(12) United States Patent
Kawakami et al.

(10) Patent No.: US 8,592,053 B2
(45) Date of Patent: *Nov. 26, 2013

(54) ANTHRACENE DERIVATIVE, LIGHT-EMITTING ELEMENT, LIGHT-EMITTING DEVICE, AND ELECTRONIC APPLIANCE

(75) Inventors: Sachiko Kawakami, Kanagawa (JP); Tsunenori Suzuki, Kanagawa (JP); Nobuharu Ohsawa, Kanagawa (JP); Satoko Shitagaki, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 6625 days.

This patent is subject to a terminal disclaimer.

(21) Appl. No.: 12/427,118

(22) Filed: Apr. 21, 2009

(65) Prior Publication Data

US 2009/0267498 A1  Oct. 29, 2009

(30) Foreign Application Priority Data

Apr. 24, 2008  (JP) ................. 2008-114057

(51) Int. Cl.
*H01L 51/54* (2006.01)

(52) U.S. Cl.
USPC ........... 428/690; 428/917; 313/504; 313/505; 313/506; 257/40; 257/E51.05; 257/E51.026; 257/E51.032; 548/418; 548/440

(58) Field of Classification Search
USPC .................. 428/690, 917; 313/504, 505, 506; 257/40, E51.032, E51.05, E51.026; 548/418, 440
See application file for complete search history.

(56) References Cited

U.S. PATENT DOCUMENTS 8,202,632 B2  6/2012  Kawakami et al.
(Continued)

FOREIGN PATENT DOCUMENTS

| EP | 2 031 036 A1 | 3/2009 |
| EP | 2 051 310 A1 | 4/2009 |

(Continued)

OTHER PUBLICATIONS

International Search Report re application No. PCT/JP2009/058113, dated Jun. 2, 2009.
(Continued)

*Primary Examiner* — Gregory Clark
(74) *Attorney, Agent, or Firm* — Husch Blackwell LLP

(57) ABSTRACT

Novel anthracene derivatives are provided. Further, a light-emitting element, a light-emitting device, and an electronic appliance each using the novel anthracene derivative are provided. Anthracene derivatives represented by general formulae (G11) and (G21) are provided. The anthracene derivatives represented by the general formulae (G11) and (G21) each emit blue light with high color purity and have a carrier-transporting property. Therefore, each of the anthracene derivatives represented by the general formulae (G11) and (G21) is suitable for use in a light-emitting element, a light-emitting device, and an electronic appliance.

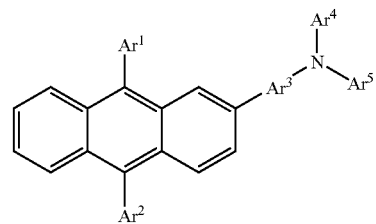

(G11)

20 Claims, 50 Drawing Sheets

(56) References Cited

U.S. PATENT DOCUMENTS

| | | | |
|---|---|---|---|
| 8,231,942 B2 | 7/2012 | Shitagaki et al. | |
| 8,288,012 B2 | 10/2012 | Nomura et al. | |
| 2005/0260442 A1 | 11/2005 | Yu et al. | |
| 2006/0192198 A1* | 8/2006 | Uckert | 257/40 |
| 2007/0205412 A1* | 9/2007 | Bae et al. | 257/40 |
| 2009/0058278 A1 | 3/2009 | Ushikubo et al. | |
| 2009/0085479 A1 | 4/2009 | Ushikubo | |
| 2009/0102366 A1 | 4/2009 | Ushikubo et al. | |
| 2009/0146139 A1* | 6/2009 | Stoessel et al. | 257/40 |
| 2009/0243476 A1 | 10/2009 | Nomura et al. | |
| 2009/0253916 A1 | 10/2009 | Kawakami et al. | |

FOREIGN PATENT DOCUMENTS

| | | | |
|---|---|---|---|
| JP | 2003-146951 | * | 5/2003 |
| JP | 2004-91334 | | 3/2004 |
| JP | 2004-95850 | | 3/2004 |
| JP | 2006-41103 | | 2/2006 |
| JP | 2009-76450 | | 4/2009 |
| JP | 2009-99966 | | 5/2009 |
| WO | WO 2007/102683 A1 | | 9/2007 |
| WO | WO 2007/110129 | * | 10/2007 |
| WO | WO 2007/110129 A1 | | 10/2007 |

OTHER PUBLICATIONS

Written Opinion re application No. PCT/JP2009/058113, dated Jun. 2, 2009.

* cited by examiner

ANTHRACENE DERIVATIVE, LIGHT-EMITTING ELEMENT, LIGHT-EMITTING DEVICE, AND ELECTRONIC APPLIANCE

TECHNICAL FIELD

The present invention relates to an anthracene derivative, and a light-emitting element, a light-emitting device, and an electronic appliance each using the anthracene derivative.

BACKGROUND ART

Organic compounds can take various structures compared with inorganic compounds, and can be used to synthesize a material having a variety of functions with appropriate molecular design. Because of these types of advantages, attention has been focused on photo electronics and electronics in which functional organic compounds are used in recent years.

For example, as examples of electronic devices in which organic compounds are used as functional organic materials, there are solar cells, light-emitting elements, organic transistors, and the like. These devices use the electrical properties and optical properties of organic compounds. Among them, in particular, tremendous progress has been made in light-emitting elements.

It is said that the light emission mechanism of a light-emitting element is as follows: by application of a voltage between a pair of electrodes with a light-emitting layer interposed therebetween, electrons injected from a cathode and holes injected from an anode recombine in the luminescence center of the light-emitting layer to form excitons in molecules, and when the excitons in molecules relax to a ground state, energy is released to emit light. A singlet excited state and a triplet excited state are known as excited states, and it is thought that light emission can be obtained through either of the excited states.

In an attempt to improve the properties of such a light-emitting element, there are many problems depending on a material. In order to solve these problems, improvement of an element structure, development of a material, etc. have been carried out.

For example, in Patent Document 1, an anthracene derivative that emits green light is disclosed. However, in Patent Document 1, only the PL spectrum of the anthracene derivative is disclosed, and the properties of a light-emitting element to which the anthracene derivative is applied are not disclosed.

Further, in Patent Document 2, a light-emitting element using an anthracene derivative for a charge-transporting layer is disclosed. However, in Patent Document 2, there is no description of the lifetime of the light-emitting element.

In view of commercialization, an increase in lifetime is an important object, and development of a light-emitting element having better properties is desired.

[Patent Document 1]
United States Patent Application Laid-Open No. 2005-0260442
[Patent Document 2]
Japanese Published Patent Application No. 2004-91334

DISCLOSURE OF INVENTION

In view of the above, according to an embodiment of the present invention, novel anthracene derivatives are provided.

Further, according to an embodiment of the present invention, a light-emitting element, a light-emitting device, and an electronic appliance each using any of the novel anthracene derivatives are provided.

An embodiment of the present invention is an anthracene derivative represented by a general formula (G11).

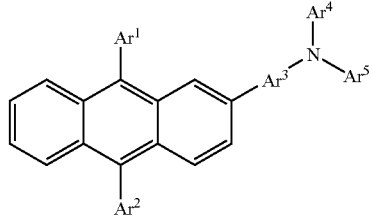

(G11)

In the formula, $Ar^1$ and $Ar^2$ independently represent a substituted or unsubstituted aryl group having 6 to 13 carbon atoms, $Ar^3$ represents a substituted or unsubstituted arylene group having 6 to 13 carbon atoms, $Ar^4$ represents a substituted or unsubstituted aryl group having 6 to 13 carbon atoms, $Ar^5$ represents a substituted or unsubstituted aryl group having 6 to 13 carbon atoms, and a direct bond between $Ar^3$ and $Ar^4$, between $Ar^3$ and $Ar^5$, or between $Ar^4$ and $Ar^5$ forms a five-membered ring to form a carbazole skeleton.

Further, an embodiment of the present invention is an anthracene derivative represented by a general formula (G12-1).

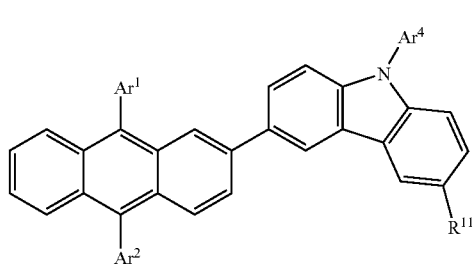

(G12-1)

In the formula, $Ar^1$ and $Ar^2$ independently represent a substituted or unsubstituted aryl group having 6 to 13 carbon atoms, $Ar^4$ represents a substituted or unsubstituted aryl group having 6 to 13 carbon atoms, and $R^{11}$ represents hydrogen, an alkyl group having 1 to 4 carbon atoms, or a substituted or unsubstituted aryl group having 6 to 13 carbon atoms.

Further, an embodiment of the present invention is an anthracene derivative represented by a general formula (G12-2).

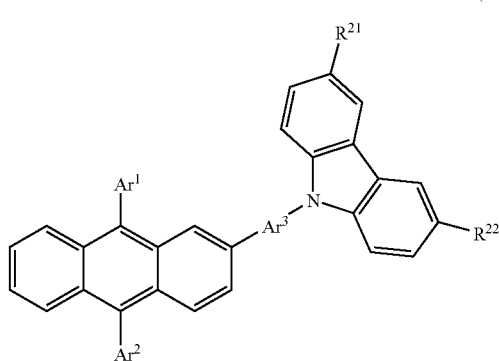

(G12-2)

In the formula, $Ar^1$ and $Ar^2$ independently represent a substituted or unsubstituted aryl group having 6 to 13 carbon atoms, $Ar^3$ represents a substituted or unsubstituted arylene group having 6 to 13 carbon atoms, and $R^{21}$ and $R^{22}$ independently represent hydrogen, an alkyl group having 1 to 4 carbon atoms, or a substituted or unsubstituted aryl group having 6 to 13 carbon atoms.

Further, an embodiment of the present invention is an anthracene derivative represented by a general formula (G13-1).

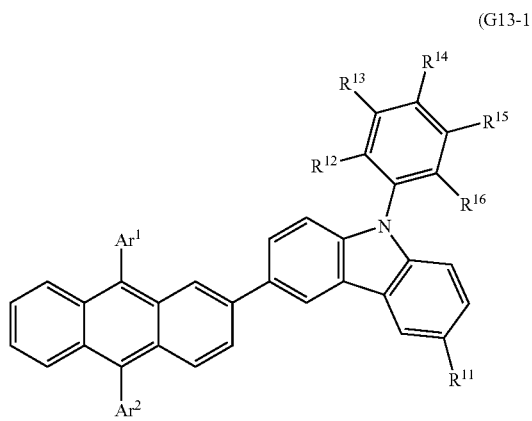

(G13-1)

In the formula, $Ar^1$ and $Ar^2$ independently represent a substituted or unsubstituted aryl group having 6 to 13 carbon atoms, $R^{11}$ represents hydrogen, an alkyl group having 1 to 4 carbon atoms, or a substituted or unsubstituted aryl group having 6 to 13 carbon atoms, and $R^{12}$ to $R^{16}$ independently represent hydrogen, an alkyl group having 1 to 4 carbon atoms, or a substituted or unsubstituted aryl group having 6 to 10 carbon atoms.

Further, an embodiment of the present invention is an anthracene derivative represented by a general formula (G13-2).

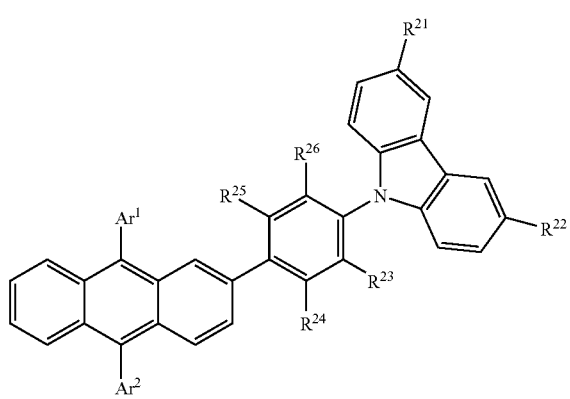

(G13-2)

In the formula, $Ar^1$ and $Ar^2$ independently represent a substituted or unsubstituted aryl group having 6 to 13 carbon atoms, $R^{21}$ and $R^{22}$ independently represent hydrogen, an alkyl group having 1 to 4 carbon atoms, or a substituted or unsubstituted aryl group having 6 to 13 carbon atoms, and $R^{23}$ to $R^{26}$ independently represent hydrogen, an alkyl group having 1 to 4 carbon atoms, or a substituted or unsubstituted phenyl group.

Further, an embodiment of the present invention is an anthracene derivative represented by a general formula (G14-1).

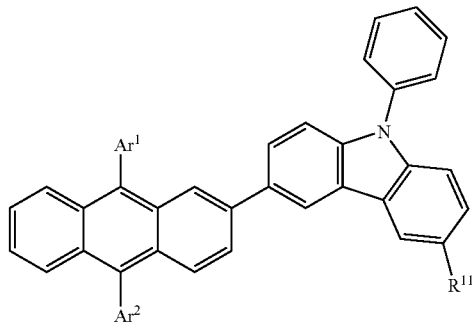

(G14-1)

In the formula, $Ar^1$ and $Ar^2$ independently represent a substituted or unsubstituted aryl group having 6 to 13 carbon atoms, and $R^{11}$ represents hydrogen, an alkyl group having 1 to 4 carbon atoms, or a substituted or unsubstituted aryl group having 6 to 13 carbon atoms.

Further, an embodiment of the present invention is an anthracene derivative represented by a general formula (G14-2).

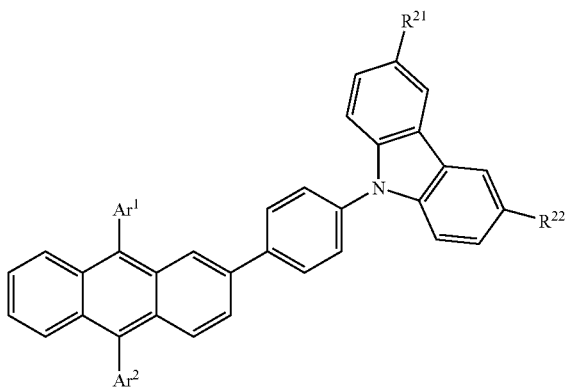

(G14-2)

In the formula, $Ar^1$ and $Ar^2$ independently represent a substituted or unsubstituted aryl group having 6 to 13 carbon atoms, and $R^{21}$ and $R^{22}$ independently represent hydrogen, an allyl group having 1 to 4 carbon atoms, or a substituted or unsubstituted aryl group having 6 to 13 carbon atoms.

Further, an embodiment of the present invention is an anthracene derivative represented by a general formula (G15-1).

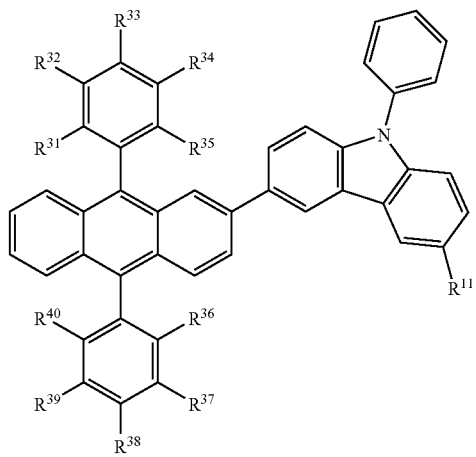

(G15-1)

In the formula, $R^{11}$ represents hydrogen, an alkyl group having 1 to 4 carbon atoms, or a substituted or unsubstituted aryl group having 6 to 13 carbon atoms, and $R^{31}$ to $R^{40}$ independently represent hydrogen, an alkyl group having 1 to 4 carbon atoms, a substituted or unsubstituted aryl group having 6 to 10 carbon atoms, halogen, or a haloalkyl group having 1 to 4 carbon atoms.

Further, an embodiment of the present invention is an anthracene derivative represented by a general formula (G15-2).

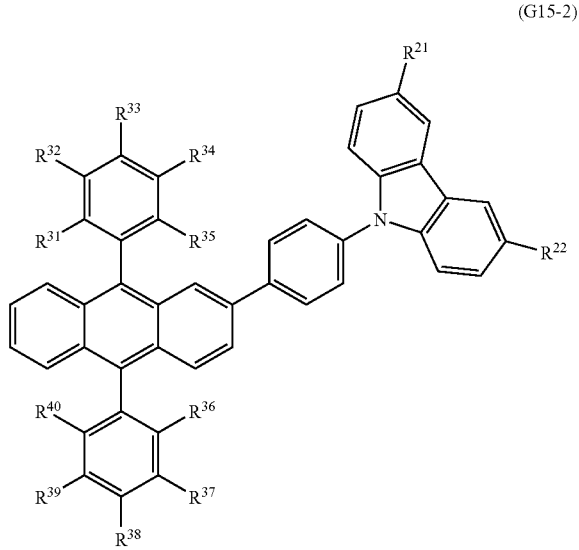

(G15-2)

In the formula, $R^{21}$ and $R^{22}$ independently represent hydrogen, an alkyl group having 1 to 4 carbon atoms, or a substituted or unsubstituted aryl group having 6 to 13 carbon atoms, and $R^{31}$ to $R^{40}$ independently represent hydrogen, an alkyl group having 1 to 4 carbon atoms, a substituted or unsubstituted aryl group having 6 to 10 carbon atoms, halogen, or a haloalkyl group having 1 to 4 carbon atoms.

Further, an embodiment of the present invention is an anthracene derivative represented by a general formula (G21).

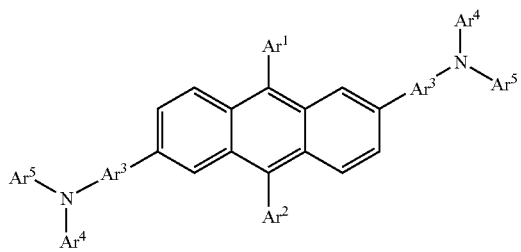

(G21)

In the formula, $Ar^1$ and $Ar^2$ independently represent a substituted or unsubstituted aryl group having 6 to 13 carbon atoms, $Ar^3$ represents a substituted or unsubstituted arylene group having 6 to 13 carbon atoms, $Ar^4$ represents a substituted or unsubstituted aryl group having 6 to 13 carbon atoms, $Ar^5$ represents a substituted or unsubstituted aryl group having 6 to 13 carbon atoms, and a direct bond between $Ar^3$ and $Ar^4$, between $Ar^3$ and $Ar^5$, or between $Ar^4$ and $Ar^5$ forms a five-membered ring to form a carbazole skeleton.

Further, an embodiment of the present invention is an anthracene derivative represented by a general formula (G22-1).

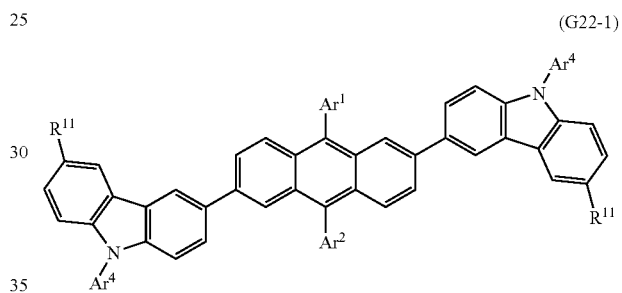

(G22-1)

In the formula, $Ar^1$ and $Ar^2$ independently represent a substituted or unsubstituted aryl group having 6 to 13 carbon atoms, $Ar^4$ represents a substituted or unsubstituted aryl group having 6 to 13 carbon atoms, and $R^{11}$ represents hydrogen, an alkyl group having 1 to 4 carbon atoms, or a substituted or unsubstituted aryl group having 6 to 13 carbon atoms.

Further, an embodiment of the present invention is an anthracene derivative represented by a general formula (G22-2).

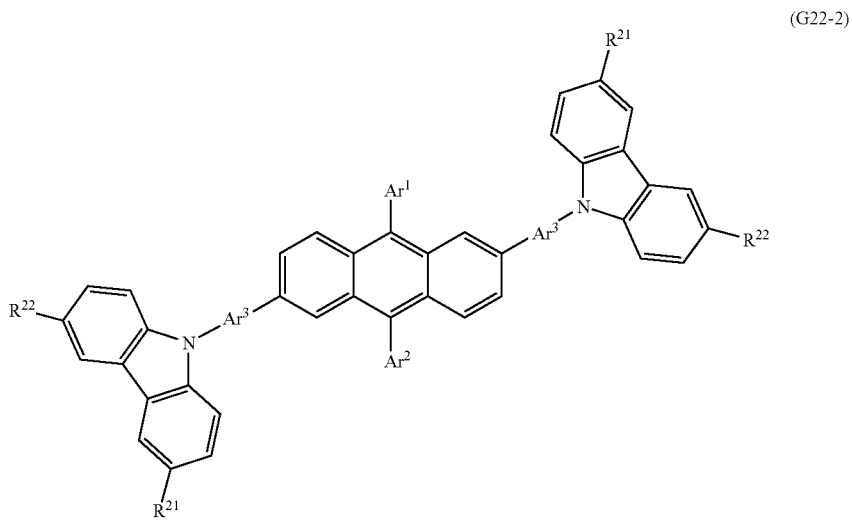

(G22-2)

In the formula, $Ar^1$ and $Ar^2$ independently represent a substituted or unsubstituted aryl group having 6 to 13 carbon atoms, $Ar^3$ represents a substituted or unsubstituted arylene group having 6 to 13 carbon atoms, and $R^{21}$ and $R^{22}$ independently represent hydrogen, an alkyl group having 1 to 4 carbon atoms, or a substituted or unsubstituted aryl group having 6 to 13 carbon atoms.

Further, an embodiment of the present invention is an anthracene derivative represented by a general formula (G23-1).

having 6 to 13 carbon atoms, and $R^{12}$ to $R^{16}$ independently represent hydrogen, an alkyl group having 1 to 4 carbon atoms, or a substituted or unsubstituted aryl group having 6 to 10 carbon atoms.

Further, an embodiment of the present invention is an anthracene derivative represented by a general formula (G23-2).

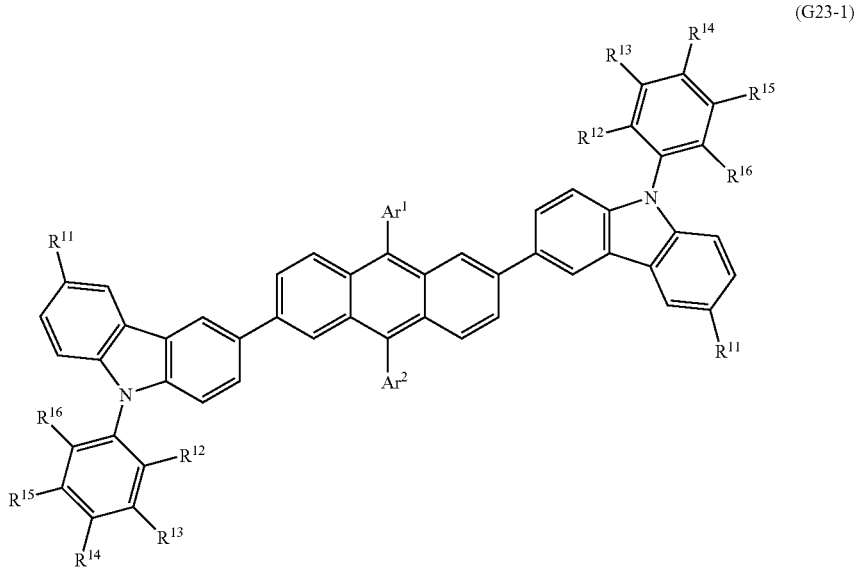

(G23-1)

In the formula, $Ar^1$ and $Ar^2$ independently represent a substituted or unsubstituted aryl group having 6 to 13 carbon atoms, $R^{11}$ represents hydrogen, an alkyl group having 1 to 4 carbon atoms, or a substituted or unsubstituted aryl group

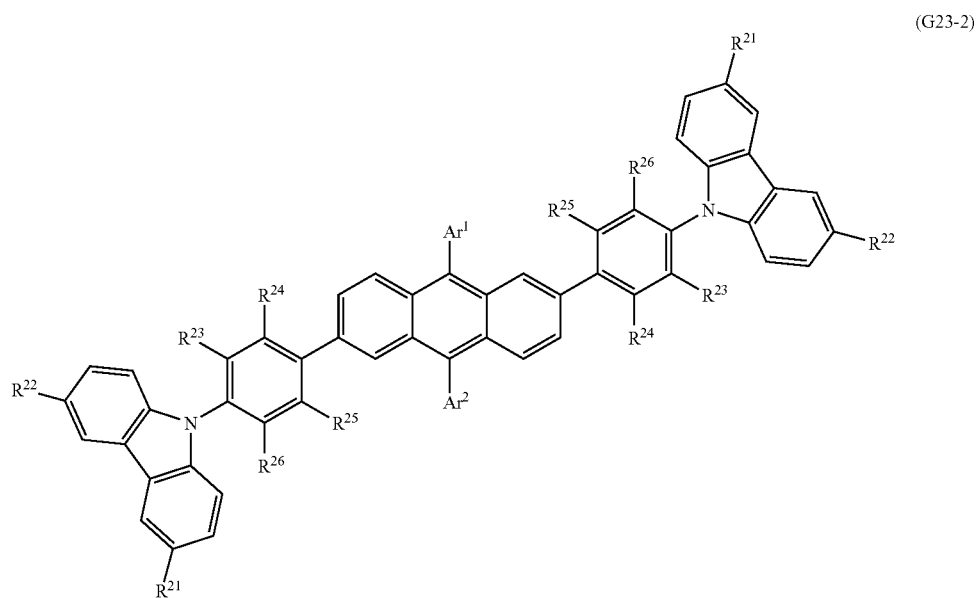

(G23-2)

In the formula, $Ar^1$ and $Ar^2$ independently represent a substituted or unsubstituted aryl group having 6 to 13 carbon atoms, $R^{21}$ and $R^{22}$ independently represent hydrogen, an alkyl group having 1 to 4 carbon atoms, or a substituted or unsubstituted aryl group having 6 to 13 carbon atoms, and $R^{23}$ to $R^{26}$ independently represent hydrogen, an alkyl group having 1 to 4 carbon atoms, or a substituted or unsubstituted phenyl group.

Further, an embodiment of the present invention is an anthracene derivative represented by a general formula (G24-1).

In the formula, $Ar^1$ and $Ar^2$ independently represent a substituted or unsubstituted aryl group having 6 to 13 carbon atoms, and $R^{11}$ represents hydrogen, an alkyl group having 1 to 4 carbon atoms, or a substituted or unsubstituted aryl group having 6 to 13 carbon atoms.

Further, an embodiment of the present invention is an anthracene derivative represented by a general formula (G24-2).

In the formula, $Ar^1$ and $Ar^2$ independently represent a substituted or unsubstituted aryl group having 6 to 13 carbon atoms, and $R^{21}$ and $R^{22}$ independently represent hydrogen, an alkyl group having 1 to 4 carbon atoms, or a substituted or unsubstituted aryl group having 6 to 13 carbon atoms.

Further, an embodiment of the present invention is an anthracene derivative represented by a general formula (G25-1).

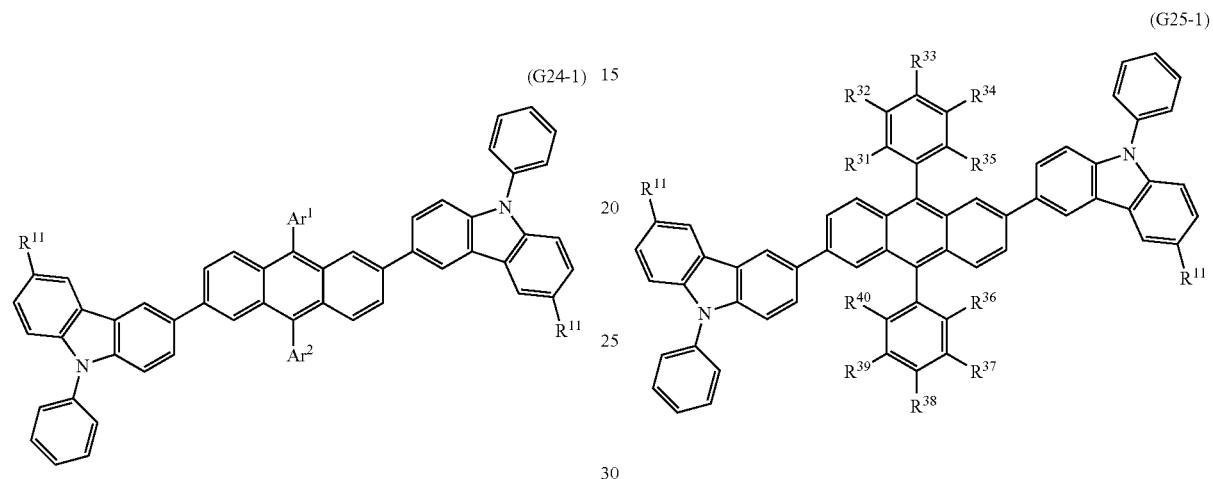

(G25-1)

In the formula, $R^{11}$ represents hydrogen, an alkyl group having 1 to 4 carbon atoms, or a substituted or unsubstituted aryl group having 6 to 13 carbon atoms, and $R^{31}$ to $R^{40}$ independently represent hydrogen, an alkyl group having 1 to 4 carbon atoms, a substituted or unsubstituted aryl group having 6 to 10 carbon atoms, halogen, or a haloalkyl group having 1 to 4 carbon atoms.

Further, an embodiment of the present invention is an anthracene derivative represented by a general formula (G25-2).

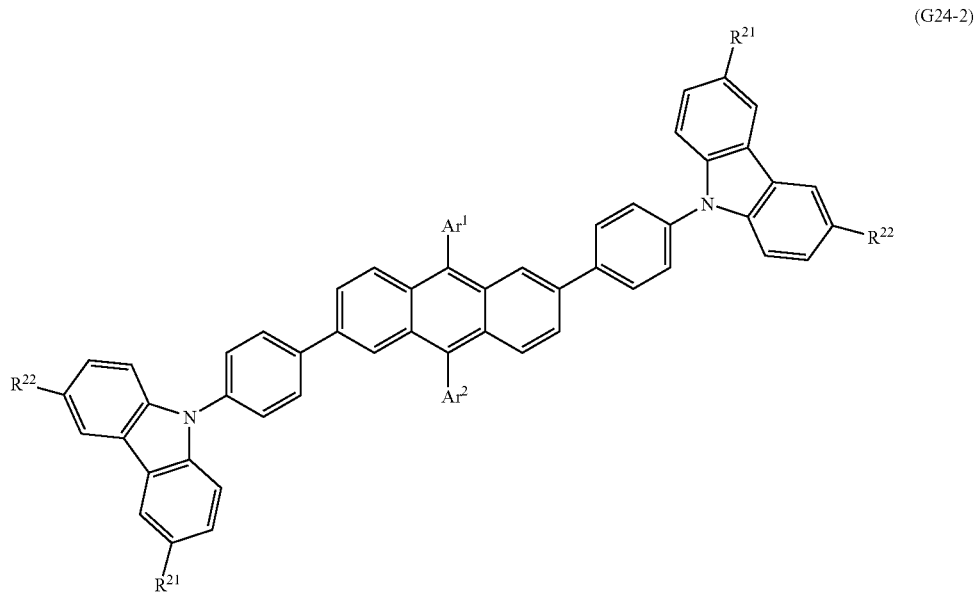

(G24-2)

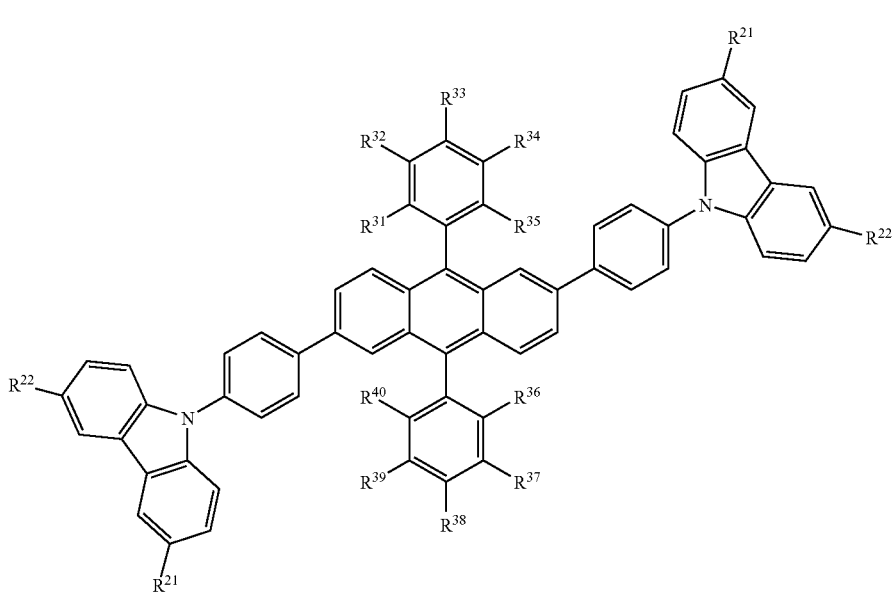
(G25-2)

In the formula, $R^{21}$ and $R^{22}$ independently represent hydrogen, an alkyl group having 1 to 4 carbon atoms, or a substituted or unsubstituted aryl group having 6 to 13 carbon atoms, and $R^{31}$ to $R^{40}$ independently represent hydrogen, an alkyl group having 1 to 4 carbon atoms, a substituted or unsubstituted aryl group having 6 to 10 carbon atoms, halogen, or a haloalkyl group having 1 to 4 carbon atoms.

For easy synthesis, $Ar^1$ and $Ar^2$ in each above structure are preferably substituents each having the same structure.

Further, an embodiment of the present invention is an anthracene derivative represented by a structural formula (101).

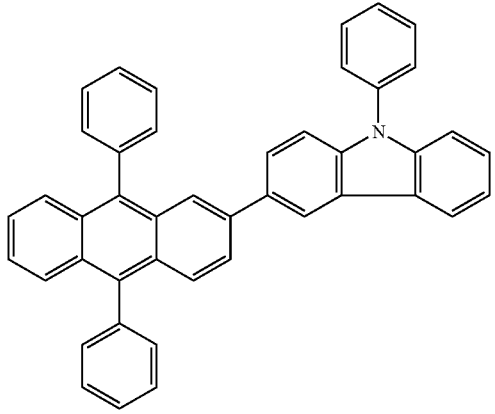
(101)

Furthermore, an embodiment of the present invention is an anthracene derivative represented by a structural formula (201).

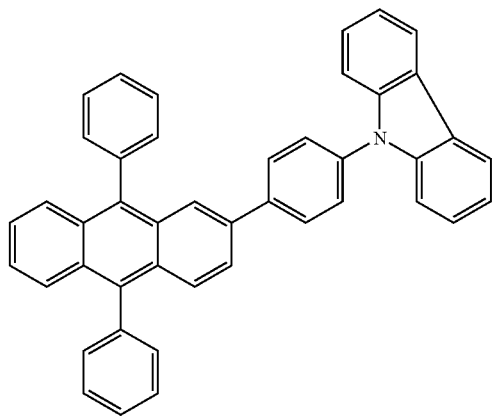
(201)

Moreover, an embodiment of the present invention is a light-emitting element using any of the above anthracene derivatives. In specific, the light-emitting element includes any of the above anthracene derivatives between a pair of electrodes.

Further, an embodiment of the present invention is a light-emitting element having a light-emitting layer between a pair of electrodes. The light-emitting layer includes any of the above anthracene derivatives. In particular, the anthracene derivative is preferably used as a light-emitting substance. That is, a structure is preferably employed in which the anthracene derivative emits light.

Furthermore, in a light-emitting device of the present invention, a light-emitting element that includes, between a pair of electrodes, an EL layer including any of the above anthracene derivatives and a control circuit configured to control light emission from the light-emitting element are included. Note that the category of a light-emitting device in this specification includes an image display device and a light source (e.g., a lighting apparatus). In addition, the following are all included in the category of a light-emitting device: a module in which a connector, for example, a flexible printed circuit (FPC), a tape automated bonding (TAB) tape, or a tape carrier package (TCP) is attached to a panel, a module provided with a printed wiring board at the end of a TAB tape or a TCP, and a module in which an integrated circuit (IC) is directly mounted to a light-emitting element by a chip on glass (COG) method.

Further, an electronic appliance using a light-emitting element of the present invention in a display portion is also included in the scope of the present invention. Accordingly, an electronic appliance of the present invention includes a display portion. The display portion includes a light-emitting element as described above and a control circuit configured to control light emission from the light-emitting element.

The anthracene derivatives of the present invention each emit blue light with high color purity and further have a carrier-transporting property. Therefore, any of the anthracene derivatives of the present invention is suitable for use in a light-emitting element, a light-emitting device, and an electronic appliance.

BEST MODE FOR CARRYING OUT THE INVENTION

Figure 1A:
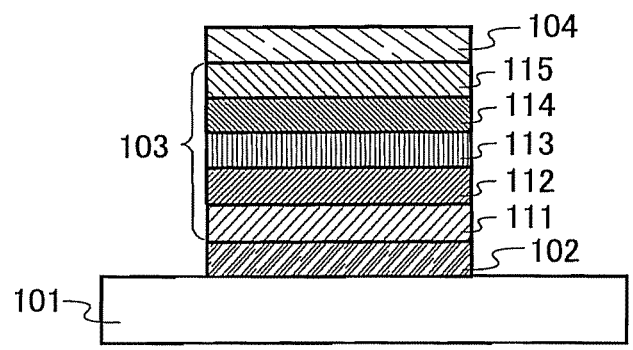
FIGS. 1A and 1B each illustrate a light-emitting element according to an embodiment of the present invention.

Hereinafter, embodiments of the present invention will be described in detail with reference to the accompanying drawings. Note that the present invention is not limited to the description below, and it is readily understood by those skilled in the art that a variety of changes and modifications can be made without departing from the spirit and scope of the present invention. Therefore, the present invention should not be interpreted as being limited to the content of the embodiments described below.

Embodiment 1

In Embodiment 1, the anthracene derivatives of the present invention will be described.

An embodiment of the present invention is the anthracene derivative represented by the general formula (G11).

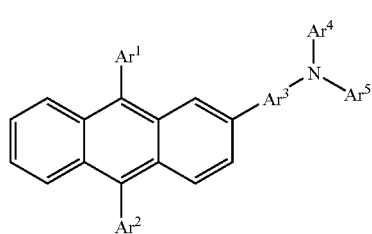

(G11)

In the formula, $Ar^1$ and $Ar^2$ independently represent a substituted or unsubstituted aryl group having 6 to 13 carbon atoms, $Ar^3$ represents a substituted or unsubstituted arylene group having 6 to 13 carbon atoms, $Ar^4$ represents a substituted or unsubstituted aryl group having 6 to 13 carbon atoms, $Ar^5$ represents a substituted or unsubstituted aryl group having 6 to 13 carbon atoms, and a direct bond between $Ar^3$ and $Ar^4$, between $Ar^3$ and $Ar^5$, or between $Ar^4$ and $Ar^5$ forms a five-membered ring to form a carbazole skeleton.

As the anthracene derivative represented by the general formula (G11), specifically, there are anthracene derivative represented by general formulae (G11-1) to (G11-3).

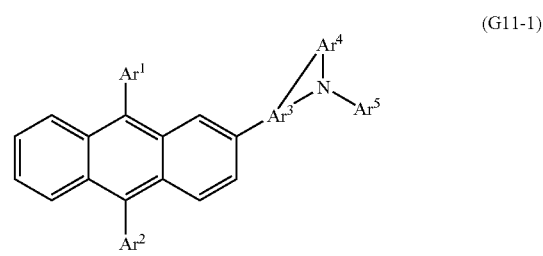

(G11-1)

In the general formula (G11-1), $Ar^1$ and $Ar^2$ independently represent a substituted or unsubstituted aryl group having 6 to 13 carbon atoms, $Ar^3$ has a benzene ring, $Ar^4$ has a benzene ring, a direct bond between $Ar^3$ and $Ar^4$ forms a five-membered ring to form a carbazole skeleton, and $Ar^5$ represents a substituted or unsubstituted aryl group having 6 to 13 carbon atoms.

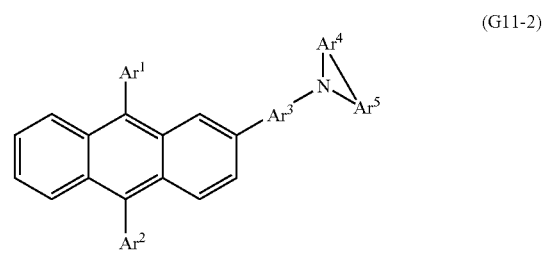

(G11-2)

In the general formula (G11-2), $Ar^1$ and $Ar^2$ independently represent a substituted or unsubstituted aryl group having 6 to 13 carbon atoms, $Ar^3$ represents a substituted or unsubstituted aryl group having 6 to 13 carbon atoms, $Ar^4$ has a benzene ring, $Ar^5$ has a benzene ring, and a direct bond between $Ar^4$ and $Ar^5$ forms a five-membered ring to form a carbazole skeleton.

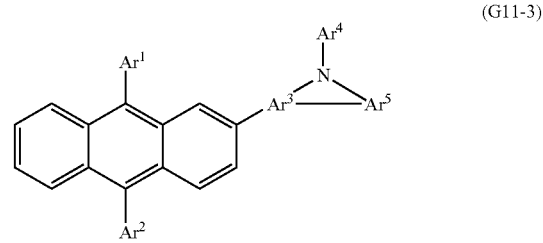

(G11-3)

In the general formula (G11-3), $Ar^1$ and $Ar^2$ independently represent a substituted or unsubstituted aryl group having 6 to 13 carbon atoms, $Ar^4$ represents a substituted or unsubstituted aryl group having 6 to 13 carbon atoms, $Ar^3$ has a benzene ring, $Ar^5$ has a benzene ring, and a direct bond between $Ar^3$ and $Ar^5$ forms a five-membered ring to form a carbazole skeleton.

Another embodiment of the present invention is the anthracene derivative represented by the general formula (G21).

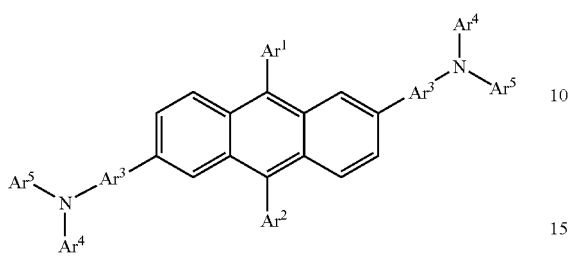

(G21)

In the formula, $Ar^1$ and $Ar^2$ independently represent a substituted or unsubstituted aryl group having 6 to 13 carbon atoms, $Ar^3$ represents a substituted or unsubstituted arylene group having 6 to 13 carbon atoms, $Ar^4$ represents a substituted or unsubstituted aryl group having 6 to 13 carbon atoms, $Ar^5$ represents a substituted or unsubstituted aryl group having 6 to 13 carbon atoms, and a direct bond between $Ar^3$ and $Ar^4$, between $Ar^3$ and $Ar^5$, or between $Ar^4$ and $Ar^5$ forms a five-membered ring to form a carbazole skeleton.

As the anthracene derivative represented by the general formula (G21), specifically, there are anthracene derivative represented by general formulae (G21-1) to (G21-3).

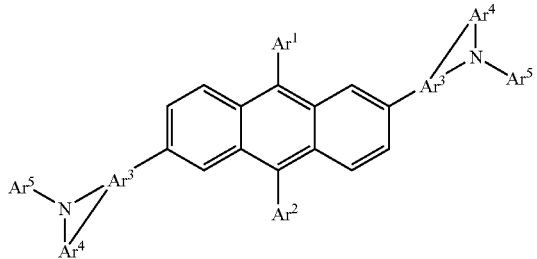

(G21-1)

In the general formula (G21-1), $Ar^1$ and $Ar^2$ independently represent a substituted or unsubstituted aryl group having 6 to 13 carbon atoms, $Ar^3$ has a benzene ring, $Ar^4$ has a benzene ring, a direct bond between $Ar^3$ and $Ar^4$ forms a five-membered ring to form a carbazole skeleton, and $Ar^5$ represents a substituted or unsubstituted aryl group having 6 to 13 carbon atoms.

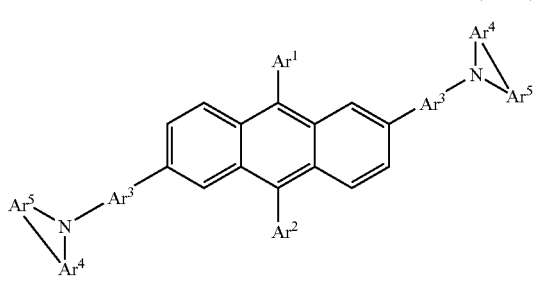

(G21-2)

In the general formula (G21-2), $Ar^1$ and $Ar^2$ independently represent a substituted or unsubstituted aryl group having 6 to 13 carbon atoms, $Ar^3$ has a benzene ring, $Ar^4$ has a benzene ring, a direct bond between $Ar^4$ and $Ar^5$ forms a five-membered ring to form a carbazole skeleton, and $Ar^5$ represents a substituted or unsubstituted aryl group having 6 to 13 carbon atoms.

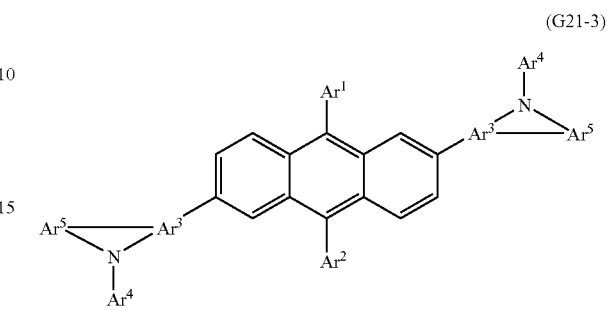

(G21-3)

In the general formula (G21-3), $Ar^1$ and $Ar^2$ independently represent a substituted or unsubstituted aryl group having 6 to 13 carbon atoms, and $Ar^4$ represents a substituted or unsubstituted aryl group having 6 to 13 carbon atoms, $Ar^3$ has a benzene ring, $Ar^5$ has a benzene ring, and a direct bond between $Ar^3$ and $Ar^5$ forms a five-membered ring to form a carbazole skeleton.

Note that the carbon atoms of the aryl group or of the arylene group which is described in this specification refer to carbon atoms forming a ring of the main skeleton, not to carbon atoms of a substituent bonded to the ring of the main skeleton. As examples of a substituent bonded to the aryl group or to the arylene group, there are an alkyl group having 1 to 4 carbon atoms and an aryl group having 6 to 13 carbon atoms; specifically, a methyl group, an ethyl group, a propyl group, a butyl group, a phenyl group, a naphthyl group, a fluorenyl group, and the like. Further, the aryl group or the arylene group may have one or more substituents. If the aryl group or the arylene group has two substituents, the substituents may be bonded to each other to form a ring. For example, if the aryl group is a fluorenyl group, the carbon atom at the 9-position may have two phenyl groups, and the two phenyl groups may be bonded to each other to form a spiro ring structure.

In the general formulae (G11) and (G21), aryl groups each having 6 to 13 carbon atoms may independently have a substituent. If aryl groups each having 6 to 13 carbon atoms independently have a plurality of substituents, the substituents may be bonded to form a ring. Further, if a carbon atom has two substituents, the substituents may be bonded to each other to form a spiro ring. For example, there are substituents represented by the structural formulae (11-1) to (11-16).

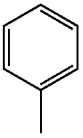

(11-1)

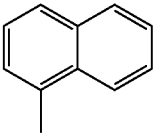

(11-2)

-continued
(11-3)
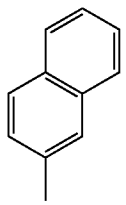
(11-4)
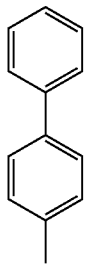
(11-5)
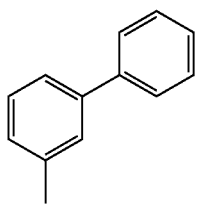
(11-6)
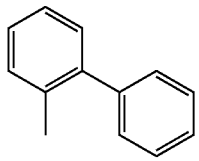
(11-7)
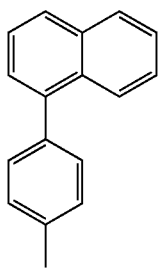
(11-8)
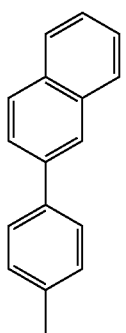
-continued
(11-9)
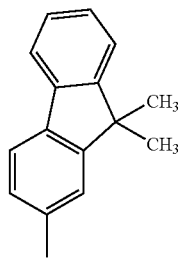
(11-10)
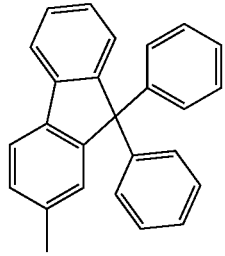
(11-11)
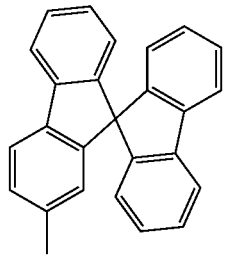
(11-12)
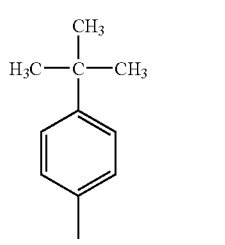
(11-13)
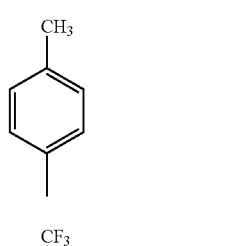
(11-14)
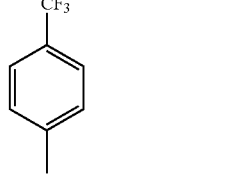
(11-15)
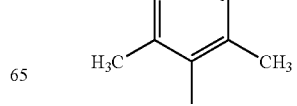

(11-16)
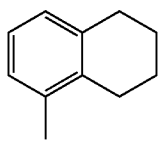

Moreover, in the general formulae (G11) and (G21), an arylene groups having 6 to 13 carbon atoms may independently have a substituent. If arylene group having 6 to 13 carbon atoms has a plurality of substituents, the substituents may be bonded to form a ring. Further, if a carbon atom has two substituents, the substituents may be bonded to each other to form a Spiro ring. For example, there are substituents represented by the structural formulae (12-1) to (12-9).

(12-1)
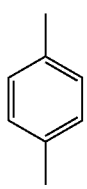

(12-2)
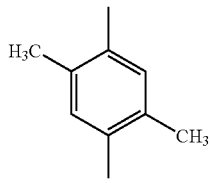

(12-3)
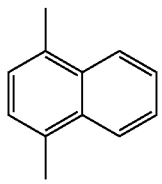

(12-4)
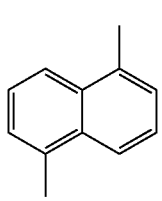

(12-5)
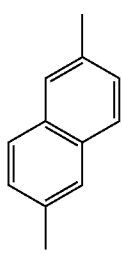

(12-6)
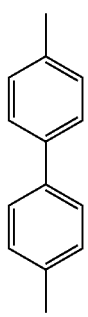

(12-7)
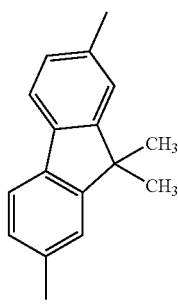

(12-8)
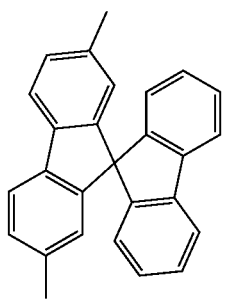

(12-9)
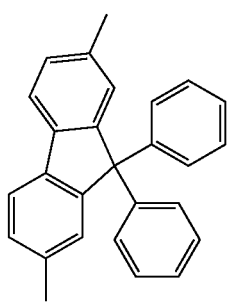

The anthracene derivative represented by the general formula (G11) is preferably an anthracene derivative represented by the general formula (G12-1) or (G12-2), for easy synthesis and purification.

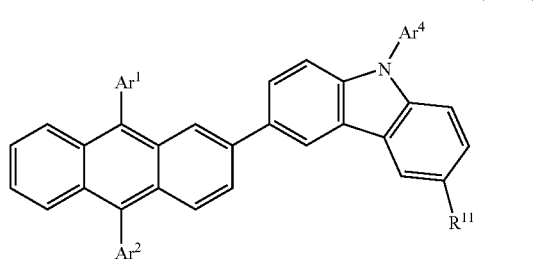

(G12-1)

In the formula, Ar¹ and Ar² independently represent a substituted or unsubstituted aryl group having 6 to 13 carbon atoms, Ar⁴ represents a substituted or unsubstituted aryl group having 6 to 13 carbon atoms, and R¹¹ represents hydrogen, an alkyl group having 1 to 4 carbon atoms, or a substituted or unsubstituted aryl group having 6 to 13 carbon atoms.

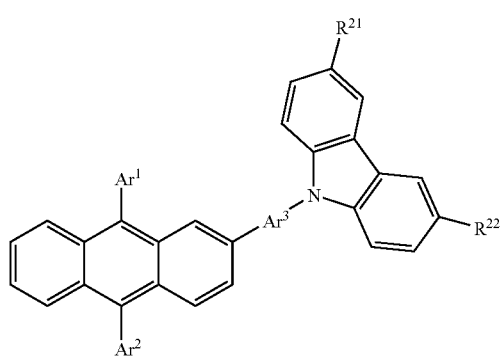

(G12-2)

In the formula, Ar¹ and Ar² independently represent a substituted or unsubstituted aryl group having 6 to 13 carbon atoms, Ar³ represents a substituted or unsubstituted arylene group having 6 to 13 carbon atoms, and R²¹ and R²² independently represent hydrogen, an alkyl group having 1 to 4 carbon atoms, or a substituted or unsubstituted aryl group having 6 to 13 carbon atoms.

Also, the anthracene derivative represented by the general formula (G21) is preferably the anthracene derivative represented by the general formula (G22-1) or (G22-2), for easy synthesis and purification.

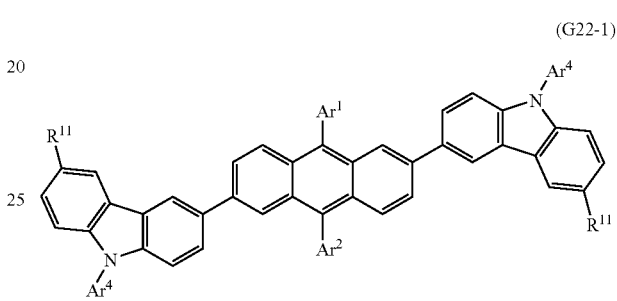

(G22-1)

In the formula, Ar¹ and Ar² independently represent a substituted or unsubstituted aryl group having 6 to 13 carbon atoms, Ar⁴ represents a substituted or unsubstituted aryl group having 6 to 13 carbon atoms, and R¹¹ represents hydrogen, an alkyl group having 1 to 4 carbon atoms, or a substituted or unsubstituted aryl group having 6 to 13 carbon atoms.

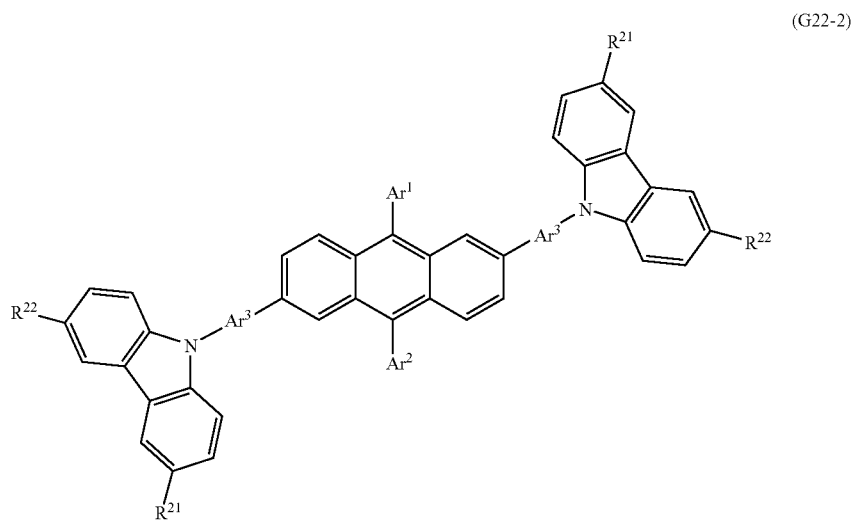

(G22-2)

In the formula, $Ar^1$ and $Ar^2$ independently represent a substituted or unsubstituted aryl group having 6 to 13 carbon atoms, $Ar^3$ represents a substituted or unsubstituted arylene group having 6 to 13 carbon atoms, and $R^{21}$ and $R^{22}$ independently represent hydrogen, an alkyl group having 1 to 4 carbon atoms, or a substituted or unsubstituted aryl group having 6 to 13 carbon atoms.

Further, in the anthracene derivative represented by the general formula (G11), it is preferable that $Ar^3$ be a substituted or unsubstituted benzene ring, $Ar^4$ be a substituted or unsubstituted benzene ring, and $Ar^5$ be a substituted or unsubstituted benzene ring, for easy synthesis and purification. That is, the anthracene derivative represented by the general formula (G13-1) or (G13-2) is preferable.

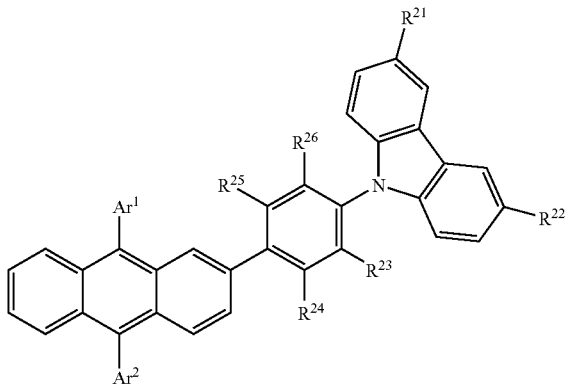

(G13-2)

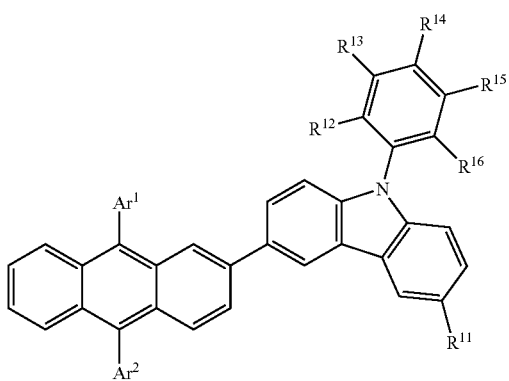

(G13-1)

In the formula, $Ar^1$ and $Ar^2$ independently represent a substituted or unsubstituted aryl group having 6 to 13 carbon atoms, $R^{21}$ and $R^{22}$ independently represent hydrogen, an alkyl group having 1 to 4 carbon atoms, or a substituted or unsubstituted aryl group having 6 to 13 carbon atoms, and $R^{23}$ to $R^{26}$ independently represent hydrogen, an alkyl group having 1 to 4 carbon atoms, or a substituted or unsubstituted phenyl group.

Also in the anthracene derivative represented by the general formula (G21), it is preferable that $Ar^3$ be a substituted or unsubstituted benzene ring, $Ar^4$ be a substituted or unsubstituted benzene ring, and $Ar^5$ be a substituted or unsubstituted benzene ring, for easy synthesis and purification. That is, an anthracene derivative represented by the general formula (G23-1) or (G23-2) is preferable.

(G23-1)

In the formula, $Ar^1$ and $Ar^2$ independently represent a substituted or unsubstituted aryl group having 6 to 13 carbon atoms, $R^{11}$ represents hydrogen, an alkyl group having 1 to 4 carbon atoms, or a substituted or unsubstituted aryl group having 6 to 13 carbon atoms, and $R^{12}$ to $R^{16}$ independently represent hydrogen, an alkyl group having 1 to 4 carbon atoms, or a substituted or unsubstituted aryl group having 6 to 10 carbon atoms.

In the formula, $Ar^1$ and $Ar^2$ independently represent a substituted or unsubstituted aryl group having 6 to 13 carbon atoms, $R^{11}$ represents hydrogen, an alkyl group having 1 to 4 carbon atoms, or a substituted or unsubstituted aryl group having 6 to 13 carbon atoms, and $R^{12}$ to $R^{16}$ independently represent hydrogen, an alkyl group having 1 to 4 carbon atoms, or a substituted or unsubstituted aryl group having 6 to 10 carbon atoms.

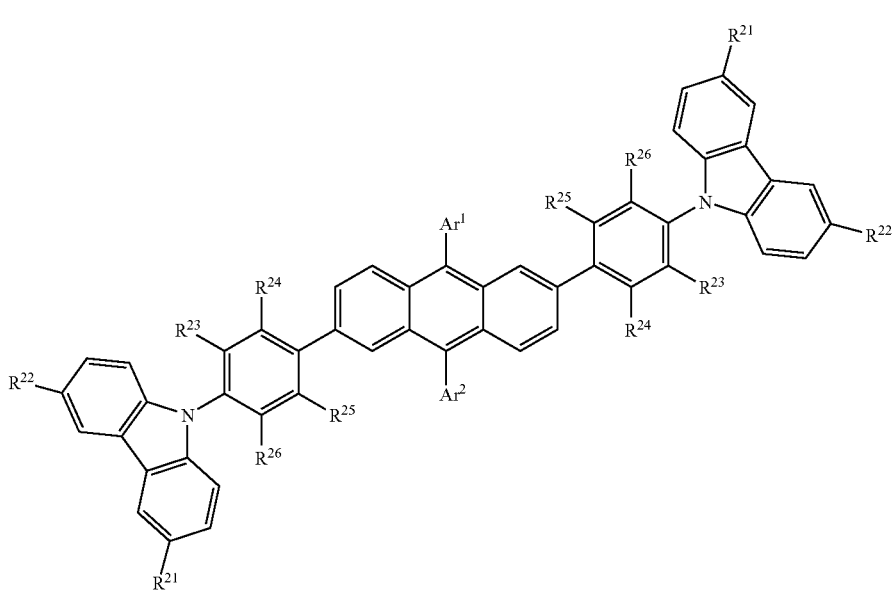
(G23-2)

In the formula, $Ar^1$ and $Ar^2$ independently represent a substituted or unsubstituted aryl group having 6 to 13 carbon atoms, $R^{21}$ and $R^{22}$ independently represent hydrogen, an alkyl group having 1 to 4 carbon atoms, or a substituted or unsubstituted aryl group having 6 to 13 carbon atoms, and $R^{23}$ to $R^{26}$ independently represent hydrogen, an alkyl group having 1 to 4 carbon atoms, or a substituted or unsubstituted phenyl group.

As the substituted or unsubstituted aryl groups each having 6 to 10 carbon atoms in the general formulae (G13-1), (G13-2), (G23-1), and (G23-2), there are substituents represented by structural formulae (13-1) to (13-8), for example.

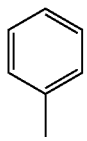
(13-1)

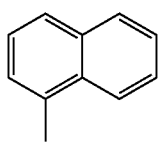
(13-2)

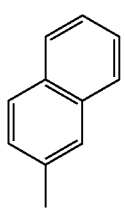
(13-3)

-continued

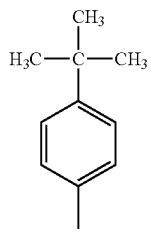
(13-4)

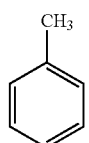
(13-5)

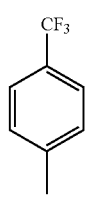
(13-6)

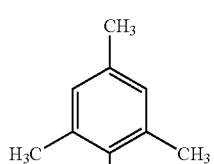
(13-7)

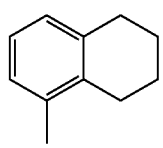
(13-8)

The anthracene derivative represented by the general formula (G11) is preferably the anthracene derivative represented by the general formula (G14-1) or (G14-2), for easy synthesis and purification.

(G14-1)

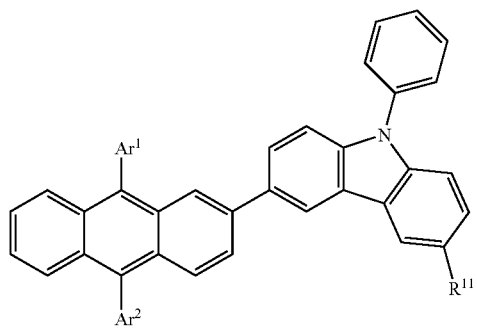

In the formula, Ar¹ and Ar² independently represent a substituted or unsubstituted aryl group having 6 to 13 carbon atoms, and $R^{11}$ represents hydrogen, an alkyl group having 1 to 4 carbon atoms, or a substituted or unsubstituted aryl group having 6 to 13 carbon atoms.

(G14-2)

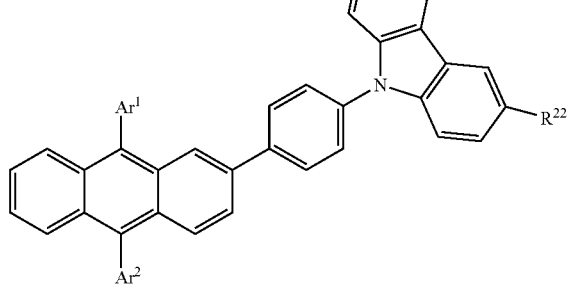

In the formula, Ar¹ and Ar² independently represent a substituted or unsubstituted aryl group having 6 to 13 carbon atoms, and $R^{21}$ and $R^{22}$ independently represent hydrogen, an alkyl group having 1 to 4 carbon atoms, or a substituted or unsubstituted aryl group having 6 to 13 carbon atoms.

Also, the anthracene derivative represented by the general formula (G21) is preferably the anthracene derivative represented by the general formula (G24-1) or (G24-2) for easy synthesis and purification.

(G24-1)

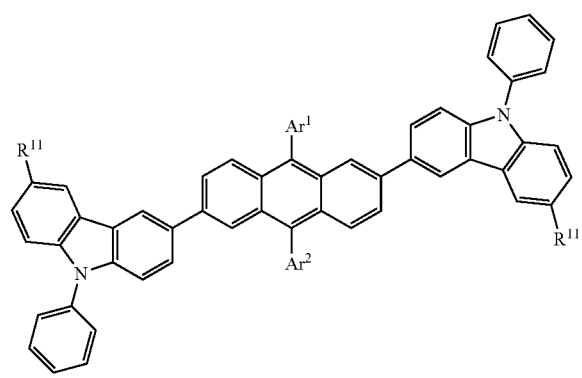

In the formula, Ar¹ and Ar² independently represent a substituted or unsubstituted aryl group having 6 to 13 carbon atoms, and $R^{11}$ represents hydrogen, an alkyl group having 1 to 4 carbon atoms, or a substituted or unsubstituted aryl group having 6 to 13 carbon atoms.

(G24-2)

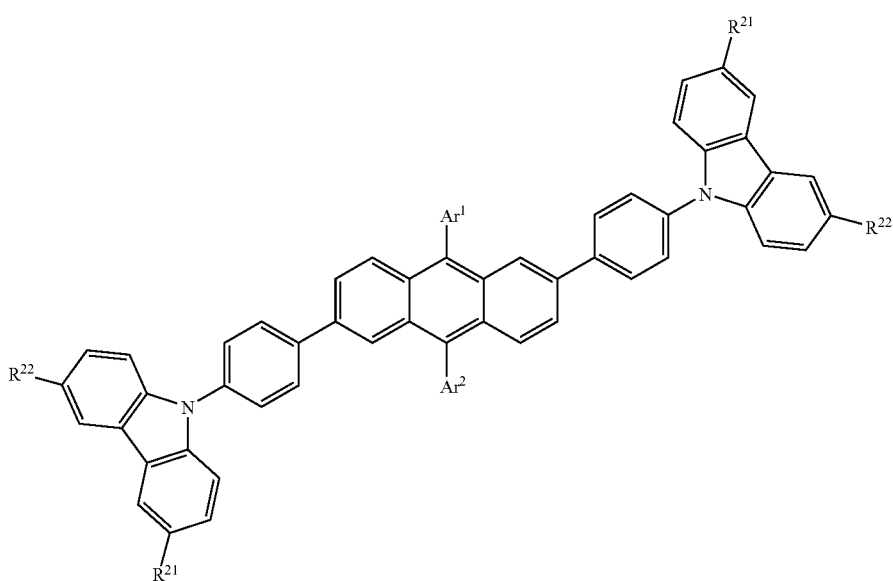

In the formula, $Ar^1$ and $Ar^2$ independently represent a substituted or unsubstituted aryl group having 6 to 13 carbon atoms, and $R^{21}$ and $R^{22}$ independently represent hydrogen, an alkyl group having 1 to 4 carbon atoms, or a substituted or unsubstituted aryl group having 6 to 13 carbon atoms.

Further, in the anthracene derivative represented by the general formula (G11), it is preferable that $Ar^1$ and $Ar^2$ be independently a substituted or unsubstituted phenyl group for easy synthesis and purification. That is, the anthracene derivative represented by the general formula (G15-1) or (G15-2) is preferable.

(G15-1)

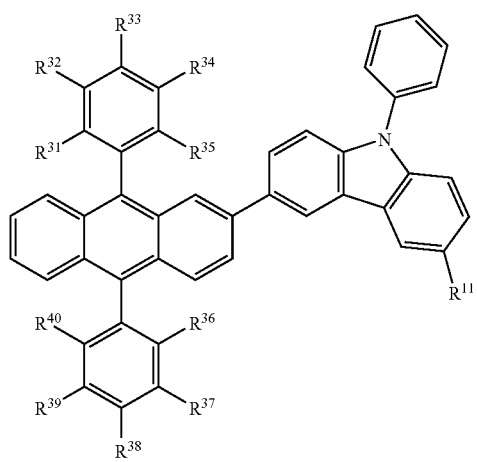

In the formula, $R^{11}$ represents hydrogen, an alkyl group having 1 to 4 carbon atoms, or a substituted or unsubstituted aryl group having 6 to 13 carbon atoms, and $R^{31}$ to $R^{40}$ independently represent hydrogen, an alkyl group having 1 to 4 carbon atoms, a substituted or unsubstituted aryl group having 6 to 10 carbon atoms, halogen, or a haloalkyl group having 1 to 4 carbon atoms.

(G15-2)

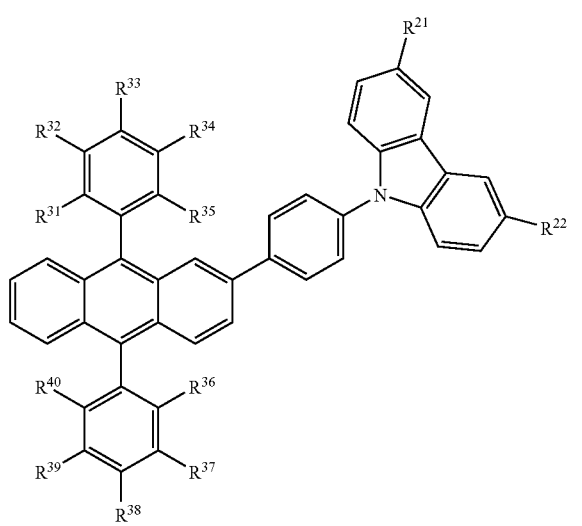

In the formula, $R^{21}$ and $R^{22}$ independently represent hydrogen, an alkyl group having 1 to 4 carbon atoms, or a substituted or unsubstituted aryl group having 6 to 13 carbon atoms, and $R^{31}$ to $R^{40}$ independently represent hydrogen, an alkyl group having 1 to 4 carbon atoms, a substituted or unsubstituted aryl group having 6 to 10 carbon atoms, halogen, or a haloalkyl group having 1 to 4 carbon atoms.

Also, in the anthracene derivative represented by the general formula (G21), it is preferable that $Ar^1$ and $Ar^2$ be independently a substituted or unsubstituted phenyl 5 group for easy synthesis and purification. That is, an anthracene derivative represented by the general formula (G25-1) or (G25-2) is preferable.

(G25-1)

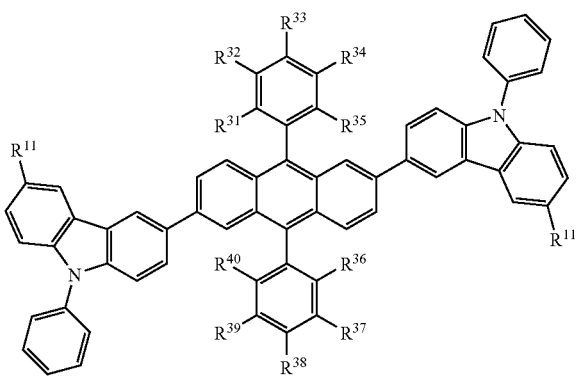

In the formula, $R^{11}$ represents hydrogen, an alkyl group having 1 to 4 carbon atoms, or a substituted or unsubstituted aryl group having 6 to 13 carbon atoms, and $R^{31}$ to $R^{40}$ independently represent hydrogen, an alkyl group having 1 to 4 carbon atoms, a substituted or unsubstituted aryl group having 6 to 10 carbon atoms, halogen, or a haloalkyl group having 1 to 4 carbon atoms.

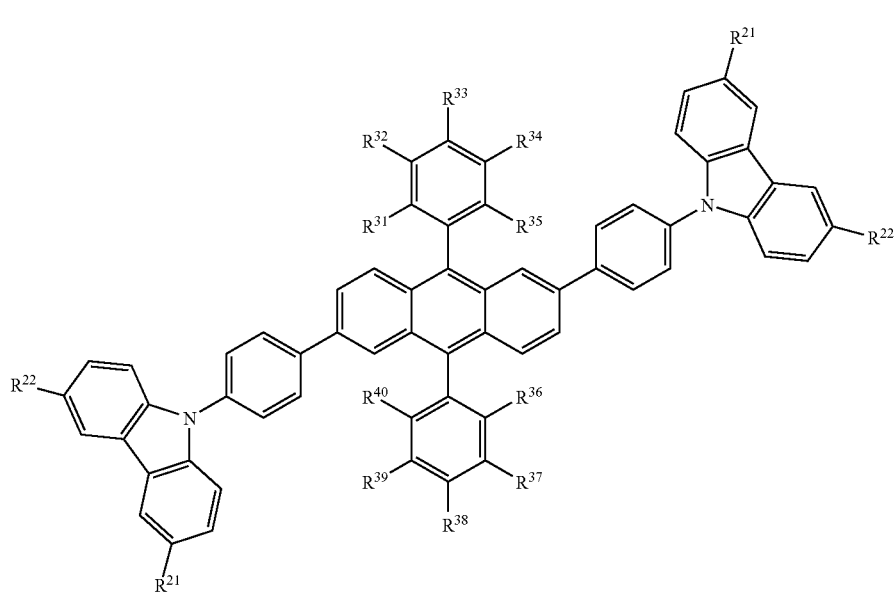

(G25-2)

In the formula, $R^{21}$ and $R^{22}$ independently represent hydrogen, an alkyl group having 1 to 4 carbon atoms, or a substituted or unsubstituted aryl group having 6 to 13 carbon atoms, and $R^{31}$ to $R^{40}$ independently represent hydrogen, an alkyl group having 1 to 4 carbon atoms, a substituted or unsubstituted aryl group having 6 to 10 carbon atoms, halogen, or a haloalkyl group having 1 to 4 carbon atoms.

As the haloalkyl group having 1 to 4 carbon atoms in each of the general formulae (G15-1), (G15-2), (G25-1), and (G25-2), there is a trifluoromethyl group and the like.

Further, in the anthracene derivative represented by the general formula (G11), $Ar^1$ and $Ar^2$ are preferably substituents each having the same structure, for easy synthesis and purification.

Also in the anthracene derivative represented by the general formula (G21), $Ar^1$ and $Ar^2$ are preferably substituents each having the same structure, for easy synthesis and purification.

Specific examples of the anthracene derivative represented by the general formula (G11) include, but not limited to, anthracene derivatives represented by structural formulae (101) to (149) and (201) to (242). Specific examples of the anthracene derivative represented by the general formula (G21) include, but not limited to, anthracene derivatives represented by structural formulae (301) to (349) and (401) to (441).

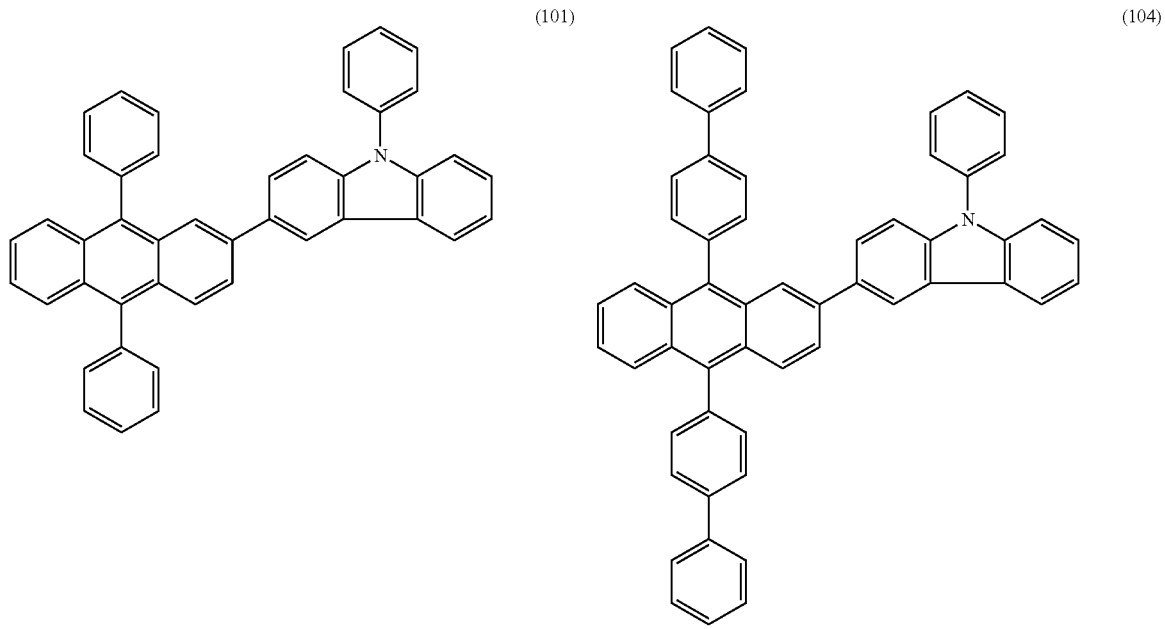

-continued
(102)
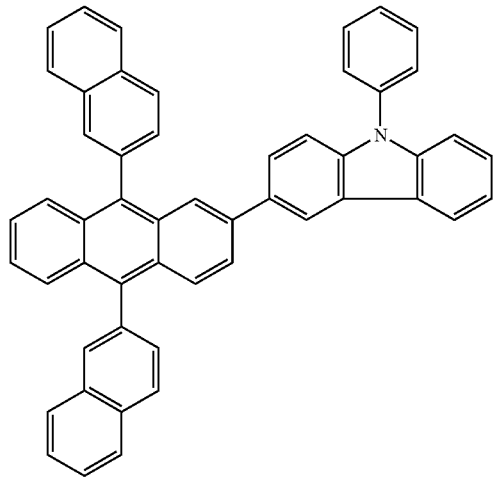
(105)
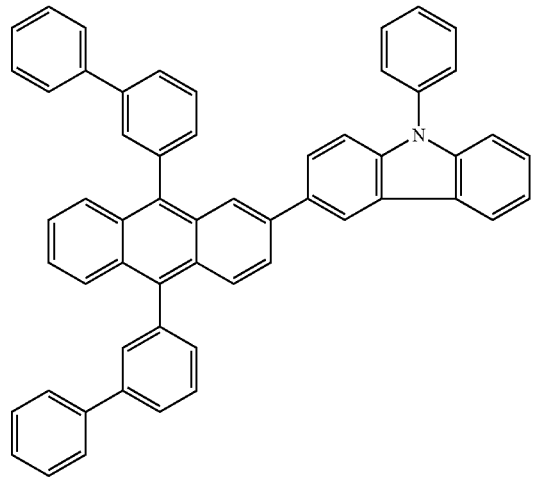
(103)
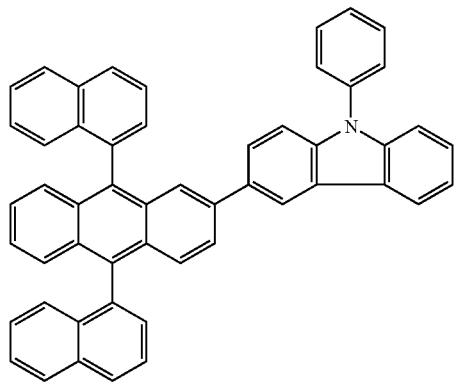
(106)
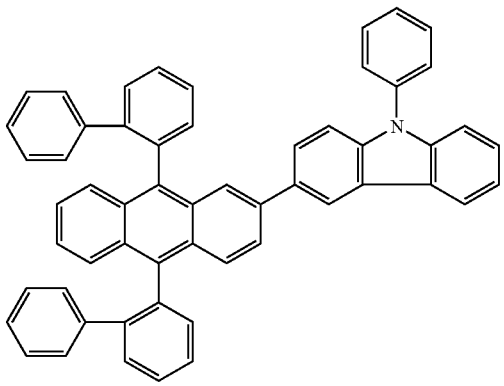
(107)
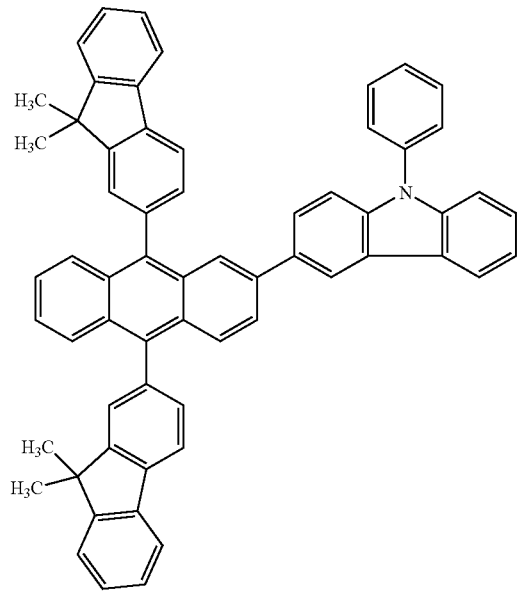
(110)
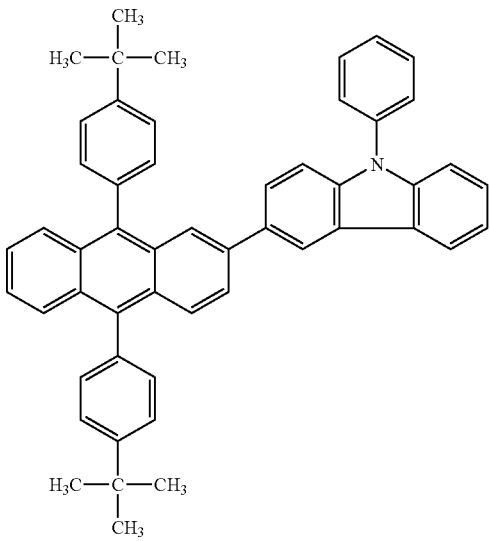

-continued
(108)
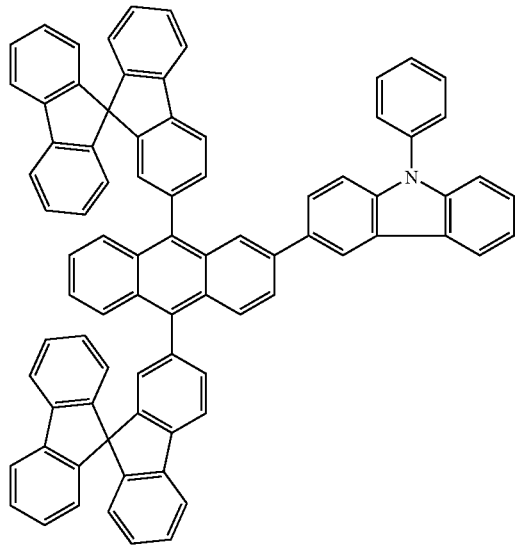
(111)
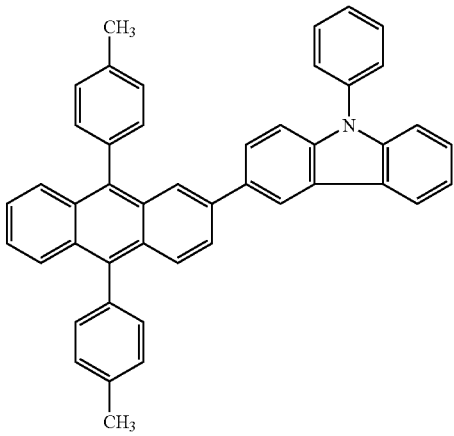
(109)
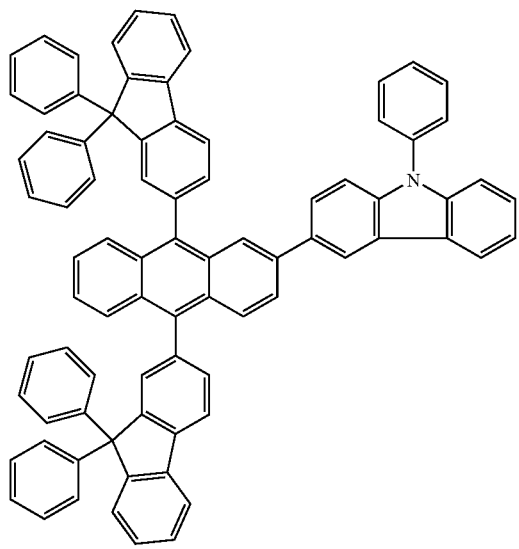
(112)
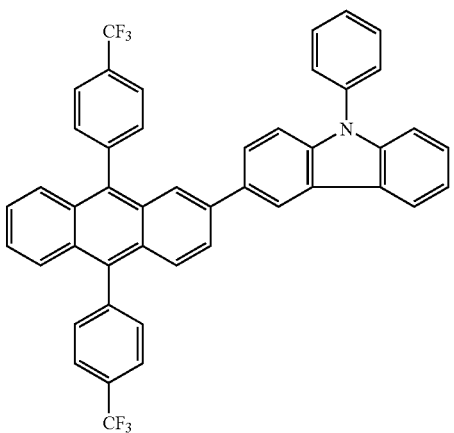
(113)
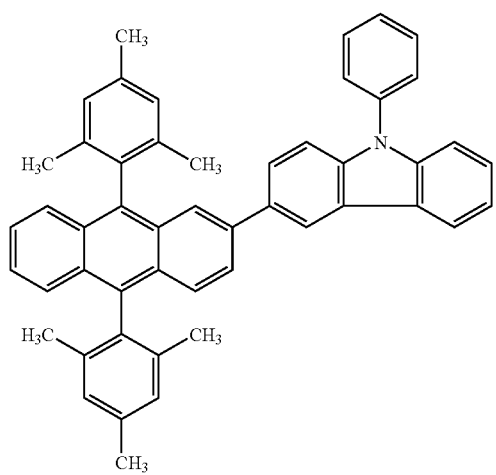
(115)
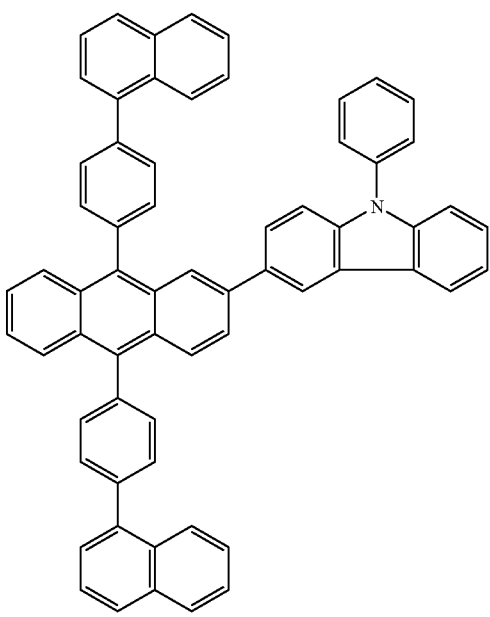

-continued
(114)
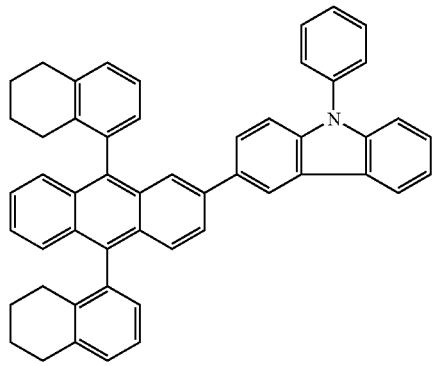
(116)
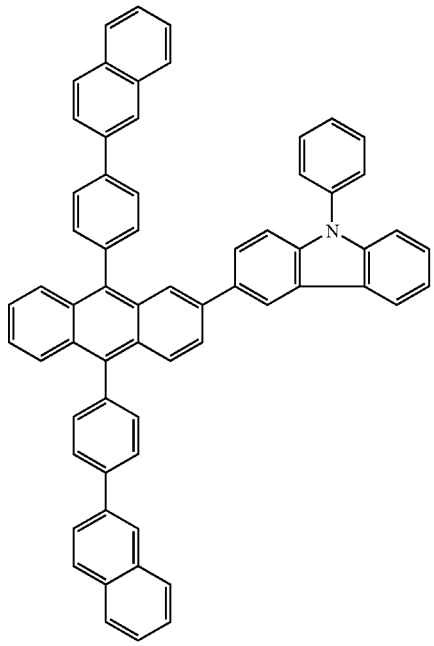
(117)
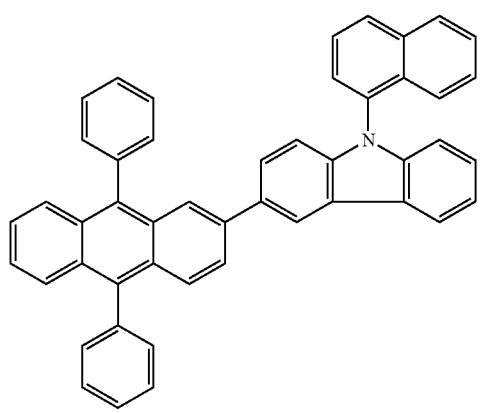
(120)
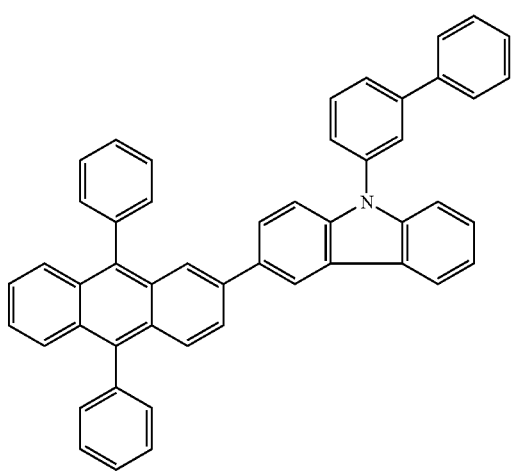
(118)
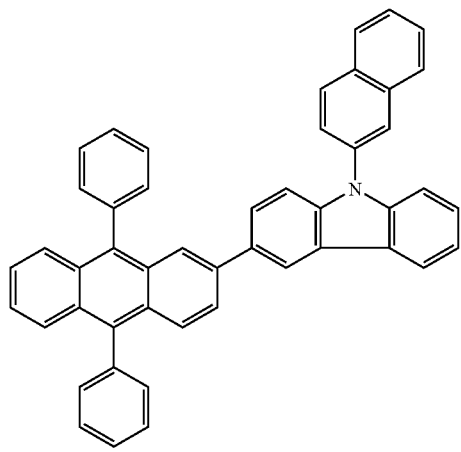
(121)
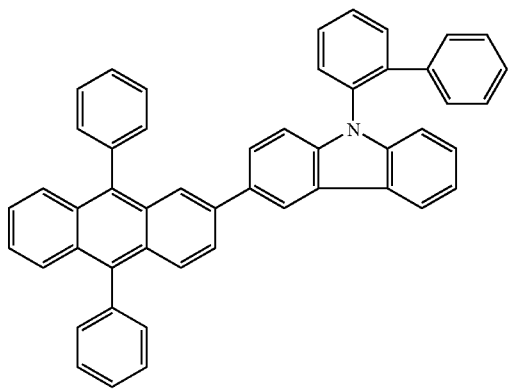

-continued
(119) 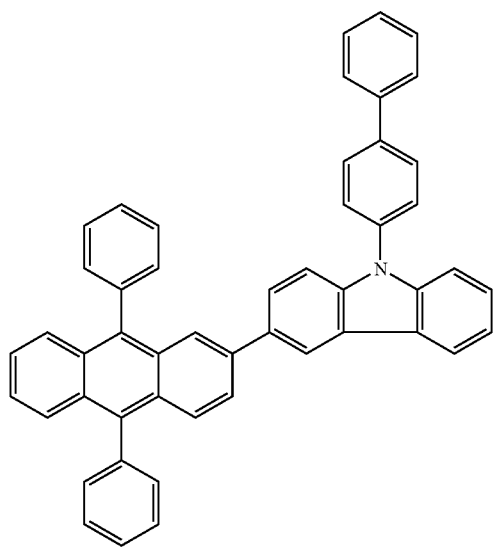
(122) 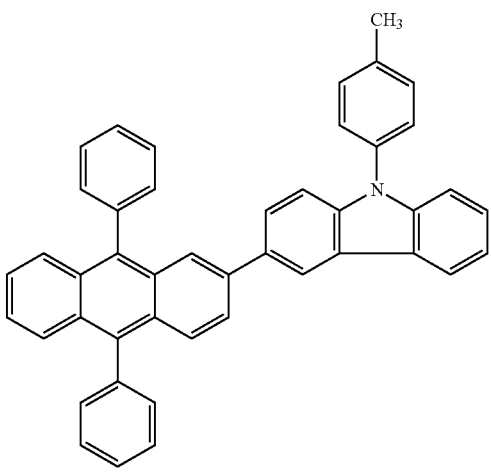
(123) 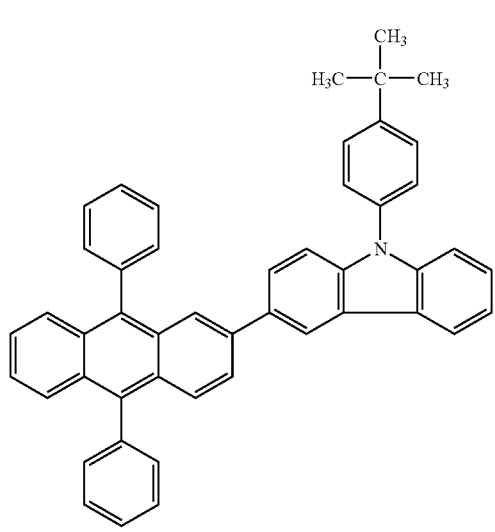
(126) 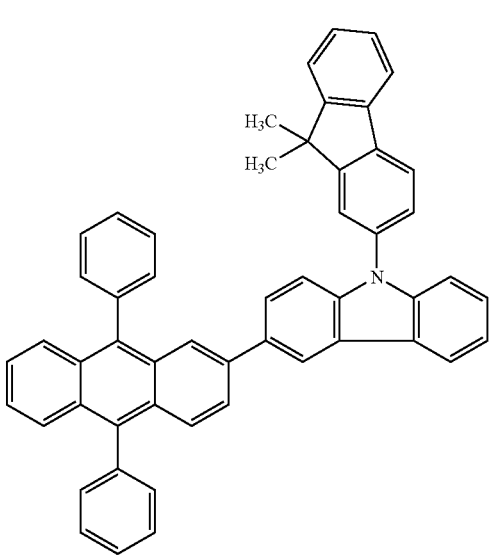
(124) 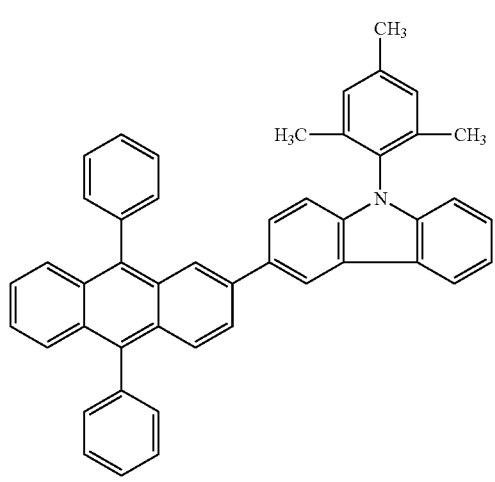
(127) 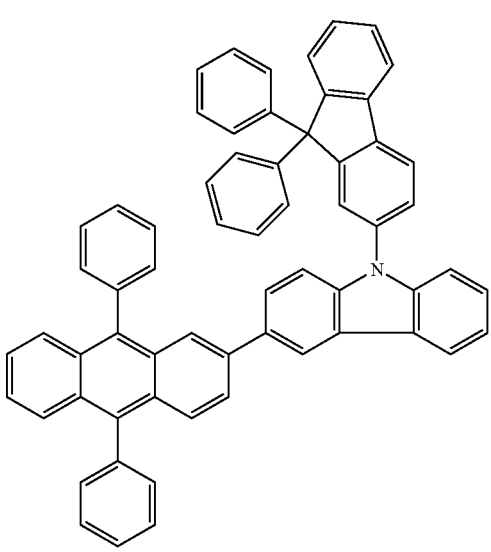

-continued
(125)
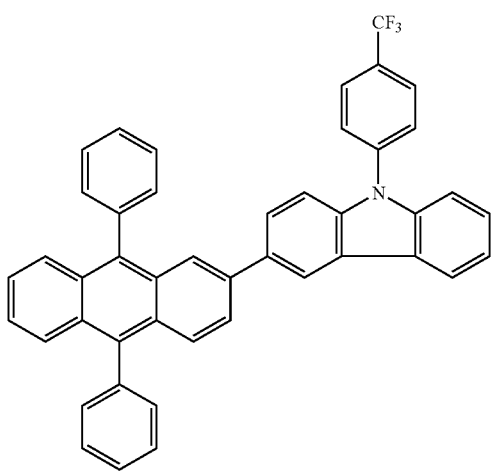
(128)
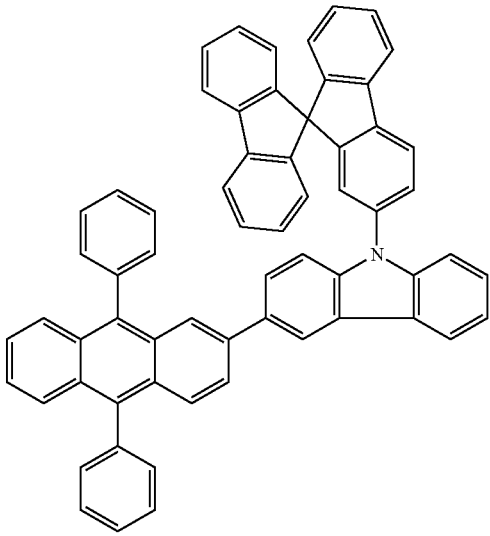
(129)
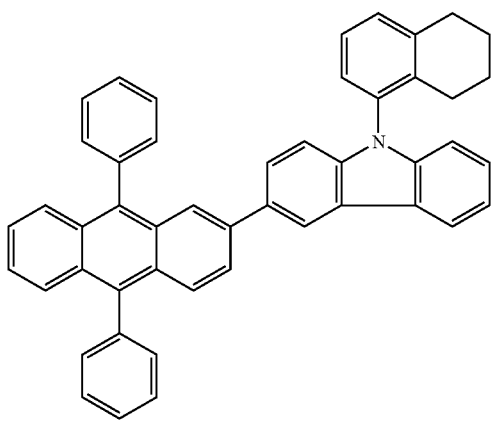
(131)
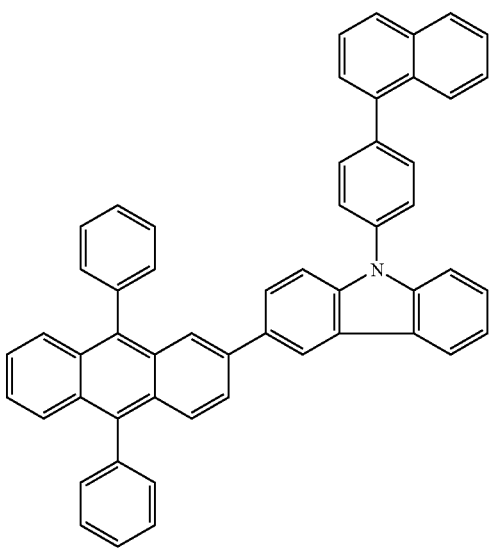
(130)
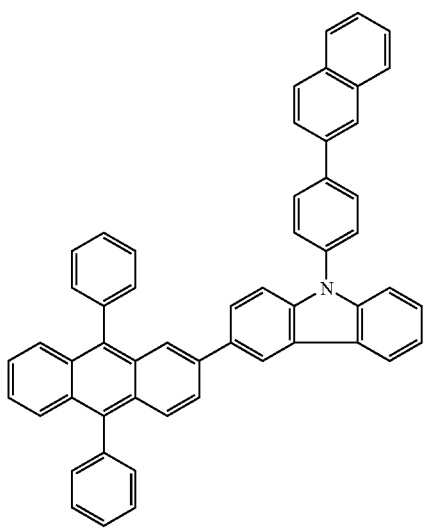
(132)

(135)
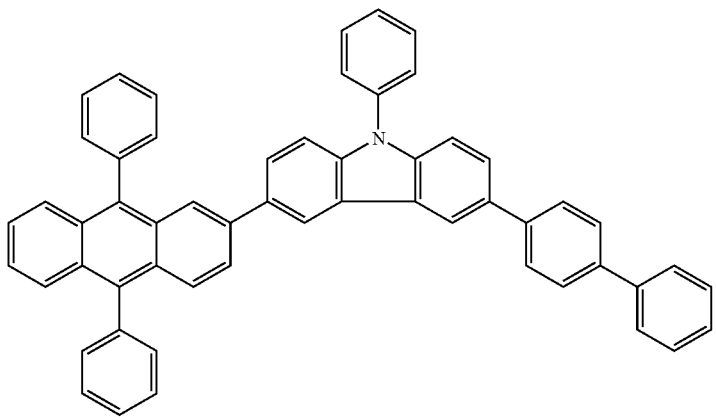
(133)
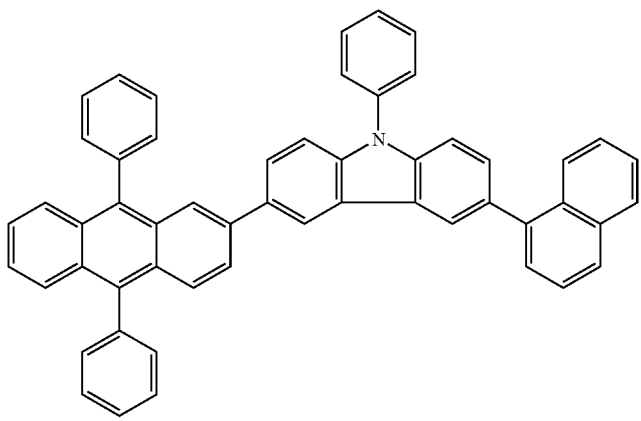
(136)
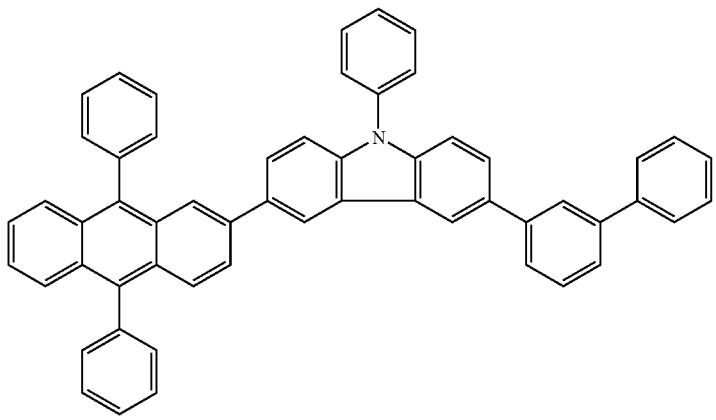
(134)
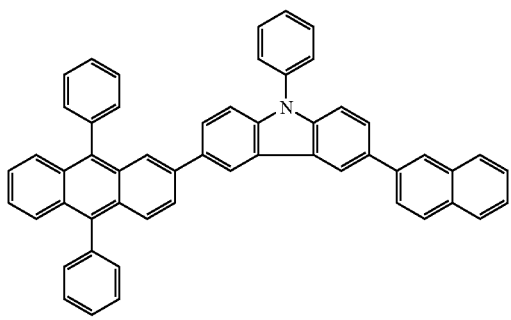
(137)
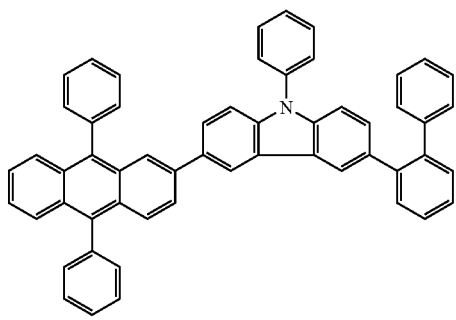

(138)
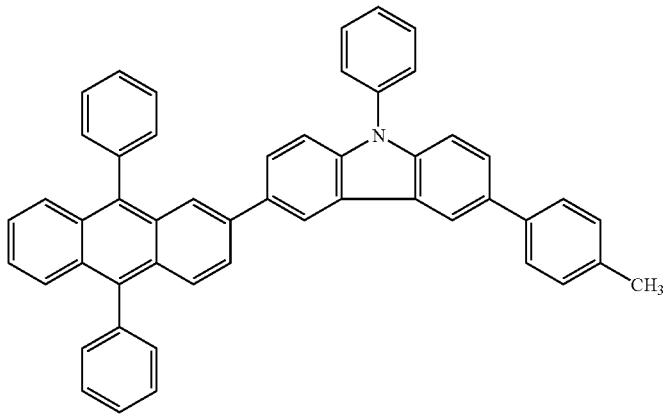
(141)
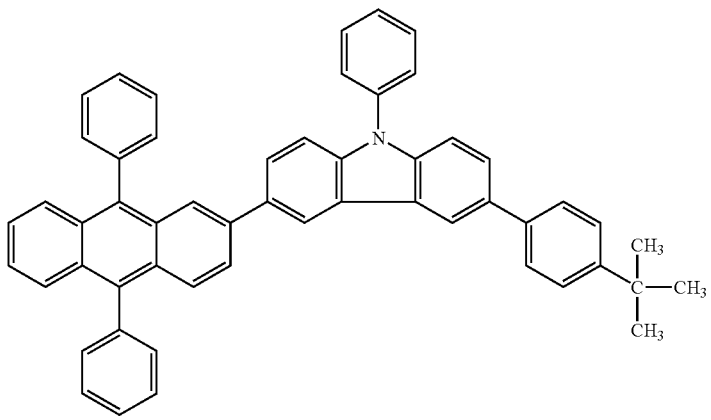
(139)
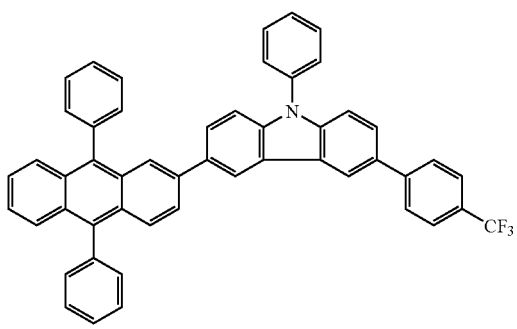
(142)
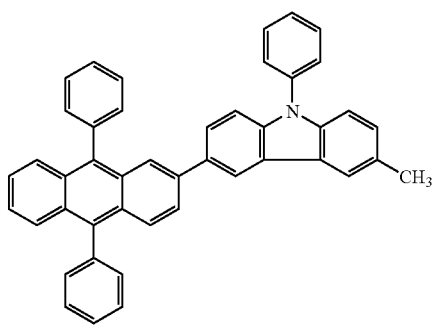
(140)
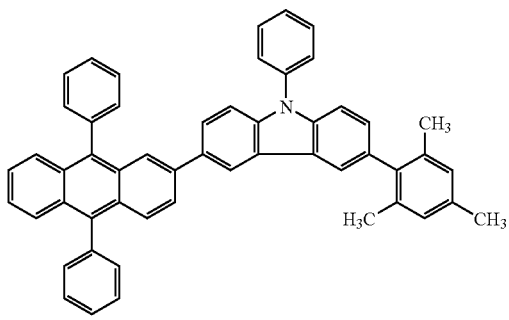
(143)
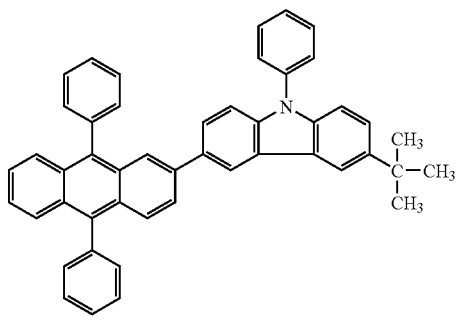

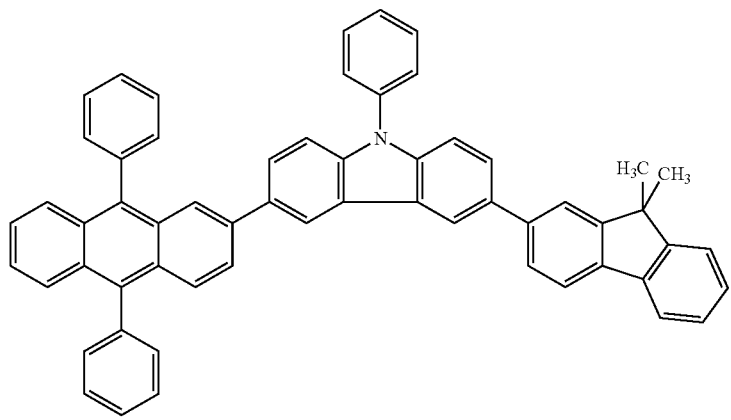
(144)
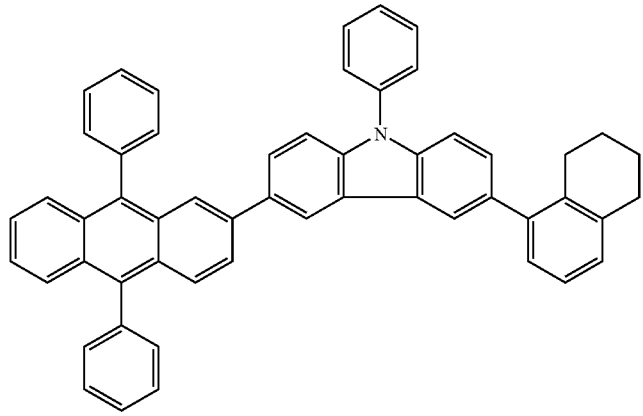
(147)
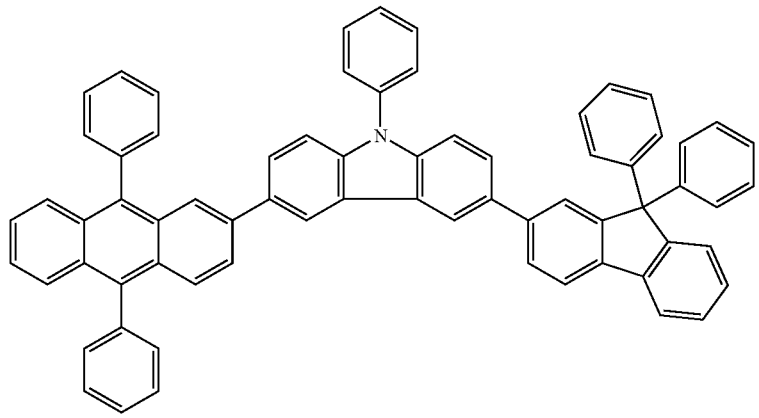
(145)
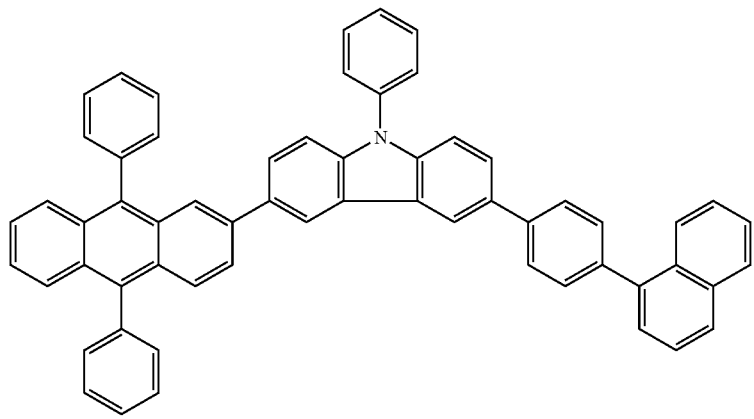
(148)

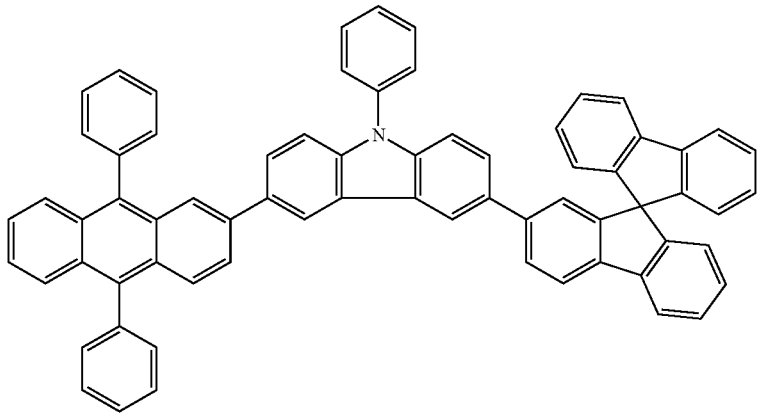
(146)
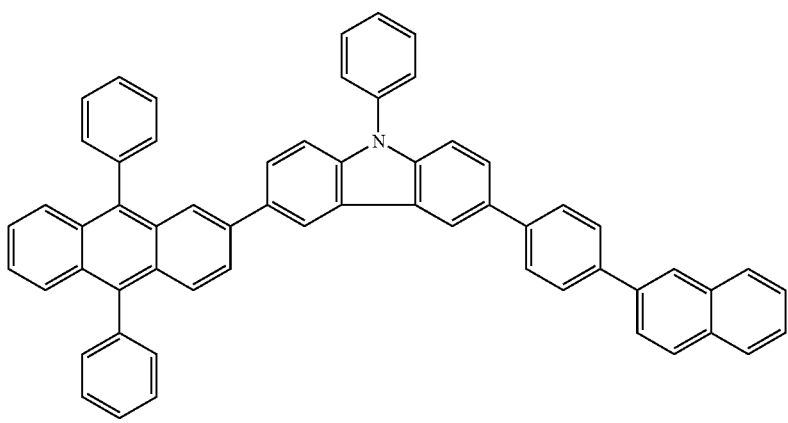
(149)
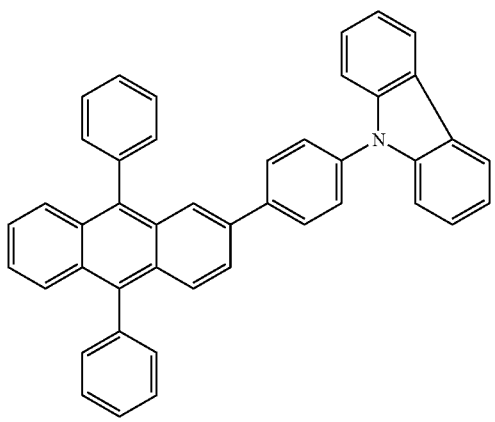
(201)
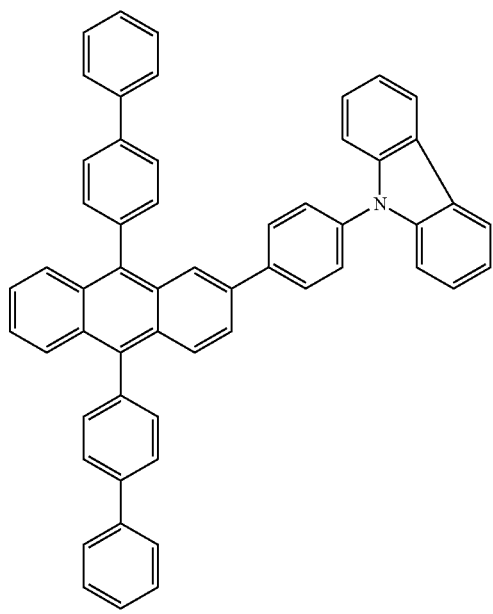
(204)

(202) 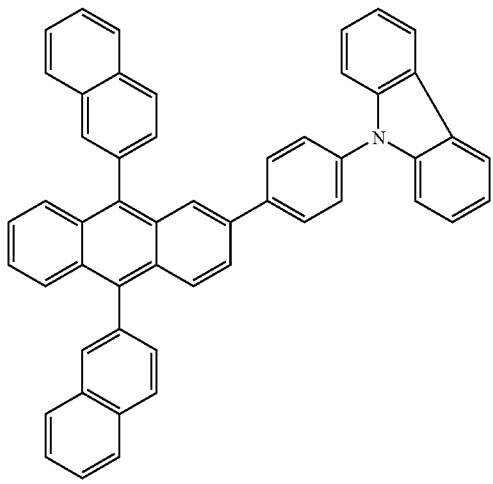
(205) 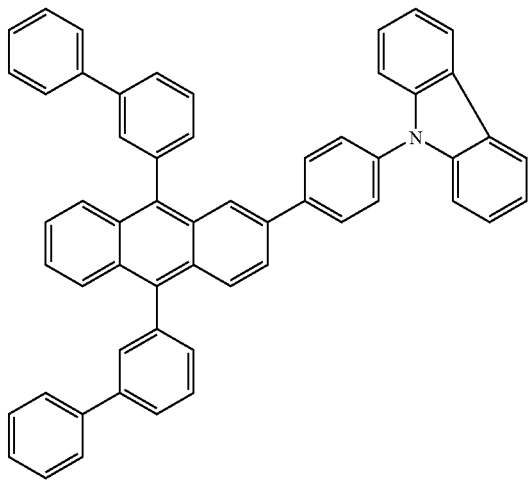
(203) 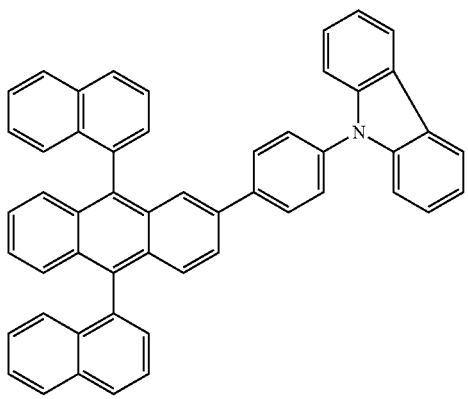
(206) 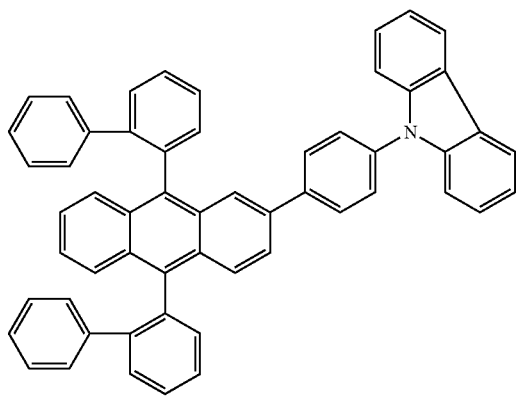
(207) 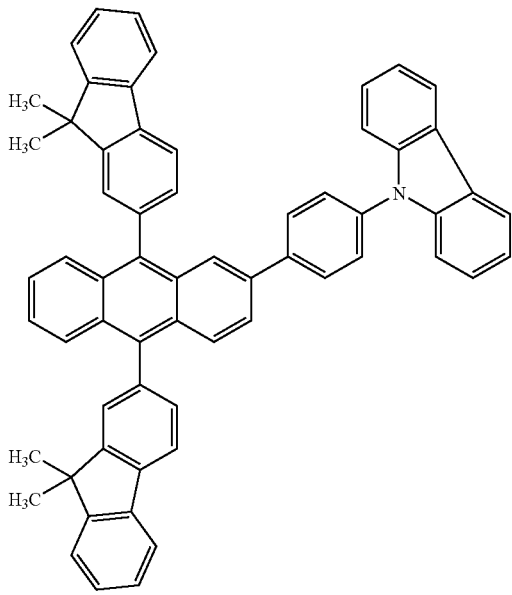
(210) 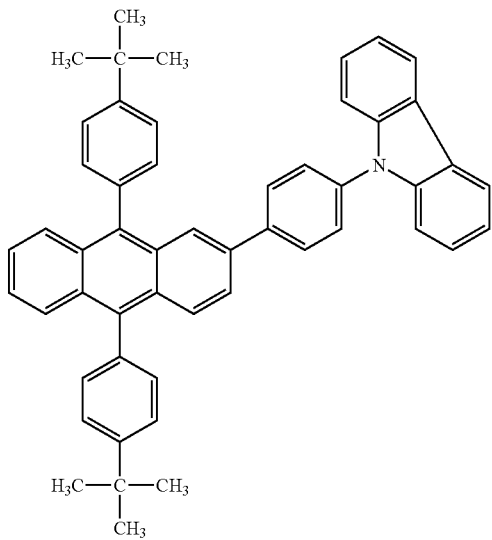

-continued
(208)
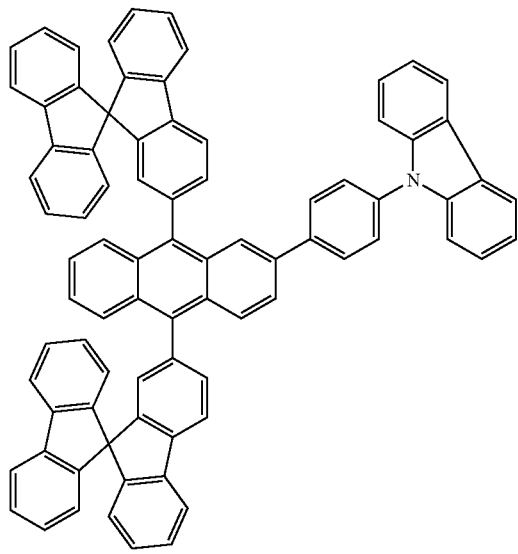
(209)
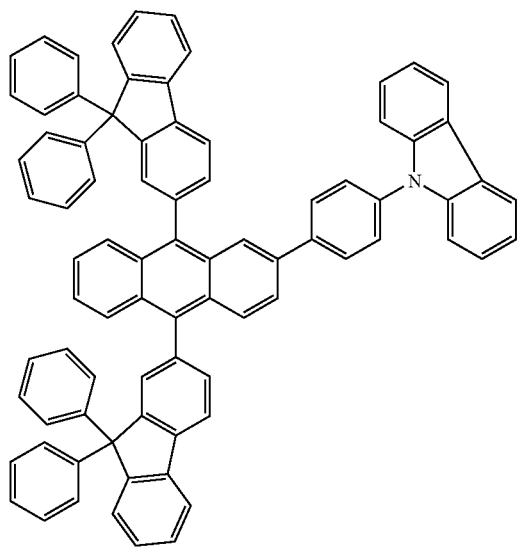
(211)
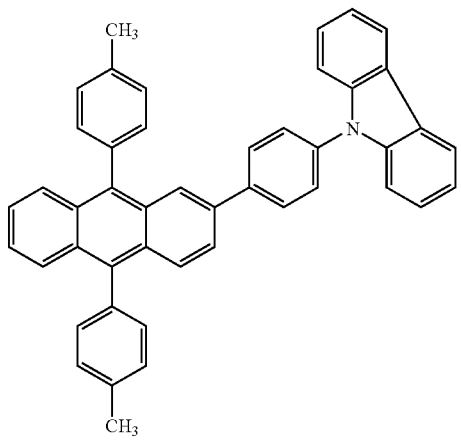
(212)
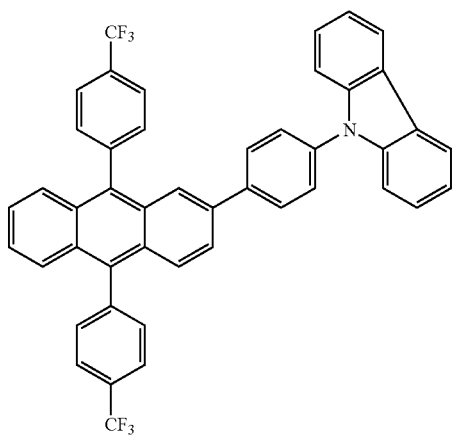

-continued
(213)
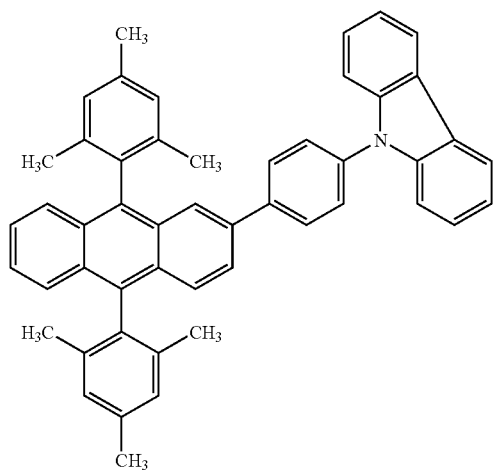
(215)
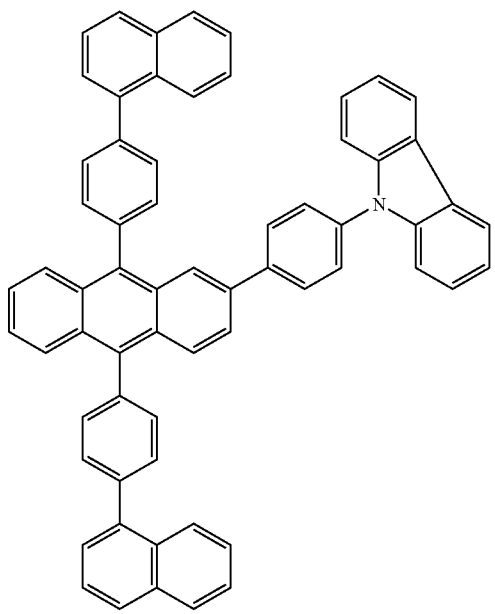
(214)
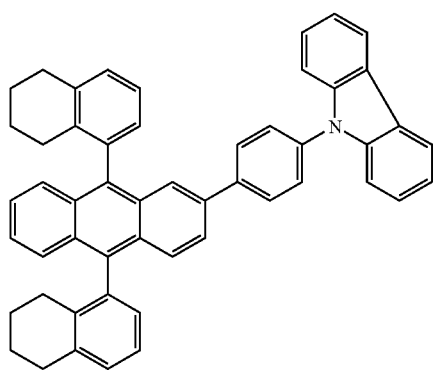
(216)
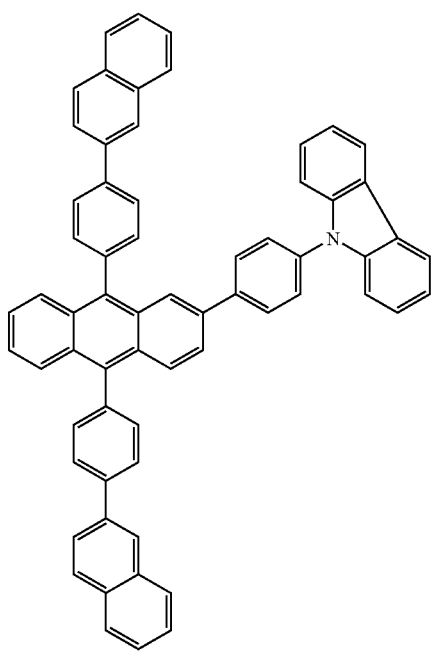
(217)
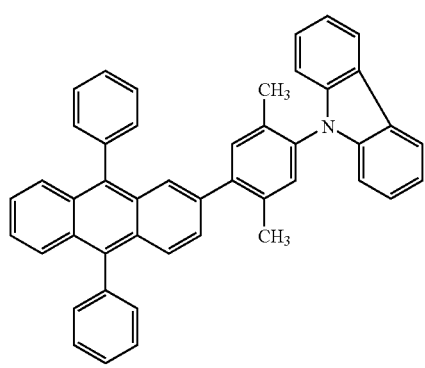
(221)
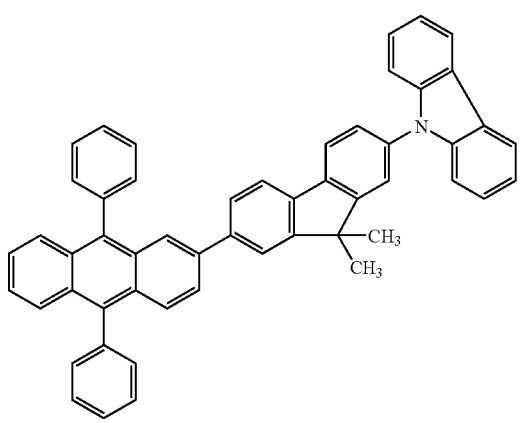

-continued
(218)
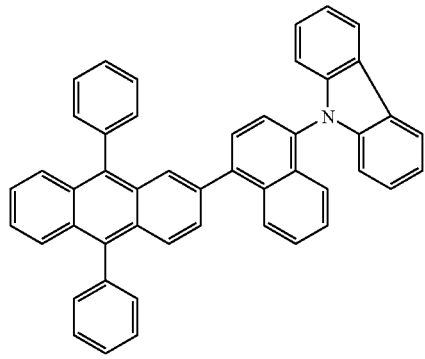
(219)
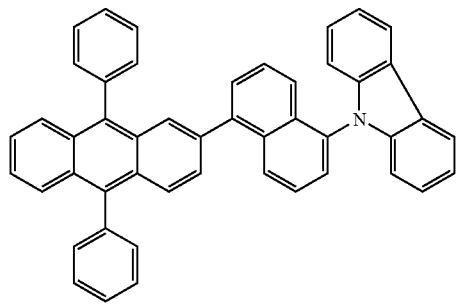
(220)
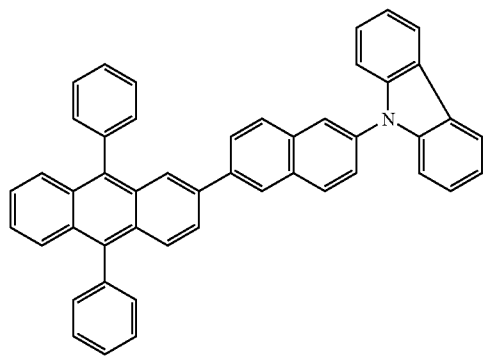
(222)
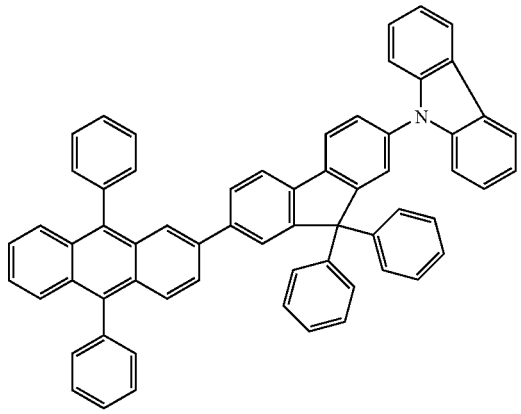
(223)
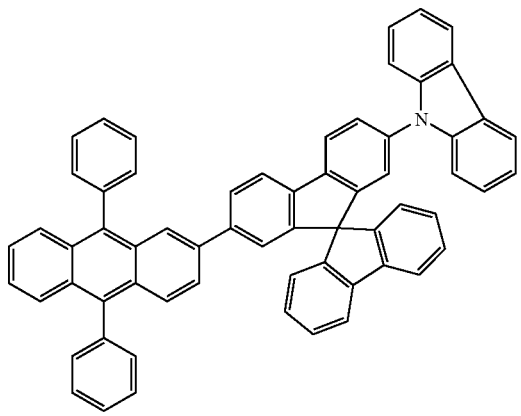
(224)
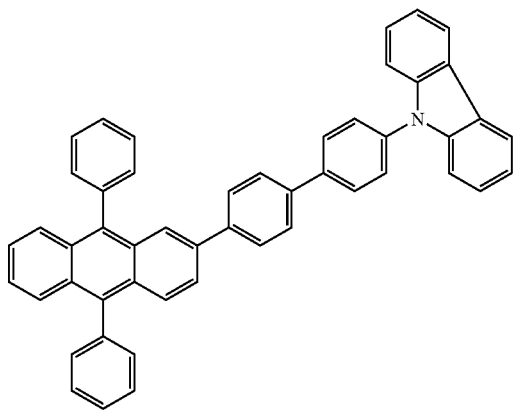

(225)
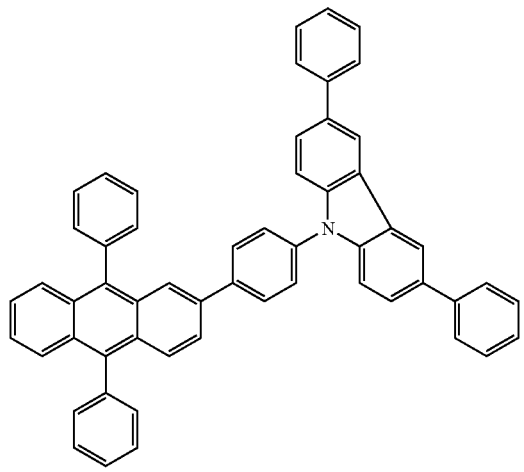
(228)
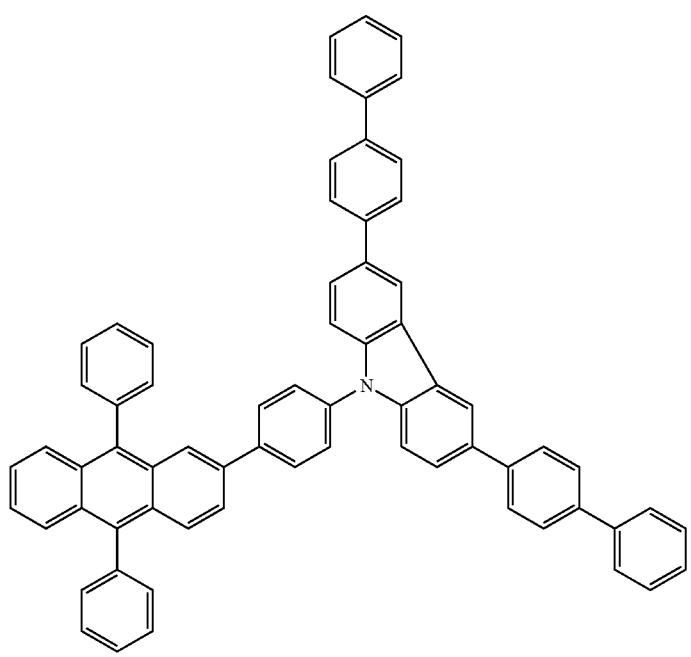
(226)
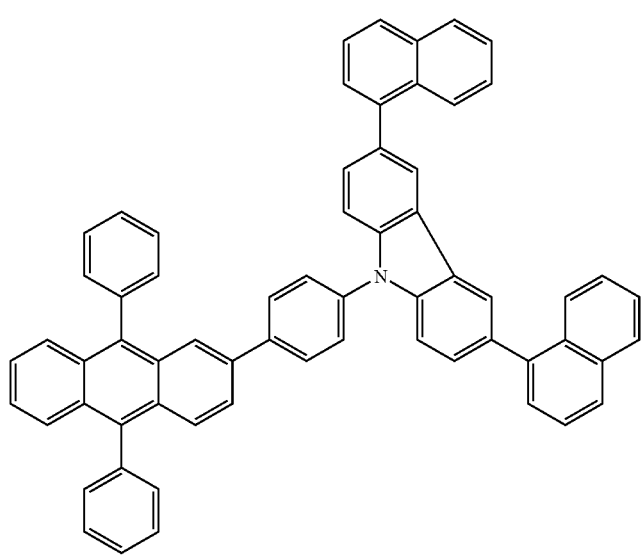

(229)
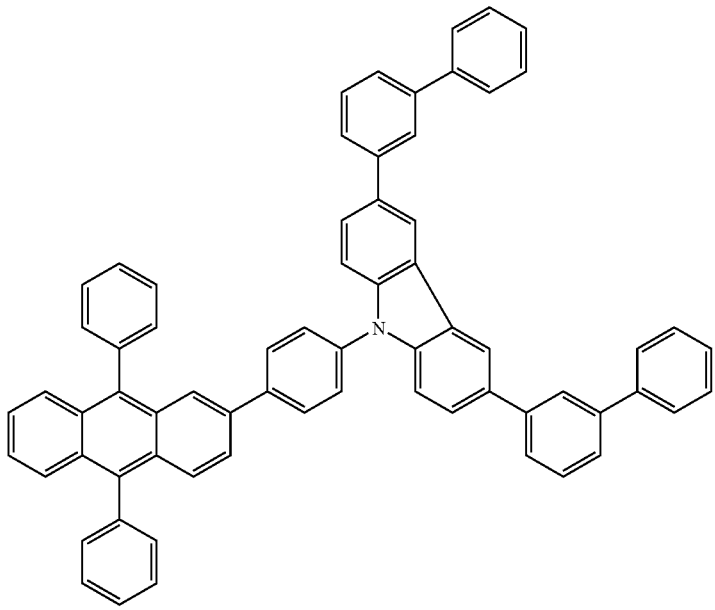
(227)
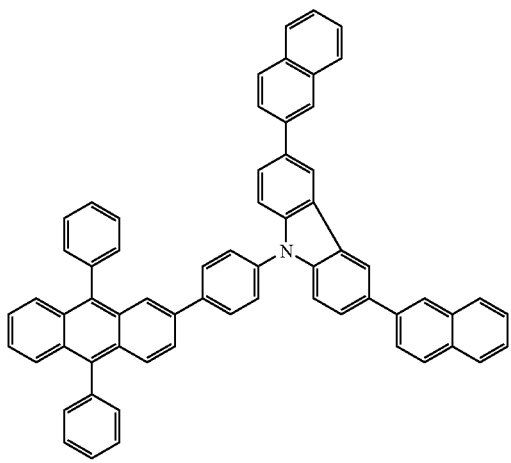
(230)
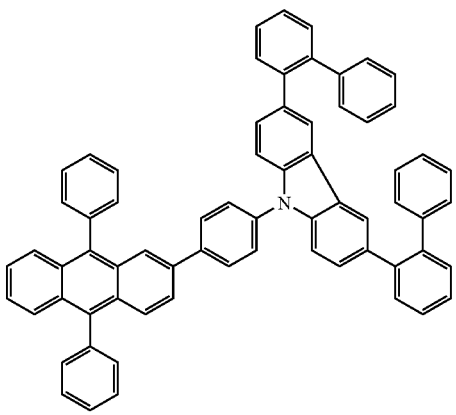
(231)
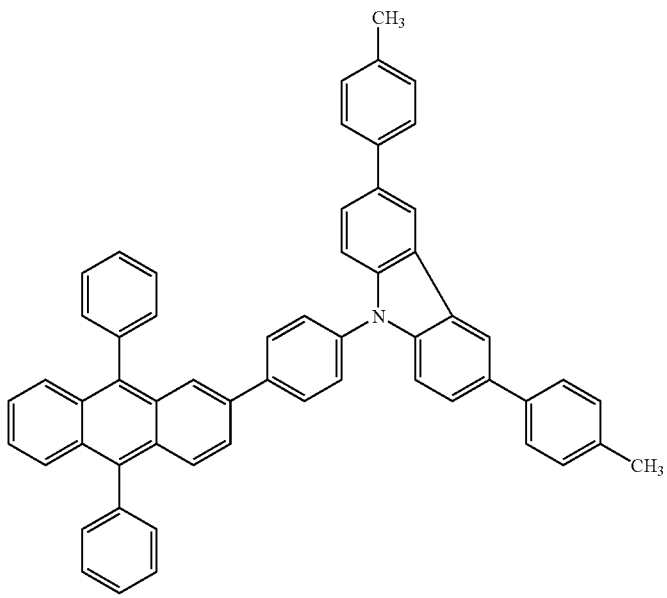

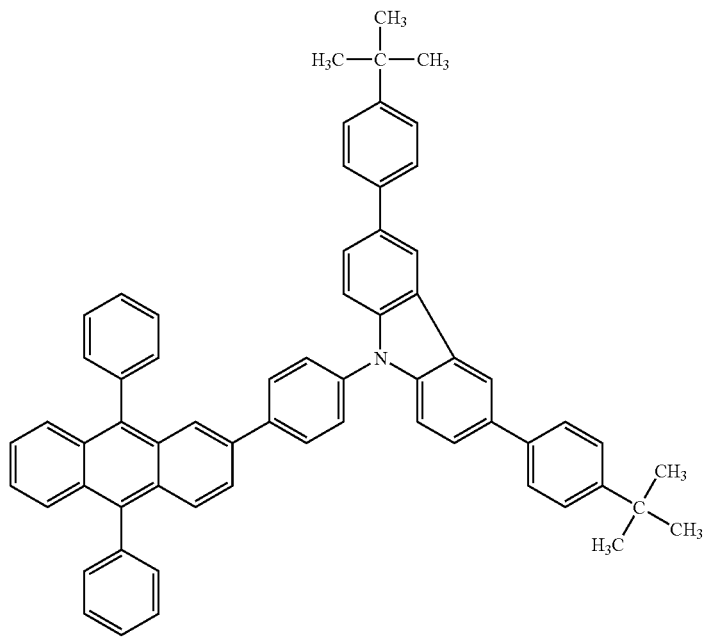
(234)
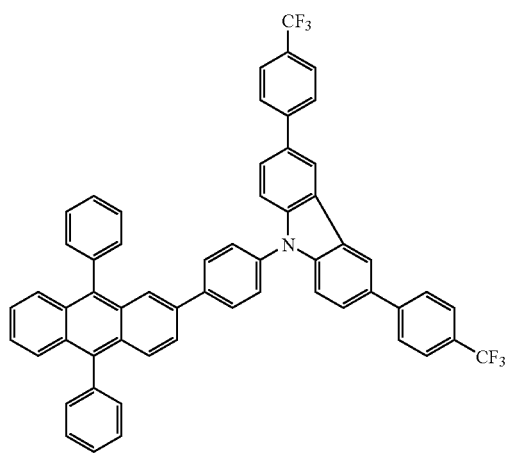
(232)
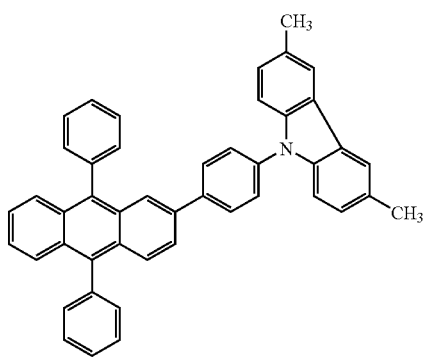
(235)
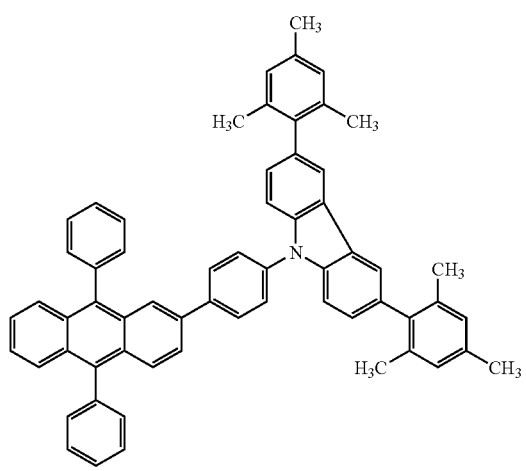
(233)
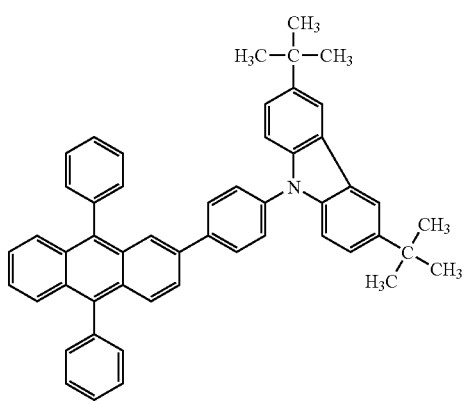
(236)

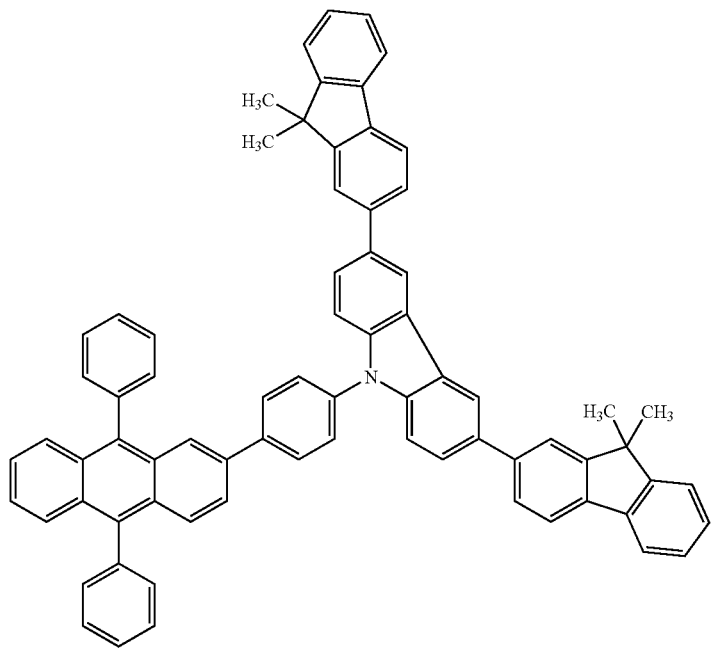
(237)
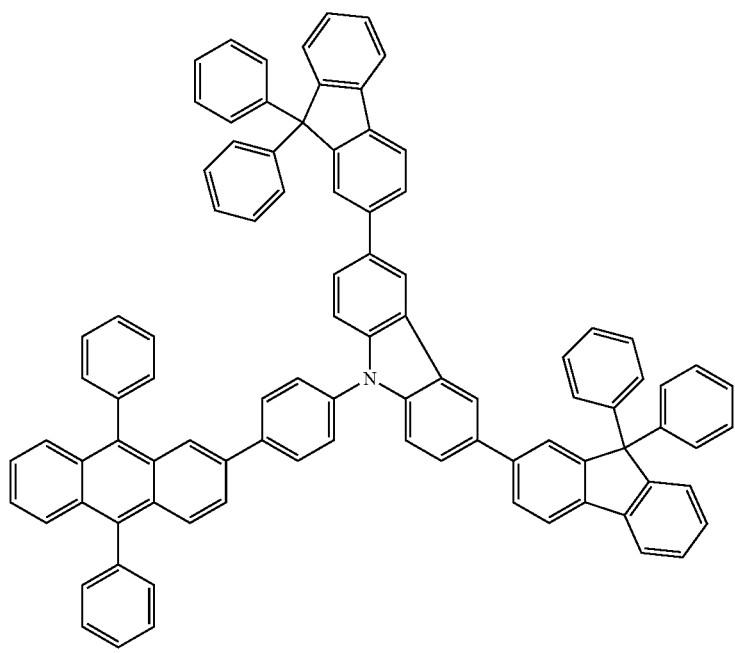
(238)

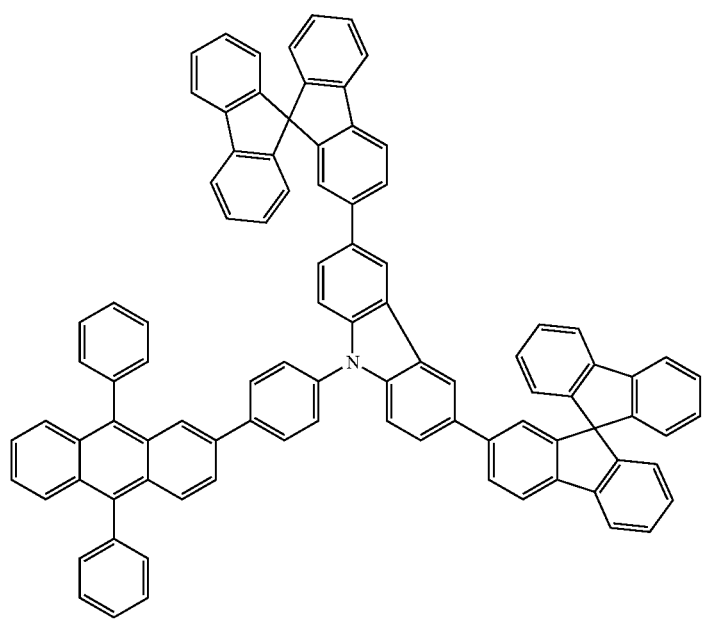
(239)
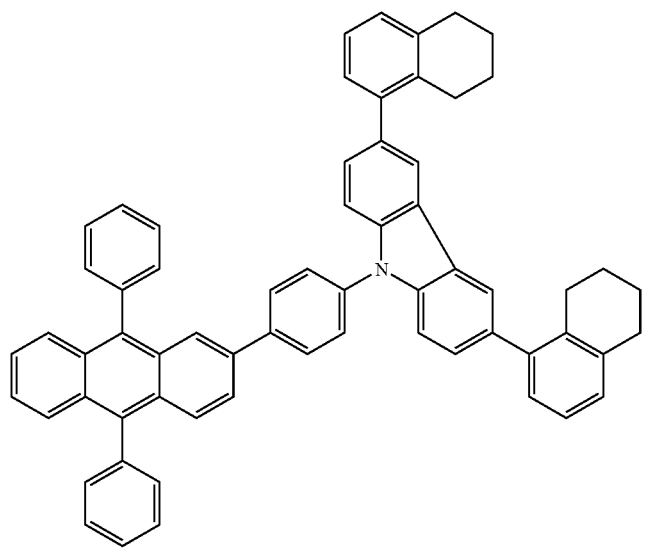
(240)

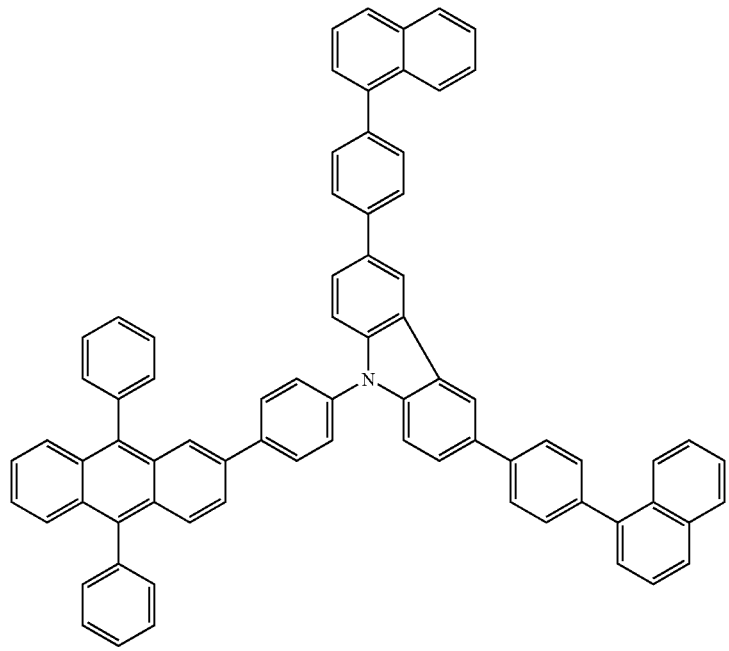
(241)
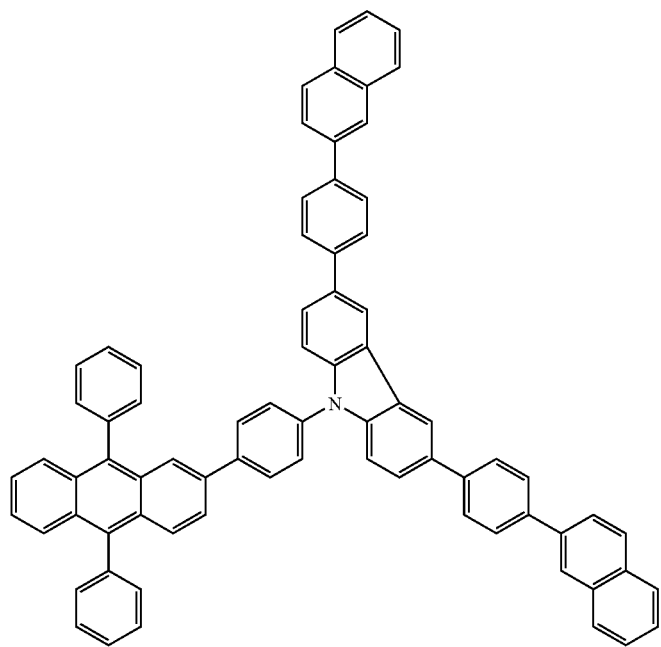
(242)

(301)
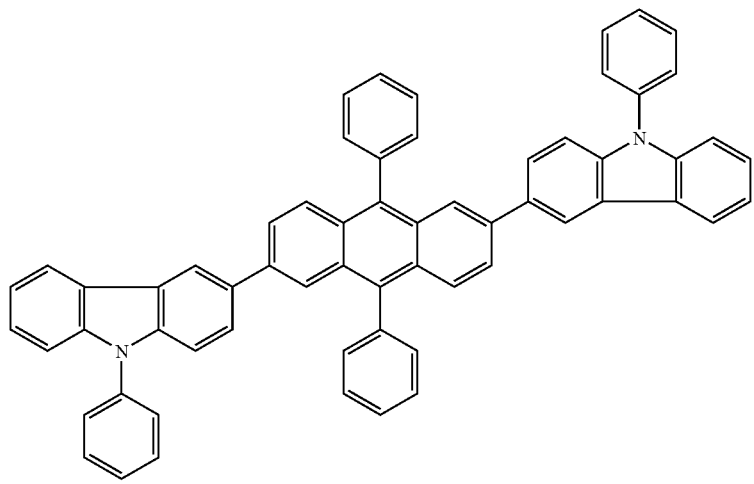
(304)
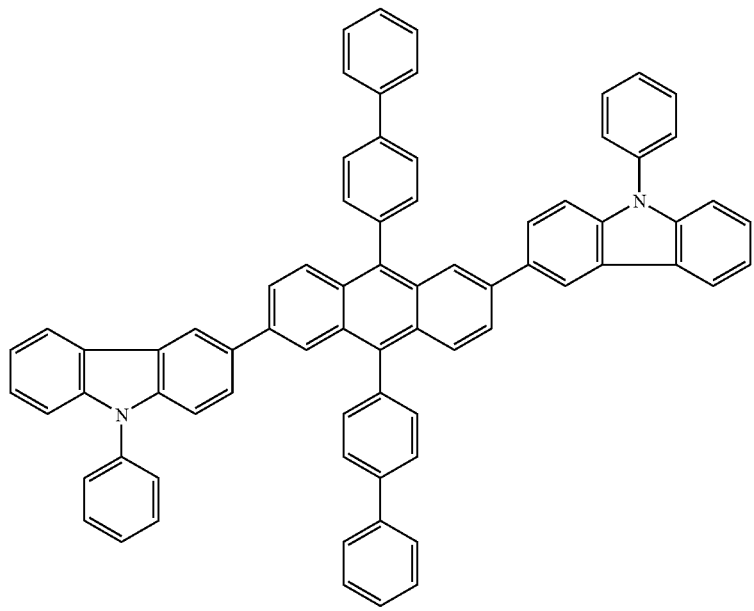
(302)
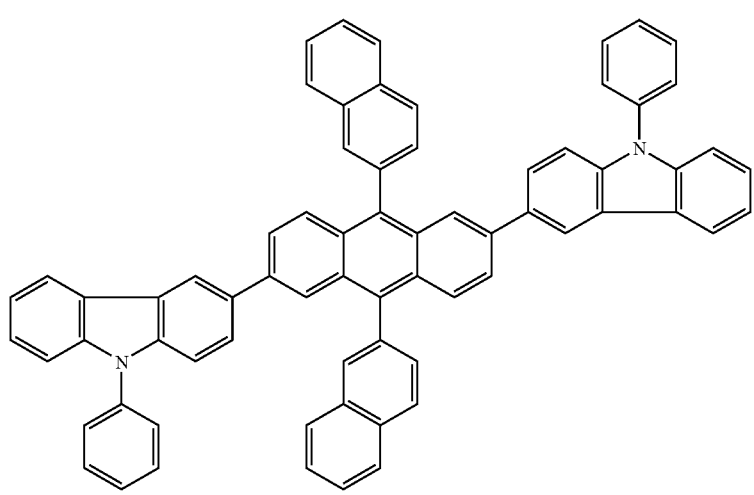

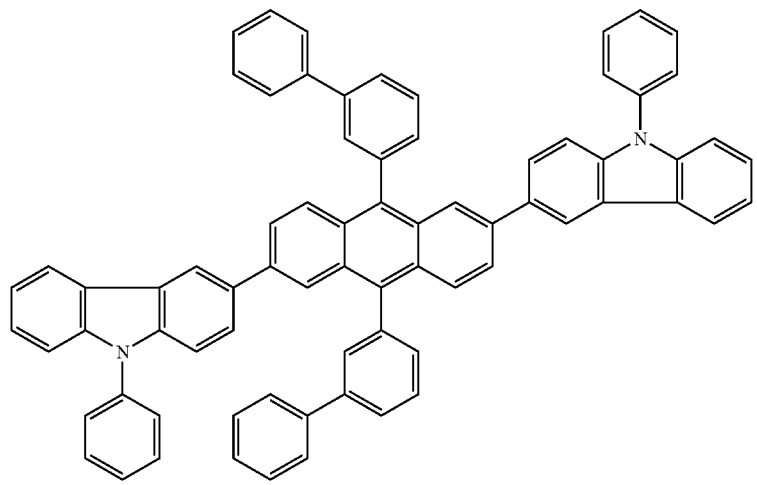
(305)
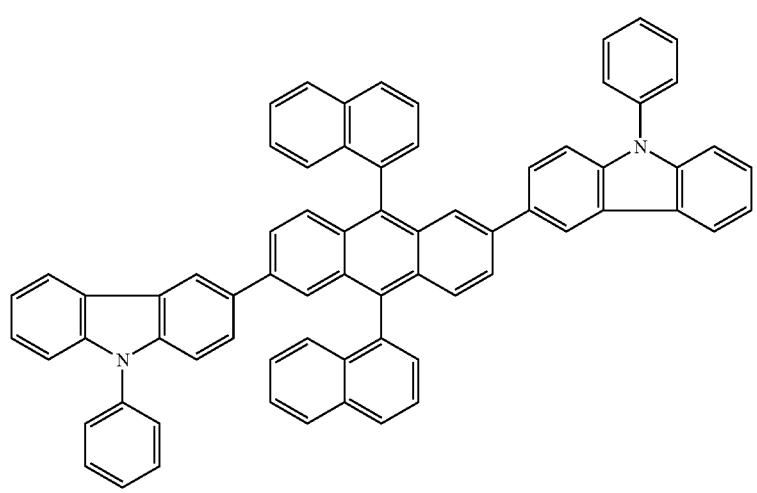
(303)
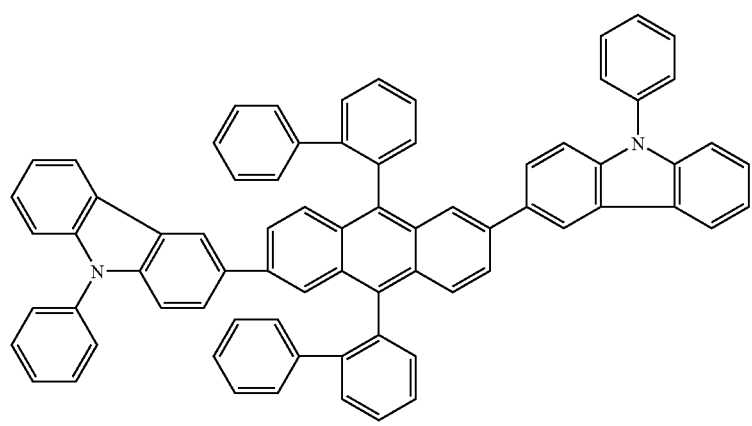
(306)

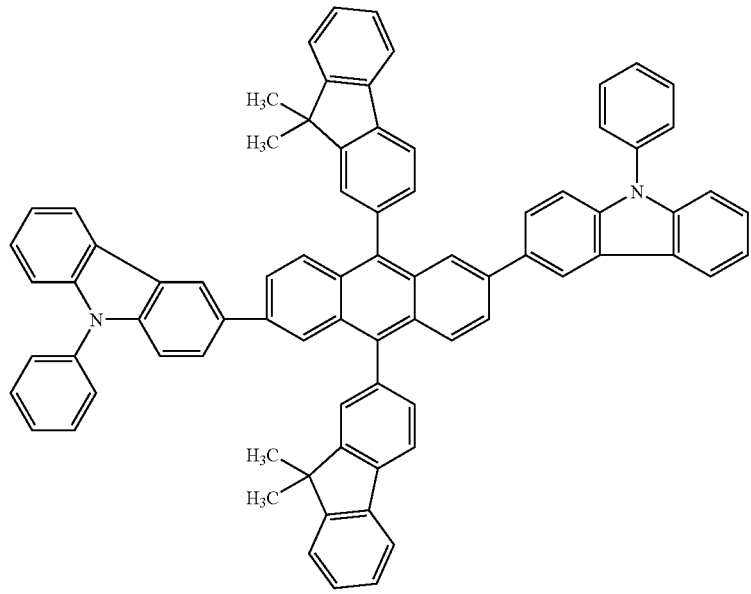
(307)
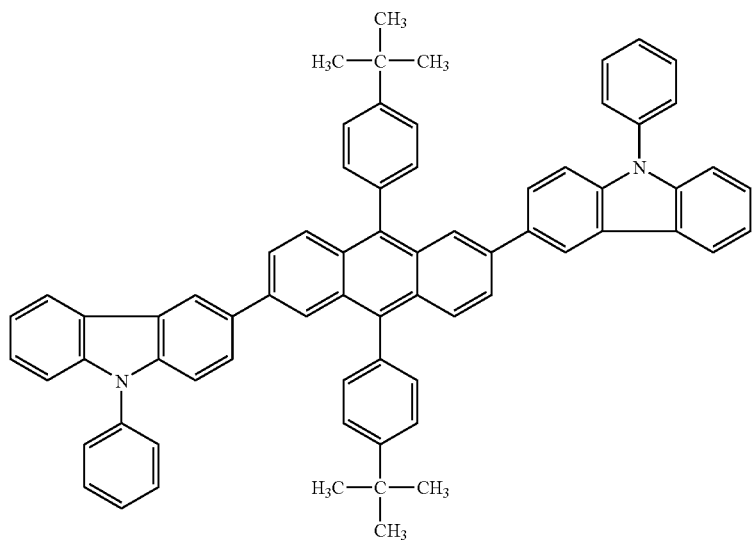
(310)

(308)
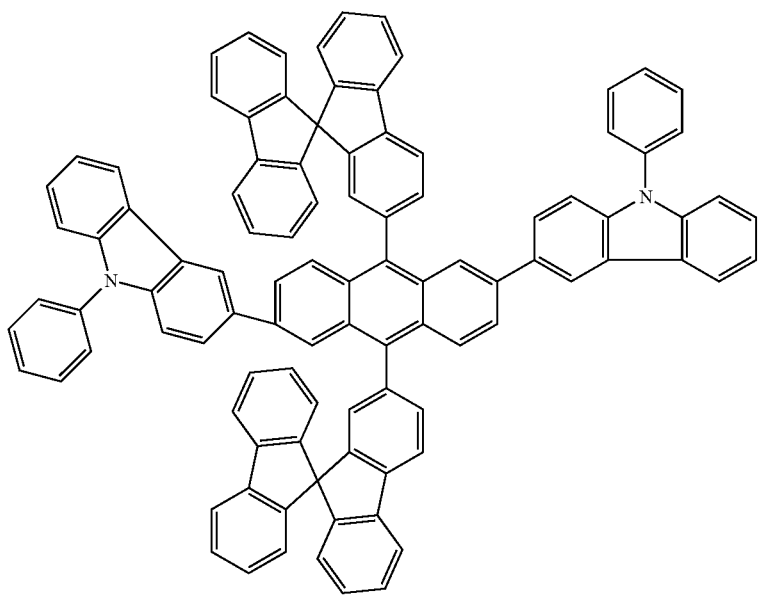
(311)
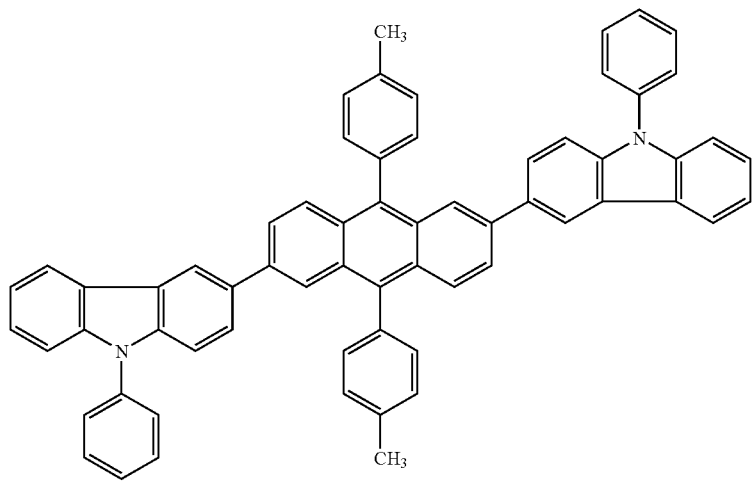
(309)
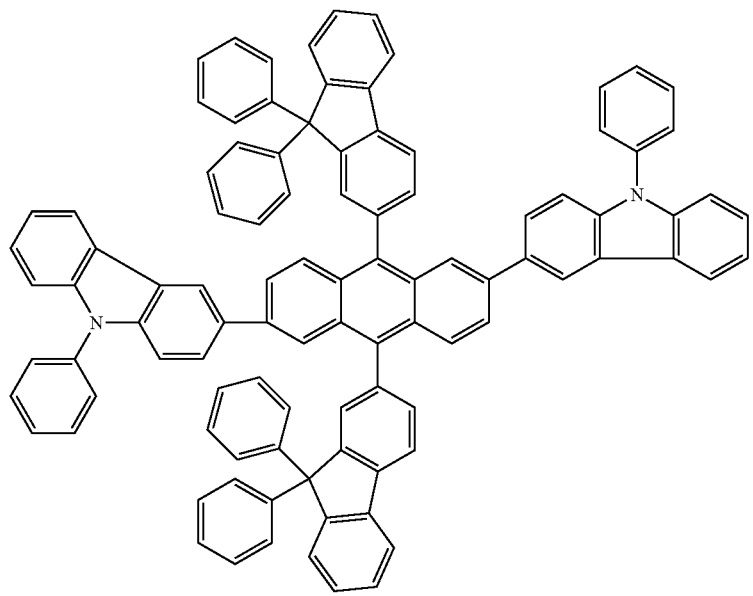

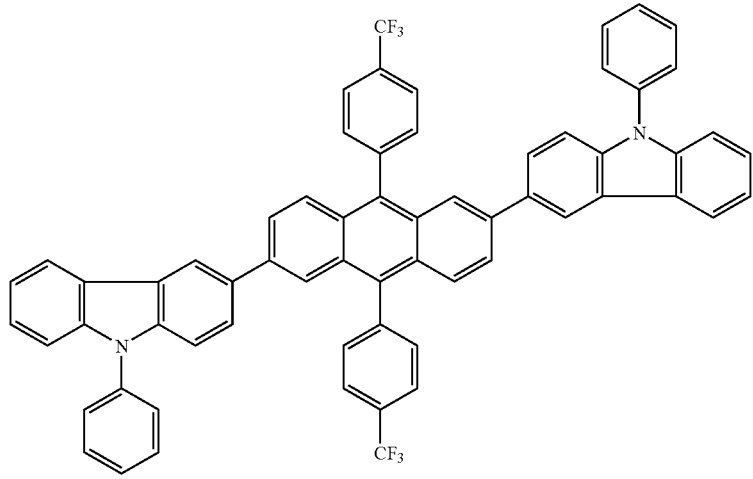
(312)
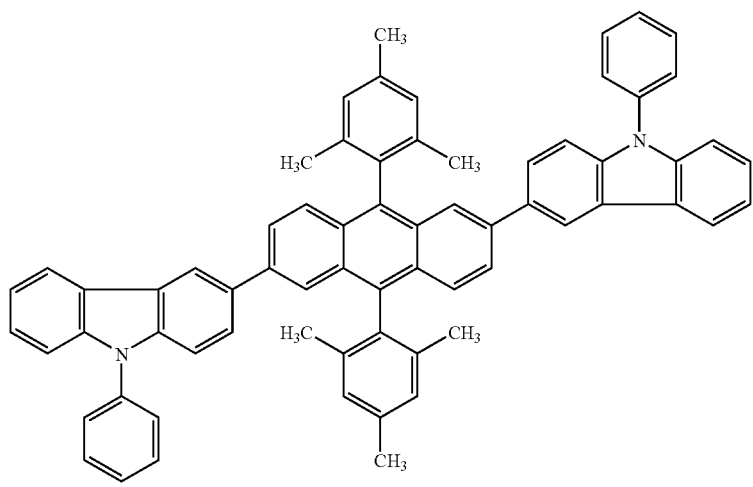
(313)
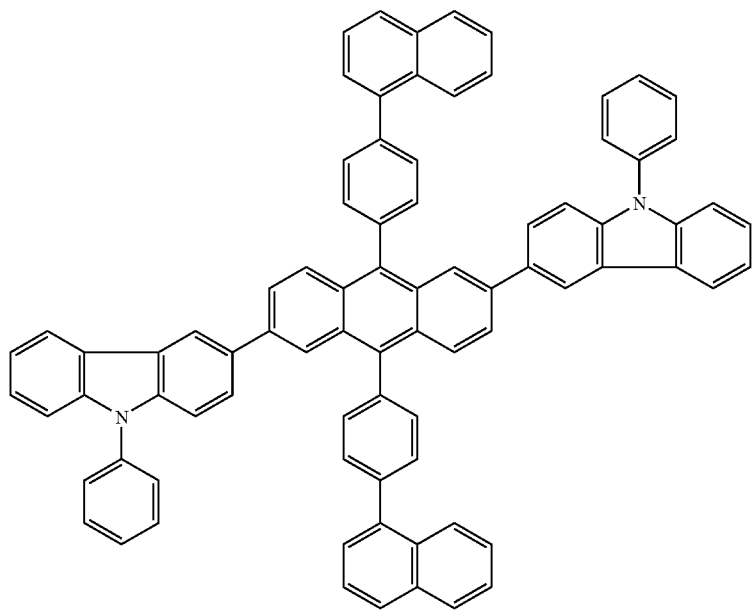
(315)

(314)
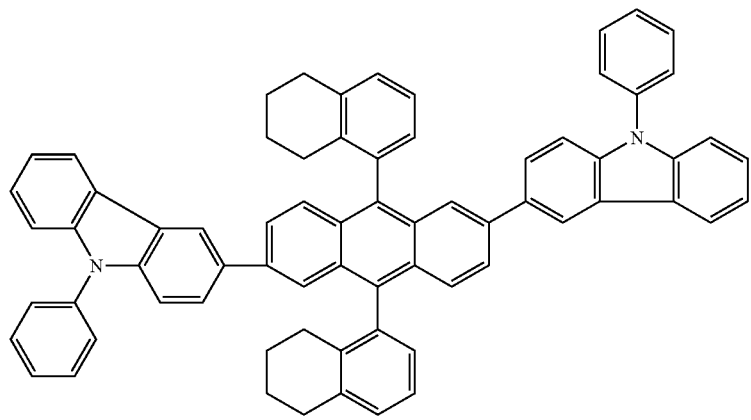
(316)
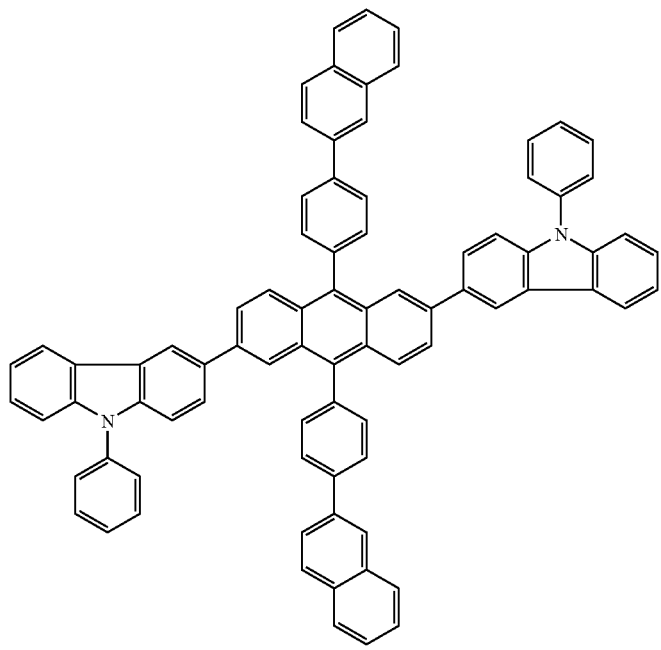
(317)
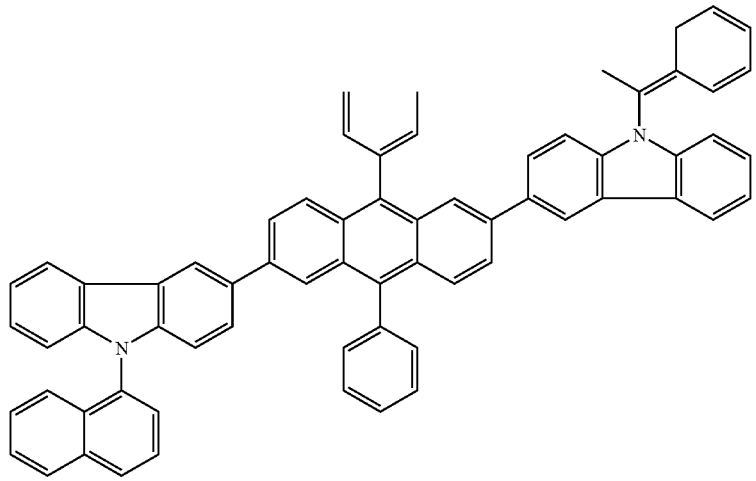

-continued
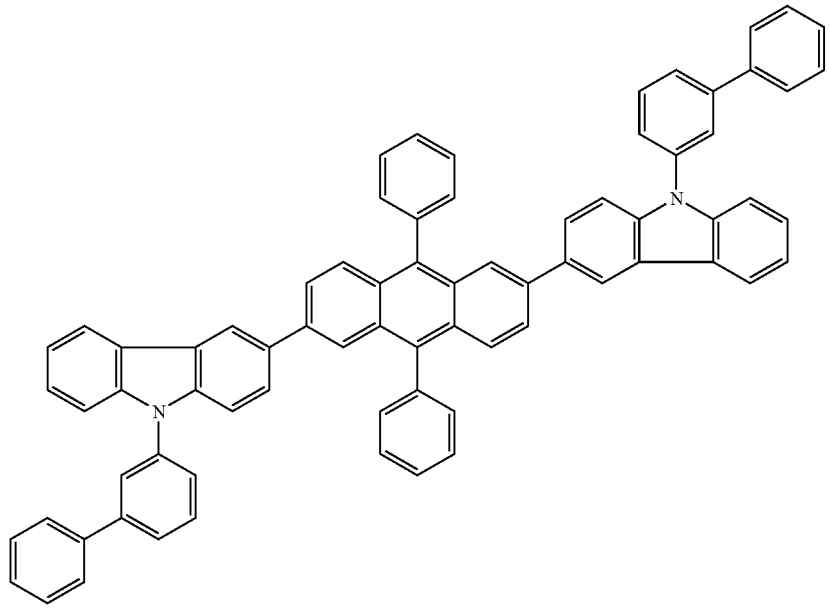
(320)
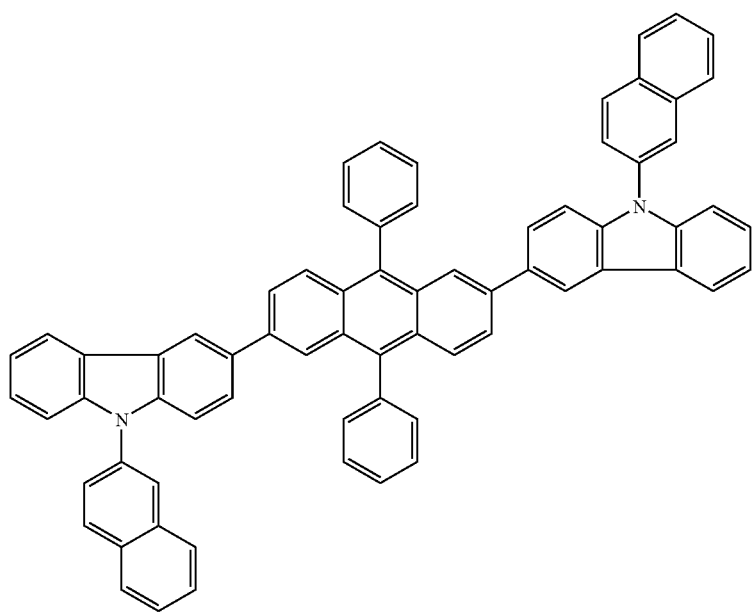
(318)

-continued
(321)
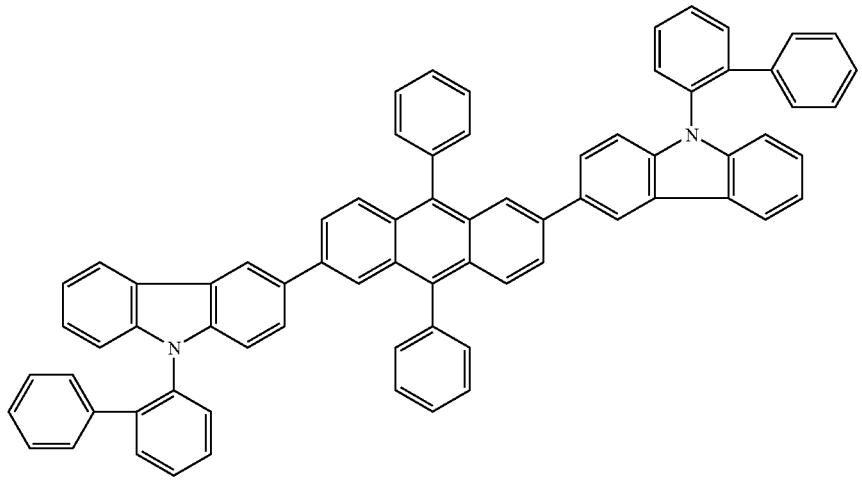
(319)
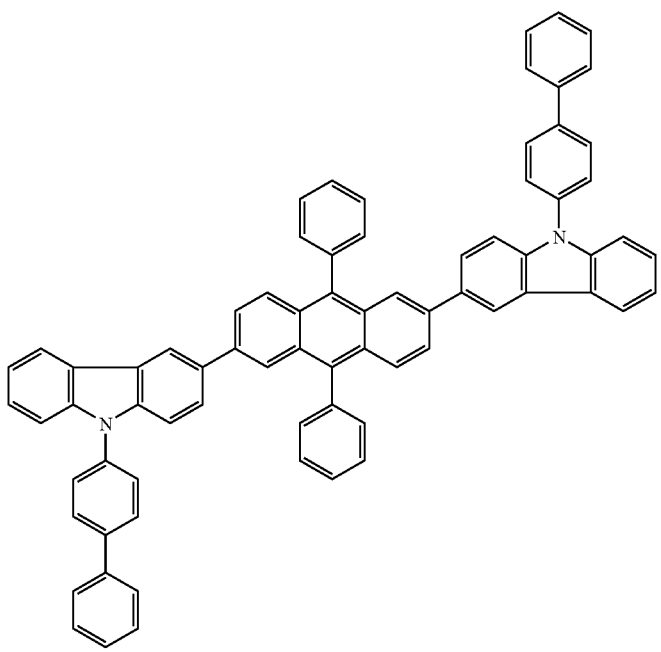
(322)
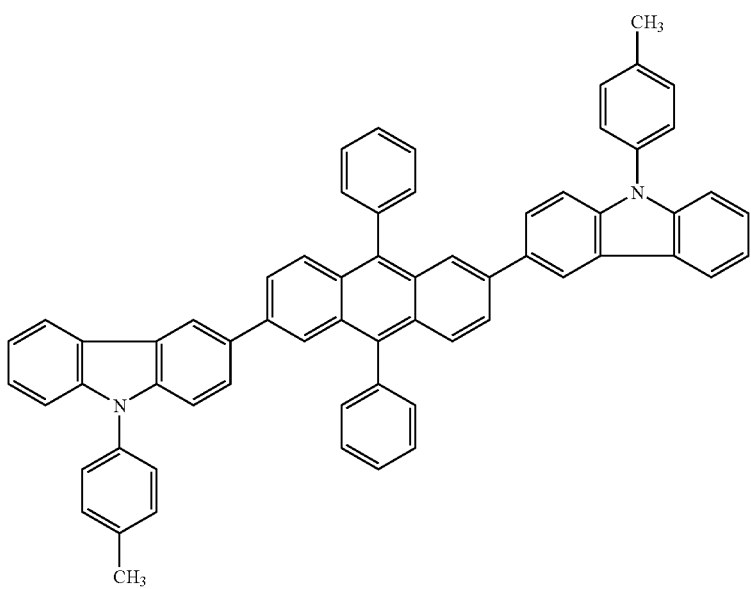

(323)
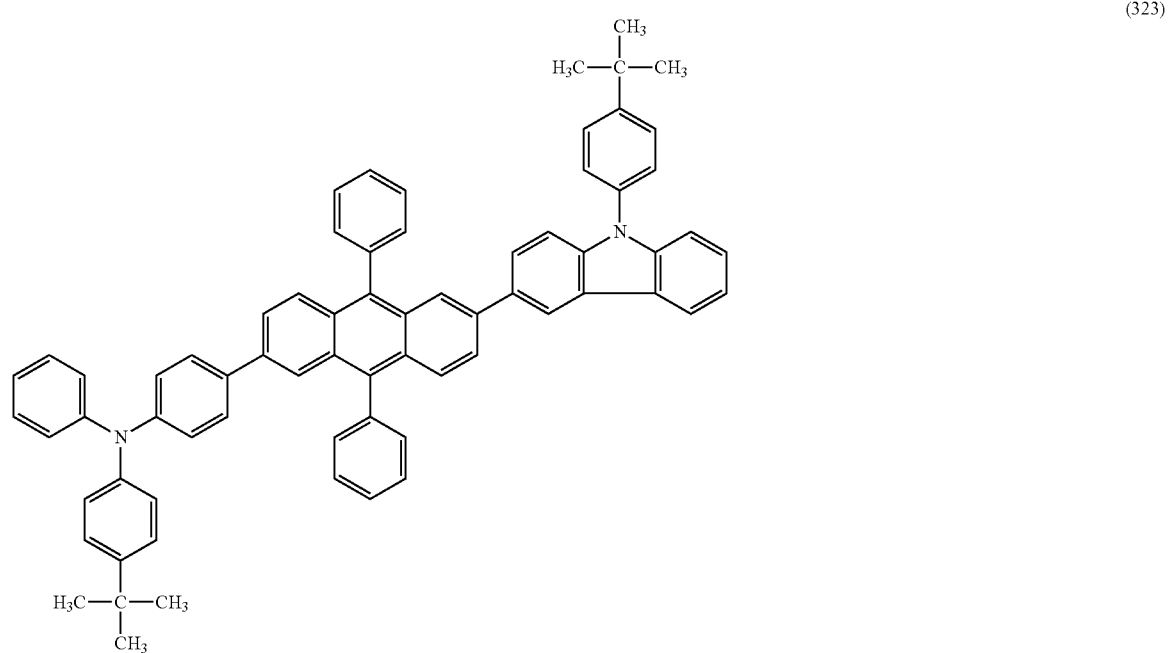
(326)
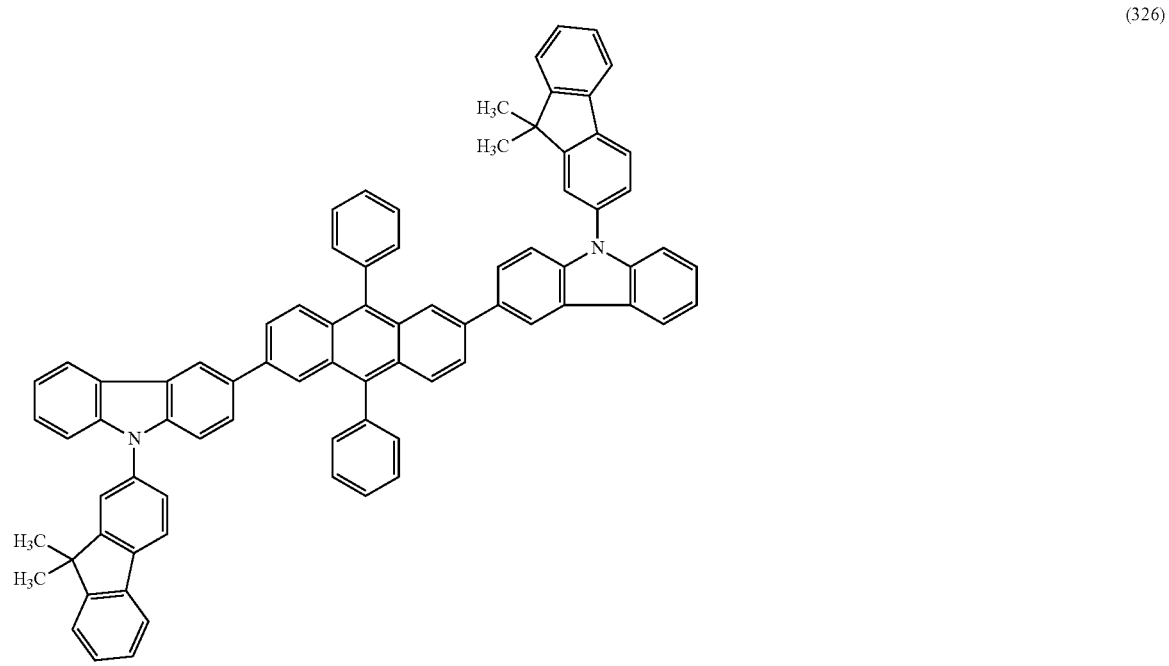

-continued
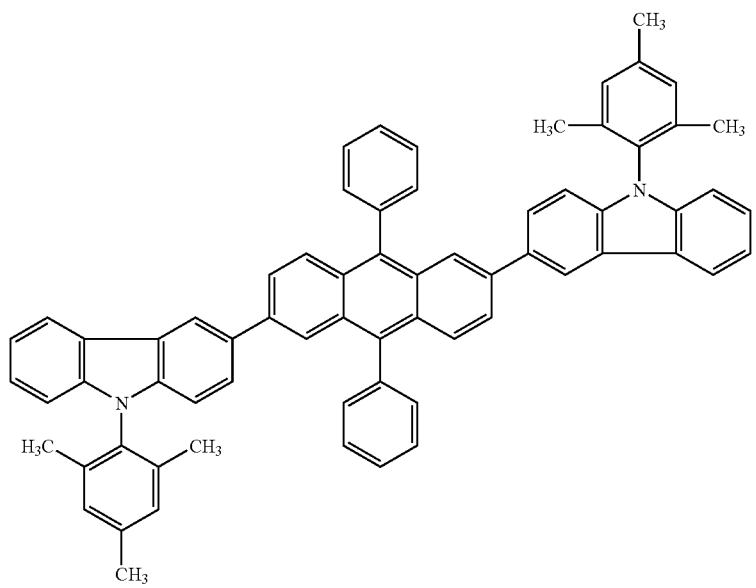
(324)
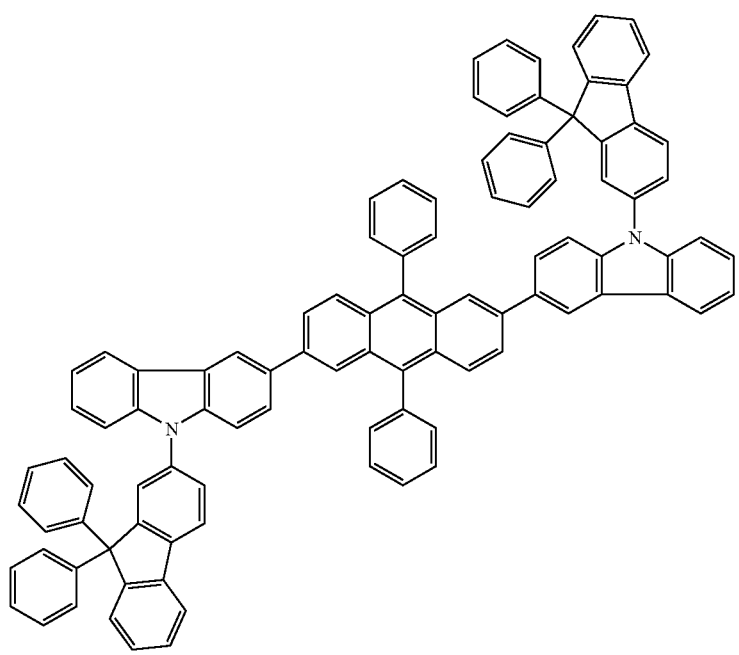
(327)

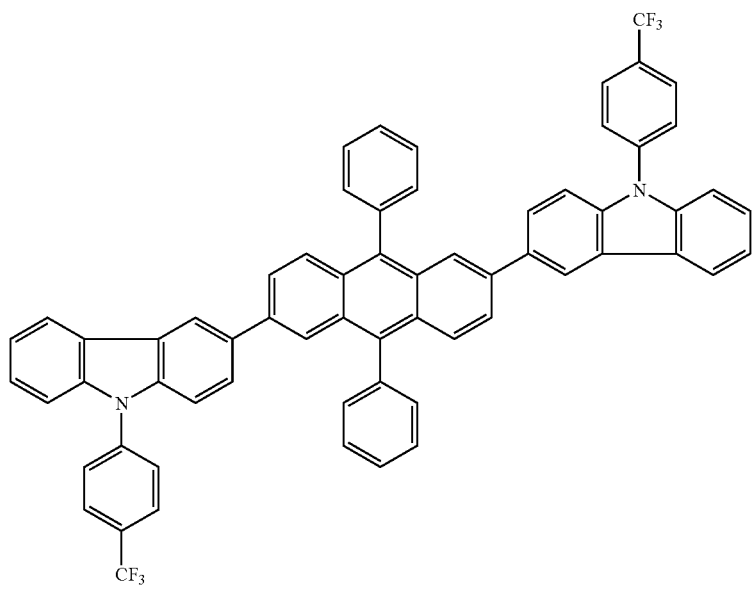
(325)
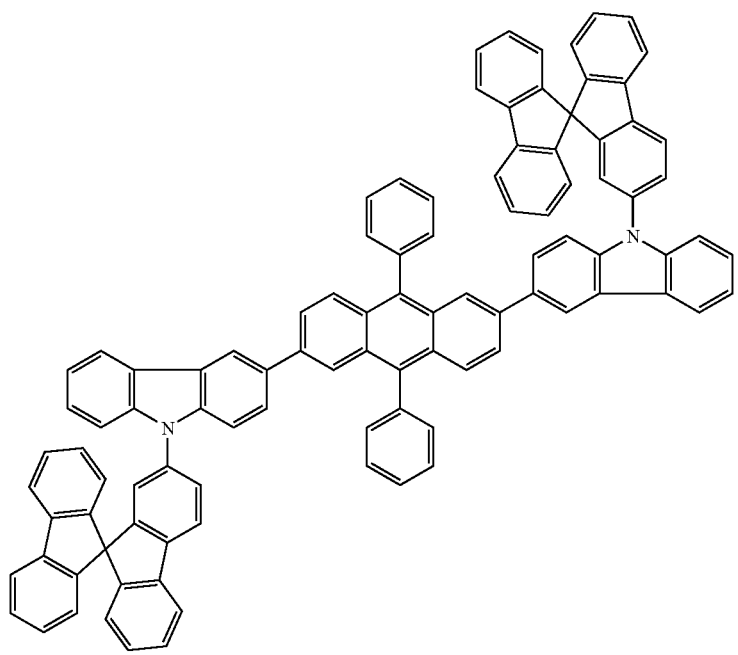
(328)

(329)
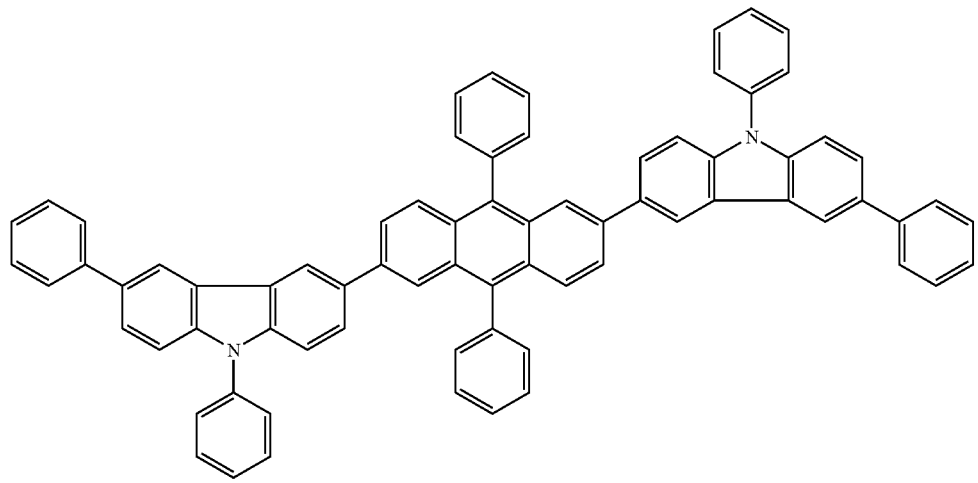
(330)
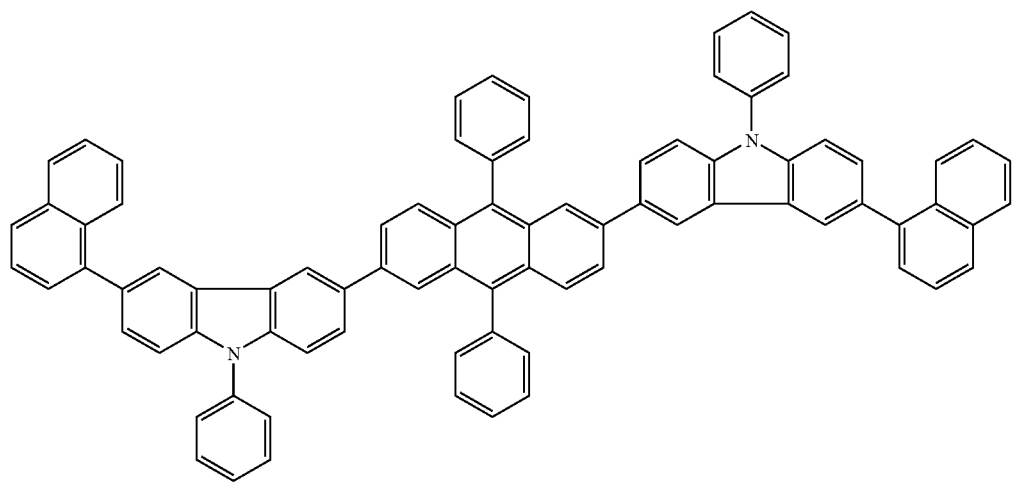
(331)
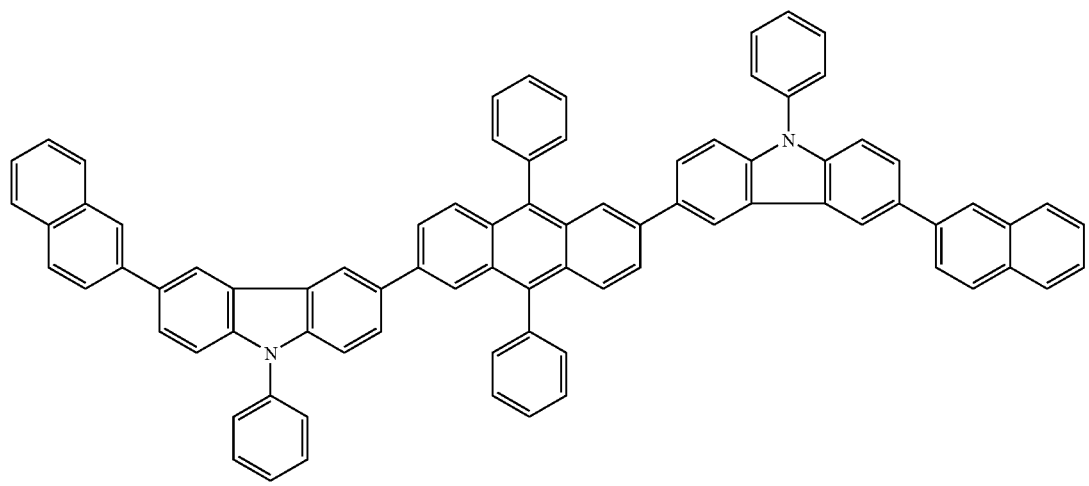

(332)
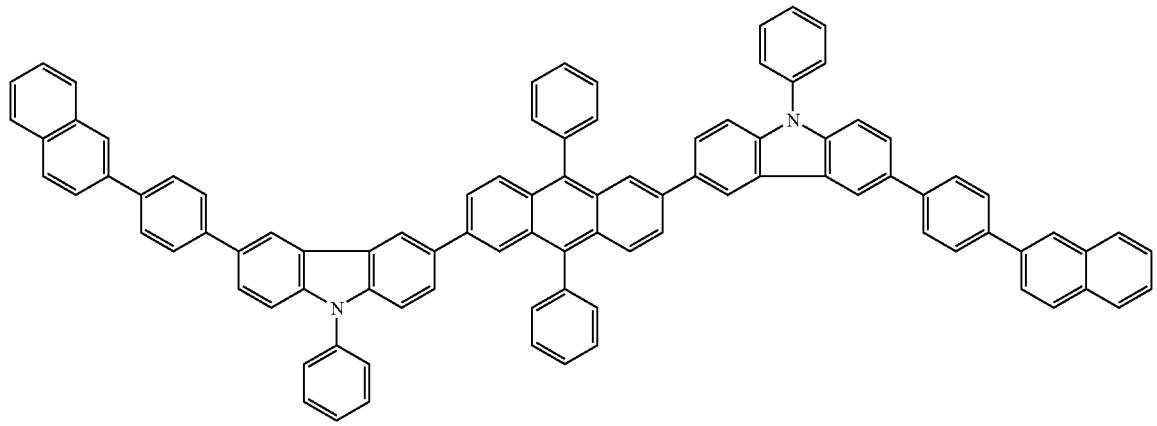
(333)
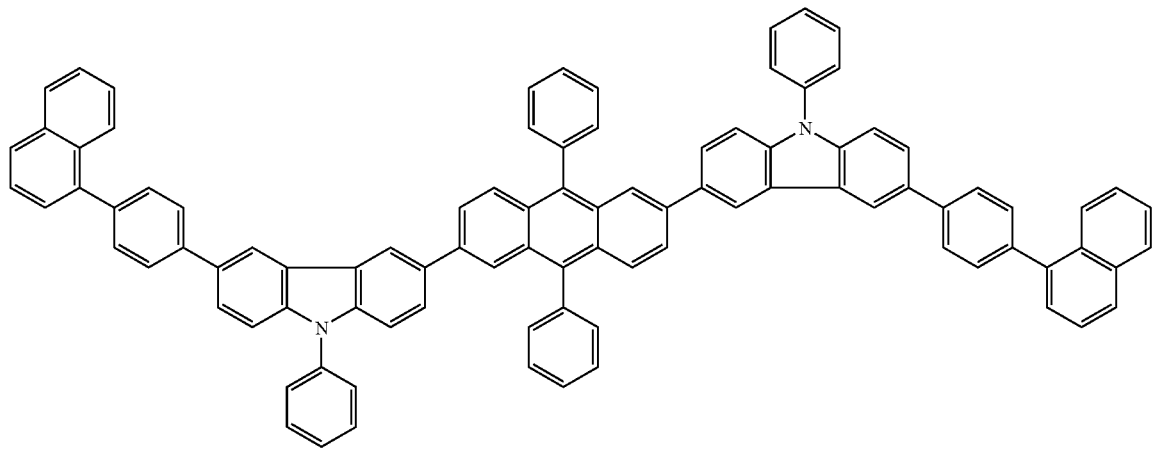
(334)
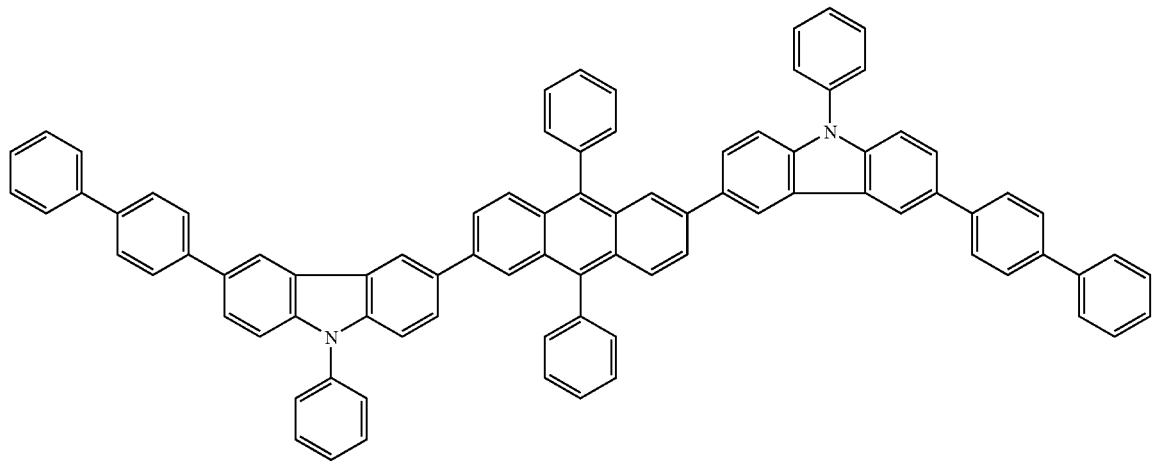

(335)
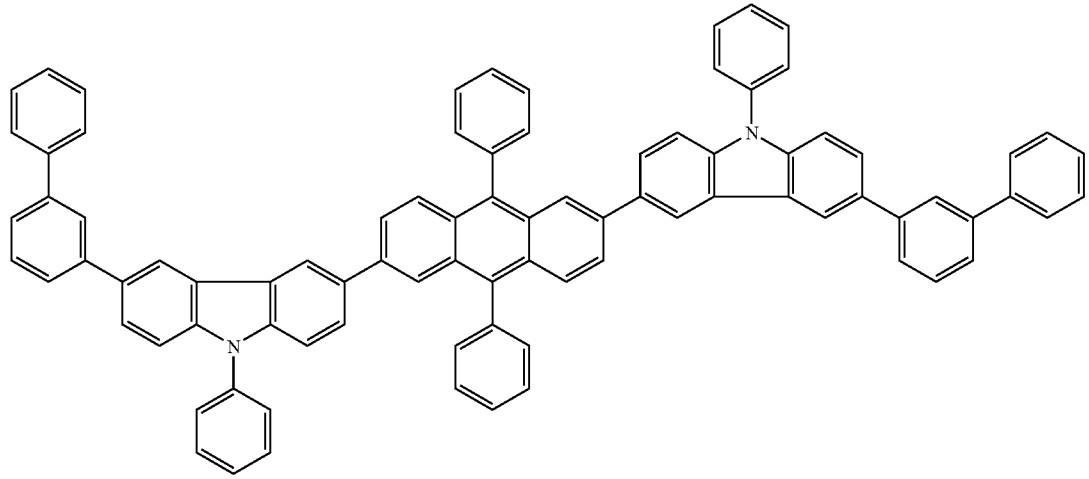
(336)
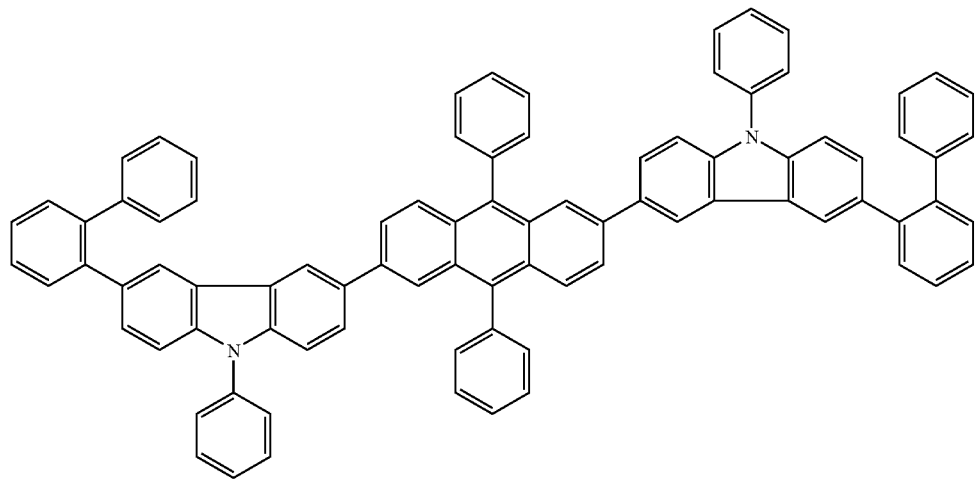
(337)
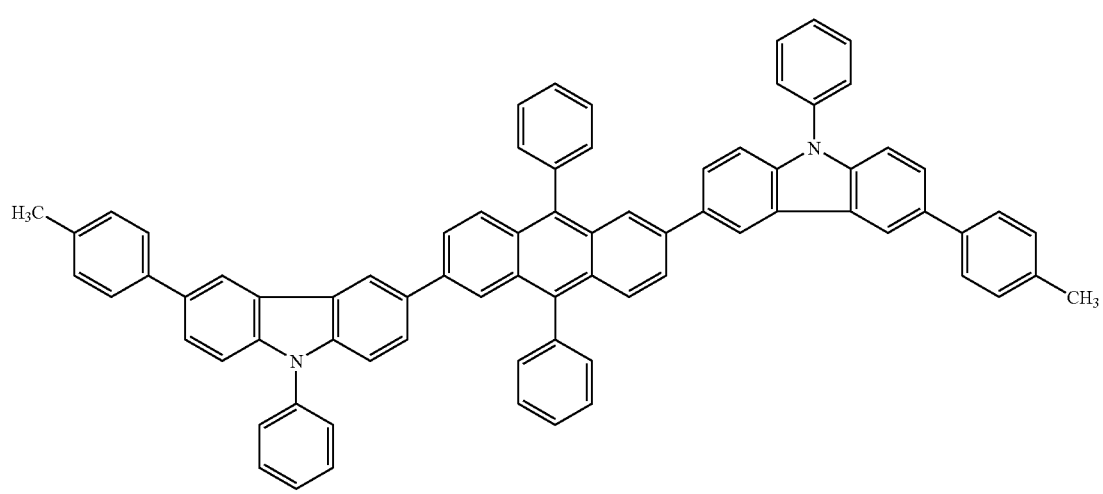

(338)
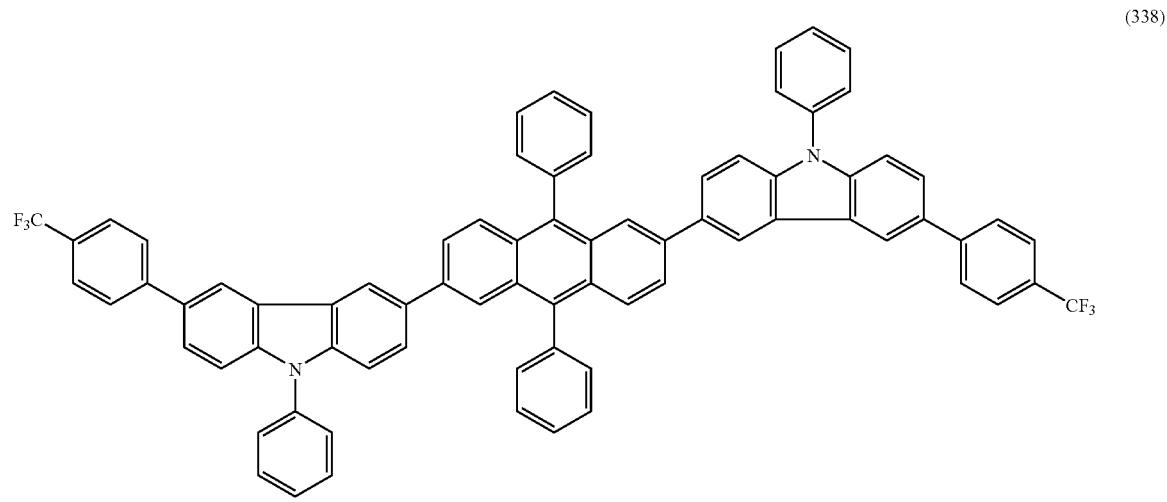
(339)
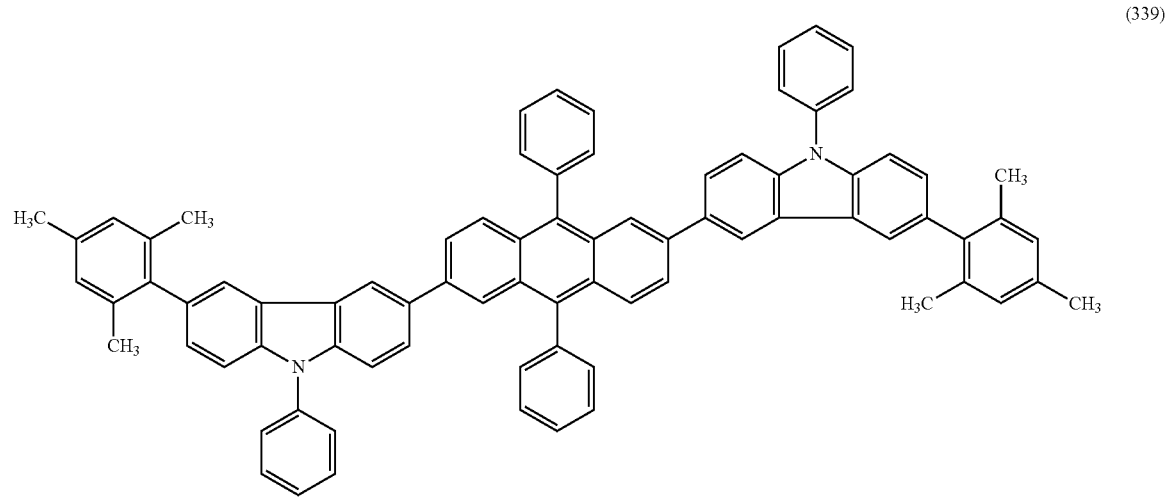
(340)
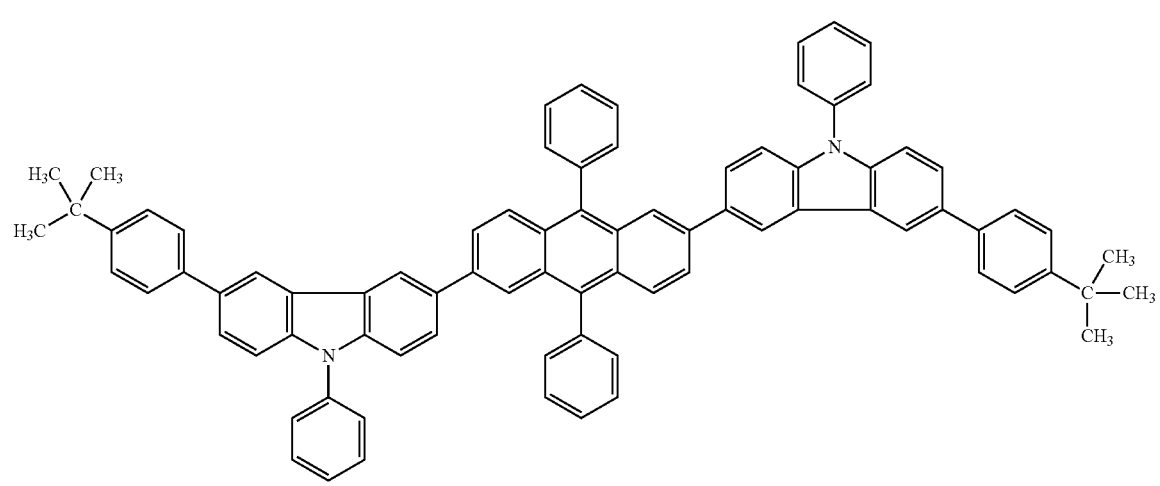

(341)
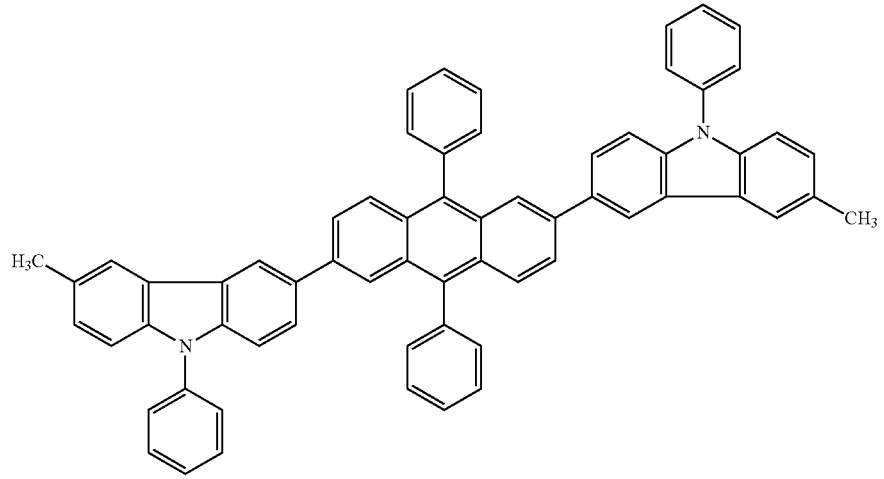
(342)
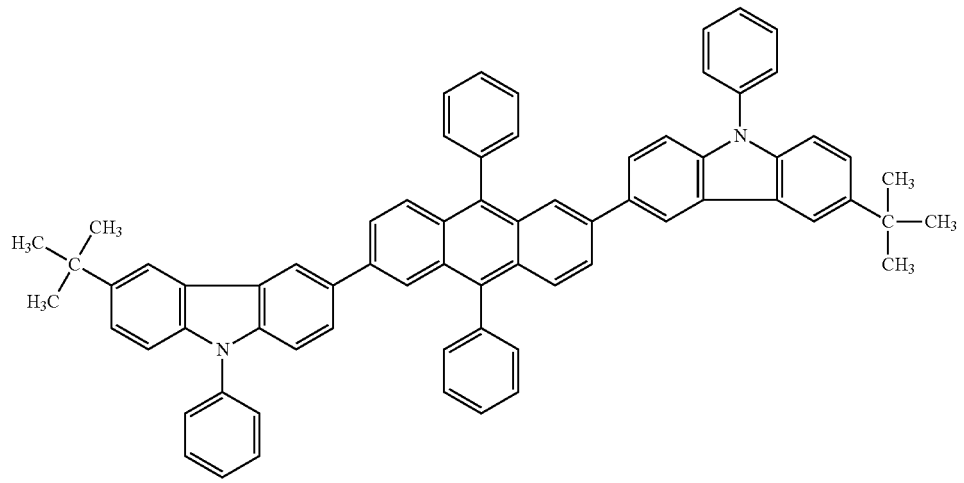
(343)
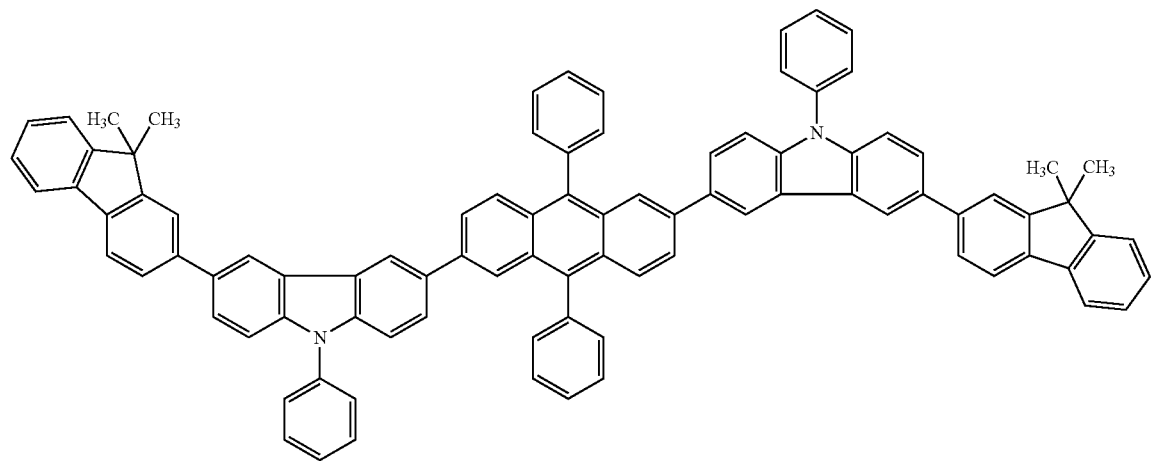

(344)
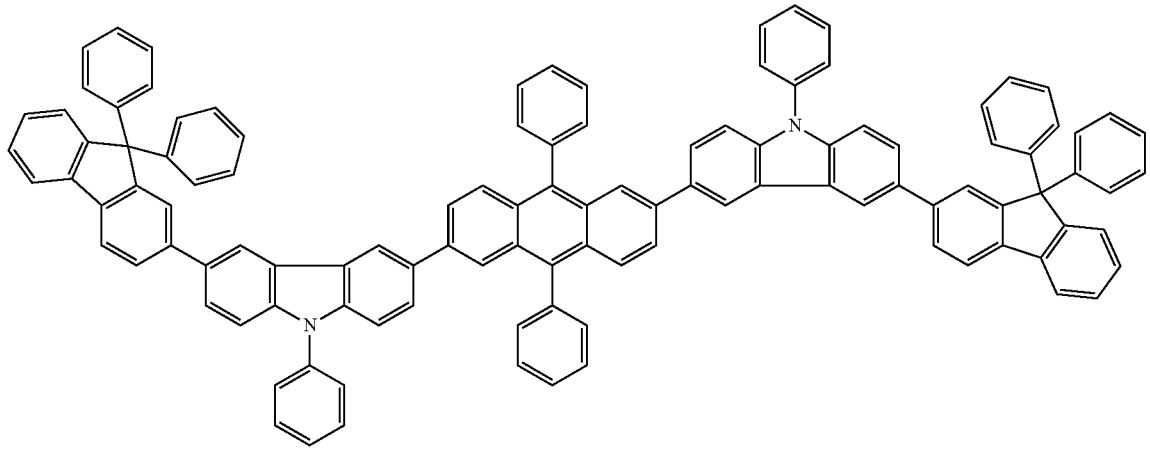
(345)
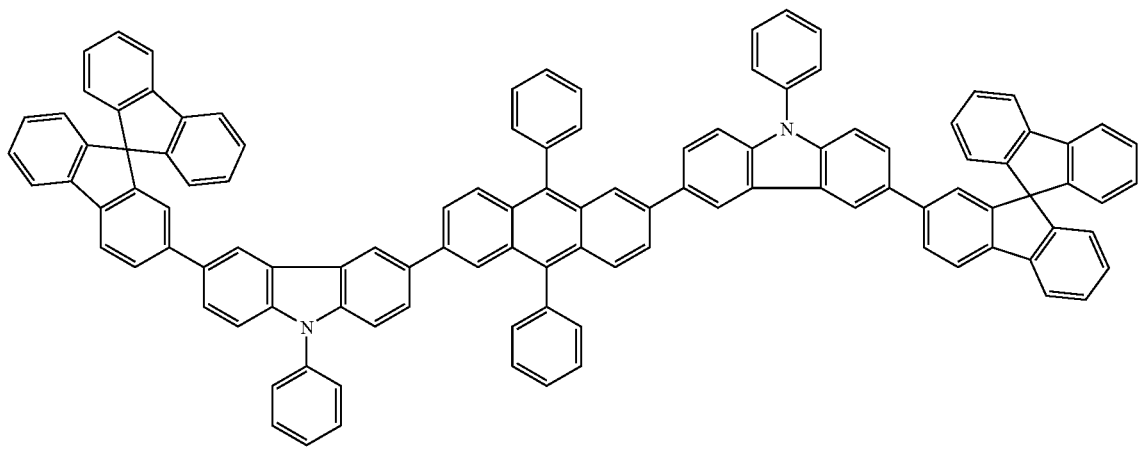
(346)
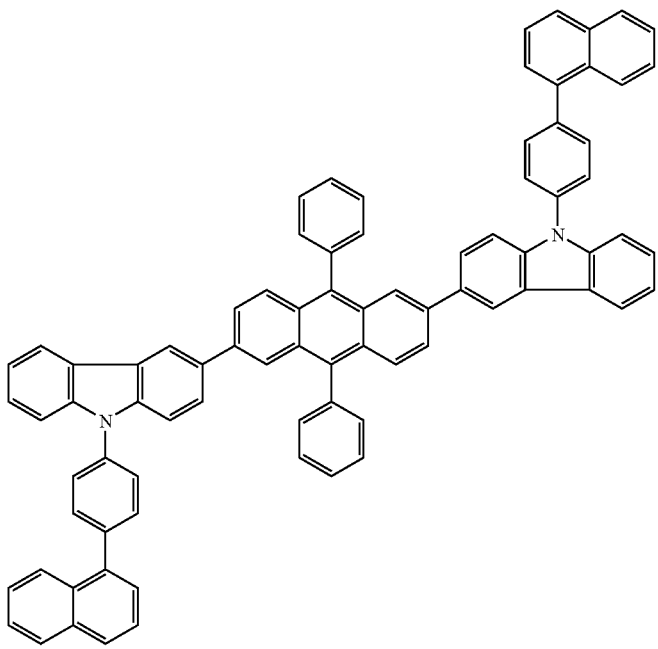

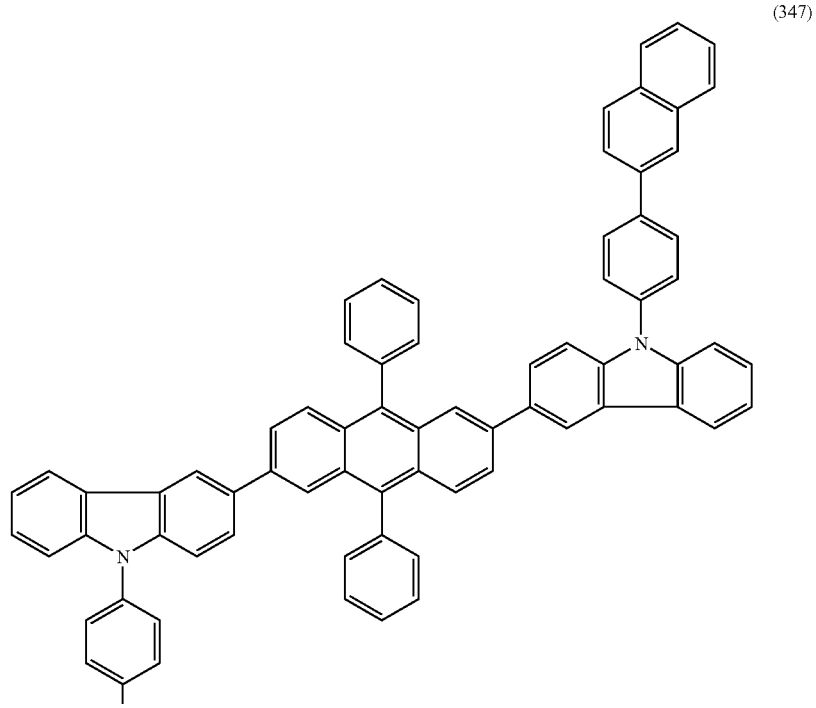
(347)
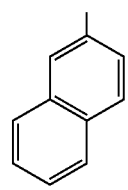
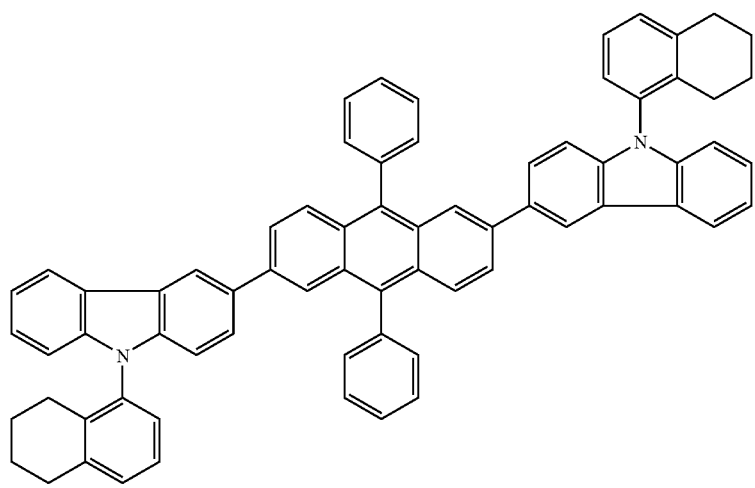
(348)

(349)
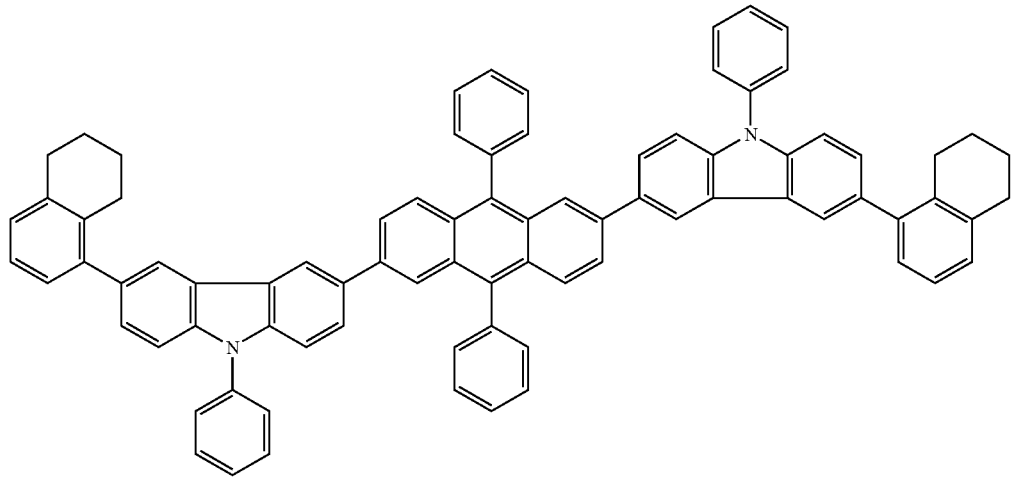
(401)
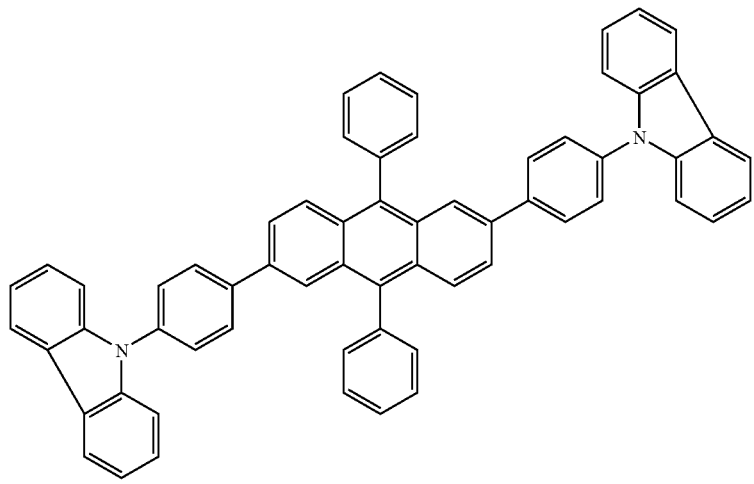
(404)
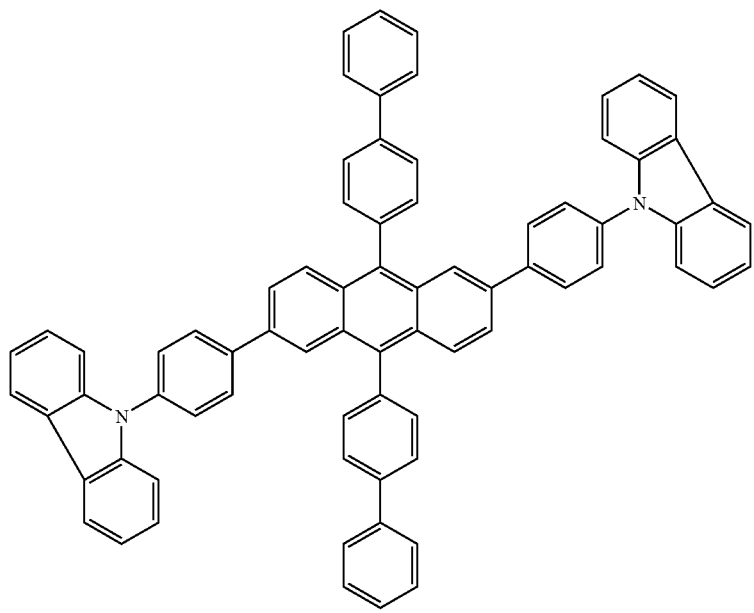

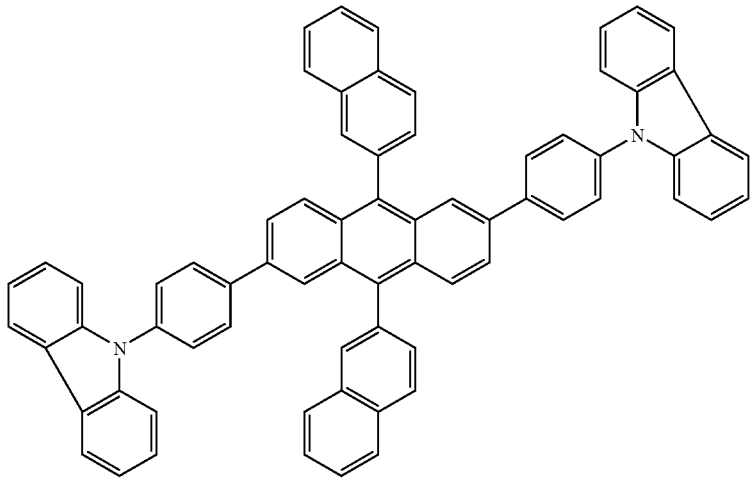
(402)
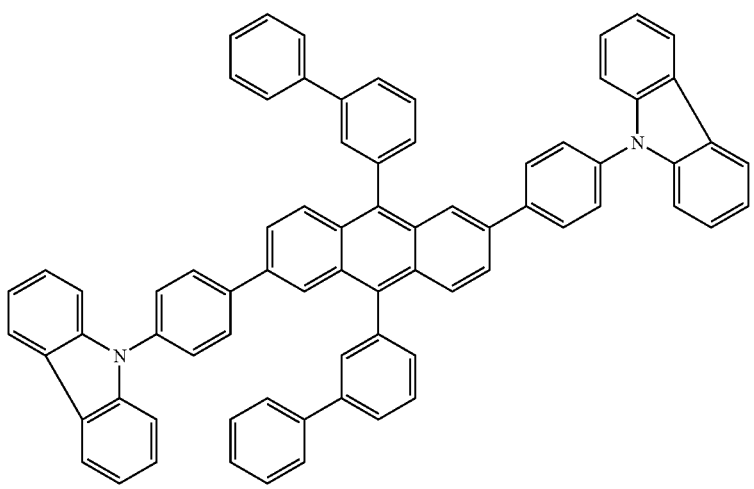
(405)
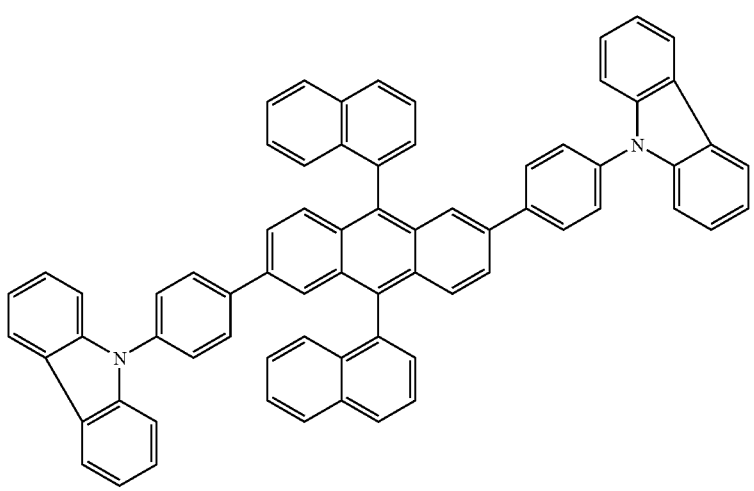
(403)

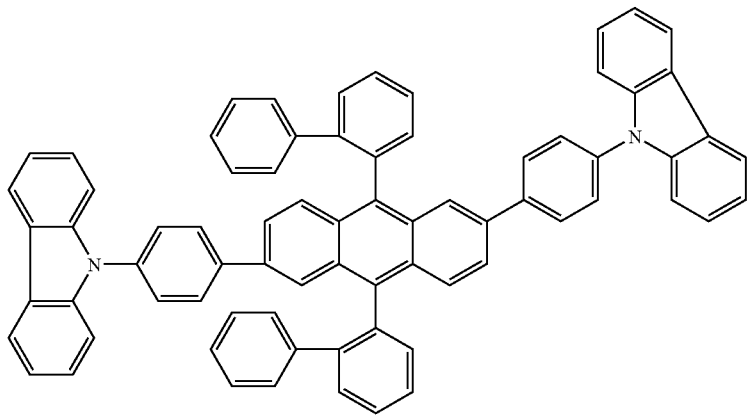
(406)
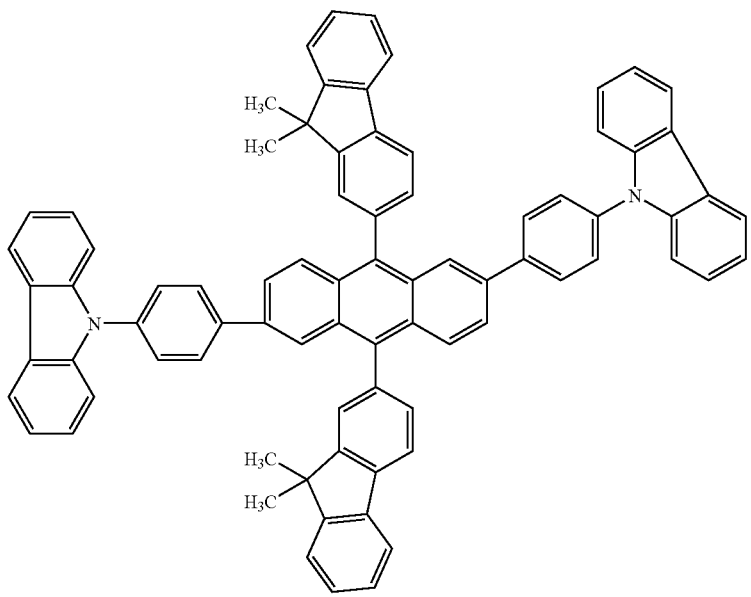
(407)
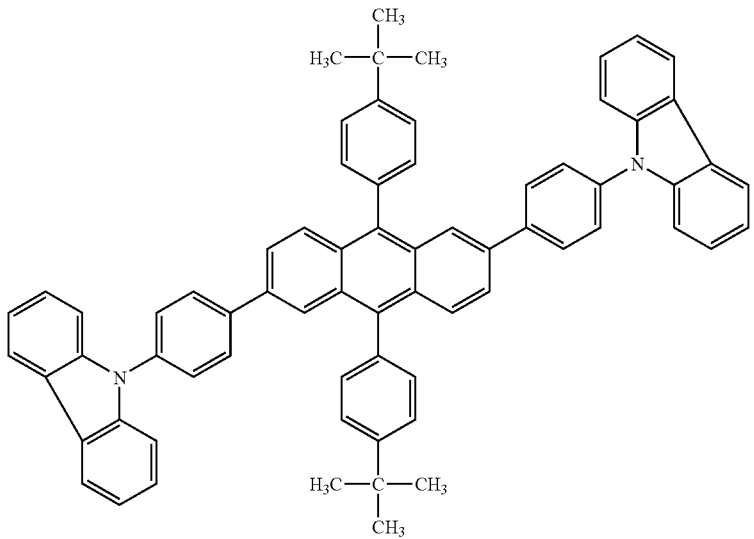
(410)

(408)
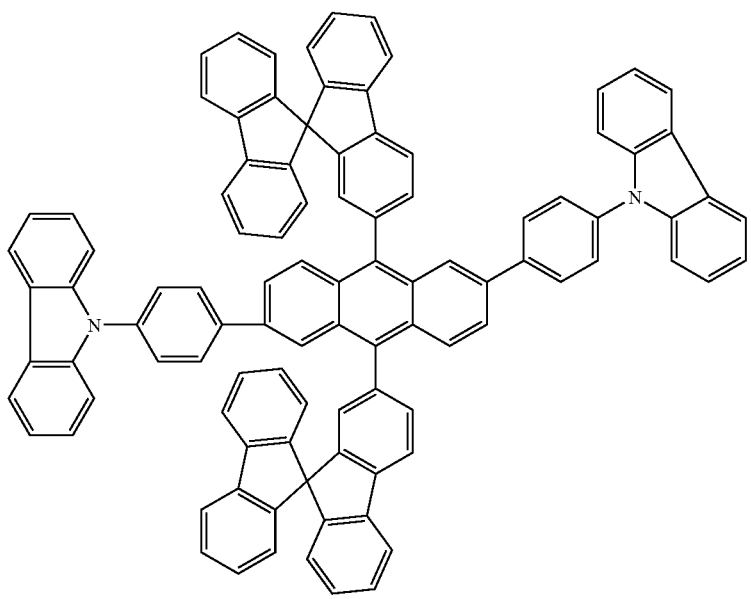
(411)
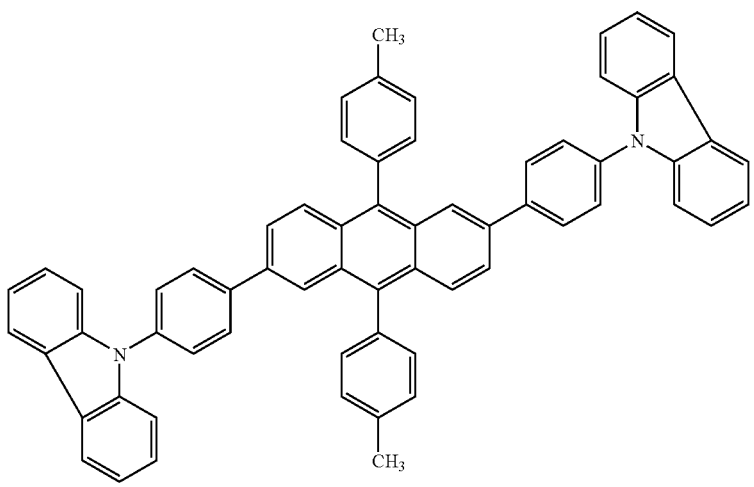
(409)
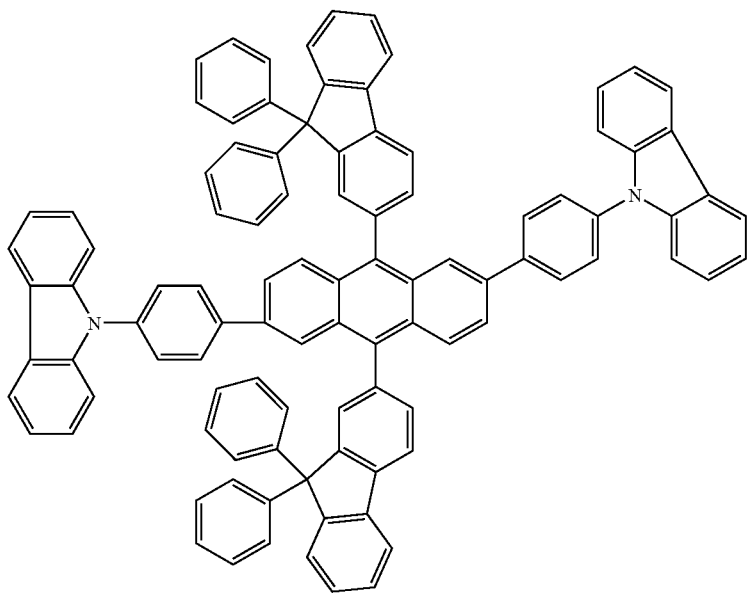

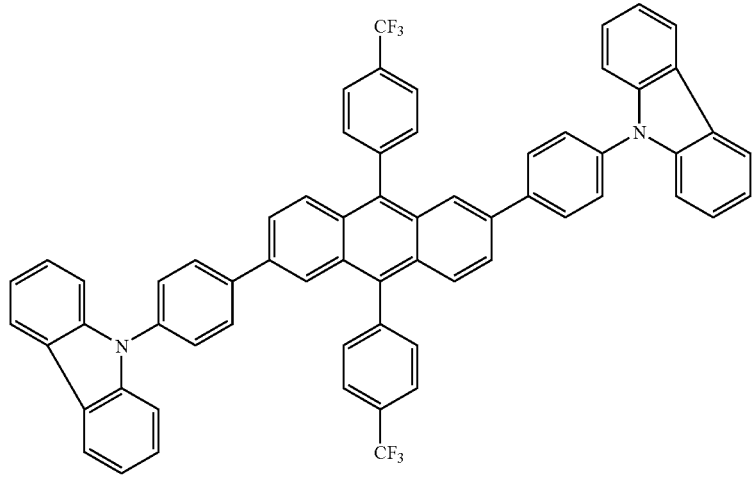
(412)
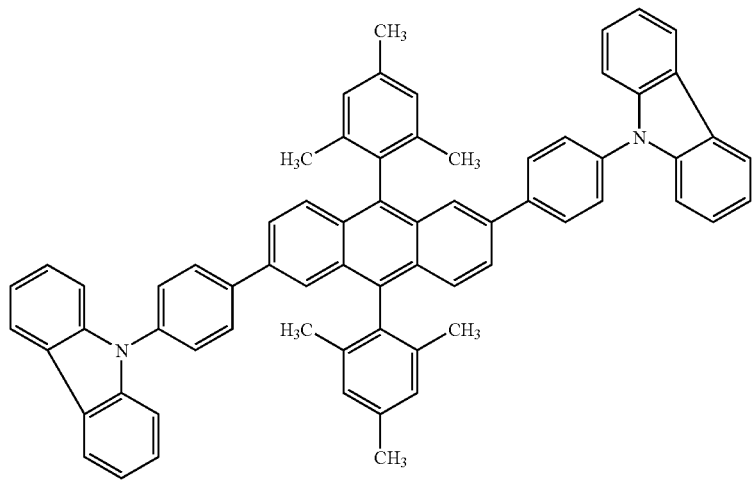
(413)
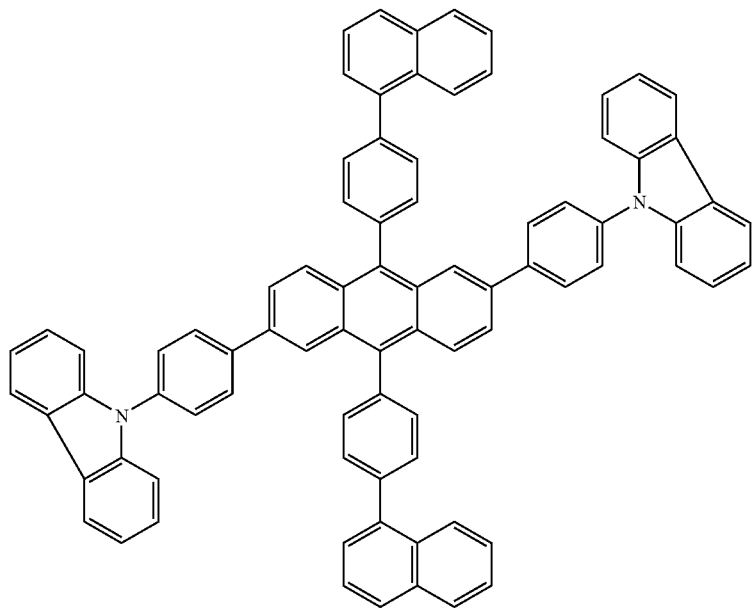
(415)

-continued
(414)
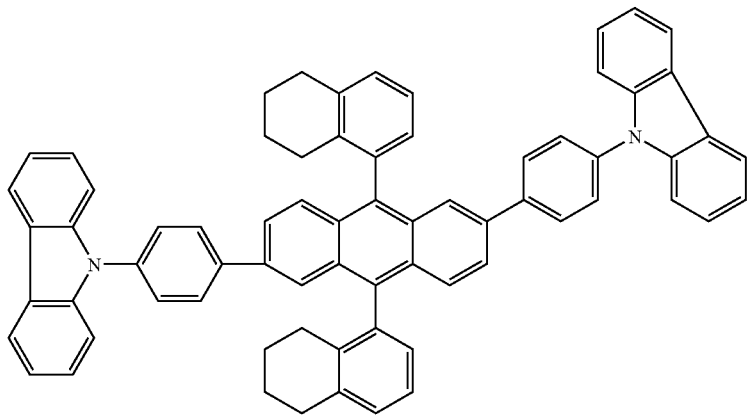
(416)
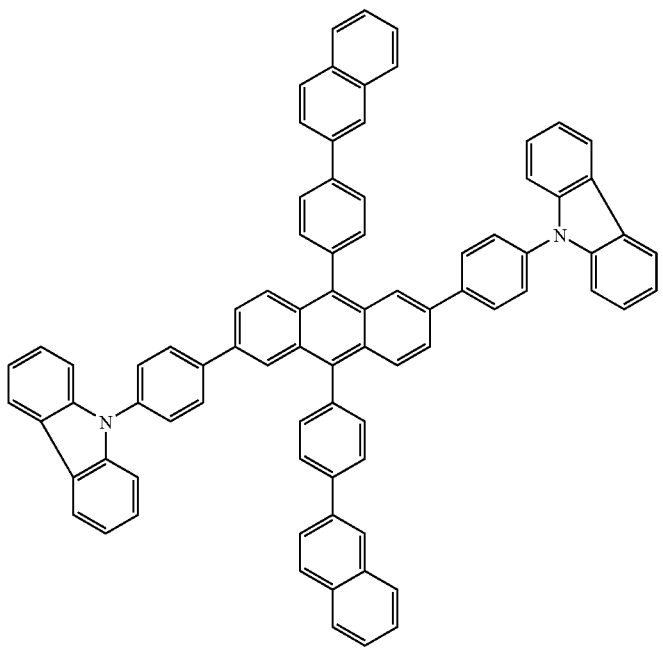
(417)
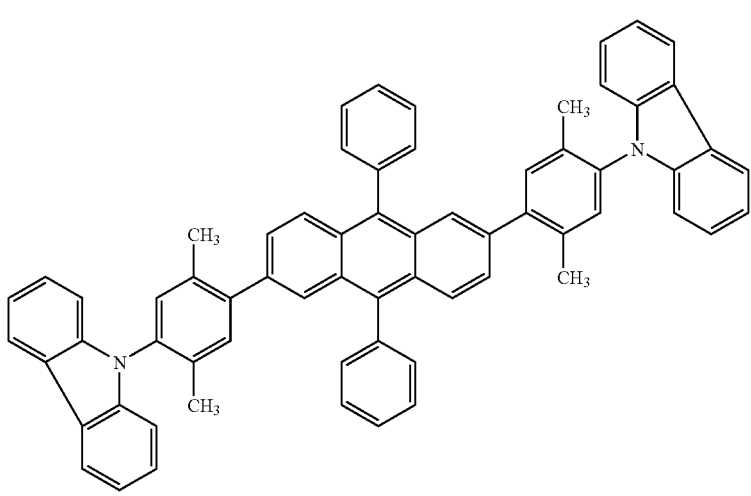

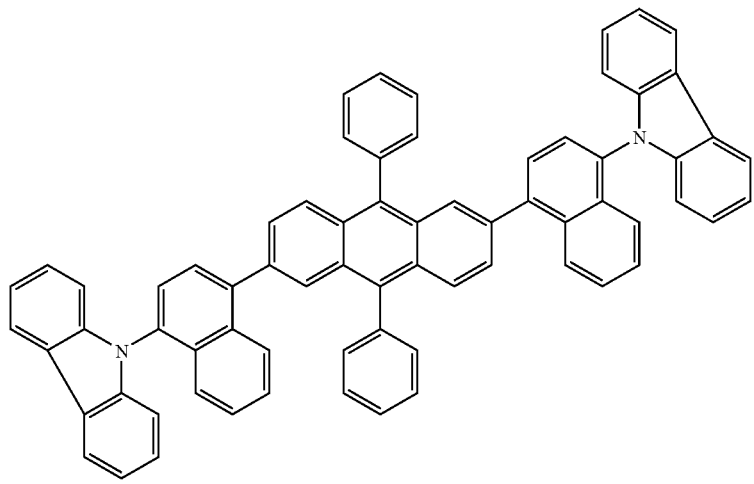
(418)
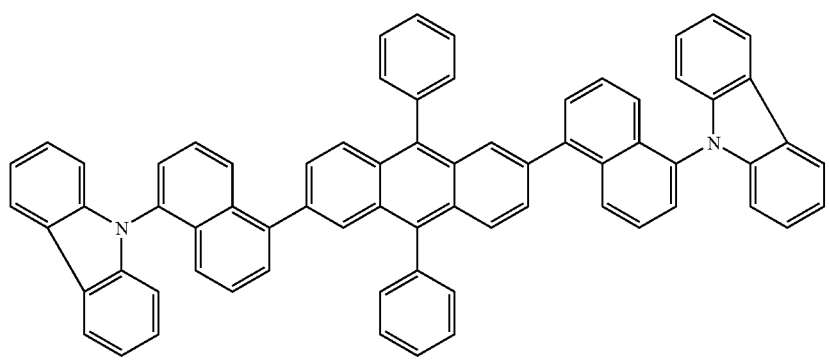
(419)
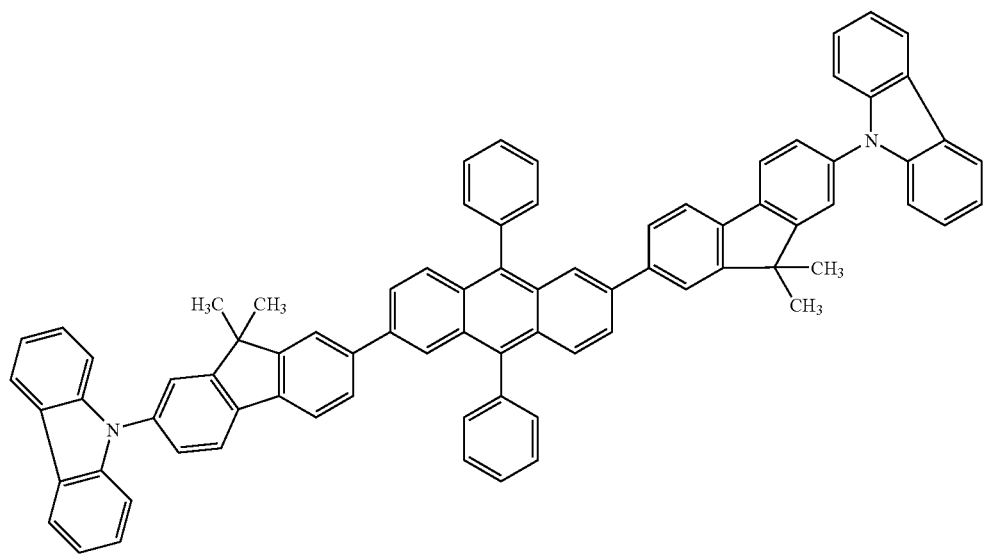
(420)

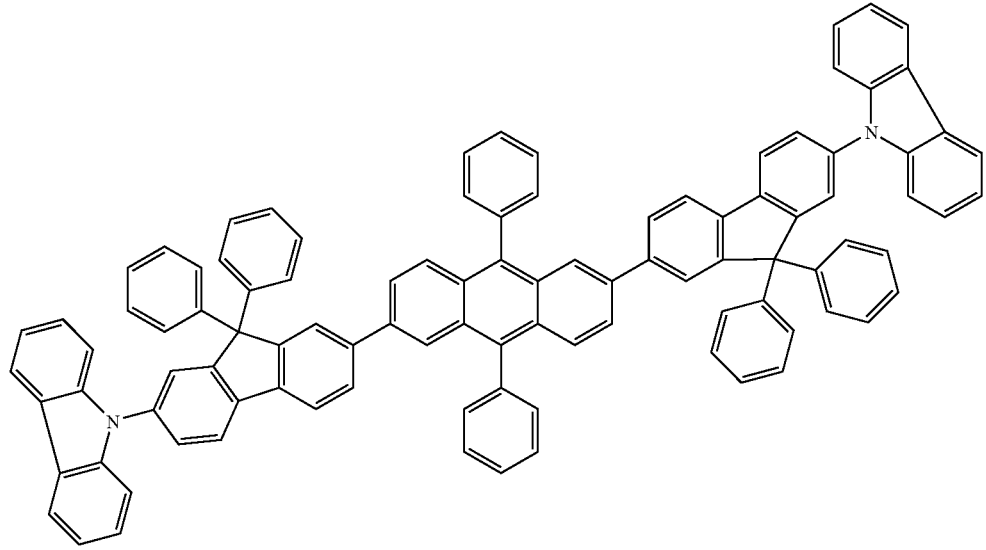
(421)
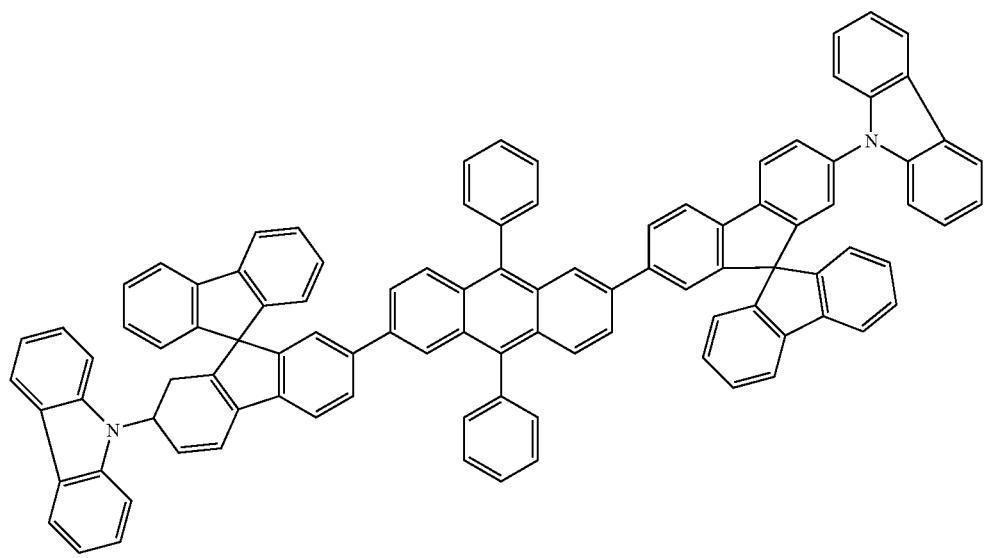
(422)

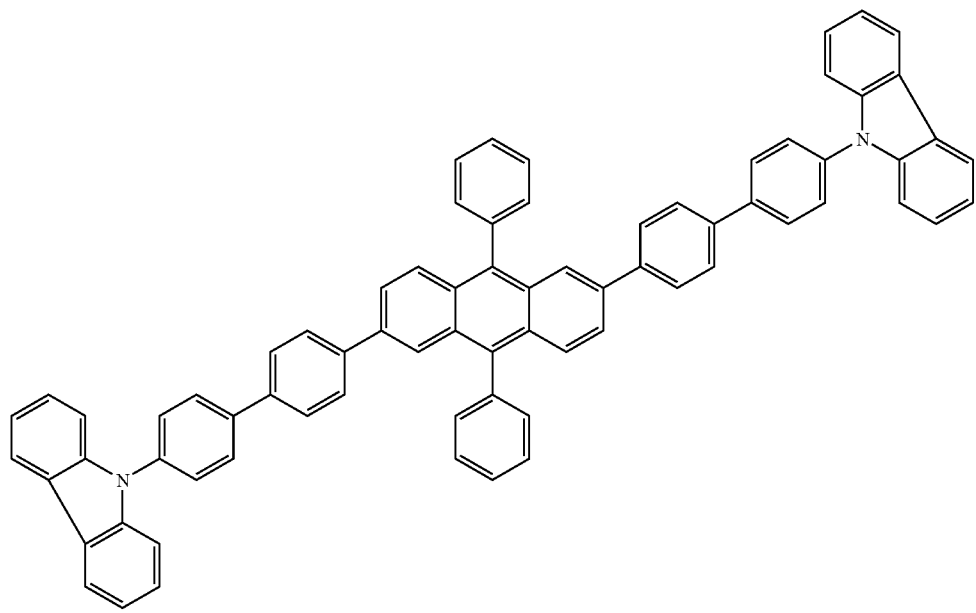
(423)
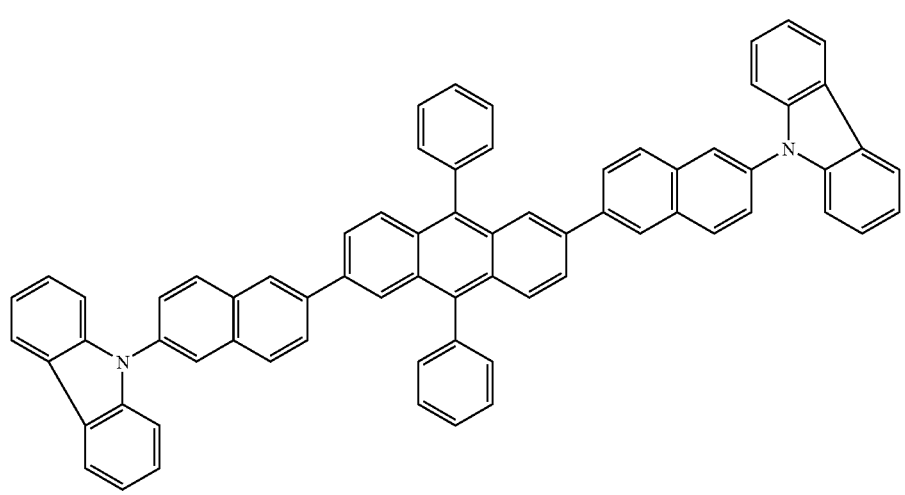
(424)

-continued
(425)
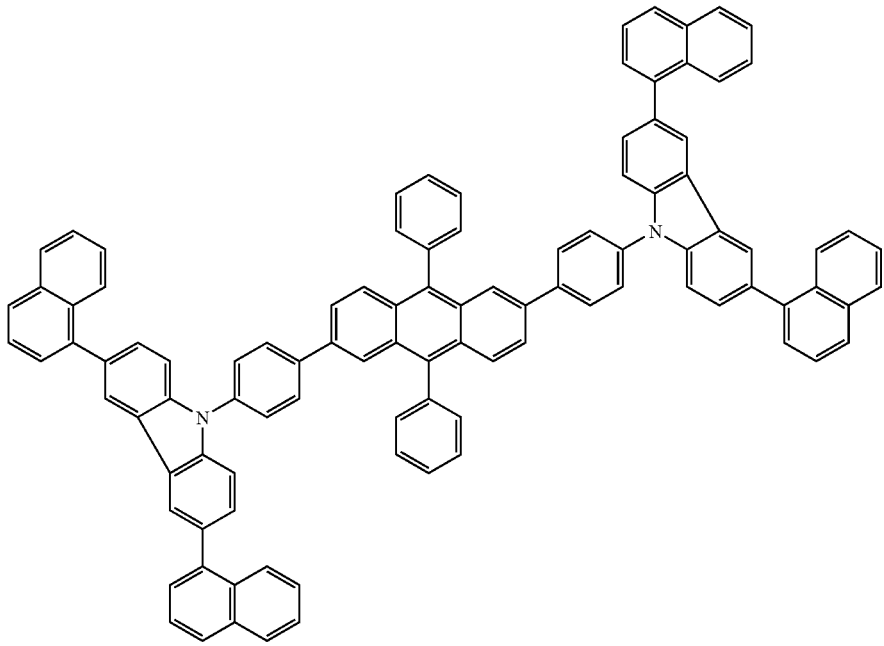
(426)
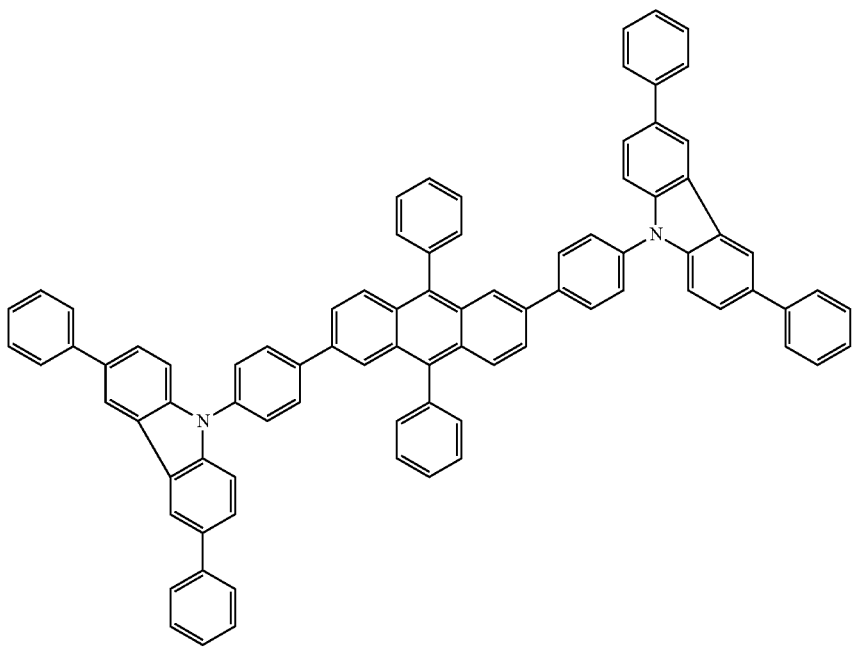
(427)
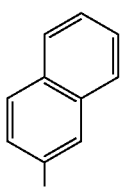

-continued
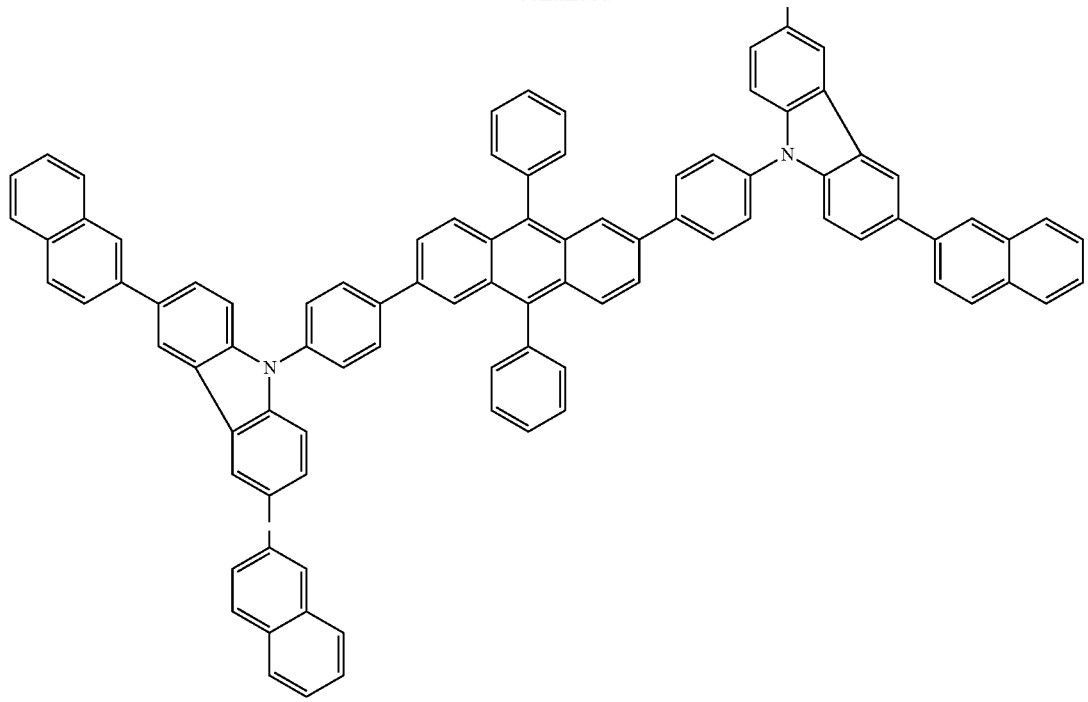
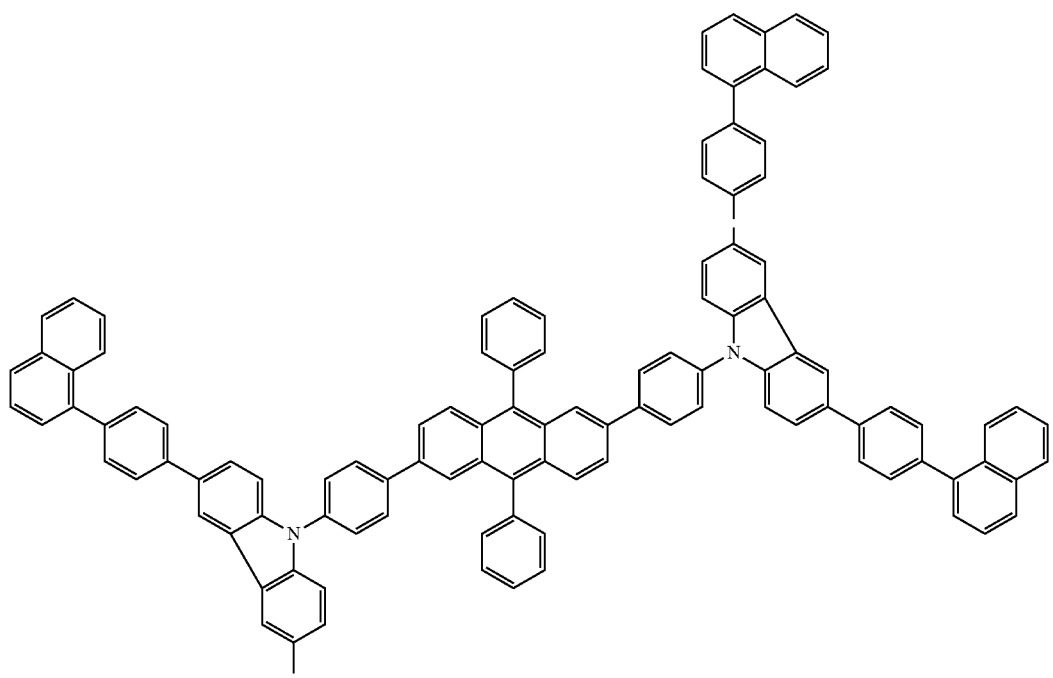
(428)
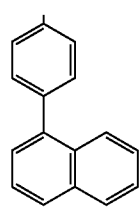

(429)
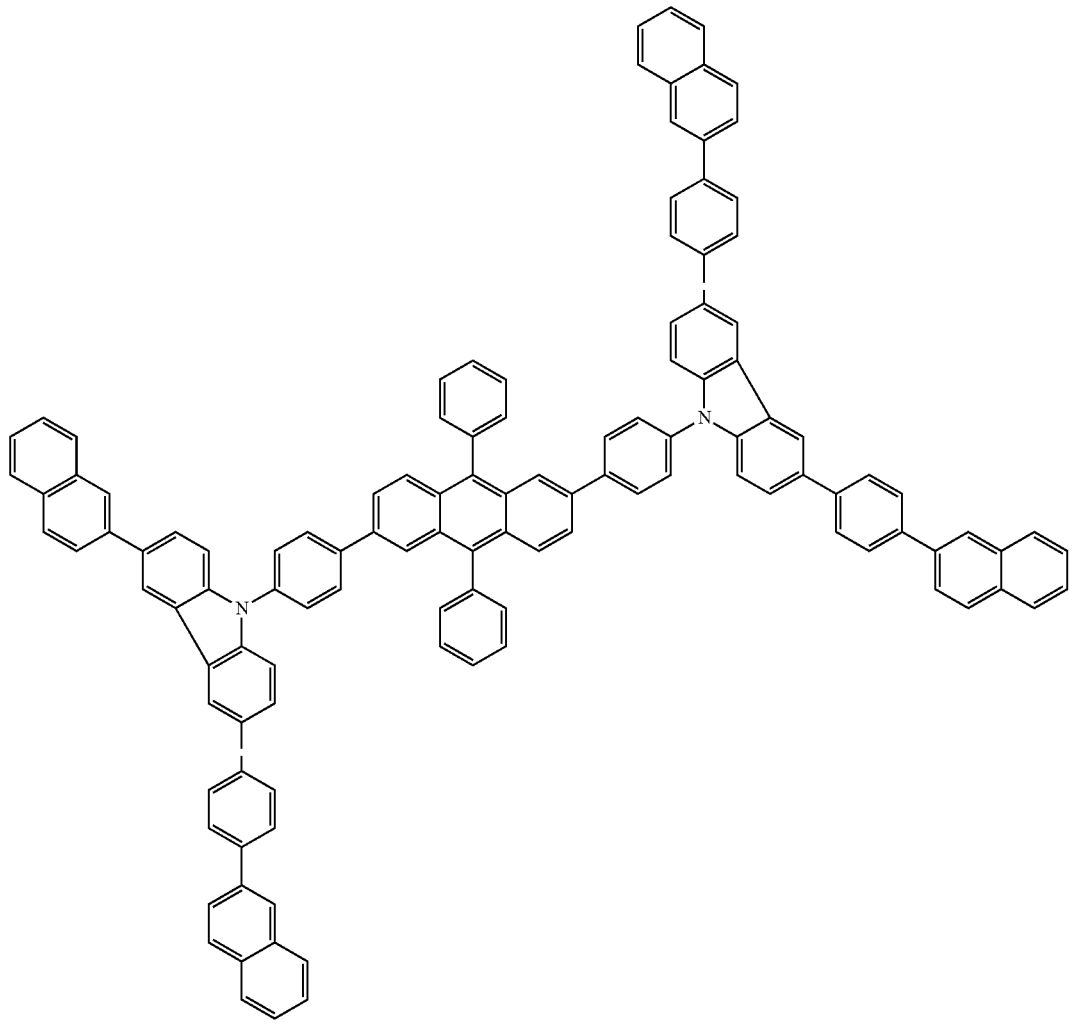
(430)
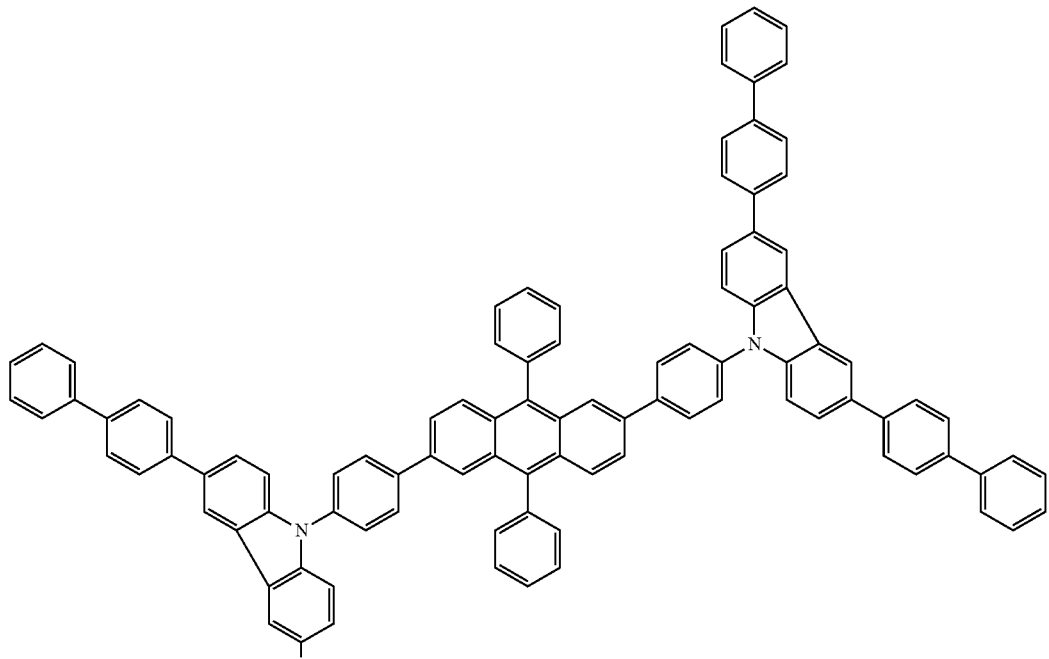

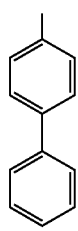
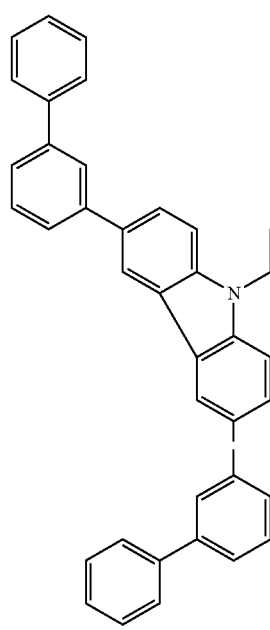
(431)
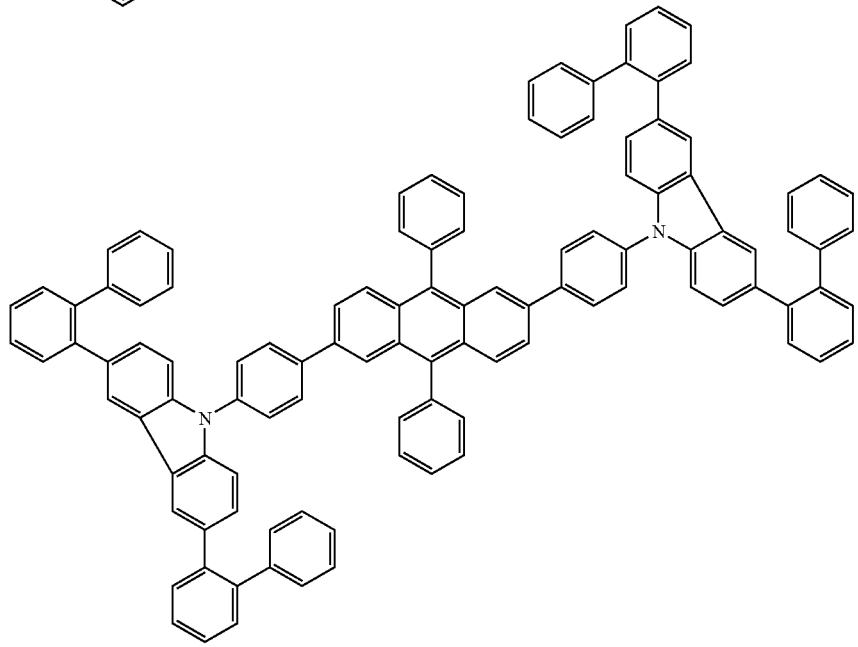
(432)

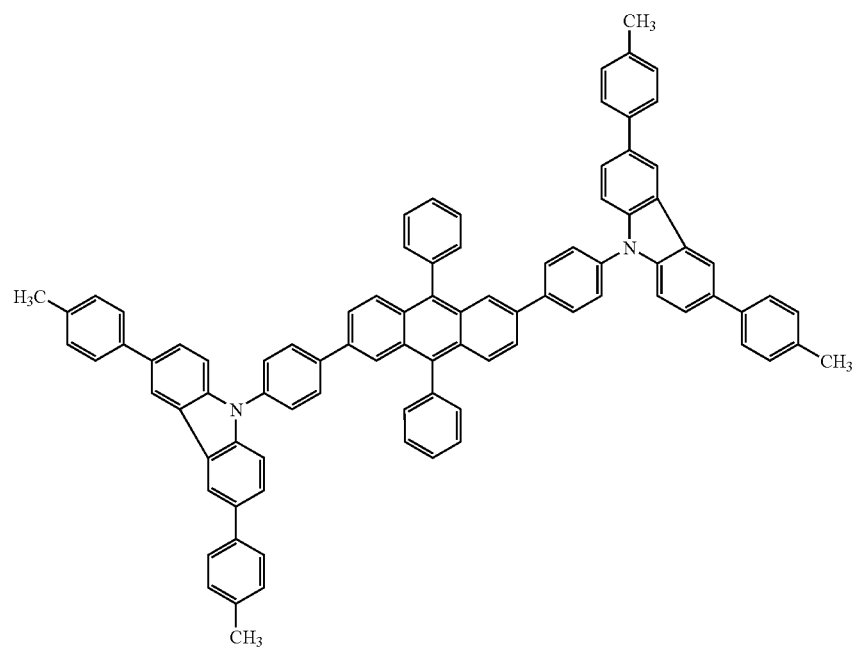
(433)
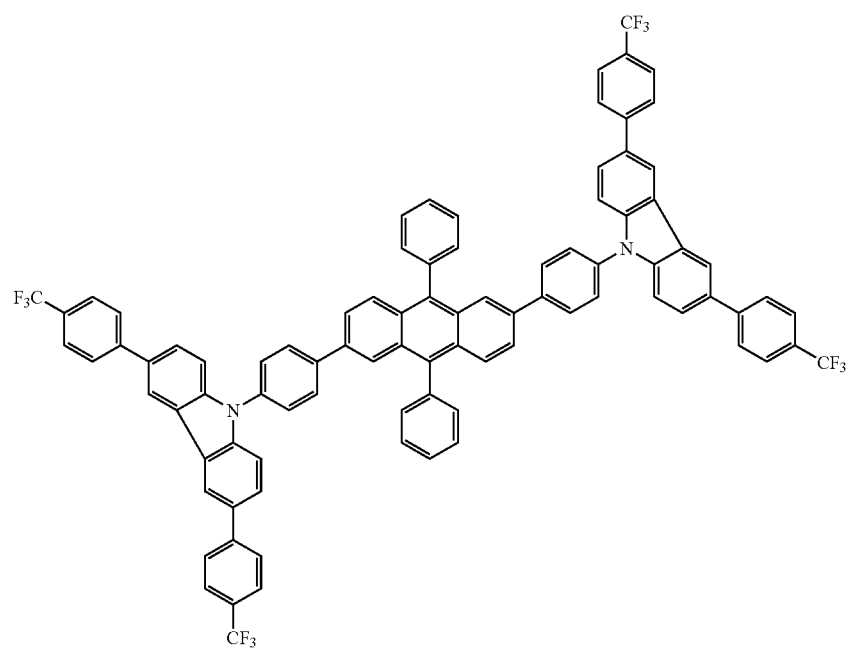
(434)

(435)
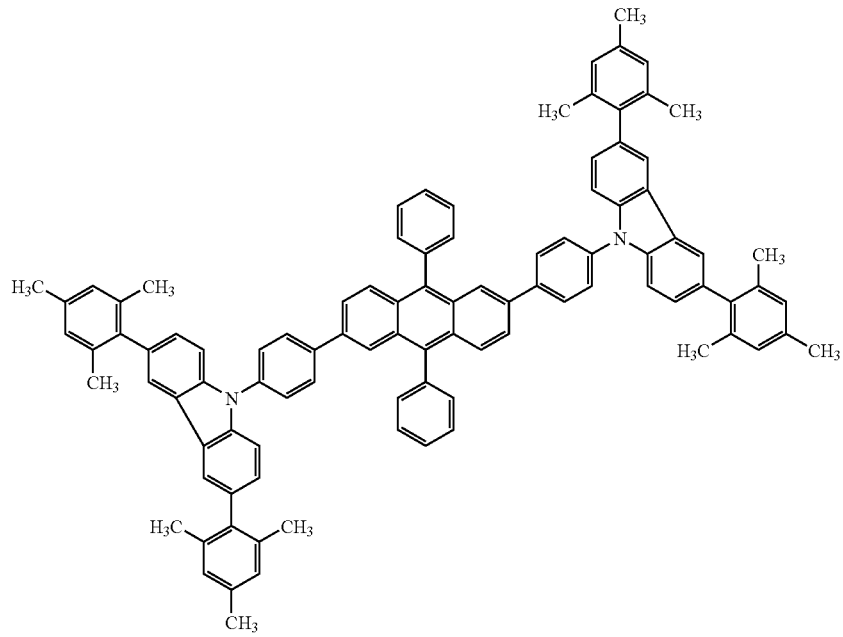
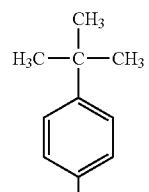
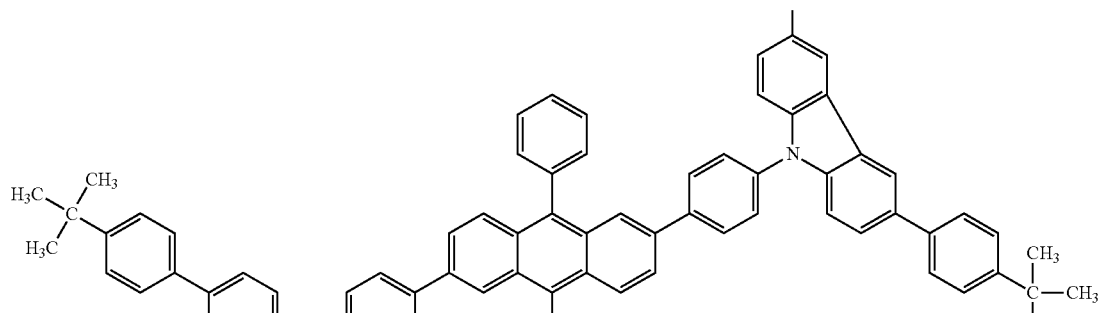
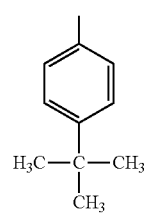

(437)
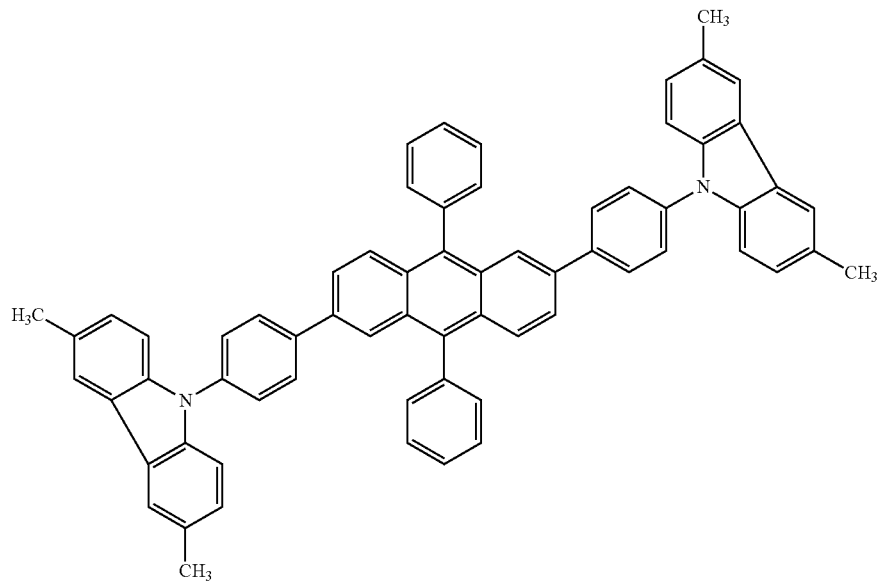
(438)
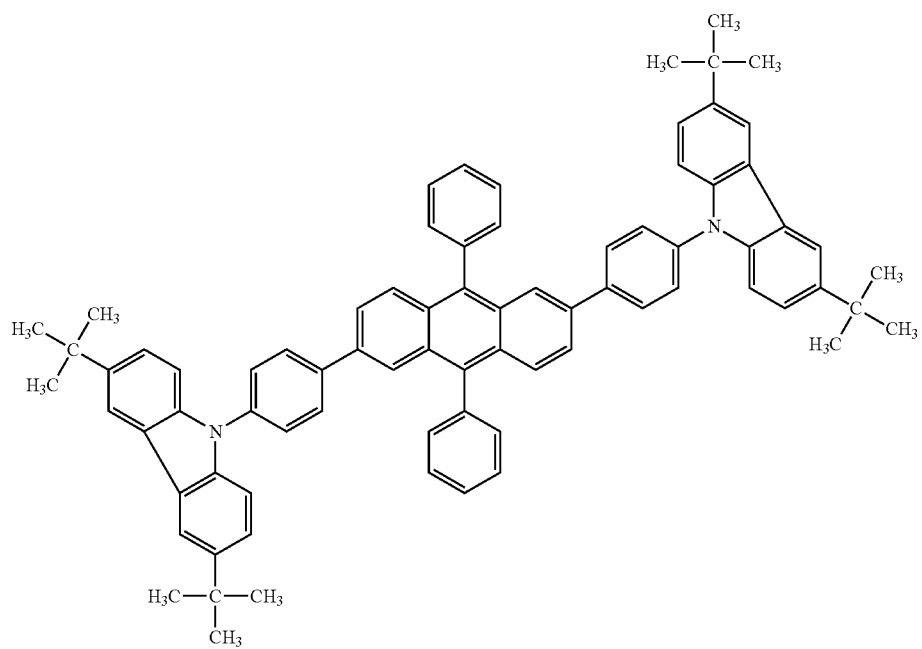
(439)
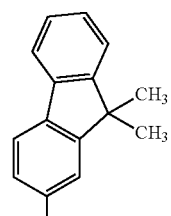

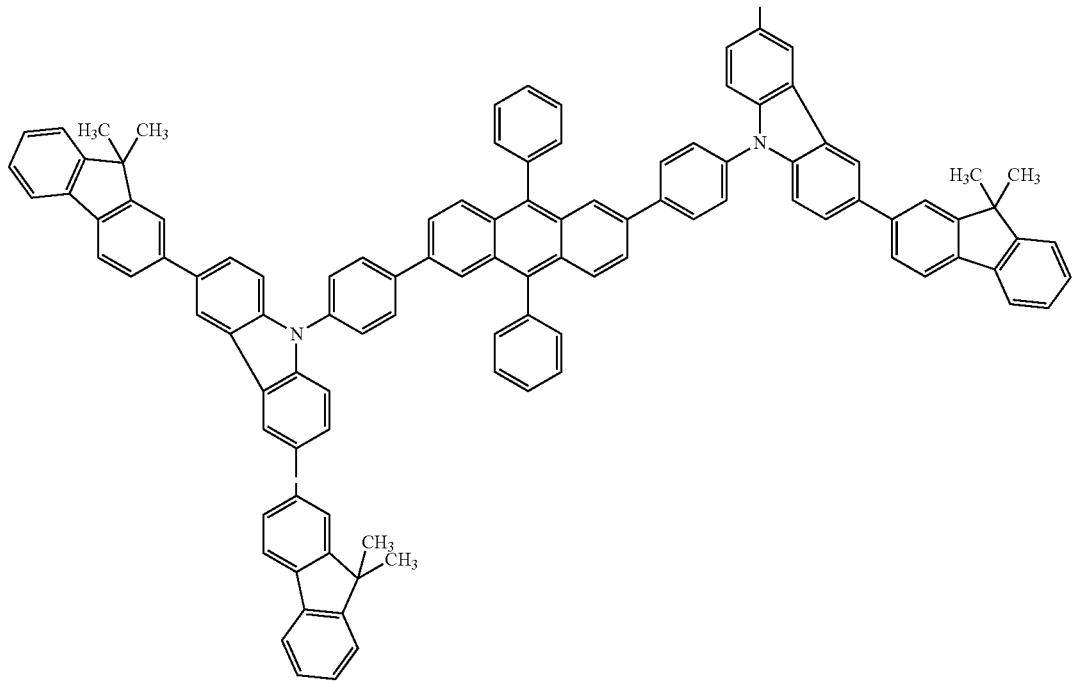
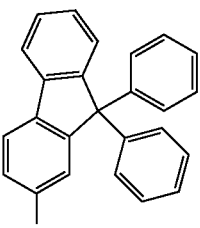
(440)
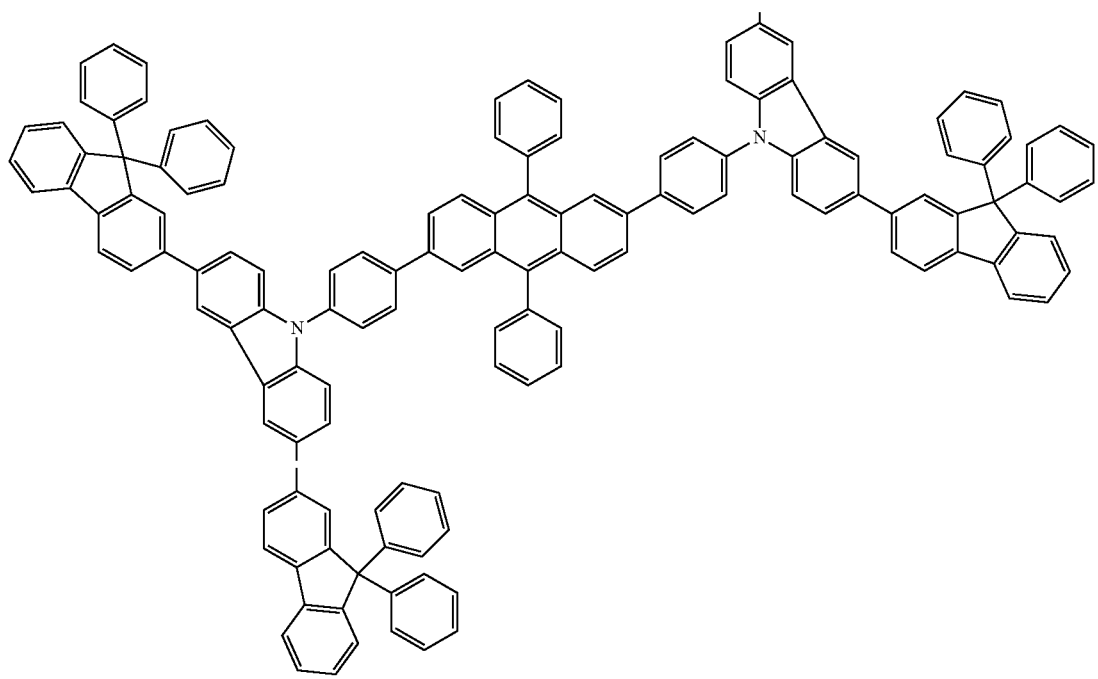

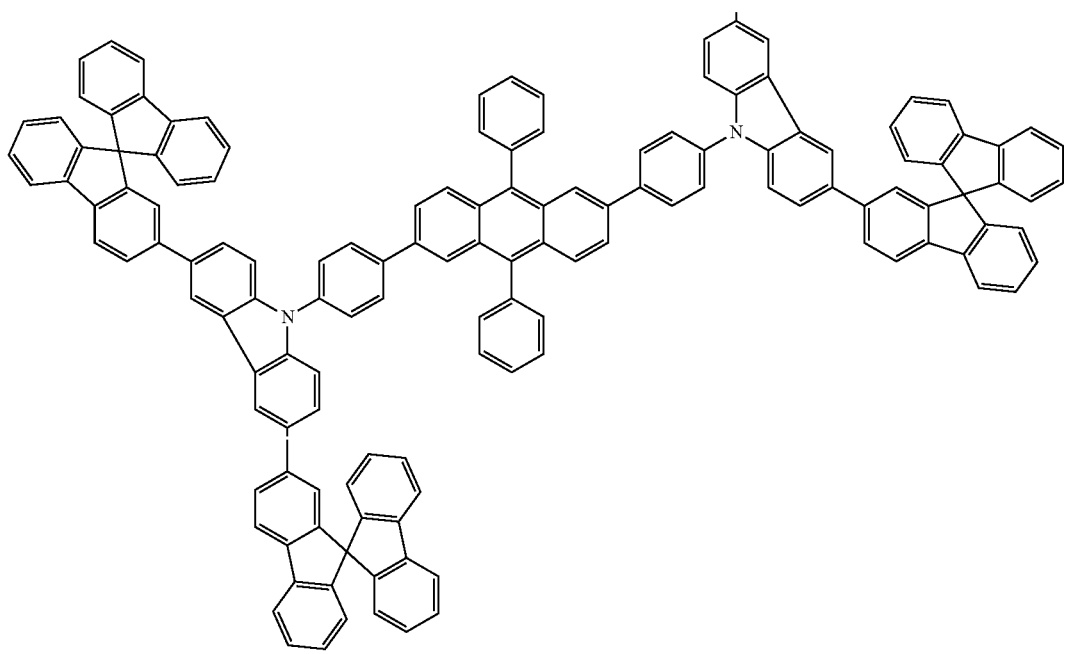

(441)

The anthracene derivatives represented by the structural formulae (101) to (149) are specific examples in the case of the bond between Ar$^3$ and Ar$^4$ or between Ar$^3$ and Ar$^5$ in the general formula (G11). The anthracene derivatives represented by the structural formulae (201) to (242) are specific examples in the case of the bond between Ar$^4$ and Ar$^5$ in the general formula (G11).

The anthracene derivatives represented by the structural formulae (301) to (349) are specific examples in the case of the bond between Ar$^3$ and Ar$^4$ or between Ar$^3$ and Ar$^5$ in the general formula (G21). The anthracene derivatives represented by the structural formulae (401) to (441) are specific examples in the case of the bond between Ar$^4$ and Ar$^5$ in the general formula (G21).

A variety of reactions can be applied to methods of synthesizing the anthracene derivatives of the present invention. For example, the anthracene derivatives of the present invention can be synthesized by synthesis reactions described hereinafter. Note that methods of synthesizing the anthracene derivatives of the present invention are not limited to the synthesis methods below.

<Synthesis of Anthracene Derivative Represented by General Formula (G11)>

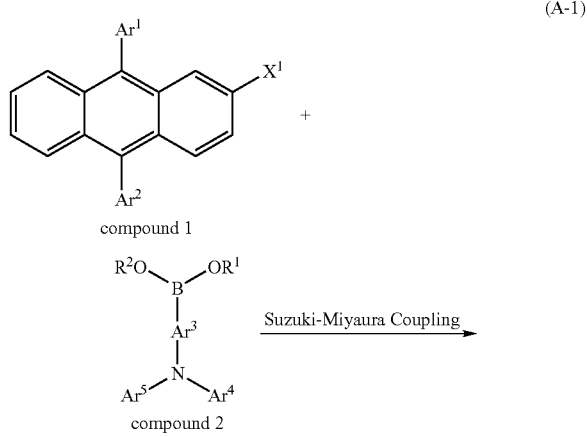

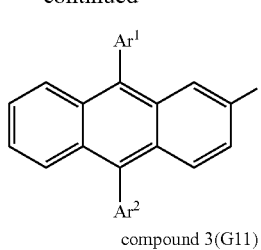

compound 3(G11)

As illustrated in a synthesis scheme (A-1), an anthracene derivative (compound 1) and a carbazole derivative with a boronic acid or organoboron (compound 2) are coupled by a Suzuki-Miyaura reaction, whereby an anthracene derivative in which a carbazole skeleton is bonded to the 2-position (compound 3), which is the object of the synthesis, can be obtained. In the synthesis scheme (A-1), $X^1$ represents halogen or a triflate group, $Ar^1$ and $Ar^2$ independently represent a substituted or unsubstituted aryl group having 6 to 13 carbon atoms, $Ar^3$ represents a substituted or unsubstituted arylene group having 6 to 13 carbon atoms, $Ar^4$ represents a substituted or unsubstituted aryl group having 6 to 13 carbon atoms, $Ar^5$ represents a substituted or unsubstituted aryl group having 6 to 13 carbon atoms, and a direct bond between $Ar^3$ and $Ar^4$, between $Ar^3$ and $Ar^5$, or between $Ar^4$ and $Ar^5$ forms a five-membered ring to form a carbazole skeleton. In addition, in the case where $X^1$ is halogen, $X^1$ is preferably chlorine, bromine, or iodine.

Examples of a palladium catalyst that can be used in the synthesis scheme (A-1) include, but not limited to, palladium (II) acetate, tetrakis(triphenylphosphine)palladium(0), and the like. Examples of a ligand of the palladium catalyst which can be used in the synthesis scheme (A-1) include, but not limited to, tri(ortho-tolyl)phosphine, triphenylphosphine, tricyclohexylphosphine, and the like. Examples of a base that can be used in the synthesis scheme (A-1) include, but not limited to, an organic base such as sodium t-butoxide, an inorganic base such as potassium carbonate, and the like. Examples of a solvent that can be used in the synthetic scheme (A-1) include, but not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as ethylene glycol dimethyl ether and water; and the like. In addition, use of a mixed solvent of toluene and water or a mixed solvent of toluene, ethanol, and water is more preferable.

<Synthesis of Anthracene Derivative Represented by General Formula (G21)>

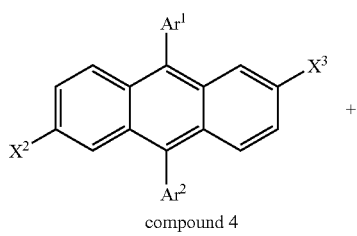

compound 4

(A-2)

+

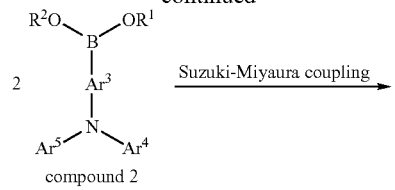

compound 2

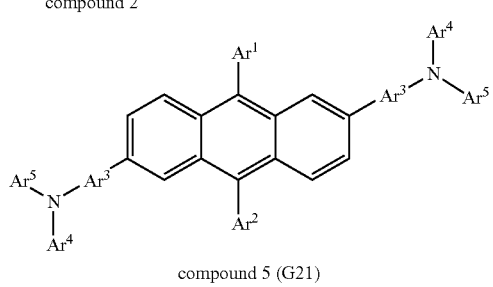

compound 5 (G21)

As illustrated in a synthesis scheme (A-2), an anthracene derivative (compound 4) and a carbazole derivative with a boronic acid or organoboron (compound 2) are coupled by a Suzuki-Miyaura reaction, whereby an anthracene derivative in which two carbazole skeletons are bonded to the 2- and 6-positions (compound 5), which is the object of the synthesis, can be obtained. In the synthesis scheme (A-2), $X^2$ and $X^3$ independently represent halogen or a triflate group, $Ar^1$ and $Ar^2$ independently represent a substituted or unsubstituted aryl group having 6 to 13 carbon atoms, $Ar^3$ represents a substituted or unsubstituted arylene group having 6 to 13 carbon atoms, $Ar^4$ represents a substituted or unsubstituted aryl group having 6 to 13 carbon atoms, $Ar^5$ represents a substituted or unsubstituted aryl group having 6 to 13 carbon atoms, and a direct bond between $Ar^3$ and $Ar^4$, between $Ar^3$ and $Ar^5$, or between $Ar^4$ and $Ar^5$ forms a five-membered ring to form a carbazole skeleton. In addition, in the case where $X^2$ and $X^3$ are each halogen, $X^2$ and $X^3$ are preferably chlorine, bromine, or iodine and may be the same or different from each other.

Examples of a palladium catalyst that can be used in the synthesis scheme (A-2) include, but not limited to, palladium (II) acetate, tetrakis(triphenylphosphine)palladium(0), and the like. Examples of a ligand of the palladium catalyst which can be used in the synthesis scheme (A-2) include, but not limited to, tri(ortho-tolyl)phosphine, triphenylphosphine, tricyclohexylphosphine, and the like. Examples of a base that can be used in the synthesis scheme (A-2) include, but not limited to, an organic base such as sodium t-butoxide, an inorganic base such as potassium carbonate, and the like. Examples of a solvent that can be used in the synthetic scheme (A-2) include, but not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as ethylene glycol dimethyl ether and water; and the like. In addition, use of a mixed solvent of toluene and water or a mixed solvent of toluene, ethanol, and water is more preferable.

The anthracene derivatives of the present invention emit blue light with high color purity. Thus, each anthracene derivative is suitable for use in a light-emitting element. Furthermore, the anthracene derivatives of the present invention are stable against repetition of oxidation reactions and reduction reactions. Thus, by using any of the anthracene derivatives of the present invention for a light-emitting element, a light-emitting element with a long lifetime can be obtained. Also, since the anthracene derivatives of the present invention can emit blue light with high color purity, each anthracene derivative is suitable for use in a light-emitting element for a full-color display.

The anthracene derivatives of the present invention have solubility in a wide variety of solvents, such as dichloroethane, chloroform, tetrahydrofuran, cyclohexanone, dimethylformamide, dimethyl sulfoxide, acetone, dioxane, anisole, ethyl acetate, toluene, xylene, tetralin, chlorobenzene, dichlorobenzene, fluorobenzene, etc. and nitrobenzene, pyridine, methyl isobutyl ketone, diglyme etc. Therefore, a layer including any of the anthracene derivatives of the present invention can be formed by forming a film of a mixture of such a solvent and the anthracene derivative by a wet method.

Embodiment 2

In Embodiment 2, one embodiment of a light-emitting element using any of the anthracene derivatives of the present invention will be described with reference to FIGS. 1A and 1B.

A light-emitting element described in Embodiment 2 has a plurality of layers between a pair of electrodes. The plurality of layers are a stack of layers each including a substance with a high carrier-injecting property or a substance having a high carrier-transporting property such that a light-emitting region is formed in a region away from the electrodes, i.e., such that carriers recombine in an area away from the electrodes.

In Embodiment 2, the light-emitting element includes a first electrode 102, a second electrode 104, and an EL layer 103 formed between the first electrode 102 and the second electrode 104. Note that in Embodiment 2, hereinafter, it is assumed that the first electrode 102 functions as an anode and the second electrode 104 functions as a cathode. In other words, in the description below, it is assumed that light emission is obtained when a voltage is applied to the first electrode 102 and the second electrode 104 so that the potential of the first electrode 102 is higher than that of the second electrode 104.

A substrate 101 is used as a support of the light-emitting element. For the substrate 101, glass, plastic, or the like can be used, for example. Note that any other material may be used as long as it functions as a support of the light-emitting element. Note that when light emission from the light-emitting element is extracted outside through the substrate, a light-transmitting substrate is preferably used as the substrate 101.

Preferably, the first electrode 102 is formed using any of metals, alloys, or electrically conductive compounds, a mixture thereof, or the like having a high work function (specifically, greater than or equal to 4.0 eV is preferable). For example, there are indium oxide-tin oxide (ITO), indium oxide-tin oxide containing silicon or silicon oxide, indium oxide-zinc oxide (IZO), indium oxide containing tungsten oxide and zinc oxide (IWZO), and the like. Films of such electrically conductive metal oxide are normally formed by sputtering, but may also be formed by an inkjet method, a spin coating method, or the like by applying a sol-gel method or the like. For example, a film of indium oxide-zinc oxide (IZO) can be formed using a target in which 1 to 20 wt % of zinc oxide is added to indium oxide by a sputtering method. In addition, a film of indium oxide containing tungsten oxide and zinc oxide (IWZO) can be formed using a target in which 0.5 to 5 wt % tungsten oxide and 0.1 to 1 wt % zinc oxide are added to indium oxide by a sputtering method. Further, there are gold (Au), platinum (Pt), nickel (Ni), tungsten (W), chromium (Cr), molybdenum (Mo), iron (Fe), cobalt (Co), copper (Cu), palladium (Pd), titanium (Ti), nitride of a metal material (e.g., titanium nitride), and the like.

Further, when a layer including a composite material described later is used as a layer that is in contact with the first electrode 102, any of a variety of metals, alloys, electrically conductive compounds, or a mixture thereof can be used for the first electrode 102 regardless of the work functions. For example, aluminum (Al), silver (Ag), an alloy containing aluminum (e.g., AlSi), or the like can be used. Alternatively, it is possible to use any of elements belonging to Group 1 or 2 of the periodic table which have a low work function, i.e., alkali metals such as lithium (Li) and cesium (Cs); alkaline earth metals such as magnesium (Mg), calcium (Ca), and strontium (Sr); alloys containing any of these metals (e.g., MgAg and AlLi); rare earth metals such as europium (Eu) and ytterbium (Yb); alloys containing any of these metals; or the like. A film of an alkali metal, an alkaline earth metal, or an alloy containing any of these metals can be formed by a vacuum evaporation method. Alternatively, a film of an alloy containing an alkali metal or an alkaline earth metal can be formed by a sputtering method. Further, a film can be formed using silver paste or the like by an inkjet method or the like.

The EL layer 103 described in Embodiment 2 includes a hole-injecting layer 111, a hole-transporting layer 112, a light-emitting layer 113, an electron-transporting layer 114, and an electron-injecting layer 115. Note that as long as the EL layer 103 includes any of the anthracene derivatives described in Embodiment 1, there is no limitation on the stack structure of the other layers. In other words, there is no limitation on the stack structure of the EL layer 103 as long as the EL layer 103 has a structure in which any of the anthracene derivatives described in Embodiment 1 is used in combination with a layer including a substance with a high electron-transporting property, a substance with a high hole-transporting property, a substance with a high electron-injecting property, a substance with a high hole-injecting property, a bipolar substance (a substance with a high electron-transporting property and a high hole-transporting property), or the like, as appropriate. For example, the structure can be formed by combining a hole-injecting layer, a hole-transporting layer, a light-emitting layer, an electron-transporting layer, an electron-injecting layer, etc., as appropriate. Materials for the layers are specifically given below.

The hole-injecting layer 111 is a layer including a substance with a high hole-injecting property. As a substance having a high hole-injecting property, molybdenum oxide, vanadium oxide, ruthenium oxide, tungsten oxide, manganese oxide, or the like can be used. Besides, as examples of low molecular organic compounds, there are phthalocyanine-based compounds such as phthalocyanine (abbreviation: $H_2Pc$), copper(II) phthalocyanine (abbreviation: CuPc), and vanadyl(IV) phthalocyanine (VOPc), aromatic amine compounds such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1), and the like.

Alternatively, the hole-injecting layer 111 can be formed using a composite material in which an acceptor substance is included in a substance having a high hole-transporting property. Note that, by using a material in which an acceptor substance is included in a substance having a high hole-transporting property, a material used for forming the electrode may be selected regardless of the work function. In other words, besides a material with a high work function, a material with a low work function may also be used for the first electrode 102. Such composite materials can be formed by co-evaporation of a substance having a high hole-transporting property and an acceptor substance.

Note that in this specification, the term "composite" refers not only to a state in which two kinds of materials are simply mixed, but also to a state in which charges can be given and received between materials by mixture of a plurality of materials.

As an organic compound used for the composite material, any of a variety of compounds such as aromatic amine compounds, carbazole derivatives, aromatic hydrocarbons, or high molecular compounds (oligomers, dendrimers, polymers, etc.) can be used. Note that an organic compound used for the composite material preferably has a high hole-transporting property. Specifically, a substance having a hole mobility of $10^{-6}$ cm$^2$/Vs or more is preferably used. Further, any other substance may be used as long as it is a substance in which the hole-transporting property is higher than the electron-transporting property. Organic compounds that can be used for the composite material are specifically given below.

For example, any of the following organic compounds can be used for the composite material: aromatic amine compounds such as MTDATA, TDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), and N,N'-bis(3-methylphenyl)-N,N'-diphenyl-[1,1'-biphenyl]-4,4'-diamine (abbreviation: TPD); carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl-2,3,5,6-tetraphenylbenzene; and aromatic hydrocarbon compounds such as 2-tert-butyl-9,10-di(2-naphthyl)anthracene (abbreviation: t-BuDNA), 2-tert-butyl-9,10-di(1-naphthyl) anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl) anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butyl-anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl) anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis[4-(2,2-diphenylvinyl)phenyl]anthracene (abbreviation: DPVPA).

Further, examples of the acceptor substance are as follows: organic compounds such as 7,7,8,8-tetracyano-2,3,5,6-tetrafluoroquinodimethane (abbreviation: F$_4$-TCNQ) and chloranil, and transition metal oxides. Furthermore, other examples are oxides of metals belonging to Group 4 to Group 8 of the periodic table. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in air and its hygroscopic property is low so that it can be easily handled.

Alternatively, for the hole-injecting layer 111, any of high molecular compounds (oligomers, dendrimers, polymers, etc.) can be used. Examples of high molecular compounds include poly(N-vinylcarbazole) (abbreviation: PVK), poly (4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine (abbreviation: Poly-TPD). Alternatively, a high molecular compound to which acid is added, such as poly(3,4-ethylenedioxythiophene)/poly(styrenesulfonic acid) (PEDOT/PSS) or polyaniline/poly(styrenesulfonic acid) (PAni/PSS), can be used.

Alternatively, for the hole-injecting layer 111, a composite material formed using any of the above-mentioned high molecular compounds such as PVK, PVTPA, PTPDMA, or Poly-TPD and any of the above-mentioned acceptor substances may be used.

The hole-transporting layer 112 is a layer including a substance with a high hole-transporting property. As a substance having a high hole-transporting property, a low molecular organic compound can be used, and examples thereof include aromatic amine compounds such as NPB (or α-NPD), TPD, 4,4'-bis[N-(9,9-dimethylfluoren-2-yl)-N-phenylamino]biphenyl (abbreviation: DFLDPBi), and 4,4'-bis[N-(spiro-9,9'-bifluoren-2-yl)-N-phenylamino]biphenyl (abbreviation: BSPB). The substances mentioned here are mainly substances having a hole mobility of $10^{-6}$ cm$^2$/Vs or more. However, any other substance may also be used as long as it is a substance in which the hole-transporting property is higher than the electron-transporting property. Note that the hole-transporting layer is not limited to a single layer and may be a stack of two or more layers including any of the above-mentioned substances.

Alternatively, for the hole-transporting layer 112, a composite material in which an acceptor substance is included in the above-mentioned substance having a high hole-transporting property may be used.

Alternatively, for the hole-transporting layer 112, a high molecular compound such as PVK, PVTPA, PTPDMA, or Poly-TPD can be used.

The light-emitting layer 113 is a layer including a substance with a high light-emitting property. In the light-emitting element described in Embodiment 2, the light-emitting layer 113 includes any of the anthracene derivatives of the present invention which are described in Embodiment 1. Since the anthracene derivatives of the present invention emit blue light with high color purity, each anthracene derivative is suitable for use in a light-emitting element as a substance with a high light-emitting property.

The electron-transporting layer 114 is a layer including a substance with a high electron-transporting property. As examples of low molecular compounds, there are metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato) beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato] zinc(II) (abbreviation: ZnBTZ). Furthermore, besides the metal complexes, there are heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ01), bathophenanthroline (abbreviation: BPhen), and bathocuproine (abbreviation: BCP). The substances mentioned here are mainly substances having an electron mobility of $10^{-6}$ cm$^2$/Vs or more. Note that any other substance may also be used as long as it is a substance in which the electron-transporting property is higher than the hole-transporting property. Further, the electron-transporting layer is not limited to a single layer and may be a stack of two or more layers including any of the above-mentioned substances.

Alternatively, a high molecular compound can be used for the electron-transporting layer 114. For example, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy), or the like can be used.

The electron-injecting layer 115 is a layer including a substance with a high electron-injecting property. As the substance having a high electron-injecting property, any of alkali metals, alkaline earth metals, or compounds thereof, such as lithium fluoride (LiF), cesium fluoride (CsF), and calcium fluoride (CaF$_2$) can be used. Alternatively, a layer that includes a substance having an electron-transporting property and a substance exhibiting an electron-donating property with respect to the substance having an electron-transporting property can be used. Specifically, a layer in which an alkali metal, an alkaline earth metal, or a compound thereof is contained in a substance having an electron-transporting property, such as a layer in which magnesium (g) is contained in Alq, can be used. Note that as the electron-injecting layer, use of a layer that includes a substance having an electron-transporting property and a substance exhibiting an electron-donating property with respect to the substance having an electron-transporting property is preferable in that injection of electrons from the second electrode 104 can be efficiently performed.

As a substance for forming the second electrode 104, a metal, an alloy, an electrically conductive compound, a mixture thereof, or the like with a low work function (specifically, a work function of 3.8 eV or less is preferable) can be used. As specific examples of such cathode materials, there are elements belonging to Group 1 or Group 2 of the periodic table, i.e., alkali metals such as lithium (Li) and cesium (Cs); alkaline earth metals such as magnesium (Mg), calcium (Ca), and strontium (Sr); alloys containing any of these metals (e.g., MgAg and AlLi); rare earth metals such as europium (Eu) and ytterbium (Yb); alloys containing any of these metals; and the like. A film of an alkali metal, an alkaline earth metal, or an alloy containing any of these metals can be formed by a vacuum evaporation method. Alternatively, a film of an alloy containing an alkali metal or an alkaline earth metal can be formed by a sputtering method. Further, a film can be formed using silver paste or the like by an inkjet method or the like.

Further, by providing the electron-injecting layer 115 which is a layer having the function of promoting injection of electrons between the second electrode 104 and the electron-transporting layer 114, the second electrode 104 can be formed using any of a variety of conductive materials such as Al, Ag, ITO, or indium oxide-tin oxide containing silicon or silicon oxide, regardless of the work functions. Films of these conductive materials can be formed by a sputtering method, an inkjet method, a spin coating method, or the like.

Further, any of a variety of methods can be employed for forming the EL layer regardless of whether the method is a dry process or a wet process. For example, a vacuum evaporation method, an inkjet method, a spin coating method, or the like may be used. Further, a different formation method may be used for each electrode or each layer.

For example, the EL layer may be formed using a high molecular compound selected from the above-described materials by a wet method. Alternatively, the EL layer can be formed using a low molecular organic compound by a wet method. Further alternatively, the EL layer may be formed using a low molecular organic compound by a dry method such as vacuum evaporation.

In addition, the electrode may be formed by a wet method using a sol-gel method, or by a wet method using paste of a metal material. Alternatively, the electrode may be formed by a dry method such as a sputtering method or a vacuum evaporation method.

For example, in order that a display device to which a light-emitting element of the present invention is applied may be manufactured using a large substrate, light-emitting layers are preferably formed by a wet method. Even with a large substrate, use of an inkjet method for forming light-emitting layers facilitates forming the light-emitting layers in different colors.

In the light-emitting element of the present invention which has a structure as described above, a current flows because of a potential difference applied between the first electrode 102 and the second electrode 104, and holes and electrons recombine in the EL layer 103, whereby light is emitted.

The emitted light is extracted out through one or both of the first electrode 102 and the second electrode 104. Therefore, one or both of the first electrode 102 and the second electrode 104 is/are an electrode having a light-transmitting property. For example, when only the first electrode 102 has a light-transmitting property, the emitted light is extracted from a substrate side through the first electrode 102. Alternatively, when only the second electrode 104 has a light-transmitting property, the emitted light is extracted from the side opposite to the substrate through the second electrode 104. When each of the first electrode 102 and the second electrode 104 has a light-transmitting property, the emitted light is extracted from both the substrate side and the side opposite to the substrate side through the first electrode 102 and the second electrode 104.

Note that the structure of layers provided between the first electrode 102 and the second electrode 104 are not limited to the above structure. Any structure instead of the above structure can be employed as long as the light-emitting region for recombination of electrons and holes is positioned away from the first electrode 102 and the second electrode 104 so as to prevent quenching due to the proximity of the light-emitting region and a metal, and any of the anthracene derivatives described in Embodiment 1 is included in the structure.

That is, there is no limitation on the stack structure of the layers, as long as any of the anthracene derivatives of the present invention is used in combination with a layer including a substance with a high electron-transporting property, a substance having a high hole-transporting property, a substance having a high electron-injecting property, a substance having a high hole-injecting property, or a substance having a bipolar property (a substance having a high electron-transporting property and a hole-transporting property), as appropriate.

Figure 1B:
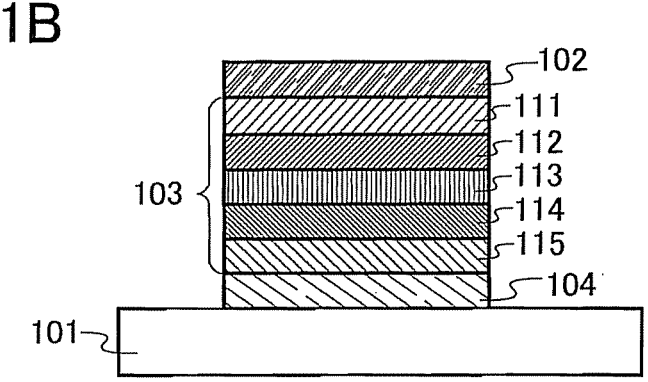

In addition, as illustrated in FIG. 1B, over the substrate 101, the second electrode 104 functioning as a cathode, the EL layer 103, and the first electrode 102 functioning as an anode may be stacked in that order. In FIG. 1B, a structure is employed in which the electron-injecting layer 115, the electron-transporting layer 114, the light-emitting layer 113, the hole-transporting layer 112, and the hole-injecting layer 111 are stacked in that order over the second electrode 104.

Note that in Embodiment 2, the light-emitting element is fabricated over a substrate formed using glass, plastic, or the like. By fabrication of a plurality of such light-emitting elements over one substrate, a passive matrix light-emitting device can be manufactured. Moreover, the light-emitting element may be fabricated over an electrode that is electrically connected to, for example, a thin film transistor (TFT) formed over a substrate formed using glass, plastic, or the like. Thus, an active matrix light-emitting device in which driving of a light-emitting element is controlled by a TFT can be manufactured. Note that there is no limitation on the structure of a TFT, and either a staggered TFT or an inverted staggered TFT may be used. Further, a driving circuit formed over a TFT substrate may be formed using an n-channel TFT and a p-channel TFT, or may be formed using any one of an n-channel TFT or a p-channel TFT. Furthermore, there is no limitation on the crystallinity of a semiconductor film used for the TFT. Either an amorphous semiconductor film or a crystalline semiconductor film may be used for the TFT. In addition, a single crystalline semiconductor film may be used. The single crystalline semiconductor film can be formed by a Smart Cut (registered trademark) method or the like.

Since the anthracene derivatives of the present invention emit blue light with high color purity, each anthracene derivative can be used for a light-emitting layer, as described in Embodiment 2, without any other light-emitting substance. By using any of the anthracene derivatives of the present invention, a light-emitting element that emits blue light with high color purity can be obtained.

Further, since the anthracene derivatives of the present invention are stable against repetition of oxidation reactions and reduction reactions, by using any of the anthracene derivatives for a light-emitting element, a light-emitting element with a long lifetime can be obtained.

Moreover, since a light-emitting element using any of the anthracene derivatives of the present invention can emit blue light with high color purity, the light-emitting element is suitable for use in a full-color display. In particular, development of blue light-emitting elements lags behind that of red or green light-emitting elements in terms of lifetime, color purity, and efficiency, and blue light-emitting elements having good properties are desired. A light-emitting element using any of the anthracene derivatives of the present invention can emit blue light with a long lifetime and is suitable for a full-color display.

Furthermore, since the anthracene derivatives of the present invention emit blue light with high color purity, a white light-emitting element can be obtained by combining any of the anthracene derivatives of the present invention with another light-emitting material and applying it to a light-emitting element.

Embodiment 3

In Embodiment 3, a structure that is different from the structure described in Embodiment 2 will be described.

When the light-emitting layer 113 described in Embodiment 2 is formed by dispersing any of the anthracene derivatives of the present invention into another substance (host material), light emission from the anthracene derivative of the present invention can be obtained. Since the anthracene derivatives of the present invention emit blue light with high color purity, a light-emitting element that emits blue light with high color purity can be obtained.

Here, as a substance in which any of the anthracene derivatives of the present invention is dispersed, any of a wide variety of materials can be used. Besides the substances having a high hole-transporting property or a high electron-transporting property which are given in Embodiment 2, there are, for example, 4,4'-bis(N-carbazolyl)biphenyl (abbreviation: CBP), 2,2',2''-(1,3,5-benzenetriyl)tris(1-phenyl-1H-benzimidazole) (abbreviation: TPBI), 9,10-di(2-naphthyl)anthracene (abbreviation: DNA), 2-tert-butyl-9,10-di(2-naphthyl)anthracene (abbreviation: t-BuDNA), 9-[4-(10-phenyl-9-antliryl)phenyl]-9H-carbazole (abbreviation: CzPA), and the like. Alternatively, as a substance in which any of the anthracene derivatives of the present invention is dispersed, a high molecular material can be used. For example, poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), poly[N,N'-bis(4-butylphenyl)-N,N'-bis(phenyl)benzidine] (abbreviation: Poly-TPD), poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy), or the like can be used.

Since the anthracene derivatives of the present invention emit blue light with high color purity, any of the anthracene derivatives can be used as a light-emitting substance. By using any of the anthracene derivatives of the present invention, a light-emitting element that emits blue light with high color purity can be obtained.

Further, since the anthracene derivatives of the present invention are stable against repetition of oxidation reactions and reduction reactions, by using any of the anthracene derivatives for a light-emitting element, a light-emitting element with a long lifetime can be obtained.

Moreover, since a light-emitting element using any of the anthracene derivatives of the present invention can emit blue light with high color purity, the light-emitting element is suitable for use in a full-color display. In particular, development of blue light-emitting elements lags behind that of red or green light-emitting elements in terms of lifetime, color purity, and efficiency, and blue light-emitting elements having good properties are desired. A light-emitting element using any of the anthracene derivatives of the present invention can emit blue light with a long lifetime and is suitable for a full-color display.

Note that for layers except the light-emitting layer 113, the structure described in Embodiment 2 can be used as appropriate.

Embodiment 4

In Embodiment 4, a structure that is different from the structures described in Embodiments 2 and 3 will be described.

When the light-emitting layer 113 described in Embodiment 2 is formed by dispersing a light-emitting substance (guest material) into any of the anthracene derivatives of the present invention, light emission from the light-emitting substance (guest material) can be obtained.

When any of the anthracene derivatives of the present invention is used as a material in which another light-emitting substance is dispersed, an emission color from the light-emitting substance can be obtained. Alternatively, a mixed color of an emission color from the anthracene derivative of the present invention and the emission color from the light-emitting substance dispersed in the anthracene derivative can be obtained.

Here, as a light-emitting substance that is to be dispersed in any of the anthracene derivatives of the present invention, any of a wide variety of materials can be used. Examples of fluorescent compounds which emit fluorescence are given below. Examples of materials for blue light emission are as follows: N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), and the like. Further, examples of materials for green light emission are as follows:

N-(9,10-diphenyl-2-anthryl)-N,N'-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like. Further, examples of materials for yellow light emission are as follows: rubrene, 5,12-bis(1,1'-biphenyl-4-yl)-6,11-diphenyltetracene (abbreviation: BPT), and the like. Further, examples of materials for red light emission are as follows: N,N,N',N'-tetrakis(4-methylphenyl)tetracene-5,11-diamine (abbreviation: p-mPhTD), 7,13-diphenyl-N,N,N',N'-tetrakis(4-methylphenyl)acenaphtho[1,2-a]fluoranthene-3, 10-diamine (abbreviation: p-mPhAFD), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), and the like. Further, examples of phosphorescent compounds which emit phosphorescence include bis[2-(2'-benzo[4,5-α]thienyl)pyridinato-N,C$^{3'}$]iridium(III) acetylacetonate (abbreviation: Ir(btp)$_2$(acac)), bis(1-phenylisoquinolinato-N,C$^{2'}$)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), 2,3,7,8,12,13,17,18-octaethyl-21H,23H-porphyrin platinum(II) (abbreviation: PtOEP), and the like.

The anthracene derivatives of the present invention each have a large energy gap. Therefore, even when a light-emitting substance that emits light at short wavelengths is dispersed in the anthracene derivative, light emission from the light-emitting substance can be obtained. That is, a substance that emits light at short wavelengths can be excited to emit light.

Further, the anthracene derivatives of the present invention are stable against repetition of oxidation reactions and reduction reactions. Accordingly, by using any of the anthracene derivatives of the present invention as a host material, a light-emitting element with a long lifetime can be obtained.

Note that for the layers except the light-emitting layer 113, the structure described in Embodiment 2 can be used as appropriate.

Embodiment 5

In Embodiment 5, a structure that is different from the structures described in Embodiments 2 to 4 is described.

The anthracene derivatives of the present invention each have a carrier-transporting property and thus can be used for a carrier-transporting layer of a light-emitting element.

The anthracene derivatives of the present invention each have an electron-transporting property. Thus, a layer including any of the anthracene derivatives of the present invention can be provided between the cathode and the light-emitting layer. Specifically, any of the anthracene derivatives of the present invention can be used for the electron-injecting layer 115 or the electron-transporting layer 114 described in Embodiment 2.

Also, when any of the anthracene derivatives of the present invention is used for the electron-injecting layer 115, the electron-injecting layer 115 preferably includes the anthracene derivative of the present invention and a substance having an electron-donating property with respect to the anthracene derivative of the present invention. Such a structure improves the electron-injecting property. Also, a material for the second electrode can be selected regardless of the work function. As a substance having an electron-donating property with respect to the anthracene derivative of the present invention, an alkali metal, an alkaline earth metal, or a compound thereof can be used.

Further, the anthracene derivatives of the present invention each have a hole-transporting property and thus can be used for the hole-transporting layer. Furthermore, a composite material in which an acceptor substance is contained in any of the anthracene derivatives of the present invention can be used for the hole-injecting layer or the hole-transporting layer. As an acceptor substance, any of the substances given in Embodiment 2 can be used.

Note that Embodiment 5 can be combined with any other embodiment as appropriate.

Embodiment 6

Figure 2:
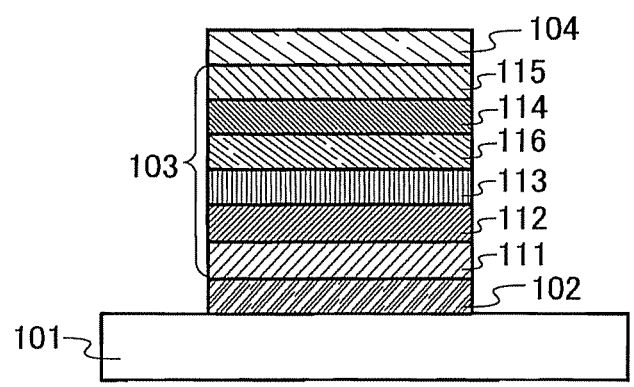
FIG. 2 illustrates a light-emitting element according to an embodiment of the present invention.

In Embodiment 6, a structure that is different from the structures described in Embodiments 2 to 5 will be described using FIG. 2.

In a light-emitting element described in Embodiment 6, a functional layer 116 is newly formed between the light-emitting layer 113 and the electron-transporting layer 114 of the light-emitting element described in Embodiment 2. The functional layer 116 controls the rate of transport of electrons injected from the second electrode 104.

The functional layer 116 includes a first organic compound and a second organic compound, and the amount of the first organic compound is larger than the amount of the second organic compound. That is, the second organic compound is dispersed in the first organic compound. Further, the layer for controlling transport of electrons is preferably provided closer to the second electrode 104 functioning as a cathode than the light-emitting layer 113 is. That is, the layer for controlling transport of electrons is preferably provided between the light-emitting layer 113 and the second electrode 104.

For the functional layer 116, a plurality of structures can be given. A first example of the structures can be a structure in which a second organic compound having the function of trapping electrons is added into a first organic compound having an electron-transporting property. In this structure, electrons are injected from the second electrode 104 serving as a cathode into the functional layer 116 through the electron-transporting layer and the like. The electrons injected into the functional layer 116 are temporarily trapped by the second organic compound, whereby the transport of the electrons is retarded; thus, injection of the electrons into the light-emitting layer 113 is controlled.

In this structure, the second organic compound included in the functional layer 116 is an organic compound having the function of trapping electrons. Therefore, the lowest unoccupied molecular orbital (LUMO) level of the second organic compound is preferably lower than the lowest unoccupied molecular orbital (LUMO) level of the first organic compound included in the functional layer 116 by 0.3 eV or more. With the second organic compound included in the functional layer 116, the rate of transport of electrons in the whole layer is lower than the case where only the first organic compound is included in this layer. That is, by addition of the second organic compound, transport of carriers can be controlled. Further, by control of the concentration of the second organic compound, the rate of transport of carriers can be controlled. Specifically, the concentration of the second organic compound is preferably in the range of 0.1 to 5 wt % or in the range of 0.1 to 5 mol %.

As the second organic compound included in the functional layer 116, for example, any of the following substances can be used: N,N'-dimethylquinacridone (abbreviation: DMQd), N,N'-diphenylquinacridone (abbreviation: DPQd), 9,18-dihydro-benzo[h]benzo[7,8]quino[2,3-b]acridine-7,16-dione (abbreviation: DMNQd-1), 9,18-dihydro-9,18-dimethyl-benzo[h]benzo[7,8]quino[2,3-b]acridine-7,16-dione (abbreviation: DMNQd-2), coumarin 30, coumarin 6, coumarin 545T, coumarin 153, and the like.

The first organic compound included in the functional layer 116 is an organic compound having an electron-transporting property. That is, the first organic compound is a compound in which the electron-transporting property is higher than the hole-transporting property. Specifically, any of the following substances can be used: metal complexes such as tris(8-quinolinolato)aluminum(III) (abbreviation: Alq), Almq$_3$, BeBq$_2$, BAlq, Znq, BAlq, ZnPBO, and ZnBTZ, heterocyclic compounds such as PBD, OXD-7, TAZ, TPBI, BPhen, and BCP, and condensed aromatic compounds such as CzPA, DPCzPA, DPPA, DNA, t-BuDNA, BANT, DPNS, DPNS2, and TPB3. Among them, metal complexes that are each stable against electrons are preferably used. Further, as mentioned earlier, the LUMO level of the second organic compound is preferably lower than the LUMO level of the first organic compound by 0.3 eV or more. Thus, as the first organic compound, an organic compound may be selected as appropriate so as to satisfy the above conditions, depending on what kind of organic compound is used as the second organic compound.

In the light-emitting element of the present invention which has a structure as described above, a current flows because of a potential difference applied between the first electrode 102 and the second electrode 104, whereby holes and electrons recombine in the EL layer 103 to emit light. Specifically, a light-emitting region is formed in a region from the light-emitting layer 113 in the EL layer 103 to the interface between the light-emitting layer 113 and the functional layer 116. This principle is described below.

Electrons are injected from the second electrode 104 into the functional layer 116 through the electron-injecting layer 115 and the electron-transporting layer 114. The transport of the electrons injected into the functional layer 116 is retarded due to the second organic compound having an electron-trapping property; thus, injection of the electrons into the light-emitting layer 113 is controlled. As a result, a light-emitting region, which has conventionally been localized in the vicinity of the interface between the hole-transporting layer 112 and the light-emitting layer 113, is formed in a region from the light-emitting layer 113 to the vicinity of the interface between the light-emitting layer 113 and the functional layer 116. Therefore, electrons are less likely to reach the hole-transporting layer 112 and to make it deteriorate. Similarly, since the light-emitting layer 113 has an electron-transporting property, holes are less likely to reach the electron-transporting layer 114 and to make it deteriorate.

A second example of the structures of the functional layer 116 can be a structure in which the first organic compound is included in greater amount than the second organic compound and the polarity of carriers transported by the first organic compound is different from that of carriers transported by the second organic compound. In the case where the functional layer 116 is provided between the light-emitting layer and the second electrode serving as a cathode, it is preferable that the first organic compound be an organic compound having an electron-transporting property, and the second organic compound be an organic compound having a hole-transporting property. Further, the difference between the lowest unoccupied molecular orbital level (LUMO level) of the first organic compound and the lowest unoccupied molecular orbital level (LUMO level) of the second organic compound is preferably less than 0.3 eV, more preferably, 0.2 eV or less. That is, thermodynamically, it is preferable that electrons, which are carriers, be easily moved between the first organic compound and the second organic compound.

In this structure, as described above, the first organic compound is preferably an organic compound having an electron-transporting property. Specifically, any of the following substances can be used: metal complexes such as Alq, Almq$_3$, BeBq$_2$, BAlq, Znq, ZnPBO, and ZnBTz; heterocyclic compounds such as PBD, OXD-7, TAZ, TPBI, BPhen, and BCP; and condensed aromatic compounds such as CzPA, DPCzPA, DPPA, DNA, t-BuDNA, BANT, DPNS, DPNS2, and TPB3.

Further, as the second organic compound, an organic compound having a hole-transporting property is preferably used. Specifically, any of the following materials can be used: condensed aromatic hydrocarbons such as 9,10-diphenylanthracene (abbreviation: DPAnth) and 6,12-dimethoxy-5,11-diphenylchrysene; aromatic amine compounds such as N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPHPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}9H-carbazol-3-amine (abbreviation: PCAPBA), N-(9,10-diphenyl-2-anthryl)-N,9-diphenyl-9H-carbazol-3-amine (abbreviation: 2PCAPA), NPB (or α-NPD), TPD, DFLDPBi, and BSPB; and compounds having an amino group such as coumarin 7 and coumarin 30.

With a combination as described above, transport of electrons from the first organic compound to the second organic compound or from the second organic compound to the first organic compound is suppressed, whereby the rate of transport of electrons in the functional layer 116 can be suppressed.

Note that among the above combinations, a combination of a metal complex as the first organic compound and an aromatic amine compound as the second organic is preferable. A metal complex has a high electron-transporting property and has large dipole moment, whereas an aromatic amine compound has a high hole-transporting property and has a comparatively small dipole moment. With a combination of such substances that are significantly different in dipole moment, the abovementioned effect of suppressing transport of electrons can be further increased. Specifically, when the dipole moment of the first organic compound is $P_1$ and the dipole moment of the second organic compound is $P_2$, a combination that satisfies one of the following expressions is preferable:

$$P_1/P_2 \geq 3$$

$$P_1/P_2 \leq 0.33$$

In the light-emitting element of the present invention which has a structure as described above, a current flows because of a potential difference applied between the first electrode 102 and the second electrode 104, whereby holes and electrons recombine in the EL layer 103 to emit light. Specifically, a light-emitting region is formed in a region from the light-emitting layer 113 in the EL layer 103 to the interface between the light-emitting layer 113 and the functional layer 116. This principle is described below.

In the functional layer 116, electrons are easy to inject into the first organic compound, which is an organic compound having an electron-transporting property, and easy to transport toward the neighboring first organic compound. That is, the rate (v) at which electrons are transported between the first organic compounds is high.

On the other hand, since the second organic compound, which is an organic compound having a hole-transporting property, has the LUMO level close to the LUMO level of the first organic compound, it is possible that electrons will be thermodynamically injected into the first organic compound. However, the rate ($v_1$) at which electrons are injected from the first organic compound, which is an organic compound having an electron-transporting property, into the second organic compound, which is an organic compound having a hole-transporting property, or the rate ($v_2$) at which electrons are injected from the second organic compound into the first organic compound is lower than the rate (v) at which electrons are transported between the first organic compounds.

Therefore, since the functional layer 116 includes the second organic compound, the rate of transport of electrons in the whole layer is lower than that in a layer including only the first organic compound. That is, by addition of the second organic compound, transport of carriers can be controlled. Further, by control of the concentration of the second organic compound, the rate of transport of carriers can be controlled.

In a conventional light-emitting element in which the functional layer 116 having either one of the above structures is not formed, electrons injected from the second electrode are injected into the light-emitting layer 113 while the transport of the electrons is not retarded. The electrons injected into the light-emitting layer 113 could reach the hole-transporting layer 112 by passing through the light-emitting layer, when the light-emitting layer 113 has an electron-transporting property, i.e., when the material the amount of which is the largest in the light-emitting layer 113 has an electron-transporting property. If electrons reach the hole-transporting layer 112, a material included in the hole-transporting layer 112 could deteriorate, leading to deterioration of the light-emitting element. Further, if this deterioration increases the number of holes that reach the electron-transporting layer 114 over time, recombination probability in the light-emitting layer 113 is decreased over time, which results in a reduction in element lifetime (luminance decay over time).

A feature of the light-emitting element described in Embodiment 6 is that the functional layer 116 is further provided. Electrons injected from the second electrode 104 are injected into the functional layer 116 through the electron-injecting layer 115 and the electron-transporting layer 114. Transport of the electrons injected into the functional layer 116 is retarded, whereby injection of the electrons into the light-emitting layer 113 is controlled. As a result, a light-emitting region, which has conventionally been localized in the vicinity of the interface between the hole-transporting layer 112 and the light-emitting layer 113, is formed in a region from the light-emitting layer 113 to the vicinity of the interface between the light-emitting layer 113 and the functional layer 116. Therefore, electrons are less likely to reach the hole-transporting layer 112 and to make it deteriorate. Similarly, since the light-emitting layer 113 has an electron-transporting property, holes are less likely to reach the electron-transporting layer 114 and to make it deteriorate.

Furthermore, with an electron-blocking layer provided between the anode and the light-emitting layer in order to prevent electrons from passing through the light-emitting layer as in a conventional case, the deterioration of the function of blocking electrons of the electron-blocking layer over time expands the recombination region to the inside of the electron-blocking layer (or inside of the hold-transporting layer). Accordingly, current efficiency is significantly decreased (i.e., luminance decays). On the other hand, in the light-emitting element described in Embodiment 6, since transport of electrons is controlled before electrons reach the light-emitting layer (between the light-emitting layer and the cathode), the recombination probability in the light-emitting layer is not easily changed even if transport of electrons is somewhat unbalanced with respect to transport of holes, whereby luminance does not easily decay.

Furthermore, it is an important point of Embodiment 6 that the functional layer 116 is formed by adding an organic compound having the function of trapping electrons or an organic compound having a hole-transporting property into an organic compound having an electron-transporting property, instead of by applying only a substance with low electron mobility. Such a structure enables not only control of the number of electrons injected into the light-emitting layer 113 but also suppression of a change over time in the controlled number of the injected electrons.

As described above, by controlling the number of electrons injected into the light-emitting layer, a phenomenon that carrier balance is decreased over time to lower the recombination probability can be prevented. This leads to an improvement of element lifetime (suppression of luminance decay over time).

Further, since the layer for controlling transport of carriers which is described in Embodiment 6 includes two or more kinds of substances, the carrier balance can be precisely controlled by controlling the combination or mixture ratio of the substances, the thickness of the layer, etc.

Furthermore, since the carrier balance can be controlled by controlling the combination or mixture ratio of the substances, the thickness of the layer, etc., the carrier balance can be more easily controlled than by a conventional technique. That is, without any change in a physical property of the substance, transport of carriers can be controlled with a mixture ratio of the substances, the thickness of the layer, etc.

Moreover, transport of carriers is controlled by using the organic compound the amount of which is the smallest of those of the two or more kinds of substances included in the layer for controlling transport of carriers. That is, the transport of carriers can be controlled with the component the amount of which is the smallest of those of the components included in the layer for controlling transport of carriers. Accordingly, a light-emitting element that does not easily deteriorate over time and has improved lifetime can be realized. In other words, as compared with the case where carrier balance is controlled by a single substance, carrier balance is not easily changed. For example, if transport of carriers is controlled with a layer formed using a single substance, the carrier balance of the whole layer is changed by a partial change in morphology, partial crystallization, or the like. Thus, the layer for controlling transport of carriers in that case easily deteriorates over time. However, by controlling the transport of carriers with the use of the component the amount of which is the smallest of those of the components included in the layer for controlling transport of carriers, as described in Embodiment 6, influence of a change in morphology, crystallization, aggregation, or the like is reduced, and thus a change over time is not easily caused. Thus, a light-emitting element with a long lifetime in which carrier balance is not easily lost over time and accordingly emission efficiency is not easily decreased over time can be obtained.

Further, the thickness of the functional layer 116 is preferably greater than or equal to 5 nm and less than or equal to 20 nm. If the functional layer 116 is too thick, transport of electrons is slowed too much, resulting in an increase in driving voltage. Alternatively, if the functional layer 116 is too thin, the function of controlling transport of electrons cannot be achieved. Therefore, the thickness of the functional layer 116 is preferably greater than or equal to 5 nm and less than or equal to 20 nm.

Furthermore, since the functional layer controls transport of electrons, the layer is preferably provided between the light-emitting layer and the electrode functioning as a cathode. More preferably, the functional layer is provided so as to be in contact with the light-emitting layer. By providing the functional layer in contact with the light-emitting layer, injection of electrons into the light-emitting layer can be directly controlled. Accordingly, a change in the carrier balance in the light-emitting layer over time can be more suppressed, whereby a larger effect on improving the lifetime of the light-emitting element can be obtained. Furthermore, the process can be simplified.

Further, the functional layer is preferably provided so as to be in contact with the light-emitting layer. In such a case, the first organic compound included in the functional layer is preferably different in kind from an organic compound the amount of which is large in the light-emitting layer. In particular, in the case where the light-emitting layer includes a substance in which a substance having a high light-emitting property is dispersed (host material) and the substance having a high light-emitting property (guest material), the host material and the first organic compound are preferably different in kind. With such a structure, transport of electrons from the functional layer to the light-emitting layer can be suppressed also between the first organic compound and the host material. Accordingly, the effect obtained by providing the layer for controlling transport of electrons can be further increased.

Since the anthracene derivatives of the present invention each have an electron-transporting property, any of the anthracene derivatives can be suitably used as a substance in which a light-emitting substance is dispersed (host material) for a light-emitting layer of the light-emitting element described in Embodiment 6. As the light-emitting substance that is to be dispersed in the anthracene derivative of the present invention (guest material), for example, any of the substances given in Embodiment 4 can be used.

Note that a layer may be formed between the light-emitting layer 113 and the functional layer 116 for controlling transport of electrons.

In the light-emitting element of Embodiment 6, the emission color of a substance having a high light-emitting property which is included in the light-emitting layer and the emission color of the second organic compound are preferably similar colors. This can keep the color purity of the light-emitting element even if the second organic compound unintendedly emits light. However, the second organic compound does not necessarily emit light. For example, in the case where emission efficiency of the substance having a high light-emitting property is higher, the concentration of the second organic compound in the functional layer 116 for controlling transport of electrons is preferably adjusted so that light emission from substantially only the substance having a high light-emitting property can be obtained (the concentration of the second organic compound is slightly reduced so that light emission from the second organic compound can be suppressed). In this case, the emission color of the substance having a high light-emitting property and the emission color of the second organic compound are similar colors (i.e., they have substantially the same level of energy gap). Therefore, energy is difficult to transfer from the substance having a high light-emitting property toward the second organic compound, whereby high emission efficiency can be obtained.

Alternatively, the second organic compound preferably emits light at a shorter wavelength than the substance having a high light-emitting property which is included in the light-emitting layer. That is, the peak wavelength of the second organic compound is preferably shorter than the peak wavelength of the substance having a high light-emitting property which is included in the light-emitting layer. In that case, the energy gap of the second organic compound is larger than the energy gap of the substance having a high light-emitting property. Accordingly, energy is difficult to transfer from the substance having a high light-emitting property toward the second organic compound; therefore, unintended light emission from the second organic compound can be suppressed.

Note that Embodiment 6 can be combined with any other embodiment as appropriate.

Embodiment 7

In Embodiment 7, a light-emitting element in which a plurality of light-emitting units according to the present invention are stacked (hereinafter, referred to as a stacked type element) is described with reference to FIG. 3. This light-emitting element is a stacked-type element including a plurality of light-emitting units between a first electrode and a second electrode. The structure of each light-emitting unit can be similar to those described in Embodiments 2 to 6. In other words, the light-emitting element described in Embodiments 2 to 6 are each a light-emitting element having one light-emitting unit. As long as the light-emitting unit includes at least a light-emitting layer, there is no particular limitation on the stack structure of other layers. In Embodiment 7, a light-emitting element having a plurality of light-emitting units will be described.

Figure 3:
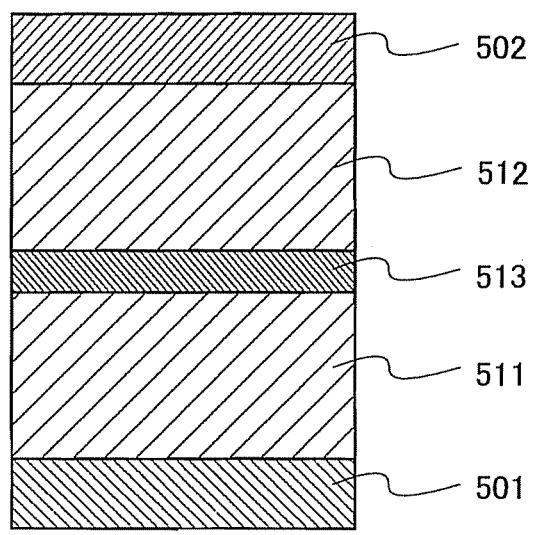
FIG. 3 illustrates a light-emitting element according to an embodiment of the present invention.

In FIG. 3, a first light-emitting unit 511 and a second light-emitting unit 512 are stacked between a first electrode 501 and a second electrode 502, and a charge generation layer 513 is provided between the first light-emitting unit 511 and the second light-emitting unit 512. Electrodes that are similar to the electrodes of Embodiment 2 can be applied to the first electrode 501 and the second electrode 502. Further, the first light-emitting unit 511 and the second light-emitting unit 512 may have either the same or different structure, which can be similar to those described in Embodiments 2 to 6.

The charge generation layer 513 is a layer that injects electrons into a light-emitting unit on one side and injects holes into a light-emitting unit on the other side when a voltage is applied to the first electrode 501 and the second electrode 502, and may be either a single layer or a stack of plural layers. As a stack structure of plural layers, a structure in which a layer that injects holes and a layer that injects electrons are stacked is preferable.

As the layer that injects holes, a semiconductor or an insulator, such as molybdenum oxide, vanadium oxide, rhenium oxide, or ruthenium oxide, can be used. Alternatively, a structure may be employed in which an acceptor substance is added to a substance having a high hole-transporting property. The layer including a substance with a high hole-transporting property and an acceptor substance is formed using the composite material described in Embodiment 2 and includes, as the acceptor substance, 7,7,8,8-tetracyano-2,3,5,6-tetrafluoroquinodimethane (abbreviation: F$_4$-TCNQ) or metal oxide such as vanadium oxide, molybdenum oxide, or tungsten oxide. As the substance having a high hole-transporting property, any of a variety of compounds such as aromatic amine compounds, carbazole derivatives, aromatic hydrocarbons, or high molecular compounds (oligomers, dendrimers, polymers, etc.) can be used. Note that a substance having a hole mobility of $10^{-6}$ cm$^2$/Vs or more is preferably applied to the substance having a high hole-transporting property. However, any other substance may also be used as long as it is a substance in which the hole-transporting property is higher than the electron-transporting property. Since the composite material of the substance having a high hole-transporting property and the acceptor substance has an excellent carrier-injecting property and an excellent carrier-transporting property, low-voltage driving and low-current driving can be realized.

As the layer that injects electrons, an insulator or a semiconductor, such as lithium oxide, lithium fluoride, or cesium carbonate, can be used. Alternatively, a structure may be employed in which a donor substance is added to a substance having a high electron-transporting property. As the donor substance, an alkali metal, an alkaline earth metal, a rare earth metal, a metal belonging to Group 13 of the periodic table, or an oxide or carbonate thereof can be used. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the donor substance. As the substance having a high electron-transporting property, any of the materials given in Embodiment 2 can be used. Note that a substance having an electron mobility of $10^{-6}$ cm$^2$/Vs or more is preferably applied to the substance having a high electron-transporting property. However, any other substance may also be used as long as it is a substance in which the electron-transporting property is higher than the hole-transporting property. Since the composite material of the substance having a high electron-transporting property and the donor substance has an excellent carrier-injecting property and an excellent carrier-transporting property, low-voltage driving and low-current driving can be realized.

Further, for the charge generation layer 513, any of the electrode materials given in Embodiment 2 can be used. For example, the charge generation layer 513 may be formed using a layer including a substance with a hole-transporting property and metal oxide in combination with a transparent conductive film. Note that the charge generation layer is preferably a layer having a high light-transmitting property in terms of light extraction efficiency.

In any case, the charge generation layer 513 interposed between the first light-emitting unit 511 and the second light-emitting unit 512 may have any structure as long as electrons can be injected into the light-emitting unit on one side and holes can be injected into the light-emitting unit on the other side when a voltage is applied between the first electrode 501 and the second electrode 502. For example, any structure is acceptable as long as the charge generation layer 513 injects electrons into the first light-emitting unit 511 and injects holes into the second light-emitting unit 512 when a voltage is applied so that the potential of the first electrode is higher than that of the second electrode.

In Embodiment 7, the light-emitting element having two light-emitting units is described. However, the present invention can be applied to a light-emitting element in which three or more light-emitting units are stacked, in a similar manner. As in the light-emitting element according to Embodiment 7, by arranging a plurality of light-emitting units between a pair of electrodes so that the plurality of light-emitting units can be partitioned by a charge generation layer, light emission in a high luminance region can be achieved with current density kept low; thus, a light-emitting element having a long lifetime can be realized. Further, when the light-emitting element is applied to a lighting apparatus, voltage drop due to the resistance of the electrode materials can be suppressed; thus, uniform light emission in a large area can be achieved. Furthermore, a light-emitting device capable of low-voltage driving with low power consumption can be realized.

Further, by forming light-emitting units to emit light of different colors from each other, a light-emitting element as a whole can provide light emission of a desired color. For example, by forming a light-emitting element having two light-emitting units such that the emission color of the first light-emitting unit and the emission color of the second light-emitting unit are complementary to each other, the light-emitting element can provide white light emission as a whole. Note that "complementary colors" refer to colors that can produce an achromatic color when mixed. In other words, when light emitted from substances that emit light of complementary colors is mixed, white light emission can be obtained. Further, the same can be applied to a light-emitting element having three light-emitting units. For example, the light-emitting element as a whole can provide white light emission when the emission color of the first light-emitting unit is red, the emission color of the second light-emitting unit is green, and the emission color of the third light-emitting unit is blue.

Note that Embodiment 7 can be combined with any other embodiment as appropriate.

Embodiment 8

In Embodiment 8, a light-emitting device manufactured using any of the anthracene derivatives of the present invention will be described.

Figure 4A:
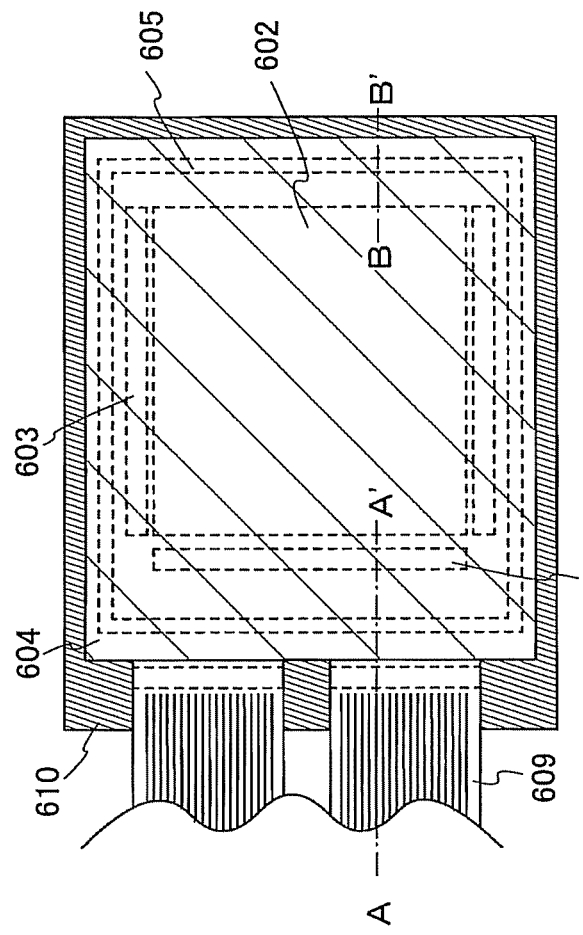
FIGS. 4A and 4B illustrate a light-emitting device according to an embodiment of the present invention.
Figure 4B:
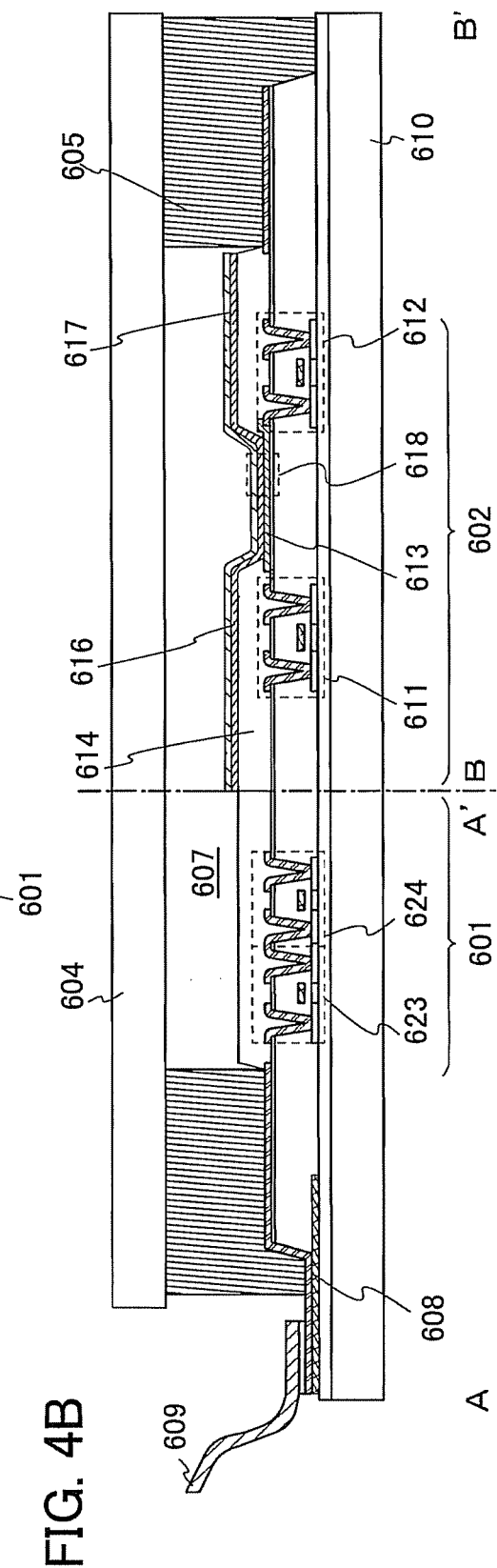

In Embodiment 8, a light-emitting device manufactured using any of the anthracene derivatives of the present invention is described using FIGS. 4A and 4B. Note that FIG. 4A is a top view illustrating the light-emitting device and FIG. 4B is a cross-sectional view of FIG. 4A taken along lines A-A' and B-B'. This light-emitting device includes a driver circuit portion (a source side driver circuit) 601, a pixel portion 602, and a driver circuit portion (a gate side driver circuit) 603, which are indicated by dotted lines, in order to control the light emission from the light-emitting element. Further, reference numeral 604 denotes a sealing substrate and reference numeral 605 denotes a sealing material. Reference numeral 607 denotes a space surrounded by the sealing material 605.

Note that a leading wiring 608 is a wiring for transmitting signals that are input to the source side driver circuit 601 and the gate side driver circuit 603. The leading wiring 608 receives video signals, clock signals, start signals, reset signals, and the like from an flexible printed circuit (FPC) 609 serving as an external input terminal. Note that although only an FPC is illustrated here, this FPC may be provided with a printed wiring board (PWB). The light-emitting device in this specification includes not only a light-emitting device itself but also a light-emitting device to which an FPC or a PWB is attached.

Then, a cross-sectional structure is described using FIG. 4B. The driver circuit portions and the pixel portion are provided over an element substrate 610, but only the source side driver circuit 601, which is the driver circuit portion, and one pixel of the pixel portion 602 are illustrated.

Further, a CMOS circuit which is a combination of an n-channel TFT 623 and a p-channel TFT 624 is formed in the source side driver circuit 601. The driver circuit may be formed using various types of circuits such as CMOS circuits, PMOS circuits, or NMOS circuits. Furthermore, in Embodiment 8, a driver-integrated type in which a driver circuit is formed over a substrate provided with a pixel portion is described; however, the present invention is not limited to this type, and the driver circuit can be formed outside the substrate instead of being formed over the substrate provided with the pixel portion.

Further, the pixel portion 602 includes a plurality of pixels each having a switching TFT 611, a current controlling TFT 612, and a first electrode 613 which is electrically connected to a drain of the current controlling TFT 612. Note that an insulator 614 is formed to cover an end portion of the first electrode 613. Here, a positive photosensitive acrylic resin film is used to form the insulator 614.

Further, in order to improve coverage, the insulator 614 is provided such that either an upper end portion or a lower end portion of the insulator 614 has a curved surface with a curvature. For example, when a positive photosensitive acrylic resin is used as a material for the insulator 614, it is preferable that only an upper end portion of the insulator 614 have a curved surface with a radius of curvature (0.2 to 3 μm). Alternatively, the insulator 614 can be formed using either a negative type resin that becomes insoluble in an etchant by light irradiation or a positive type resin that becomes soluble in an etchant by light irradiation.

An EL layer 616 and a second electrode 617 are formed over the first electrode 613. Here, any of a variety of metals, alloys, electrically conductive compounds, or a mixture thereof can be used for a material of the first electrode 613. If the first electrode is used as an anode, it is preferable that the first electrode be formed using, among such materials, any of metals, alloys, or electrically conductive compounds, a mixture thereof, or the like having a high work function (preferably, a work function of 4.0 eV or more) among such materials. For example, the first electrode 613 can be formed using a single-layer film such as an indium oxide-tin oxide film containing silicon, an indium oxide-zinc oxide film, a titanium nitride film, a chromium film, a tungsten film, a Zn film, a Pt film, or the like; a stack of a titanium nitride film and a film containing aluminum as the main component; or a three-layer structure of a titanium nitride film, a film containing aluminum as the main component, and a titanium nitride film. Note that with a stack structure, the first electrode 613 has low resistance as a wiring, forms a favorable ohmic contact, and can serve as an anode.

Further, the EL layer 616 is formed by various methods such as an evaporation method with an evaporation mask, an inkjet method, a spin coating method, or the like. The EL layer 616 includes any of the anthracene derivatives described in Embodiment 1. Further, as another material included in the EL layer 616, any of low molecular compounds or high molecular compounds (the category includes oligomers, dendrimers, polymers, etc.) may be used. Furthermore, the material used for the EL layer is not limited to an organic compound and may be an inorganic compound.

Further, as the material for the second electrode 617, various types of metals, alloys, or electrically conductive compounds, a mixture thereof, or the like can be used. If the second electrode is used as a cathode, it is preferable that the second electrode be formed using, among such materials, any of metals, alloys, or electrically conductive compounds, a mixture thereof, or the like having a low work function (preferably, a work function of 3.8 eV or less). For example, there are elements belonging to Group 1 and Group 2 of the periodic table, that is, alkali metals such as lithium (Li) and cesium (Cs); alkaline earth metals such as magnesium (Mg), calcium (Ca), and strontium (Sr); alloys containing any of these metals (e.g., MgAg and AlLi); and the like. When light generated in the EL layer 616 is transmitted through the second electrode 617, the second electrode 617 can also be formed using a stack of a thin metal film with a small thickness and a transparent conductive film (indium oxide-tin oxide (ITO), indium oxide-tin oxide containing silicon or silicon oxide, indium oxide-zinc oxide (IZO), indium oxide containing tungsten oxide and zinc oxide (IWZO), or the like).

Furthermore, by attaching the sealing substrate 604 and the element substrate 610 to each other with the sealing material 605, a light-emitting element 618 is provided in the space 607 surrounded by the element substrate 610, the sealing substrate 604, and the sealing material 605. Note that the space 607 is filled with a filler. There are cases where the space 607 may be filled with an inert gas (e.g., nitrogen or argon), or where the space 607 may be filled with the sealing material 605.

Note that as the sealing material 605, an epoxy-based resin is preferably used. In addition, it is preferable that such a material allows as little moisture or oxygen as possible to permeate. Further, as a material for the sealing substrate 604, a plastic substrate formed using fiberglass-reinforced plastics (FRP), polyvinyl fluoride (PVF), polyester, acrylic, or the like can be used instead of a glass substrate or a quartz substrate.

As described above, the light-emitting device including the light-emitting element of the present invention can be obtained.

Since any of the anthracene derivatives described in Embodiment 1 is used for the light-emitting device of the present invention, a high performance light-emitting device can be obtained. Specifically, a light-emitting device with a long lifetime can be obtained.

Moreover, since the anthracene derivatives of the present invention can emit blue light with high color purity, each anthracene derivative is suitable for use in a full-color display. By using any of the anthracene derivatives of the present invention as a light-emitting substance for a full-color display, a display device with excellent color reproducibility can be obtained.

Figure 5A:
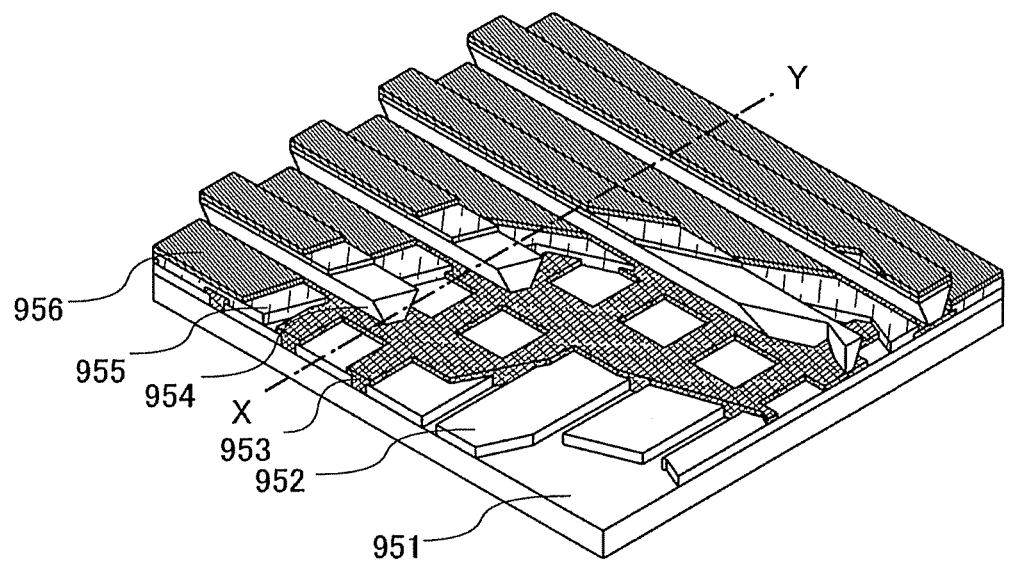
FIGS. 5A and 5B illustrate a light-emitting device according to an embodiment of the present invention.
Figure 5B:
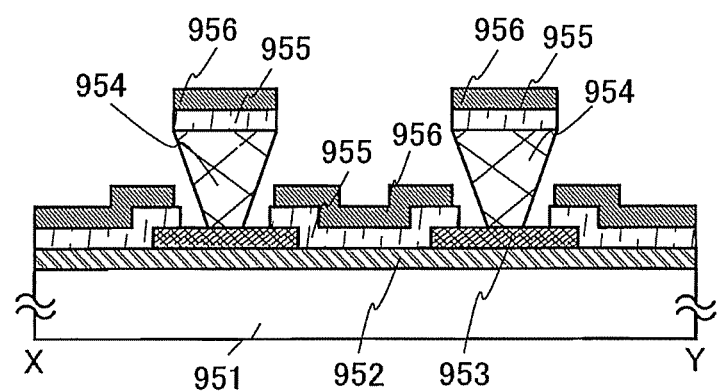

As described above, in Embodiment 8, although an active matrix light-emitting device which controls driving of a light-emitting element with a transistor is described, the light-emitting device may be a passive matrix light-emitting device. FIGS. 5A and 5B illustrate a passive matrix light-emitting device manufactured according to the present invention. Note that FIG. 5A is a perspective view of the light-emitting device and FIG. 5B is a cross-sectional view of FIG. 5A taken along a line X-Y. In FIGS. 5A and 5B, an EL layer 955 is provided between an electrode 952 and an electrode 956 over a substrate 951. An end portion of the electrode 952 is covered with an insulating layer 953. In addition, a partition layer 954 is provided over the insulating layer 953. The sidewalls of the partition layer 954 slope so that the distance between one sidewall and the other sidewall gradually decreases toward the surface of the substrate. In other words, a cross section taken along the direction of the short side of the partition layer 954 is trapezoidal, and the lower side (a side in contact with the insulating layer 953, which is one of a pair of parallel sides of the trapezoidal cross section) is shorter than the upper side (a side not in contact with the insulating layer 953, which is the other of the pair of parallel sides). Providing the partition layer 954 in this manner enables patterning of the EL layer 955 and the electrode 956. Also in the case of a passive matrix light-emitting device, by using the light-emitting element of the present invention, a light-emitting device with a long lifetime and/or high color reproducibility can be obtained.

Note that Embodiment 8 can be combined with any other embodiment as appropriate.

Embodiment 9

In Embodiment 9, electronic appliances of the present invention which each include the light-emitting device described in Embodiment 8 will be described. Electronic appliances of the present invention each have a display portion that includes any of the anthracene derivatives described in Embodiment 1 and has a long lifetime.

As examples of electronic appliances that each include a light-emitting element fabricated using any of the anthracene derivatives of the present invention, there are televisions, cameras such as video cameras and digital cameras, goggle type displays (head-mounted displays), navigation systems, audio replay devices (e.g., car audio systems and audio systems), computers, game machines, portable information terminals (e.g., mobile computers, cellular phones, portable game machines, and electronic book readers), image replay devices in which a recording medium is provided (devices that are capable of replaying recording media such as digital versatile discs (DVDs) and equipped with a display device that can display an image), and the like. Specific examples of these electronic appliances are illustrated in FIGS. 6A to 6D.

Figure 6A:
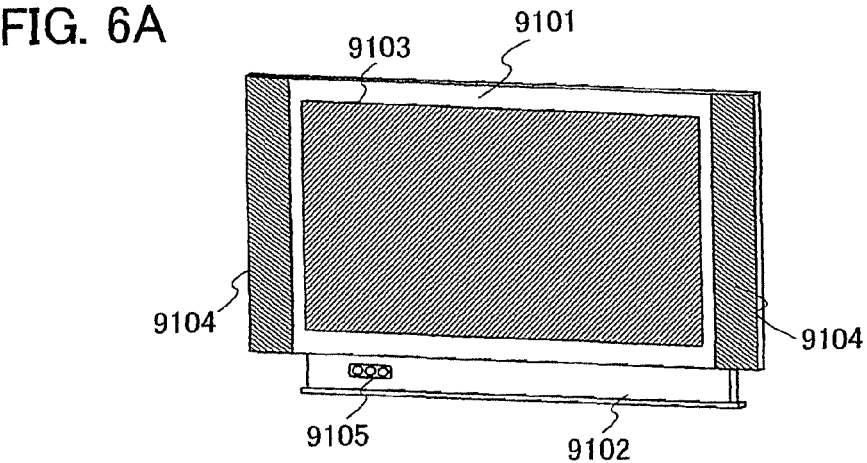
FIGS. 6A to 6D illustrate electronic appliances according to an embodiment of the present invention.

FIG. 6A illustrates a television set according to the present invention, which includes a housing 9101, a supporting base 9102, a display portion 9103, speaker portions 9104, a video input terminal 9105, and the like. In the display portion 9103 of this television set, light-emitting elements similar to those described in Embodiments 2 to 7 are arranged in matrix. A feature of the light-emitting elements is a long lifetime. Since the display portion 9103 including the light-emitting elements has a feature similar to that of the light-emitting elements, in this television set, the amount of deterioration in image quality is small. With such a feature, deterioration compensation functional circuits and power supply circuits in the television set can be greatly reduced or downsized; accordingly, a reduction in the size and weight of the housing 9101 or the supporting base 9102 can be achieved. In the television set according to the present invention, higher image quality and a reduction in size and weight are achieved; thus, a product that is suitable for living environment can be provided. Further, since the anthracene derivatives described in Embodiment 1 can emit blue light with high color purity, a television set having a display portion with high color reproducibility can be obtained.

Figure 6B:
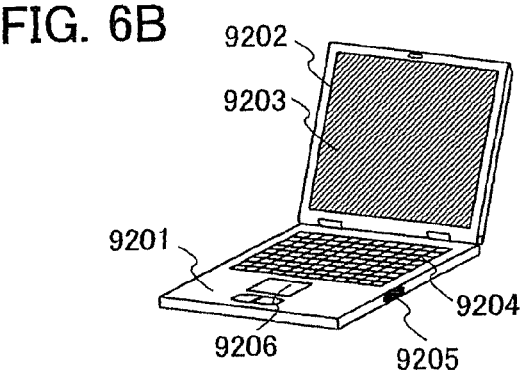

FIG. 6B illustrates a computer according to the present invention, which includes a main body 9201, a housing 9202, a display portion 9203, a keyboard 9204, an external connection port 9205, a pointing device 9206, and the like. In the display portion 9203 of this computer, light-emitting elements similar to those described in Embodiments 2 to 7 are arranged in matrix. A feature of the light-emitting elements is a long lifetime. Since the display portion 9203 including the light-emitting elements has a feature similar to that of the light-emitting elements, in this computer, the amount of deterioration in image quality is small. With such a feature, deterioration compensation functional circuits and power supply circuits in the computer can be greatly reduced or downsized; accordingly, a reduction in the size and weight of the main body 9201 and the housing 9202 can be achieved. In the computer according to the present invention, higher image quality and a reduction in size and weight are achieved; thus, a product that is suitable for the environment can be provided. Further, since the anthracene derivatives described in Embodiment 1 can emit blue light with high color purity, a computer having a display portion with high color reproducibility can be obtained.

Figure 6C:
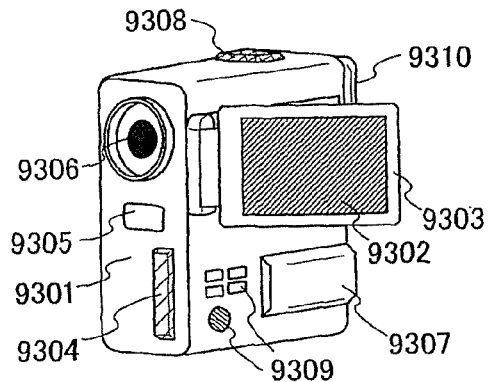

FIG. 6C illustrates a camera according to the present invention, which includes a main body 9301, a display portion 9302, a housing 9303, an external connection port 9304, a remote control receiving portion 9305, an image receiving portion 9306, a battery 9307, an audio input portion 9308, operation keys 9309, an eyepiece portion 9310, and the like. In the display portion 9302 of this camera, light-emitting elements similar to those described in Embodiments 2 to 7 are arranged in matrix. A feature of the light-emitting elements is a long lifetime. Since the display portion 9302 including the light-emitting elements has a feature similar to that of the light-emitting elements, in this camera, the amount of deterioration in image quality is small. With such a feature, deterioration compensation functional circuits and power supply circuits in the camera can be greatly reduced or downsized; accordingly, a reduction in the size and weight of the main body 9301 can be achieved. In the camera according to the present invention, higher image quality and a reduction in size and weight are achieved; thus, a product that is suitable for being carried can be provided. Further, since the anthracene derivatives described in Embodiment 1 can emit blue light with high color purity, a camera having a display portion with high color reproducibility can be obtained.

Figure 6D:
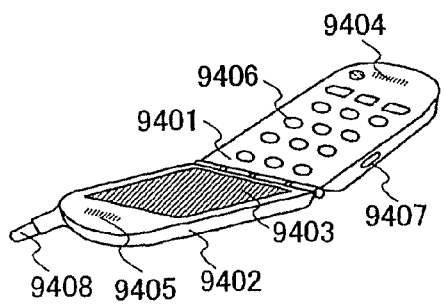

FIG. 6D illustrates a cellular phone according to the present invention, which includes a main body 9401, a housing 9402, a display portion 9403, an audio input portion 9404, an audio output portion 9405, operation keys 9406, an external connection port 9407, an antenna 9408, and the like. In the display portion 9403 of this cellular phone, light-emitting elements similar to those described in Embodiments 2 to 7 are arranged in matrix. A feature of the light-emitting elements is a long lifetime. Since the display portion 9403 including the light-emitting elements has a feature similar to that of the light-emitting elements, in this cellular phone, the amount of deterioration in image quality is small. With such a feature, deterioration compensation functional circuits and power supply circuits in the cellular phone can be greatly reduced or downsized; accordingly, a reduction in the size and weight of the main body 9401 and the housing 9402 can be achieved. In the cellular phone according to the present invention, higher image quality and a reduction in size and weight are achieved; thus, a product that is suitable for being carried can be provided. Further, since the anthracene derivatives described in Embodiment 1 can emit blue light with high color purity, a mobile phone having a display portion with high color reproducibility can be obtained.

Figure 12A:
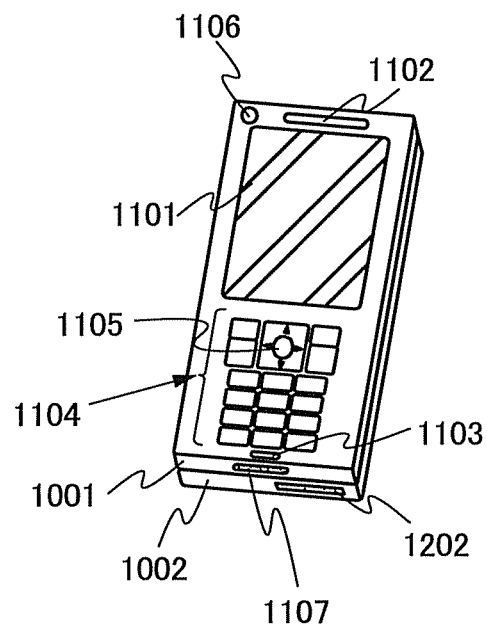
FIGS. 12A to 12C illustrate an electronic appliance according to an embodiment of the present invention.
Figure 12B:
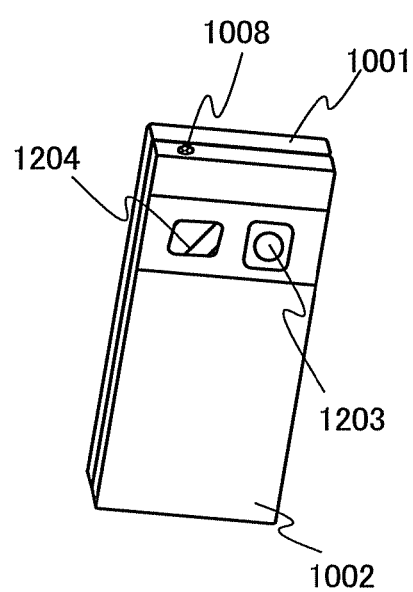
Figure 12C:
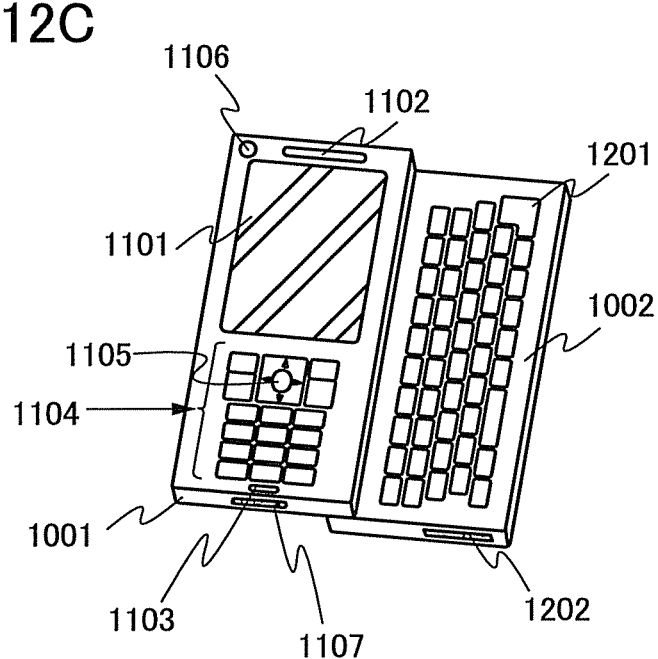

FIGS. 12A to 12C illustrate an example of a cellular phone having a structure, which is different from the structure of the cellular phone in FIG. 6D. FIG. 12A is a front view, FIG. 12B is a rear view, and FIG. 12C is a development view. The cellular phone in FIGS. 12A to 12C is a so-called smartphone which has both a function of a phone and a function of a portable information terminal, and incorporates a computer to conduct a variety of data processing in addition to voice calls.

The cellular phone illustrated in FIGS. 12A to 12C includes two housings 1001 and 1002. The housing 1001 includes a display portion 1101, a speaker 1102, a microphone 1103, operation keys 1104, a pointing device 1105, a camera lens 1106, an external connection terminal 1107, and the like, while the housing 1002 includes an earphone terminal 1008, a keyboard 1201, an external memory slot 1202, a camera lens 1203, a light 1204, and the like. In addition, an antenna is incorporated in the housing 1001.

In addition to the above structure, the cellular phone may incorporate a non-contact IC chip, a small-sized memory device, or the like.

In the display portion 1101, the light-emitting device described in Embodiment 8 can be incorporated, and a display direction can be changed as appropriate depending on the usage mode. Since the cellular phone is provided with the camera lens 1106 and the display portion 1101 on one surface, the cellular phone can be used as a videophone. Further, a still image or a moving image can be taken with the camera lens 1203 and the light 1204, using the display portion 1101 as a viewfinder. The speaker 1102 and the microphone 1103 can be used for video calls, recording, replaying, and the like without being limited to voice calls. With the use of the operation keys 1104, making and receiving calls, inputting simple information such as e-mail or the like, scrolling the screen, moving the cursor, or the like are possible. Furthermore, the housing 1001 and the housing 1002 which are overlapped with each other (FIG. 12A) can slide as illustrated in FIG. 12C, so that the cellular phone can be used as a portable information terminal. In this case, smooth operation can be conducted using the keyboard 1201 and the pointing device 1105. The external connection terminal 1107 can be connected to an AC adaptor and various types of cables such as a USB cable, and charging, data communication with a computer, or the like are possible. Furthermore, a large amount of data can be stored and moved by inserting a storage medium into the external memory slot 1202.

In addition to the above functions, the cellular phone may include an infrared communication function, a television receiving function, or the like.

Figure 7:
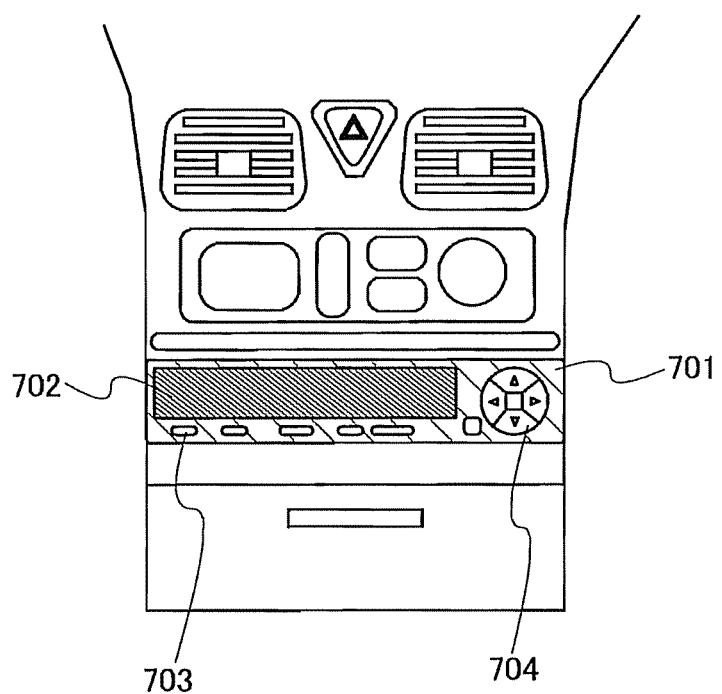
FIG. 7 illustrates an electronic appliance according to an embodiment of the present invention.

FIG. 7 illustrates an audio replay device, specifically, a car audio system which includes a main body 701, a display portion 702, and operation switches 703 and 704. The display portion 702 can be realized with the light-emitting device (passive matrix type or active matrix type) of Embodiment 8. Further, this display portion 702 may be formed using a segment type light-emitting device. In any case, by using a light-emitting element according to the present invention, a display portion having a long lifetime can be formed with the use of a vehicle power source (12 to 42 V). Furthermore, although Embodiment 9 describes an in-car audio system, a light-emitting device according to the present invention may also be used in a portable audio system or an audio system for home use.

Figure 8:
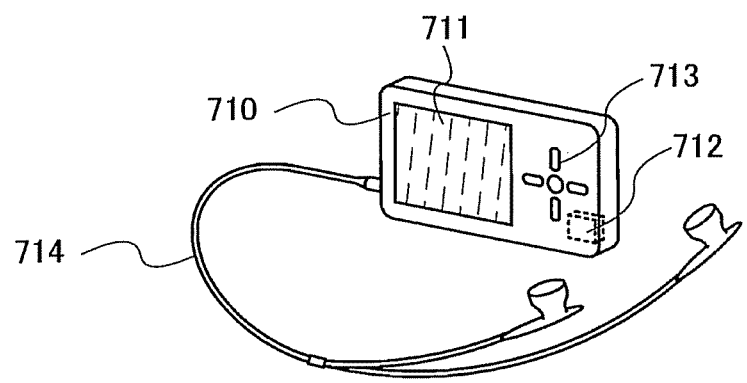
FIG. 8 illustrates an electronic appliance according to an embodiment of the present invention.

FIG. 8 illustrates a digital player as an example of an audio replay device. The digital player illustrated in FIG. 8 includes a main body 710, a display portion 711, a memory portion 712, an operation portion 713, a pair of earphones 714, and the like. Note that a pair of headphones or wireless earphones can be used instead of the pair of earphones 714. The display portion 711 can be formed by using the light-emitting device (passive matrix type or active matrix type) of Embodiment 8. Further, the display portion 711 may be formed using a segment type light-emitting device. In any case, by using a light-emitting element according to the present invention, a display portion that can display images even with the use of a secondary battery (e.g., a nickel-hydrogen battery) and has a long lifetime can be obtained. As the memory portion 712, a hard disk or a nonvolatile memory is used. For example, by using a NAND-type nonvolatile memory with a recording capacity of 20 to 200 gigabytes (GB) and by operating the operating portion 713, an image or a sound (music) can be recorded and replayed. Note that in the display portion 702 and the display portion 711, white characters are displayed against a black background, and accordingly power consumption can be reduced. This is particularly effective for portable audio systems.

As described above, the applicable range of the light-emitting device manufactured according to the present invention is wide so that the light-emitting device can be applied to electronic appliances in a wide variety of fields. By using any of the anthracene derivatives of the present invention, electronic appliances which have display portions with a long lifetime can be provided. Further, electronic appliances including a display portion having high color reproducibility can be provided.

Further, the light-emitting device of the present invention can also be used as a lighting apparatus. An embodiment in which the light-emitting device of the present invention is used as a lighting apparatus is described using FIG. 9.

Figure 9:
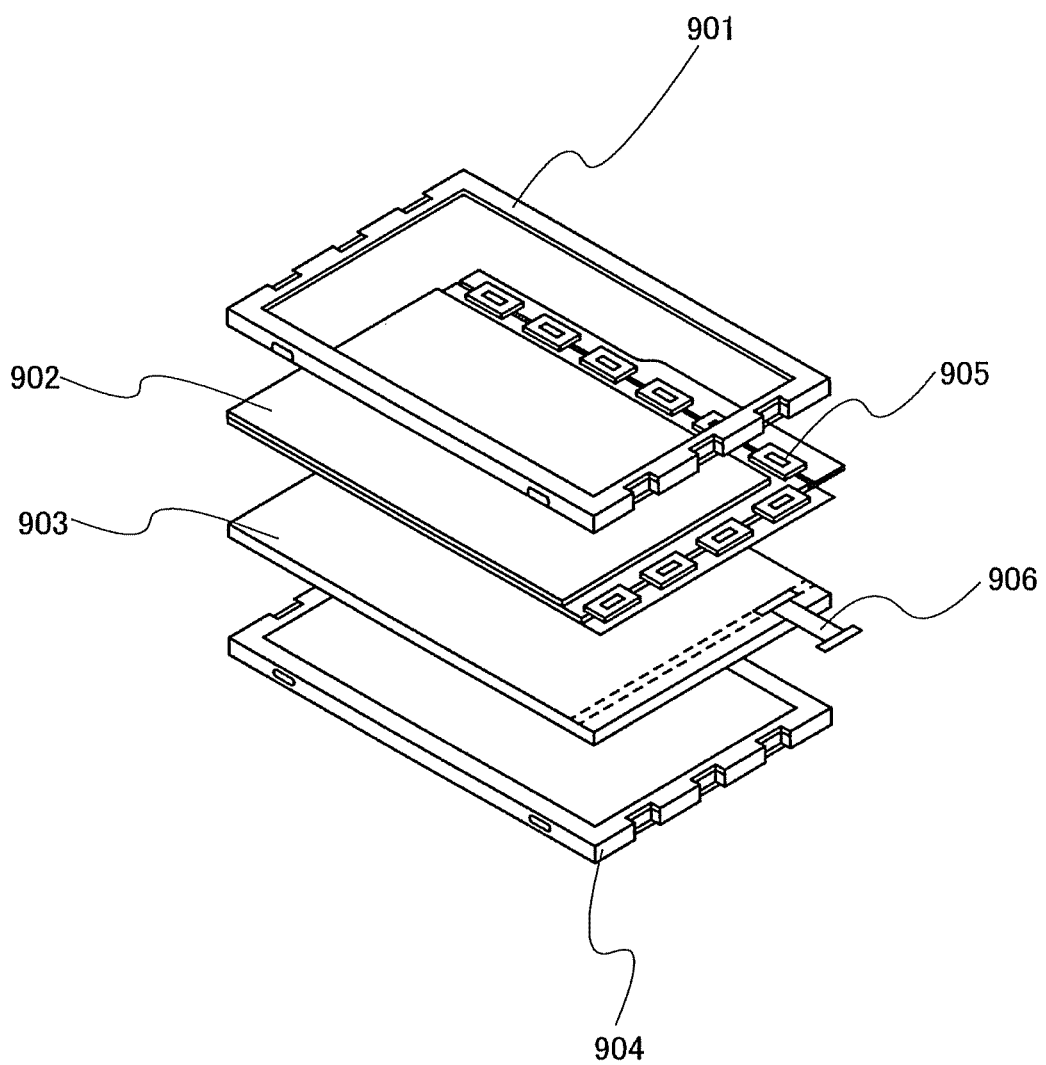
FIG. 9 illustrates an electronic appliance according to an embodiment of the present invention.

FIG. 9 illustrates a liquid crystal display device using a light-emitting device according to the present invention as a backlight, as an example of the electronic appliance using a light-emitting device according to the present invention as a lighting apparatus. The liquid crystal display device illustrated in FIG. 9 includes a housing 901, a liquid crystal layer 902, a backlight 903, and a housing 904, and the liquid crystal layer 902 is connected to a driver IC 905. Further, the light-emitting device to which the present invention is applied is used as the backlight 903, and a current is supplied through a terminal 906.

By using the light-emitting device of the present invention as the backlight of a liquid crystal display device, a backlight with reduced power consumption can be obtained. Further, since the light-emitting device of the present invention is a plane emission type lighting apparatus and can have a large area, the backlight can have a large area, whereby a liquid crystal display device having a large area can be obtained. Furthermore, since the light-emitting device of the present invention is thin and has low power consumption, a thin shape and low power consumption of a display device can also be achieved. Moreover, since the light-emitting device of the present invention has a long lifetime, a liquid crystal display device using the light-emitting device of the present invention also has a long lifetime.

Figure 10:
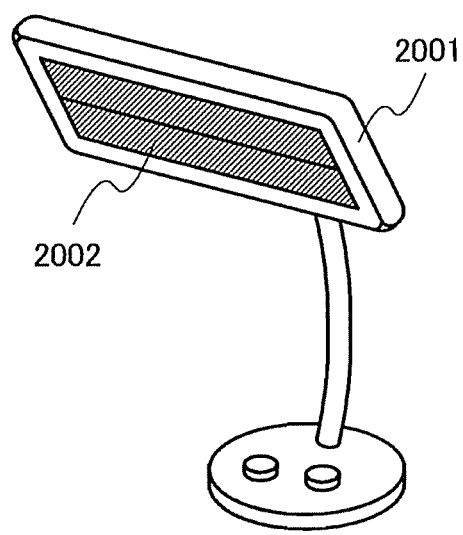
FIG. 10 illustrates a lighting apparatus according to an embodiment of the present invention.

FIG. 10 illustrates an example in which a light-emitting device to which the present invention is applied is used as a desk lamp, which is a lighting apparatus. The desk lamp illustrated in FIG. 10 includes a housing 2001 and a light source 2002, and a light-emitting device of the present invention is used as the light source 2002. Since the light-emitting device of the present invention has a long lifetime, the desk lamp also has a long lifetime.

Figure 11:
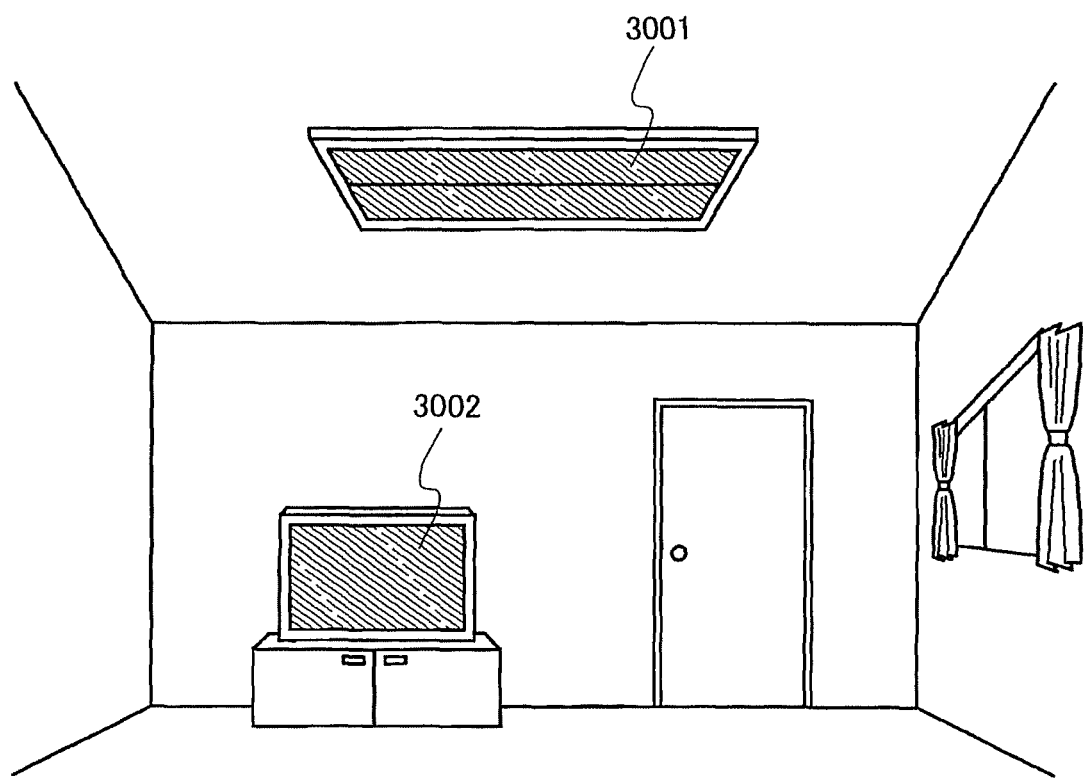
FIG. 11 illustrates a lighting apparatus according to an embodiment of the present invention.

FIG. 11 illustrates an example in which the light-emitting device to which the present invention is applied is used for an indoor lighting apparatus 3001. Since the light-emitting device of the present invention can have a large area, the light-emitting device of the present invention can be used as a lighting apparatus having a large emission area. Moreover, since the light-emitting device of the present invention is thin and has a long lifetime, the light-emitting device can be used for a lighting apparatus that is thinned and has a longer lifetime. In a room where the light-emitting device to which the present invention is thus applied is used as the indoor lighting apparatus 3001, a television set 3002 according to the present invention as described with reference to FIG. 6A is placed, so that pubic broadcasting and movies can be watched. In such a case, since each of the devices has a long lifetime, the frequency of replacing the lighting apparatus and the television set can be reduced, whereby environmental load can be reduced.

Note that Embodiment 9 can be combined with any other embodiment as appropriate.

Example 1

In Example 1, a method of synthesizing 3-(9,10-diphenyl-2-anthryl)-9-phenyl-9H-carbazole (abbreviation: 2PCzPA) represented by the structural formula (101), which is one of the anthracene derivatives of the present invention, is specifically described.

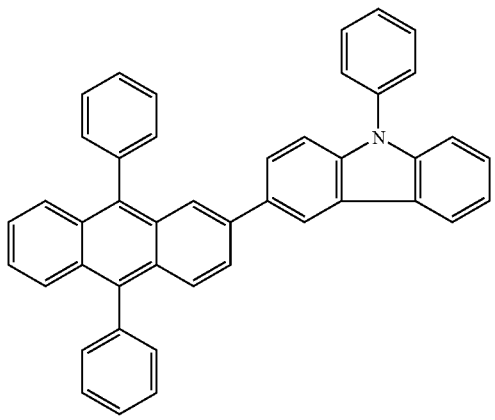

(101)

[Step 1] Synthesis of 2-Bromo-9,10-diphenylanthracene (abbreviation: 2PA unit)
(i) Synthesis of 2-Bromo-9,10-anthraquinone
A synthesis scheme of 2-bromo-9,10-anthraquinone is illustrated in (C-1).

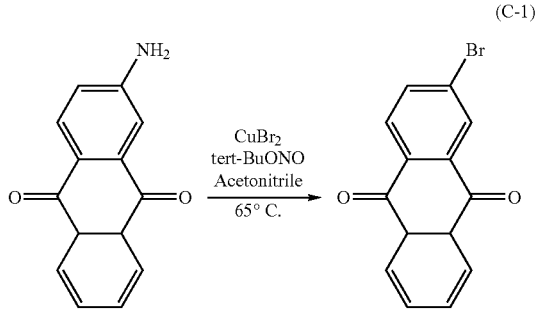 [SMILES: Nc1ccc2c(c1)C(=O)C1C=CC=CC1C2=O ; O=C1c2ccc(Br)cc2C(=O)C2C=CC=CC12]

(C-1)

In a 1L three-neck flask were put 46 g (206 mmol) of copper(II) bromide and 500 mL of acetonitrile. To the mixture was added 17.3 g (168 mmol) of tert-butyl nitrite. This mixture was heated to 65° C. While the mixture was heated, to this mixture was added 25 g (111 mmol) of 2-amino-9,10-anthraquinone. This mixture was stirred at the same temperature for 6 hours. Then, this solution was poured into about 500 mL of hydrochloric acid (3 mol/L). This mixture was stirred for 3 hours. Then, the solid precipitated from the mixture was filtered off. The obtained residue was washed with water and ethanol. Then, the residue was dissolved in toluene, and this solution was suction filtered through Florisil (a product of Wako Pure Chemical Industries, Ltd., Catalog No. 540-00135), Celite (a product of Wako Pure Chemical Industries, Ltd., Catalog No. 531-16855), and alumina. The obtained filtrate was concentrated to give a solid. The solid was recrystallized with chloroform/hexane to give 2-bromo-9,10-anthracene, which was the object of the synthesis, as 18.6 g of a light yellow powdered solid in a yield of 58%.

(ii) Synthesis of 2-Bromo-9,10-dihydroanthracene-9,10-diol
A synthesis scheme of 2-bromo-9,10-dihydroanthracene-9,10-diol is illustrated in (C-2).

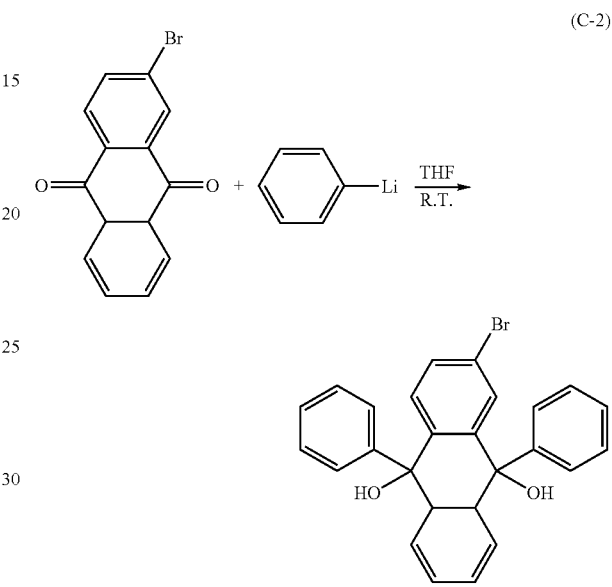

(C-2)

In a 300 mL three-neck flask was put 4.90 g (17.0 mmol) of 2-bromo-9,10-anthraquinone, and the atmosphere in the flask was replaced with nitrogen. To the flask was added 100 mL of tetrahydrofuran (THF), and 17.8 mL (37.3 mmol) of phenyllithium was dropped into this solution. After the completion of the dropping, this solution was stirred at room temperature for 15 hours. Then, this solution was washed with water, and the aqueous layer was extracted with ethyl acetate. The extract solution and the organic layer were combined and dried with magnesium sulfate. Then, this mixture was gravity filtered. The obtained filtrate was concentrated to give 2-bromo-9,10-dihydroanthracene-9,10-diol, which was the object of the synthesis.

(iii) Synthesis of 2-Bromo-9,10-diphenylanthracene.
A synthesis scheme of 2-bromo-9,10-diphenylanthracene is illustrated in (C-3).

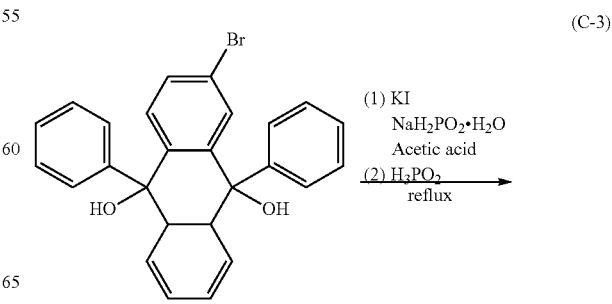

(C-3)

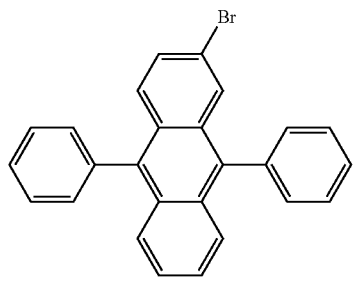

In a 500 mL three-neck flask were put 7.55 g (17.0 mmol) of 2-bromo-9,10-diphenylanthracene-9,10-diol, which was obtained, 5.06 g (30.5 mmol) of potassium iodide, 9.70 g (91.5 mmol) of sodium phosphinate monohydrate, and 50 mL of glacial acetic acid, and this mixture was stirred at 120° C. for 2 hours. Then, to this mixture was added 30 mL of 50% phosphinic acid, and this mixture was further stirred at 120° C. for 1 hour. Then, this solution was washed with water, and the aqueous layer was extracted with ethyl acetate. The extract solution and the organic layer were combined and dried with magnesium sulfate. This mixture was gravity filtered. The obtained filtrate was concentrated to give a light yellow solid. The obtained solid was dissolved in toluene, and this solution was suction filtered through Celite (a product of Wako Pure Chemical Industries, Ltd., Catalog No. 531-16855), Florisil (a product of Wako Pure Chemical Industries, Ltd., Catalog No. 540-00135), and alumina. The obtained filtrate was concentrated to give a solid. The solid was recrystallized with chloroform/hexane to give the object of the synthesis as 5.1 g of a light yellow powdered solid in a yield of 74% (which is the yield of the schemes (C-2) and (C-3)).

[Step 2] Synthesis of 2PCzPA

A synthesis scheme of 2PCzPA is illustrated in (C-4).

(C-4)

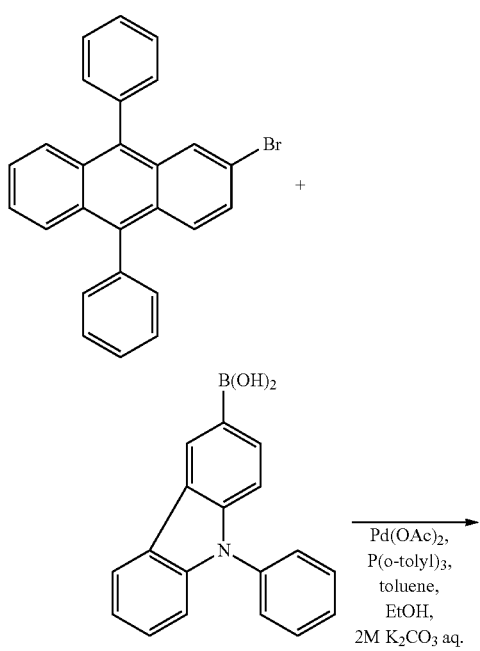

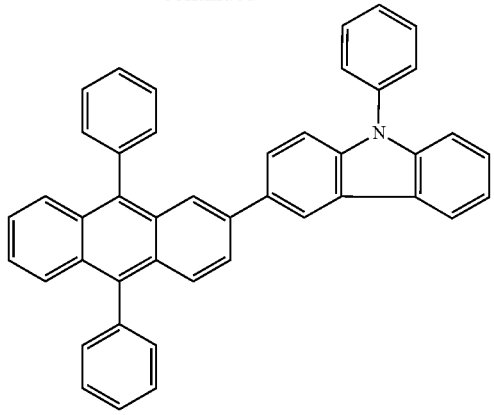

In a 100 mL three neck flask were put 1.5 g (3.7 mmol) of 2-bromo-9,10-diphenylanthracene, 1.1 g (3.7 mmol) of 4-(9H-carbazol-9-yl)phenylboronic acid, and 0.16 g (0.50 mmol) of tri(ortho-tolyl)phosphine, and the atmosphere in the flask was replaced with nitrogen. To this mixture were added 20 mL of toluene, 10 mL of ethanol, and 13 mL of an aqueous potassium carbonate solution (2.0 mol/L). This mixture was deaerated while being stirred under reduced pressure. Then, the atmosphere in the flask was replaced with nitrogen. To this mixture was added 28 mg (0.10 mmol) of palladium(II) acetate. This mixture was refluxed at 110° C. for 12 hours. Then, after this mixture was cooled to room temperature, about 20 mL of toluene was added thereto, and the mixture was filtered through Celite (a product of Wako Pure Chemical Industries, Ltd., Catalog No. 531-16855). The organic layer of the obtained mixture was washed with water and a saturated saline solution, and dried with magnesium sulfate. This mixture was gravity filtered. The obtained filtrate was concentrated to give a brown oily substance. This oily substance was purified by silica gel column chromatography (a developing solvent was a mixture of hexane and toluene in a ratio of 7:3). The obtained light yellow solid was recrystallized with ethanol to give 1.2 g of a light yellow powdered solid in a yield of 58%.

Then, 1.2 g of the obtained light-yellow powdered solid was sublimated and purified by train sublimation. For sublimation purification conditions, 2PCzPA was heated at 280° C. under a pressure of 8.7 Pa with argon gas at a flow rate of 3.0 mL/min. After the sublimation purification, 2PCzPA was recovered as 0.83 g of a light yellow solid in a yield of 74%.

By nuclear magnetic resonance (NMR) measurement, it was confirmed that this compound was 3-(9,10-diphenyl-2-anthryl)-9-phenyl-9H-carbazole (abbreviation: 2PCzPA).

Figure 13A:
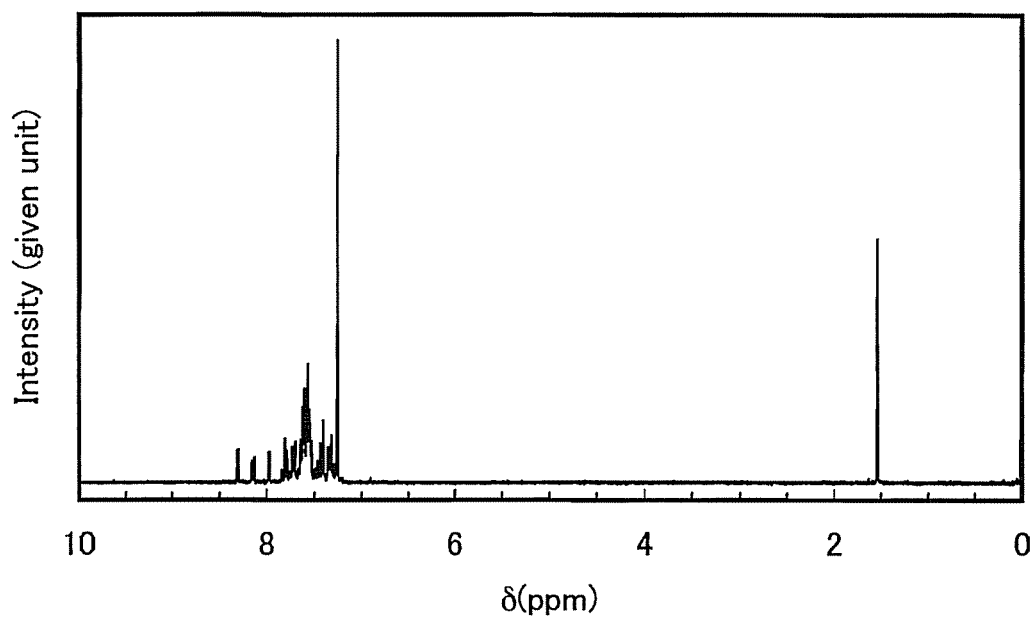
FIGS. 13A and 13B show $^1$H NMR charts of 3-(9,10-diphenyl-2-anthryl)-9-phenyl-9H-carbazole (abbreviation: 2PCzPA).
Figure 13B:
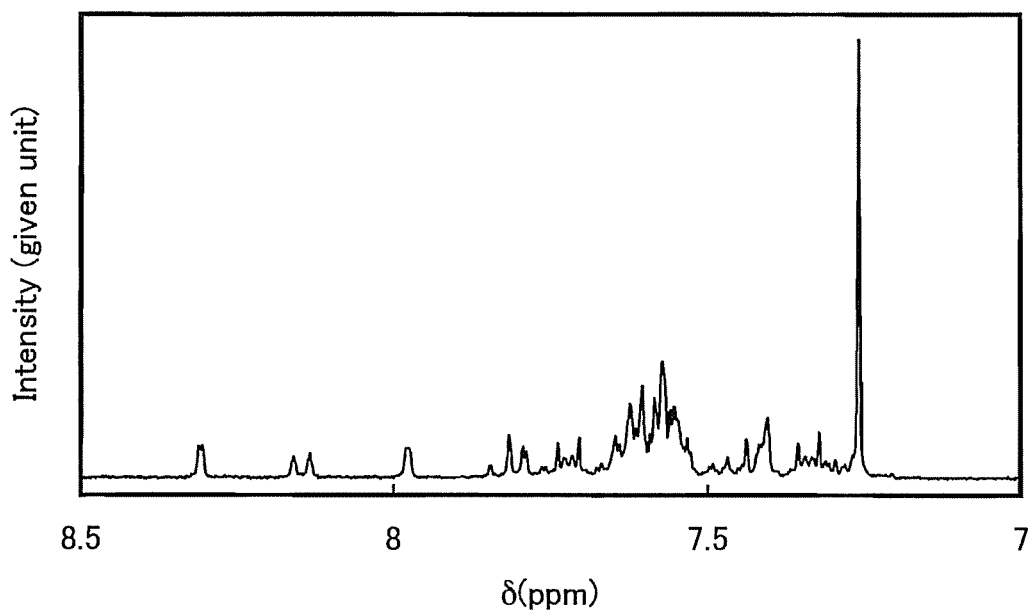

The $^1$H NMR data of 2PCzPA are shown as follows: $^1$H NMR (CDCl$_3$, 300 MHz): δ=7.30-7.34 (m, 3H), 7.41-7.49 (m, 4H), 7.53-7.65 (m, 15H), 7.70-7.74 (m, 2H), 7.79-7.84 (m, 2H), 7.98 (s, 1H), 8.15 (d, J=7.8 Hz, 1H), 8.31 (d, J=2.1 Hz, 1H). Further, FIGS. 13A and 13B show $^1$H NMR charts. Note that FIG. 13B is a chart in which the range of 7.0 to 8.5 ppm in FIG. 13A is enlarged.

Further, the decomposition temperature of 2PCzPA, which was obtained, was measured with a high vacuum differential type differential thermal balance (TG-DTA2410SA, a product of Bruker AXS K.K.). The temperature increase rate was set to 10° C./min, and the temperature was increased under normal pressure. Accordingly, a reduction in weight by 5% was seen at 416° C. Thus, 2PCzPA was found to have high thermal stability.

Figure 14:
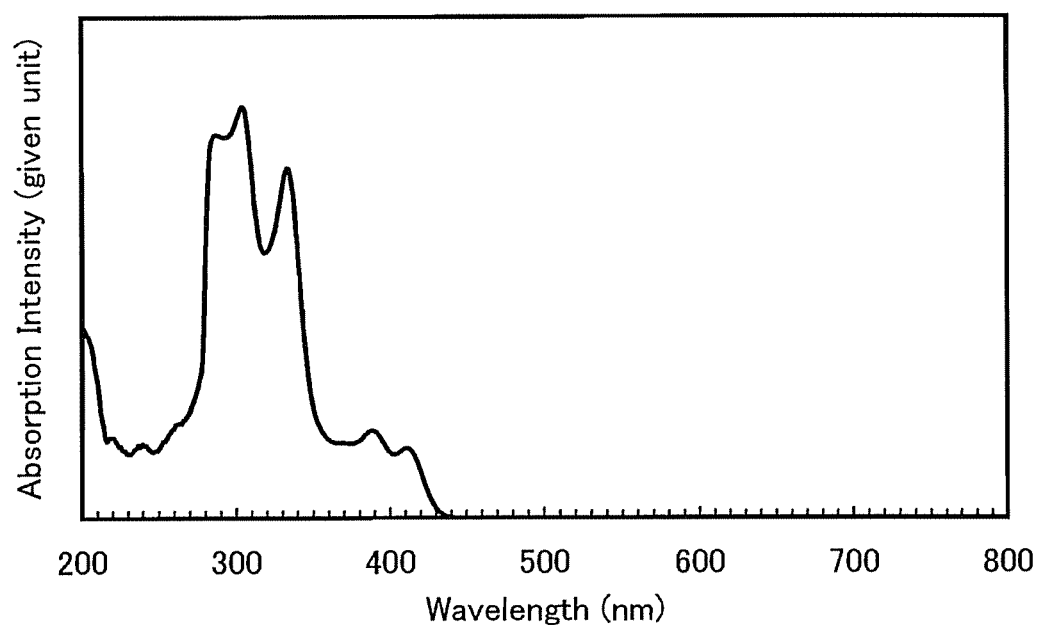
FIG. 14 shows an absorption spectrum of a toluene solution of 3-(9,10-diphenyl-2-anthryl)-9-phenyl-9H-carbazole (abbreviation: 2PCzPA).
Figure 15:
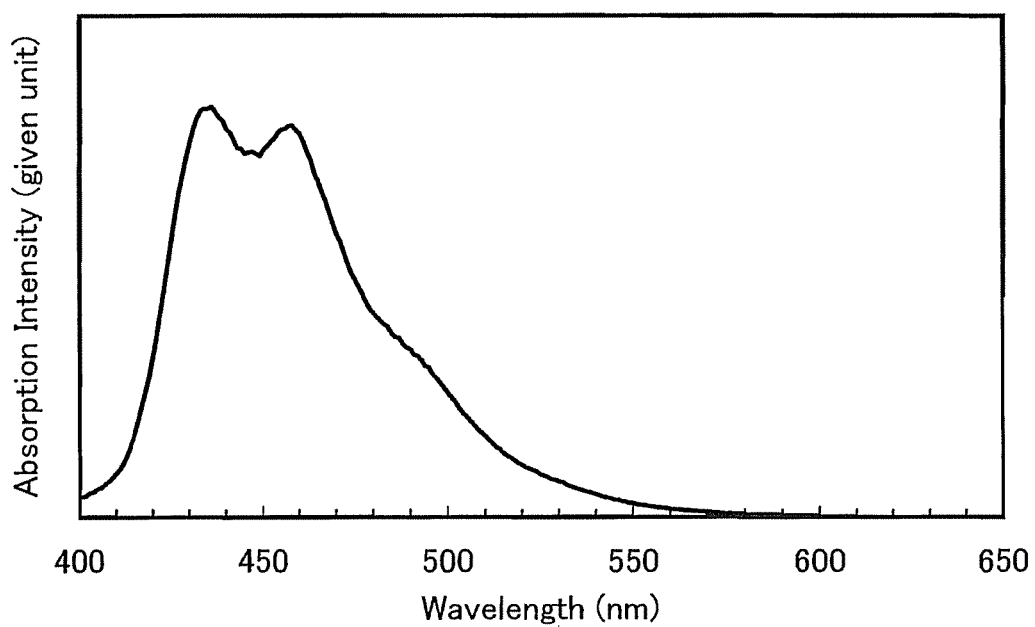
FIG. 15 shows an emission spectrum of the toluene solution of 3-(9,10-diphenyl-2-anthryl)-9-phenyl-9H-carbazole (abbreviation: 2PCzPA).

Further, FIG. 14 shows an absorption spectrum of a toluene solution of 2PCzPA, and FIG. 15 shows an emission spectrum of the toluene solution of 2PCzPA. An ultraviolet-visible spectrophotometer (V-550, a product of JASCO Corporation) was used for the measurement. The measurement was conducted with the solution put in the quartz cell. The absorption spectrum from which the absorption spectrum obtained with only toluene put in the quartz cell was subtracted is shown. In FIG. 14, the horizontal axis represents wavelength (nm) and the vertical axis represents absorption intensity (given (arbitrary) unit). In FIG. 15, the horizontal axis represents wavelength (nm) and the vertical axis represents emission intensity (given unit). With the toluene solution, absorption was observed at around 302 nm, 331 nm, 366 nm, 386 nm, and 409 nm. In addition, with the toluene solution, the peak emission wavelengths were around 436 nm and 459 nm (excitation wavelength of 370 nm).

Figure 16:
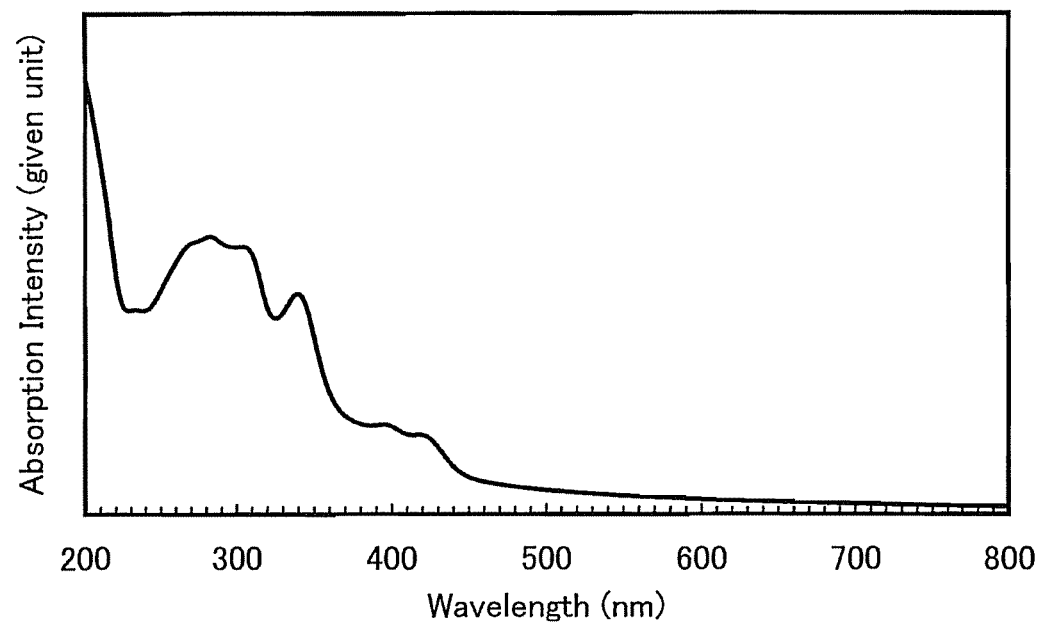
FIG. 16 shows an absorption spectrum of a thin film of 3-(9,10-diphenyl-2-anthryl)-9-phenyl-9H-carbazole (abbreviation: 2PCzPA).
Figure 17:
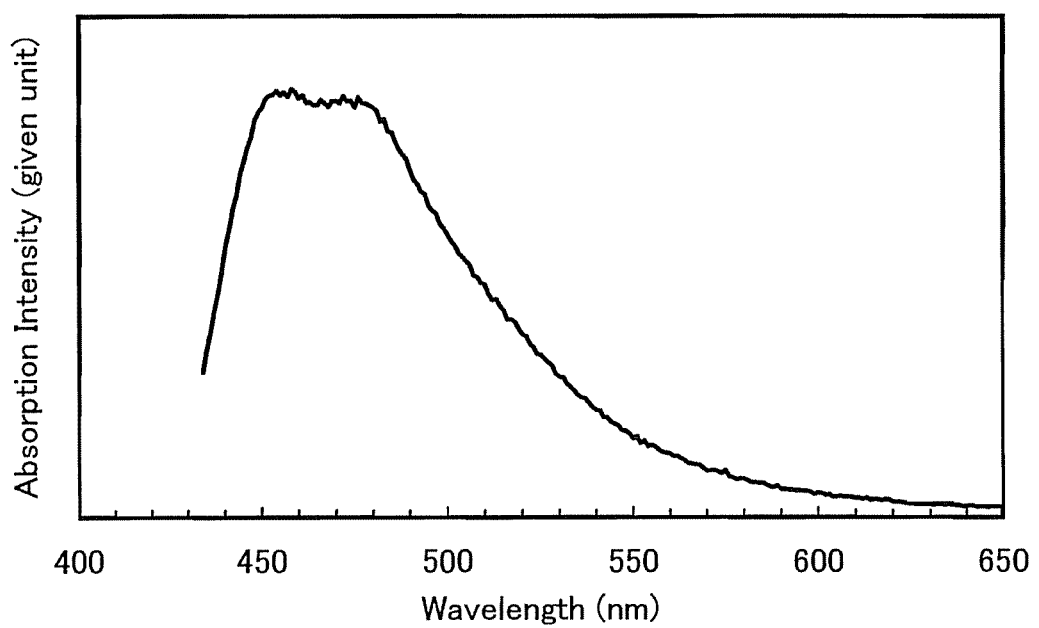
FIG. 17 shows an emission spectrum of the thin film of 3-(9,10-diphenyl-2-anthryl)-9-phenyl-9H-carbazole (abbreviation: 2PCzPA).

Further, FIG. 16 shows an absorption spectrum of a thin film of 2PCzPA, and FIG. 17 shows an emission spectrum of the thin film of 2PCzPA. An ultraviolet-visible spectrophotometer (V-550, a product of JASCO Corporation) was used for the measurement. A sample was prepared by evaporation on a quartz substrate, and the absorption spectrum from which the absorption spectrum of quartz is subtracted is shown. In FIG. 16, the horizontal axis represents wavelength (nm) and the vertical axis represents absorption intensity (given unit). In FIG. 17, the horizontal axis represents wavelength (nm) and the vertical axis represents emission intensity (given unit). With the thin film, absorption was observed at around 283 nm, 305 nm, 340 nm, 395 nm, and 423 nm. In addition, with the thin film, the peak emission wavelengths were around 456 nm and 476 nm (excitation wavelength of 418 nm).

Further, by measurement with a photoelectron spectrometer (AC-2, a product of Riken Keiki, Co., Ltd.) in the atmosphere, the ionization potential of the thin film of 2PCzPA was found to be 5.49 eV. Accordingly, it was understood that the HOMO level was −5.49 eV. Furthermore, with the use of the absorption spectrum data of the thin film of 2PCzPA, the absorption edge was obtained by a Tauc plot assuming direct 5 transition. The absorption edge was estimated as an optical energy gap, whereby the energy gap was 2.77 eV. From the obtained values of the energy gap and HOMO level, the LUMO level was −2.72 eV.

Further, the oxidation-reduction characteristics of 2PCzPA were measured by cyclic voltammetry (CV). Note that an electrochemical analyzer (ALS model 600A, a product of BAS Inc.) was used for the measurement.

For a solution used in the CV measurement, dehydrated dimethylformamide (DMF, a product of Sigma-Aldrich Inc., 99.8%, Catalog No. 22705-6) was used as a solvent, and tetra-n-butylammonium perchlorate (n-Bu$_4$NClO$_4$, a product of Tokyo Chemical Industry Co., Ltd., Catalog No. T0836), which serves as a supporting electrolyte, was dissolved in the solvent such that the concentration of tetra-n-butylammonium perchlorate was 100 mmol/L. Furthermore, 2PCzPA, which was the object of the measurement, was dissolved in the solution such that the concentration of 2PCzPA was 2 mmol/L. In addition, a platinum electrode (PTE platinum electrode, a product of BAS Inc.) was used as a working electrode, a platinum electrode (Pt counter electrode for VC-3, (5 cm), a product of BAS Inc.) was used as an auxiliary electrode, and an Ag/Ag$^+$ electrode (RE5 reference electrode for nonaqueous solvent, a product of BAS Inc.) was used as a reference electrode. Note that the measurement was conducted at room temperature.

The oxidation characteristics of 2PCzPA were examined as follows. A scan for changing the potential of the working electrode with respect to the reference electrode from −0.16 V to 1.30 V and then from 1.30 V to −0.16 V was set to one cycle, and the measurement was performed for 100 cycles. Further, the reduction characteristics of 2PCzPA were examined as follows. A scan for changing the potential of the working electrode with respect to the reference electrode from −1.02 V to −2.54 V and then from −2.54 V to −1.02 V was set to one cycle, and the measurement was performed for 100 cycles. Note that the scan rate for the CV measurement was set to 0.1 V/s.

Figure 18:
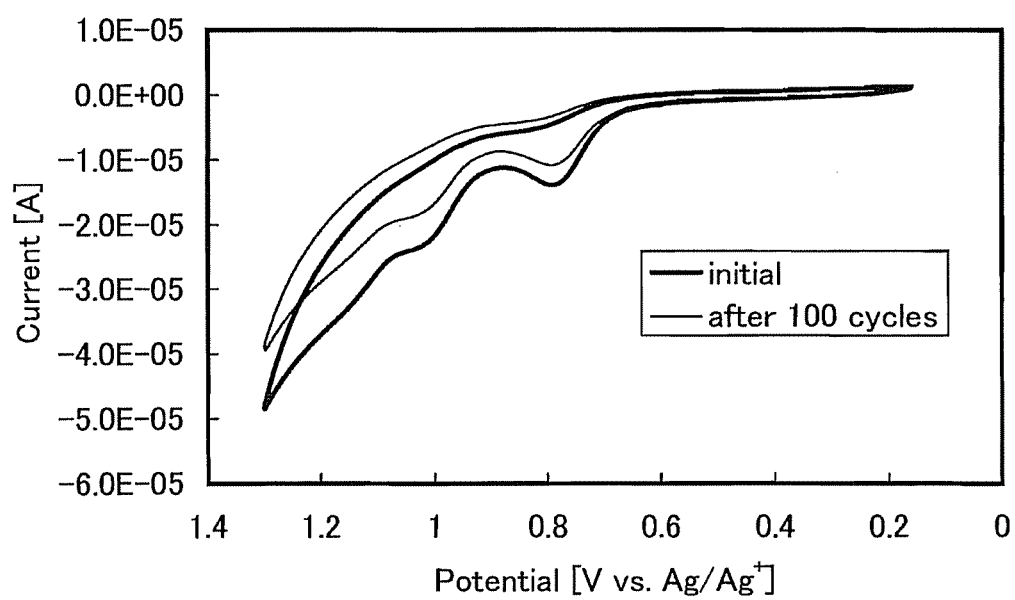
FIG. 18 shows the results of CV measurement of 3-(9,10-diphenyl-2-anthryl)-9-phenyl-9H-carbazole (abbreviation: 2PCzPA).
Figure 19:
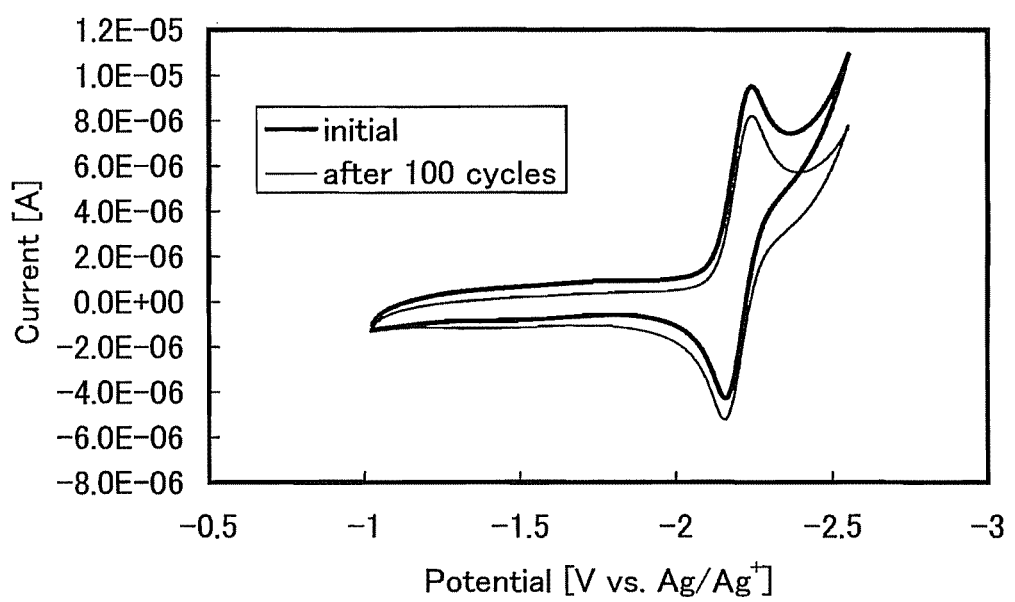
FIG. 19 shows the results of CV measurement of 3-(9,10-diphenyl-2-anthryl)-9-phenyl-9H-carbazole (abbreviation: 2PCzPA).

FIG. 18 shows CV measurement results of the oxidation characteristics of 2PCzPA. FIG. 19 shows CV measurement results of the reduction characteristics of 2PCzPA. In each of FIG. 18 and FIG. 19, the horizontal axis represents potential (V) of the working electrode with respect to the reference electrode, and the vertical axis represents the amount of current (μA) flowing between the working electrode and the auxiliary electrode. From FIG. 18, current exhibiting oxidation was observed at around 0.79 V (vs. the Ag/Ag$^+$ electrode). Further, from FIG. 19, current exhibiting reduction was observed at around −2.24 V (vs. the Ag/Ag$^+$ electrode).

Although the scan was repeated for as many as 100 cycles, significant changes in the peak position and peak intensity of the CV curves were not observed in each of the oxidation reactions and reduction reactions. This shows that the anthracene derivative of the present invention is significantly stable against repetition of oxidation reactions and reduction reactions.

Example 2

In Example 2, a method of synthesizing 9-[4-(9,10-diphenyl-2-anthryl)phenyl]-9H-carbazole (abbreviation: 2CzPPA) represented by the structural formula (201), which is one of the anthracene derivatives of the present invention, is specifically described.

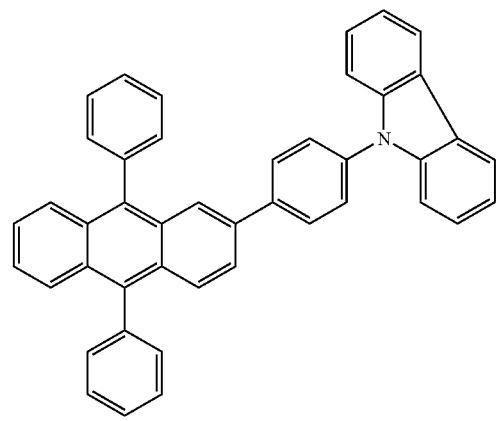

(201)

[Step 1] Synthesis of 9-[4-(9,10-Diphenyl-2-anthryl)phenyl]-9H-carbazole (abbreviation: 2CzPPA)

A synthesis scheme of 2CzPPA is illustrated in (D-1).

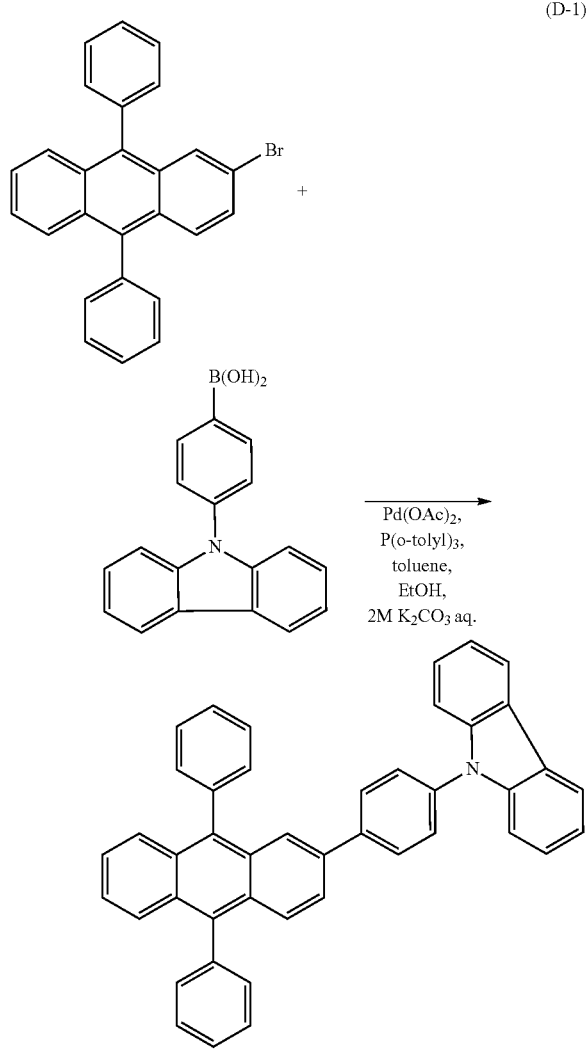

(D-1)

In a 100 mL three neck flask were put 2.0 g (4.9 mmol) of 2-bromo-9,10-diphenylanthracene, 1.4 g (4.9 mmol) of 4-(9H-carbazol-9-yl)phenylboronic acid, and 0.15 g (0.50 mmol) of tri(ortho-tolyl)phosphine, and the atmosphere in the flask was replaced with nitrogen. To this mixture were added 15 mL of toluene, 15 mL of ethanol, and 10 mL of an aqueous potassium carbonate solution (2.0 mol/L). This mixture was deaerated while being stirred under reduced pressure. Then, the atmosphere in the flask was replaced with nitrogen. To this mixture was added 23 mg (0.10 mmol) of palladium(II) acetate. This mixture was refluxed at 100° C. for 20 hours. Then, after this mixture was cooled to room temperature, about 50 mL of toluene was added thereto, and the mixture was filtered through a filter paper. The obtained mixture was washed with water, and the aqueous layer was extracted with toluene. The extract solution and the organic layer were combined and washed with a saturated saline solution, and the organic layer was dried with magnesium sulfate. This mixture was gravity filtered. The obtained filtrate was concentrated to give a light yellow solid. This solid was washed with toluene to give the object of the synthesis as 1.5 g of a light yellow powdered solid in a yield of 54%.

Then, 1.5 g of the obtained light-yellow powdered solid was sublimated and purified by train sublimation. For sublimation purification conditions, 2CzPPA was heated at 260° C. with argon gas at a flow rate of 3.0 mL/min. After the sublimation purification, 2CzPPA was recovered as 1.4 g of a light yellow solid in a yield of 94%.

By nuclear magnetic resonance (NMR) measurement, it was confirmed that this compound was 9-[4-(9,10-diphenyl-2-anthryl)phenyl]-9H-carbazole (abbreviation: 2CzPPA).

Figure 20A:
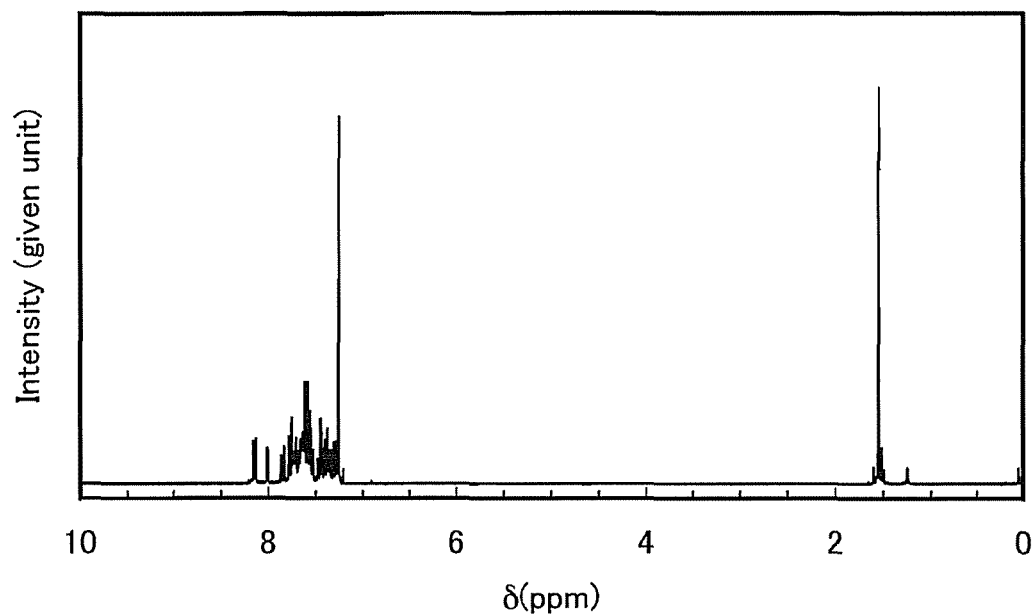
FIGS. 20A and 20B show $^1$H NMR charts of 9-[4-(9,10-diphenyl-2-anthryl)phenyl]-9H-carbazole (abbreviation: 2CzPPA).
Figure 20B:
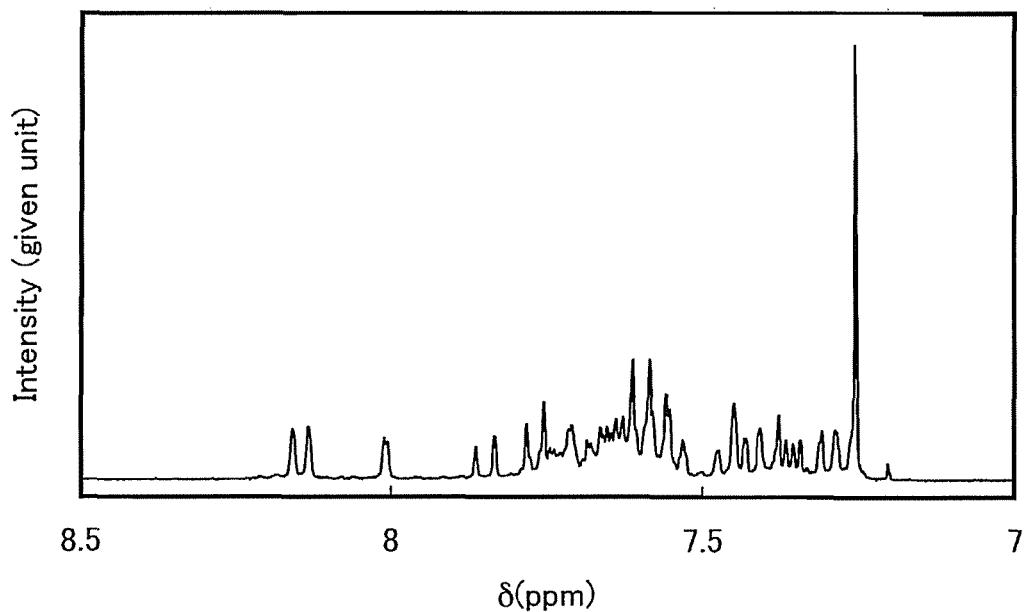

The $^1$H NMR data of 2CzPPA are shown as follows: $^1$H NMR (CDCl$_3$, 300 MHz): δ=7.30 (d, J=6.3 Hz, 2H), 7.33-7.75 (m, 21H), 7.77 (d, J=8.1 Hz, 2H), 7.85 (d, J=9.0 Hz, 1H), 8.01 (d, J=2.1 Hz, 1H), 8.15 (d, J=7.8 Hz, 2H). Further, FIGS. 20A and 20B show $^1$H NMR charts. Note that FIG. 20B is a chart in which the range of 7.0 to 8.5 ppm in FIG. 20A is enlarged.

Further, the decomposition temperature of 2CzPPA, which was obtained, was measured with a high vacuum differential type differential thermal balance (TG-DTA2410SA, a product of Bruker AXS K.K.). The temperature increase rate was set to 10° C./min, and the temperature was increased under normal pressure. Accordingly, a reduction in weight by 5% was seen at 421° C. Thus, 2CzPPA was found to have high thermal stability.

Figure 21:
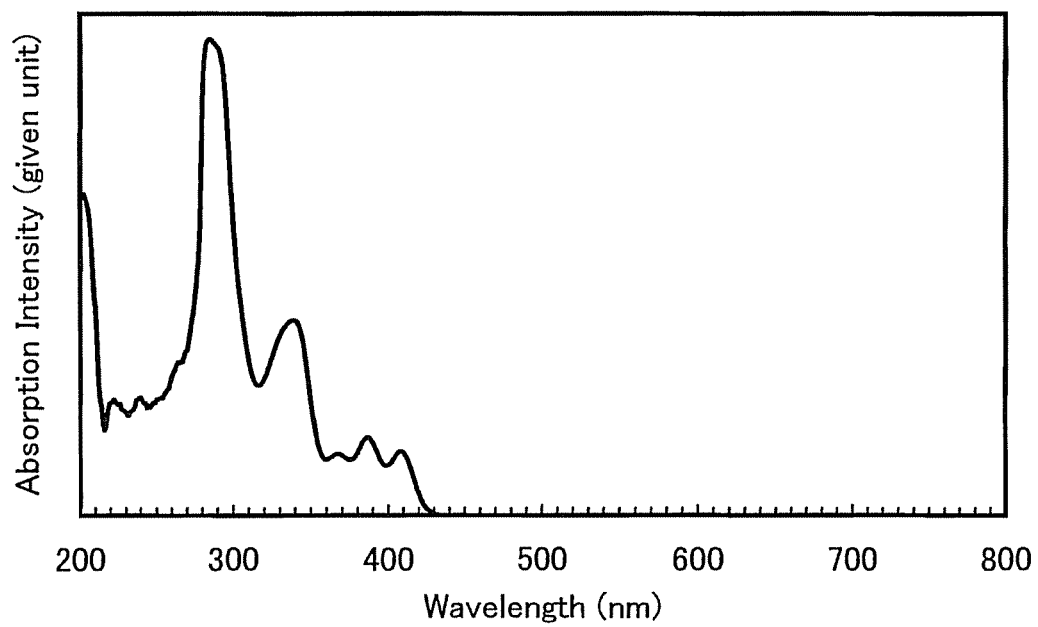
FIG. 21 shows an absorption spectrum of a toluene solution of 9-[4-(9,10-diphenyl-2-anthryl)phenyl]-9H-carbazole (abbreviation: 2CzPPA).
Figure 22:
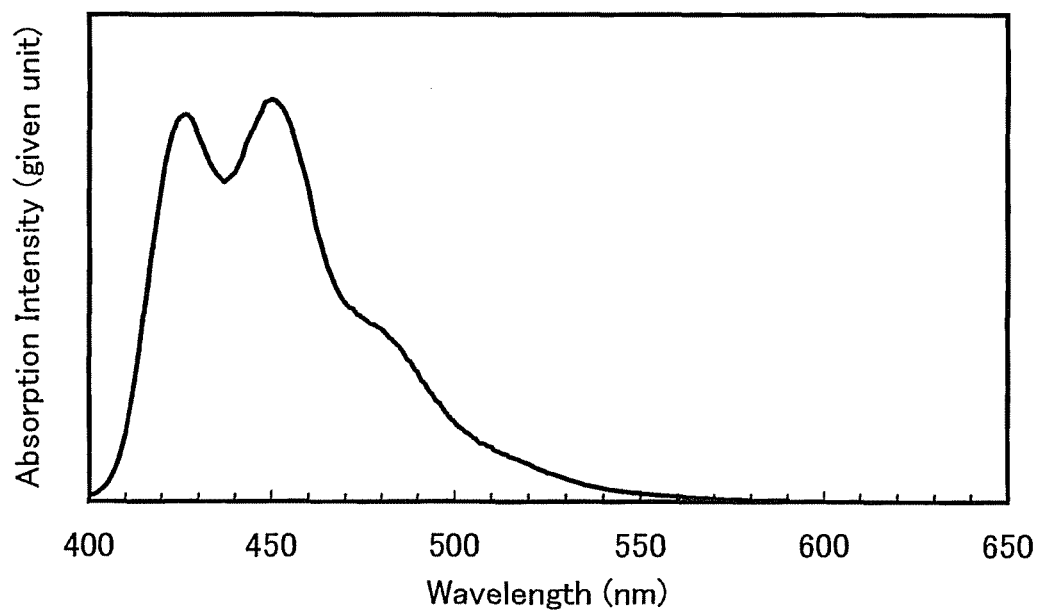
FIG. 22 shows an emission spectrum of the toluene solution of 9-[4-(9,10-diphenyl-2-anthryl)phenyl]-9H-carbazole (abbreviation: 2CzPPA).

Further, FIG. 21 shows an absorption spectrum of a toluene solution of 2CzPPA, and FIG. 22 shows an emission spectrum of the toluene solution of 2CzPPA. An ultraviolet-visible spectrophotometer (V-550, a product of JASCO Corporation) was used for the measurement. The measurement was conducted with the solution put in the quartz cell. The absorption spectrum from which the absorption spectrum obtained with only toluene put in the quartz cell was subtracted is shown. In FIG. 21, the horizontal axis represents wavelength (nm) and the vertical axis represents absorption intensity (given unit). In FIG. 22, the horizontal axis represents wavelength (nm) and the vertical axis represents emission intensity (given unit). With the toluene solution, absorption was observed at around 282 nm, 337 nm, 366 nm, 385 nm, and 407 nm. In addition, with the toluene solution, the peak emission wavelengths were 426 nm and 451 nm (excitation wavelength of 370 nm).

Figure 23:
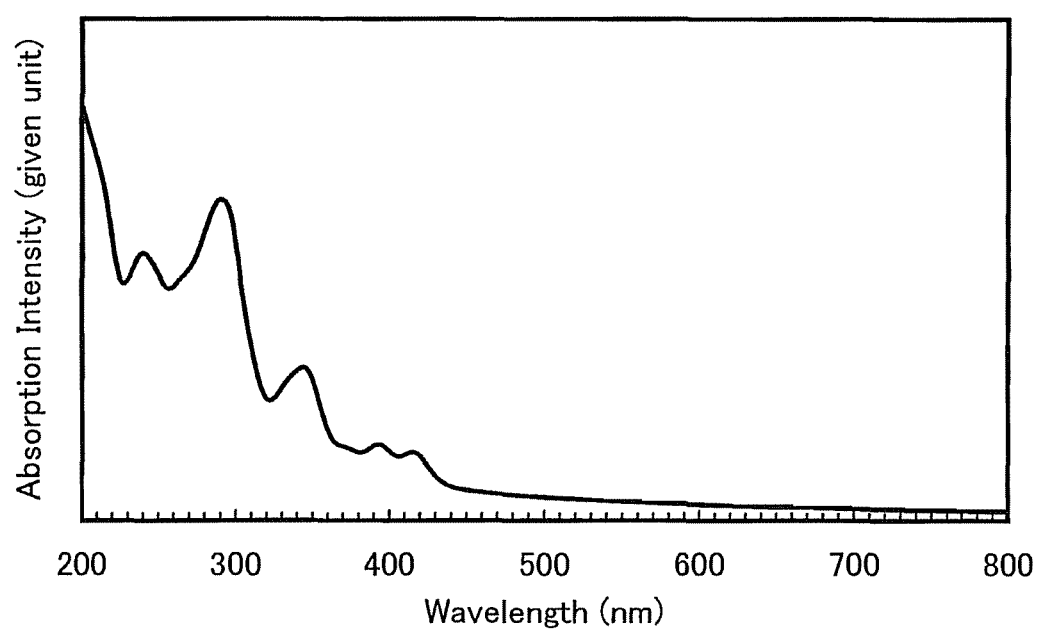
FIG. 23 shows an absorption spectrum of a thin film of 9-[4-(9,10-diphenyl-2-anthryl)phenyl]-9H-carbazole (abbreviation: 2CzPPA).
Figure 24:
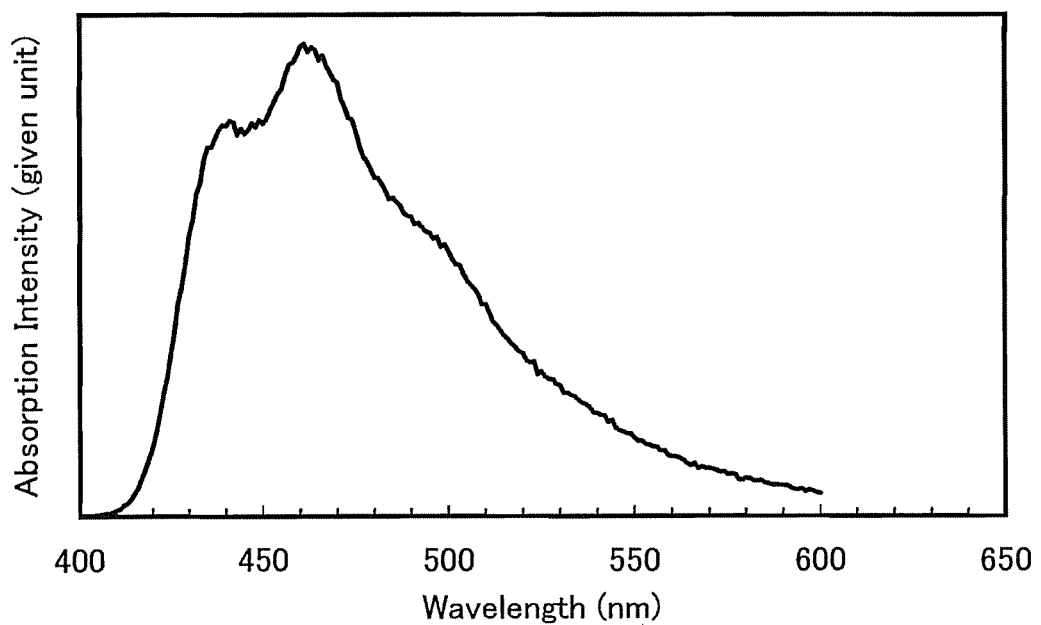
FIG. 24 shows an emission spectrum of the thin film of 9-[4-(9,10-diphenyl-2-anthryl)phenyl]-9H-carbazole (abbreviation: 2CzPPA).

Further, FIG. 23 shows an absorption spectrum of a toluene solution of 2CzPPA, and FIG. 24 shows an emission spectrum of the toluene solution of 2CzPPA. An ultraviolet-visible spectrophotometer (V-550, a product of JASCO Corporation) was used for the measurement. A sample was prepared by evaporation on a quartz substrate, and the absorption spectrum from which the absorption spectrum of quartz is subtracted is shown. In FIG. 23, the horizontal axis represents wavelength (nm) and the vertical axis represents absorption intensity (given unit). In FIG. 24, the horizontal axis represents wavelength (nm) and the vertical axis represents emission intensity (given unit). With the thin film, absorption was observed at around 240 nm, 290 nm, 344 nm, 393 nm, and 415 nm. In addition, with the thin film, the peak emission wavelength was 461 nm (excitation wavelength of 341 nm).

Further, by measurement with a photoelectron spectrometer (AC-2, a product of Riken Keiki, Co., Ltd.) in the atmosphere, the ionization potential of the thin film of 2CzPPA was found to be 5.72 eV As a result, it was understood that the HOMO level was −5.72 eV. Furthermore, with the use of the absorption spectrum data of the thin film of 2CzPPA, the absorption edge was obtained by a Tauc plot assuming direct transition. The absorption edge was estimated as an optical energy gap, whereby the energy gap was 2.84 eV. From the obtained values of the energy gap and HOMO level, the LUMO level was −2.88 eV.

Further, the oxidation-reduction characteristics of 2CzPPA were measured by cyclic voltammetry (CV). Note that an electrochemical analyzer (ALS model 600A, a product of BAS Inc.) was used for the measurement.

For a solution used in the CV measurement, dehydrated dimethylformamide (DMF, a product of Sigma-Aldrich Inc., 99.8%, Catalog No. 22705-6) was used as a solvent, and tetra-n-butylammonium perchlorate (n-Bu$_4$NClO$_4$, a product of Tokyo Chemical Industry Co., Ltd., Catalog No. T0836), which was a supporting electrolyte, was dissolved in the solvent such that the concentration of tetra-n-butylammonium perchlorate was 100 mmol/L. Furthermore, 2CzPPA, which was the object of the measurement, was dissolved in the solution such that the concentration of 2CzPPA was 2 mmol/L. In addition, a platinum electrode (PTE platinum electrode, a product of BAS Inc.) was used as a working electrode, a platinum electrode (Pt counter electrode for VC-3, (5 cm), a product of BAS Inc.) was used as an auxiliary electrode, and an Ag/Ag$^+$ electrode (RE5 reference electrode for nonaqueous solvent, a product of BAS Inc.,) was used as a reference electrode. Note that the measurement was conducted at room temperature.

The oxidation characteristics of 2CzPPA were examined as follows. A scan for changing the potential of the working electrode with respect to the reference electrode from −0.03 V to 1.30 V and then from 1.30 V to −0.03 V was set to one cycle, and the measurement was performed for 100 cycles. Further, the reduction characteristics of 2CzPPA were examined as follows. A scan for changing the potential of the working electrode with respect to the reference electrode from −1.08 V to −2.50 V and then from −2.50 V to −1.08 V was set to one cycle, and the measurement was performed for 100 cycles. Note that the scan rate for the CV measurement was set to 0.1 V/s.

Figure 25:
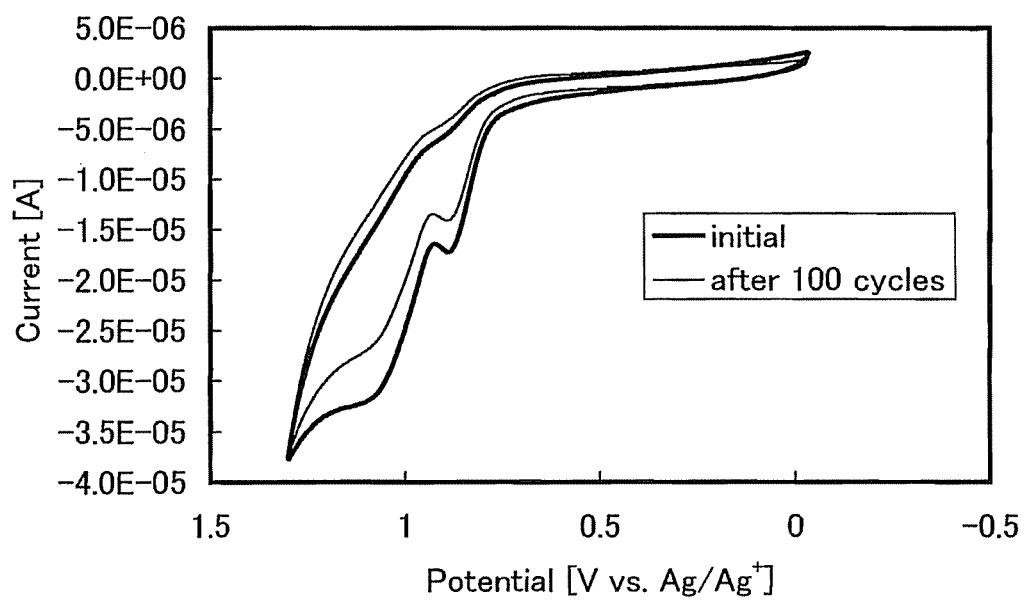
FIG. 25 shows the results of CV measurement of 9-[4-(9,10-diphenyl-2-anthryl)phenyl]-9H-carbazole (abbreviation: 2CzPPA).
Figure 26:
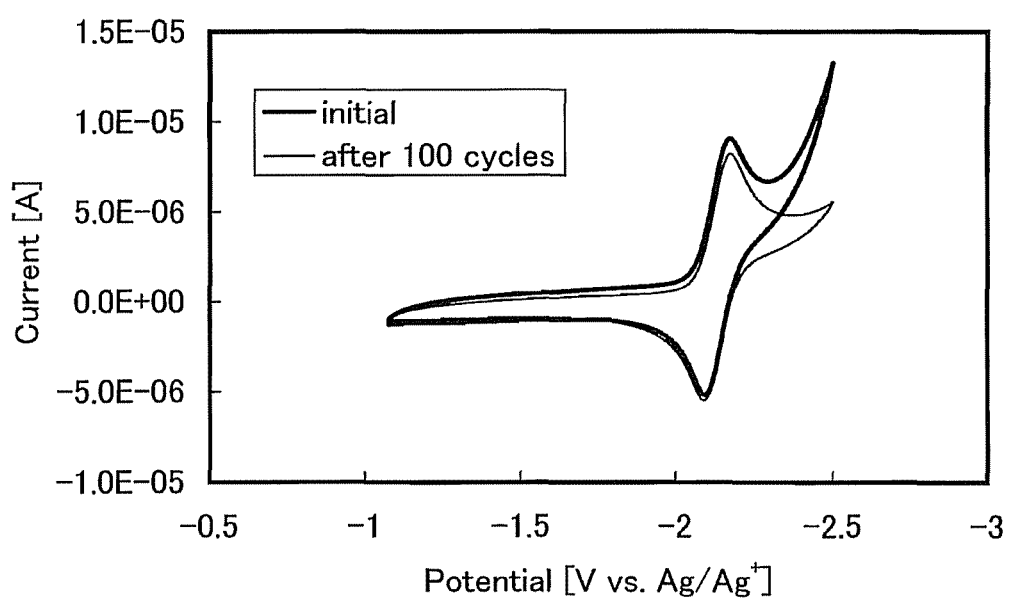
FIG. 26 shows the results of CV measurement of 9-[4-(9,10-diphenyl-2-anthryl)phenyl]-9H-carbazole (abbreviation: 2CzPPA).

FIG. 25 shows CV measurement results of the oxidation characteristics of 2CzPPA. FIG. 26 shows CV measurement results of the reduction characteristics of 2CzPPA. In each of FIG. 25 and FIG. 26, the horizontal axis represents potential (V) of the working electrode with respect to the reference electrode, and the vertical axis represents the amount of current (μA) flowing between the working electrode and the auxiliary electrode. From FIG. 25, current exhibiting oxidation was observed at around 0.89 V (vs. the Ag/Ag$^+$ electrode). Further, from FIG. 26, current exhibiting reduction was observed at around −2.17 V (vs. the Ag/Ag$^+$ electrode).

Although the scan was repeated for as many as 100 cycles, significant changes in the peak position and peak intensity of the CV curves were not observed in each of the oxidation reactions and reduction reactions. This shows that the anthracene derivative of the present invention is significantly stable against repetition of oxidation reactions and reduction reactions.

Example 3

Figure 27:
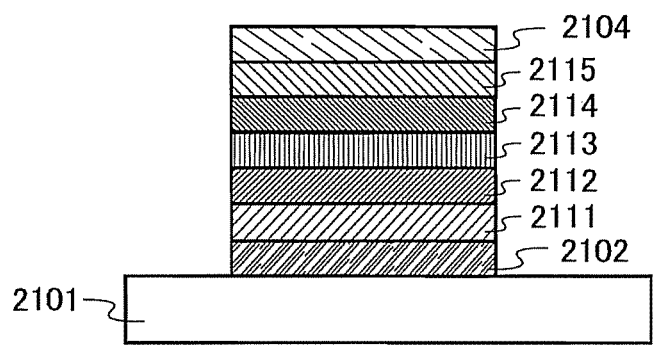
FIG. 27 illustrates a light-emitting element of Examples.

In Example 3, light-emitting elements of the present invention will be described using FIG. 27. Structural formulae of materials used in Example 3 are illustrated below.

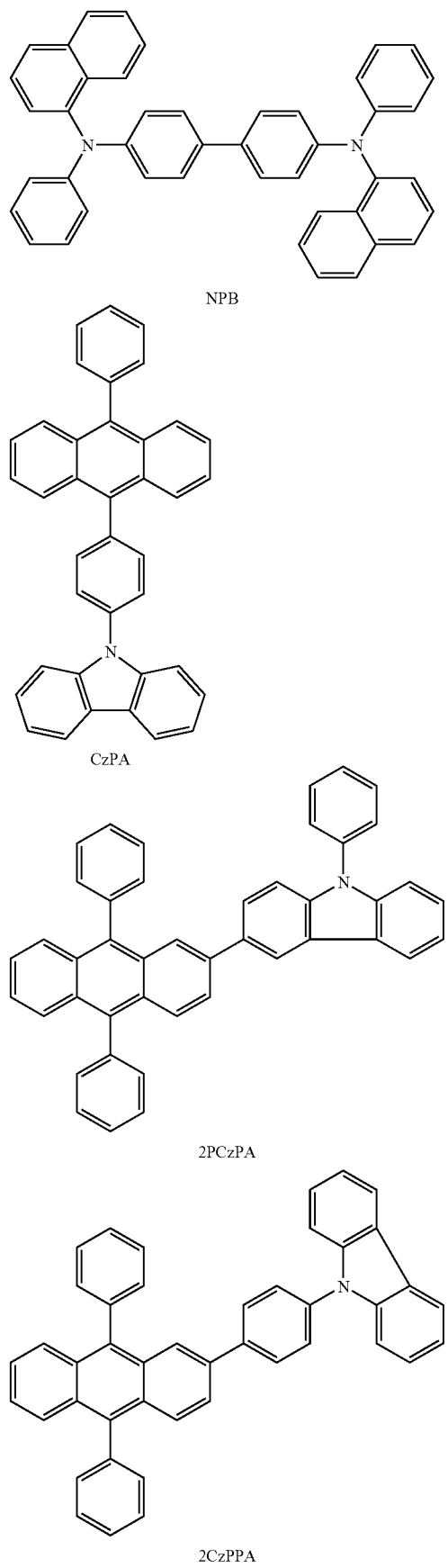 [SMILES: c1ccc(N(c2ccc(-c3ccc(N(c4ccccc4)c4cccc5ccccc45)cc3)cc2)c2cccc3ccccc23)cc1 ; "NPB" ; c1ccc(-c2c3ccccc3c(-c3ccc(-n4c5ccccc5c5ccccc54)cc3)c3ccccc23)cc1 ; c1ccc(-c2c3ccccc3c(-c3ccccc3)c3cc(-c4ccc5c(c4)c4ccccc4n5-c4ccccc4)ccc23)cc1 ; c1ccc(-c2c3ccccc3c(-c3ccccc3)c3cc(-c4ccc(-n5c6ccccc6c6ccccc65)cc4)ccc23)cc1]

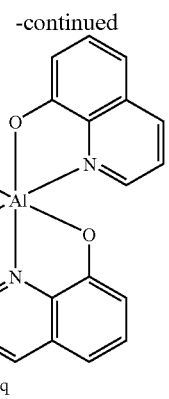

Alq

Hereinafter, a method of fabricating light-emitting elements of Example 3 is described.

(Light-Emitting Element 1)

First, a film of indium tin oxide containing silicon oxide (ITSO) was formed on a glass substrate 2101 by a sputtering method, whereby a first electrode 2102 was formed. Note that the thickness of the first electrode 2102 was set to 110 nm and the area of the electrode was set to 2 mm×2 mm.

Next, the substrate provided with the first electrode was fixed to a substrate holder provided in a vacuum evaporation apparatus such that the surface on which the first electrode 2102 was formed faced downward. After the pressure in a film formation chamber was reduced to approximately $10^{-4}$ Pa, 4,4'-bis[N-(1-naphthyl)-N-phenylamino]biphenyl (abbreviation: NPB) and molybdenum(VI) oxide were co-evaporated on the first electrode 2102, whereby a layer 2111 including a composite material of an organic compound and an inorganic compound was formed. The thickness of the layer 2111 was set to 50 nm and the mass ratio of NPB to molybdenum(VI) oxide was adjusted so as to be 4:1 (=NPB:molybdenum oxide). Note that a co-evaporation method refers to an evaporation method by which evaporation is conducted from a plurality of evaporation sources at the same time in one treatment chamber.

Next, a 10-nm-thick film of 4,4'-bis[N-(1-naphthyl)-N-phenylamino]biphenyl (abbreviation: NPB) was formed on the layer 2111 including a composite material by an evaporation method with resistance heating, whereby a hole-transporting layer 2112 was formed.

Furthermore, 9-[4-(10-phenyl-9-anthryl)phenyl]-9H-carbazole (abbreviation: CzPA) and 3-(9,10-diphenyl-2-anthryl)-9-phenyl-9H-carbazole (abbreviation: 2PCzPA) represented by the structural formula (101), which was one of the anthracene derivatives of the present invention, were co-evaporated on the hole-transporting layer 2112, whereby a 30-nm-thick light-emitting layer 2113 was formed. Here, the mass ratio of CzPA to 2PCzPA was adjusted to be 1:0.1 (=CzPA:2PCzPA).

Then, a 10-nm-thick film of tris(8-quinolinolato)aluminum(III) (abbreviation: Alq) was formed on the light-emitting layer 2113 by an evaporation method with resistance heating, whereby an electron-transporting layer 2114 was formed.

Furthermore, tris(8-quinolinolato)aluminum(II) (abbreviation: Alq) and lithium (Li) were co-evaporated on the electron-transporting layer 2114, whereby a 20-nm-thick electron-injecting layer 2115 was formed. Here, the mass ratio of Alq to Li was adjusted to be 1:0.01 (=Alq:Li).

Lastly, a 200-nm-thick aluminum film was formed on the electron-injecting layer 2115 by an evaporation method with resistance heating, whereby a second electrode 2104 was formed. Thus, a light-emitting element 1 was fabricated.

(Light-Emitting Element 2)

A light-emitting element 2 was fabricated in a manner similar to that of the light-emitting element 1 by using the same kind of substrate as the light-emitting element 1 and 9-[4-(9,10-diphenyl-2-anthryl)phenyl]-9H-carbazole (abbreviation: 2CzPPA) represented by the structural formula (201), which was one of the anthracene derivatives of the present invention, instead of 2PCzPA. That is, by co-evaporation of 9-[4-(10-phenyl-9-anthryl)phenyl]-9H-carbazole (abbreviation: CzPA) and 9-[4-(9,10-diphenyl-2-anthryl)phenyl]-9H-carbazole (abbreviation: 2CzPPA) represented by the structural formula (201), which was the anthracene derivative of the present invention, the 30-nm-thick light-emitting layer 2113 was formed on the hole-transporting layer 2112. Here, the mass ratio of CzPA to 2CzPPA was adjusted to be 1:0.1 (=CzPA:2CzPPA). The layers other than the light-emitting layer 2113 were formed in a manner similar to those of the light-emitting element 1.

The thus obtained light-emitting elements 1 and 2 were sealed in a glove box containing a nitrogen atmosphere so as not to be exposed to air. Then, operation characteristics of these light-emitting elements were measured. Note that the measurement was carried out at room temperature (in the atmosphere kept at 25° C.).

Figure 28:
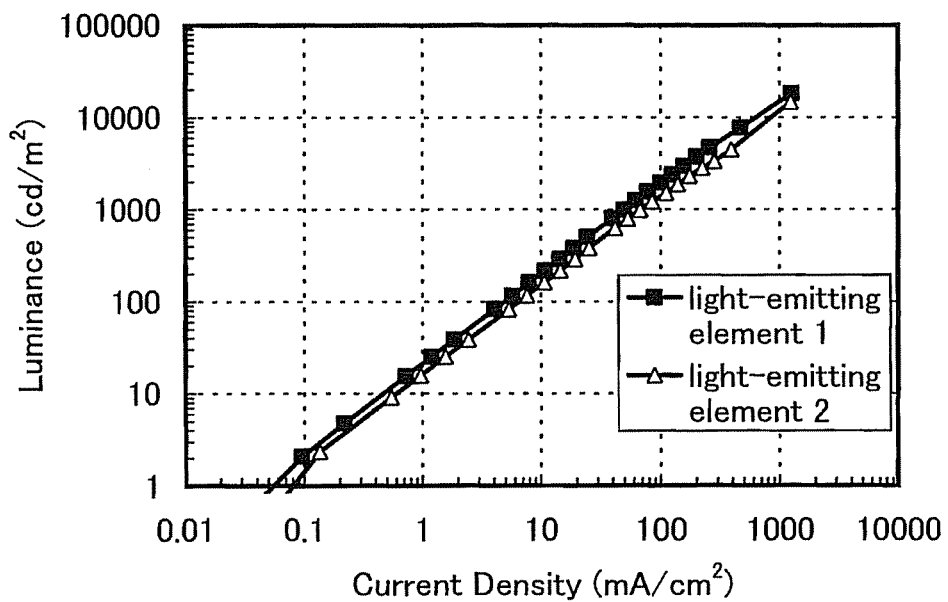
FIG. 28 shows the current density vs. luminance characteristics of light-emitting elements fabricated in Example 3.
Figure 29:
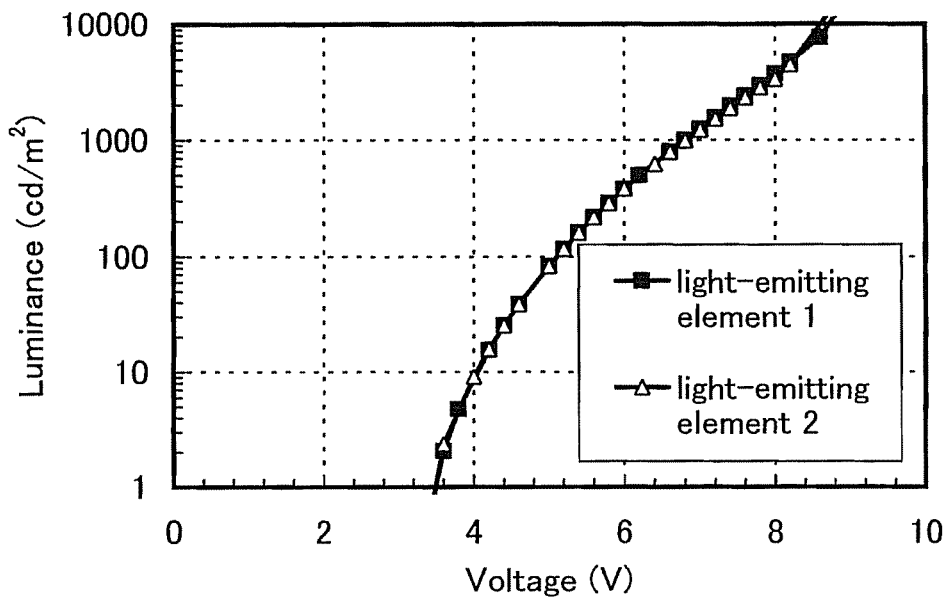
FIG. 29 shows the voltage vs. luminance characteristics of the light-emitting elements fabricated in Example 3.
Figure 30:
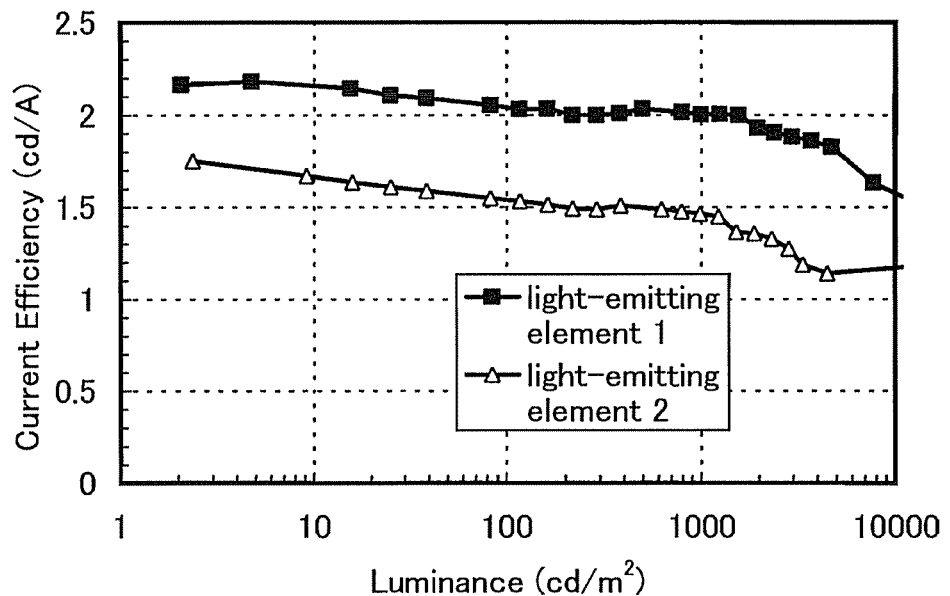
FIG. 30 shows the luminance vs. current efficiency characteristics of the light-emitting elements fabricated in Example 3.
Figure 31:
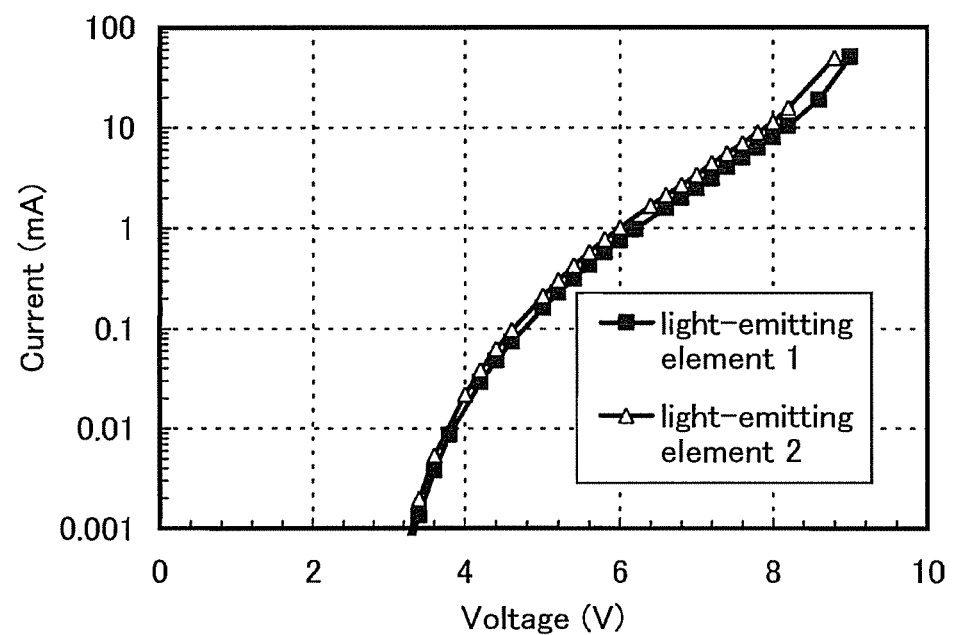
FIG. 31 shows the voltage vs. current characteristics of the light-emitting elements fabricated in Example 3.

FIG. 28 shows the current density vs. luminance characteristics of the light-emitting elements 1 and 2. FIG. 29 shows the voltage vs. luminance characteristics of the light-emitting elements 1 and 2. FIG. 30 shows the luminance vs. current efficiency characteristics of the light-emitting elements 1 and 2. FIG. 31 shows the voltage vs. current characteristics of the light-emitting elements 1 and 2.

Figure 32:
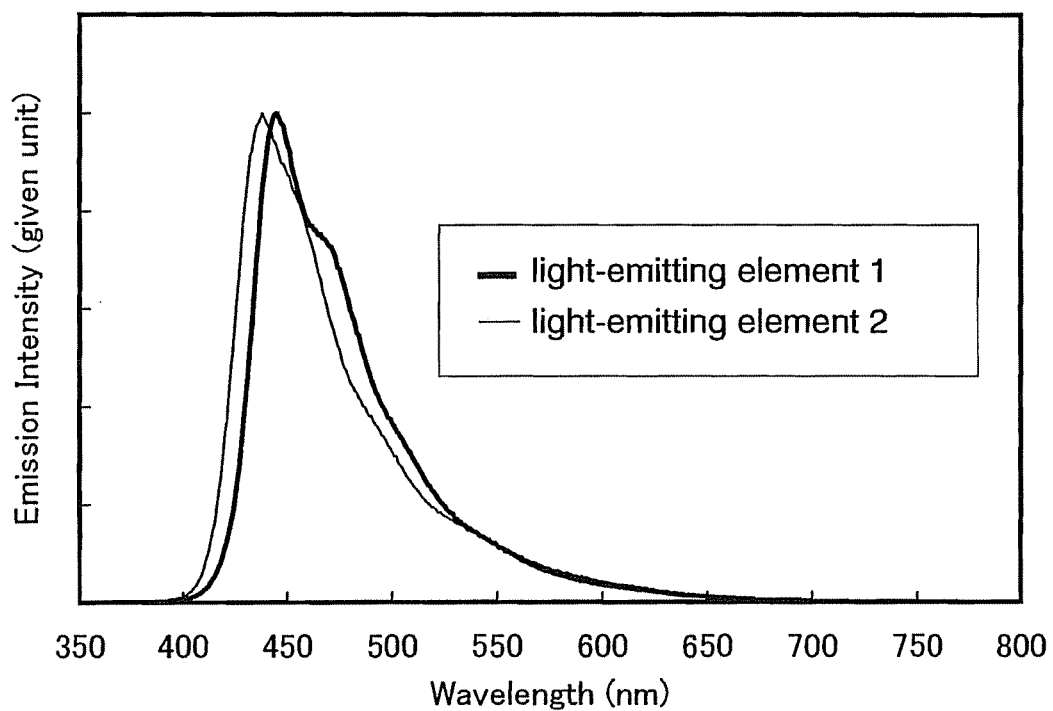
FIG. 32 shows emission spectra of the light-emitting elements fabricated in Example 3.

Further, FIG. 32 shows the emission spectra of the light-emitting elements 1 and 2 at a current of 1 mA. As apparent from FIG. 32, light emission from the light-emitting element 1 was from 2PCzPA. Further, light emission from the light-emitting element 2 was from 2CzPPA.

The CIE chromaticity coordinates of the light-emitting element 1 at a luminance of 800 cd/m$^2$ were (x=0.16, y=0.13), and blue light emission with high color purity was exhibited. Further, at a luminance of 800 cd/m$^2$, the current efficiency of the light-emitting element 1 was 2.0 cd/A, and the external quantum efficiency thereof was 1.8%. Furthermore, at a luminance of 800 cd/m$^2$, the voltage, current density, and power efficiency of the light-emitting element 1 were 6.6 V, 39.5 mA/cm$^2$, and 1.0 lm/W, respectively.

The CIE chromaticity coordinates of the light-emitting element 2 at a luminance of 990 cd/m$^2$ were (x=0.16, y=0.11), and blue light emission with high color purity was exhibited. Further, at a luminance of 990 cd/m$^2$, the current efficiency of the light-emitting element 2 was 1.5 cd/A, and the external quantum efficiency thereof was 1.4%. Furthermore, at a luminance of 990 cd/m$^2$, the voltage, current density, and power efficiency of the light-emitting element 2 were 6.8 V, 67.3 mA/cm$^2$, and 0.68 lm/W, respectively.

Thus, the light-emitting element 1 and the light-emitting element 2 each emit blue light with high color purity. Therefore, by using the anthracene derivative of the present invention as a light-emitting substance of a light-emitting layer, a light-emitting element that emits blue light with high color purity can be obtained.

Example 4

In Example 4, light-emitting elements of the present invention will be described using FIG. 27. Structural formulae of materials used in Example 4 are illustrated below. Note that the structural formulae of the materials which have already been illustrated are omitted.

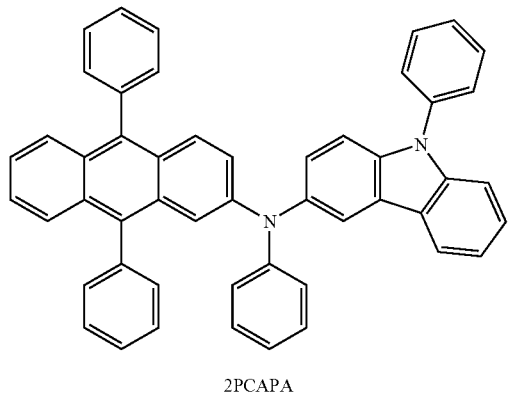 [SMILES: c1ccc(-c2c3ccccc3c(-c3ccccc3)c3cc(N(c4ccccc4)c4ccc5c(c4)c4ccccc4n5-c4ccccc4)ccc23)cc1]

2PCAPA

Hereinafter, a method of fabricating light-emitting elements of Example 4 is described.

(Light-Emitting Element 3)

First, a film of indium tin oxide containing silicon oxide (ITSO) was formed on the glass substrate 2101 by a sputtering method, whereby the first electrode 2102 was formed. Note that the thickness of the first electrode 2102 was set to 110 nm and the area of the electrode was set to 2 mm×2 mm.

Next, the substrate provided with the first electrode was fixed to a substrate holder provided in a vacuum evaporation apparatus such that the surface on which the first electrode 2102 was formed faced downward. After the pressure in a film formation chamber was reduced to approximately $10^{-4}$ Pa, 4,4'-bis[N-(1-naphthyl)-N-phenylamino]biphenyl (abbreviation: NPB) and molybdenum(VI) oxide were co-evaporated on the first electrode 2102, whereby the layer 2111 including a composite material of an organic compound and an inorganic compound was formed. The thickness of the layer 2111 was set to 50 nm and the mass ratio of NPB to molybdenum (VI) oxide was adjusted so as to be 4:1 (=NPB:molybdenum oxide). Note that a co-evaporation method refers to an evaporation method by which evaporation is conducted from a plurality of evaporation sources at the same time in one treatment chamber.

Next, a 10-nm-thick film of 4,4'-bis[N-(1-naphthyl)-N-phenylamino]biphenyl (abbreviation: NPB) was formed on the layer 2111 including a composite material by an evaporation method with resistance heating, whereby the hole-transporting layer 2112 was formed.

Furthermore, 3-(9,10-diphenyl-2-anthryl)-9-phenyl-9H-carbazole (abbreviation: 2PCzPA) represented by the structural formula (101), which was one of the anthracene derivatives of the present invention, and N-(9,10-diphenyl-2-anthryl)-N,9-diphenyl-9H-carbazol-3-amine (abbreviation: 2PCAPA) were co-evaporated on the hole-transporting layer 2112, whereby the 40-nm-thick light-emitting layer 2113 was formed. Here, the mass ratio of 2PCzPA to 2PCAPA was adjusted to be 1:0.05 (=2PCzPA:2PCAPA).

Then, a 30-nm-thick film of tris(8-quinolinolato)aluminum(III) (abbreviation: Alq) was formed on the light-emitting layer 2113 by an evaporation method with resistance heating, whereby the electron-transporting layer 2114 was formed.

Furthermore, a 1-nm-thick lithium fluoride film was formed on the electron-transporting layer 2114 by an evaporation method with resistance heating, whereby the electron-injecting layer 2115 was formed.

Lastly, a 200-nm-thick aluminum film was formed on the electron-injecting layer 2115 by an evaporation method with resistance heating, whereby the second electrode 2104 was formed. Thus, a light-emitting element 3 was fabricated.

(Light-Emitting Element 4)

A light-emitting element 4 was fabricated in a manner similar to that of the light-emitting element 3 by using the same kind of substrate as the light-emitting element 3 and 9-[4-(9,10-diphenyl-2-anthryl)phenyl]-9H-carbazole (abbreviation: 2CzPPA) represented by the structural formula (201), which was one of the anthracene derivatives of the present invention, instead of 2PCzPA. That is, by co-evaporation of 9-[4-(9,10-diphenyl-2-anthryl)phenyl]-9H-carbazole (abbreviation: 2CzPPA) represented by the structural formula (201), which was the anthracene derivative of the present invention, and N-(9,10-diphenyl-2-anthryl)-N,9-diphenyl-9H-carbazol-3-amine (abbreviation: 2PCAPA), the 40-nm-thick light-emitting layer 2113 was formed on the hole-transporting layer 2112. Here, the mass ratio of 2CzPPA to 2PCAPA was adjusted to be 1:0.05 (=2CzPPA:2PCAPA). The layers other than the light-emitting layer 2113 were formed in a manner similar to those of the light-emitting element 3.

The thus obtained light-emitting elements 3 and 4 were sealed in a glove box containing a nitrogen atmosphere so as not to be exposed to air. Then, operation characteristics of these light-emitting elements were measured. Note that the measurement was carried out at room temperature (in the atmosphere kept at 25° C.).

Figure 33:
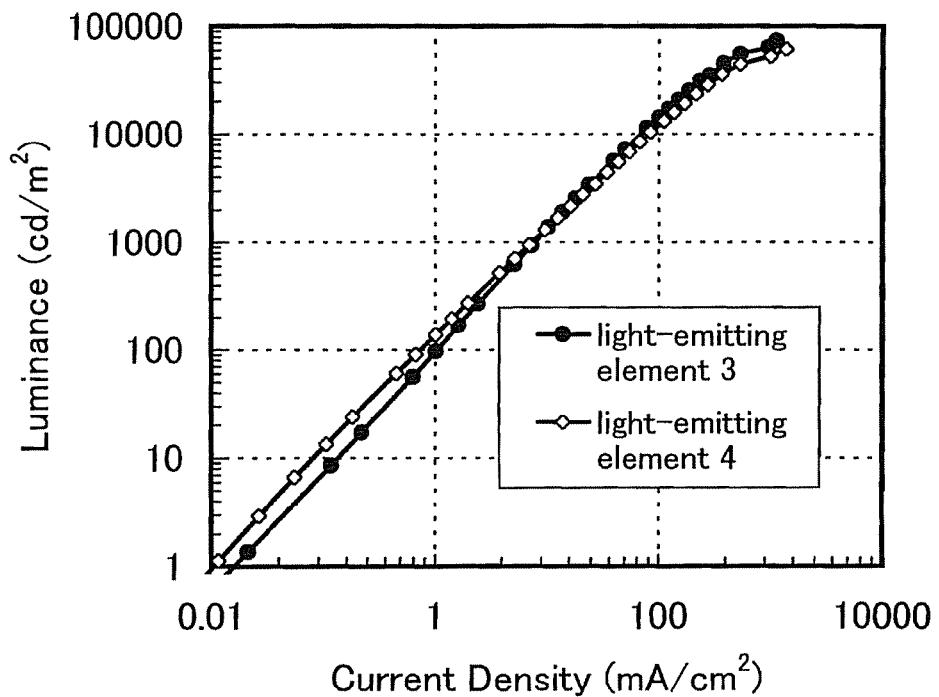
FIG. 33 shows the current density vs. luminance characteristics of light-emitting elements fabricated in Example 4.
Figure 34:
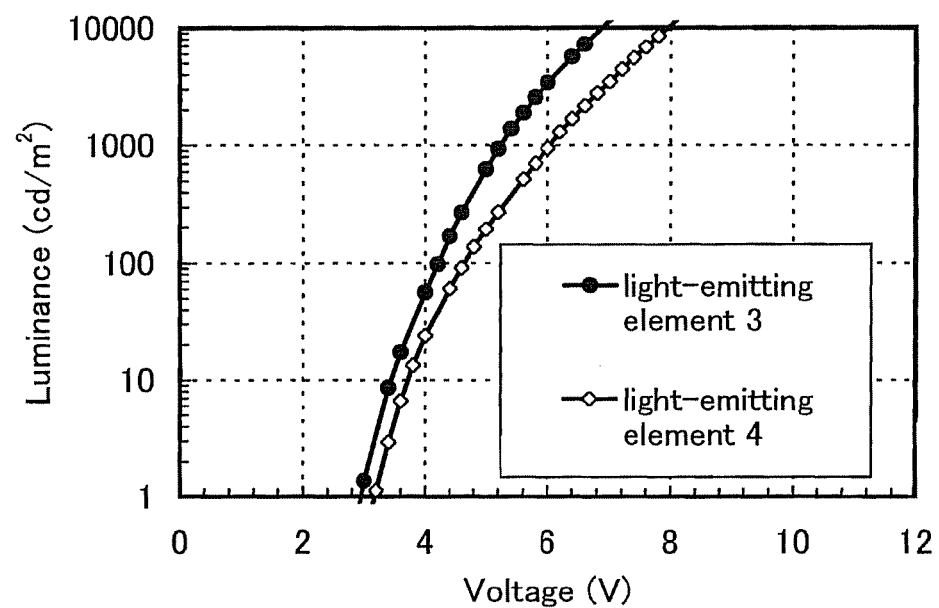
FIG. 34 shows the voltage vs. luminance characteristics of the light-emitting elements fabricated in Example 4.
Figure 35:
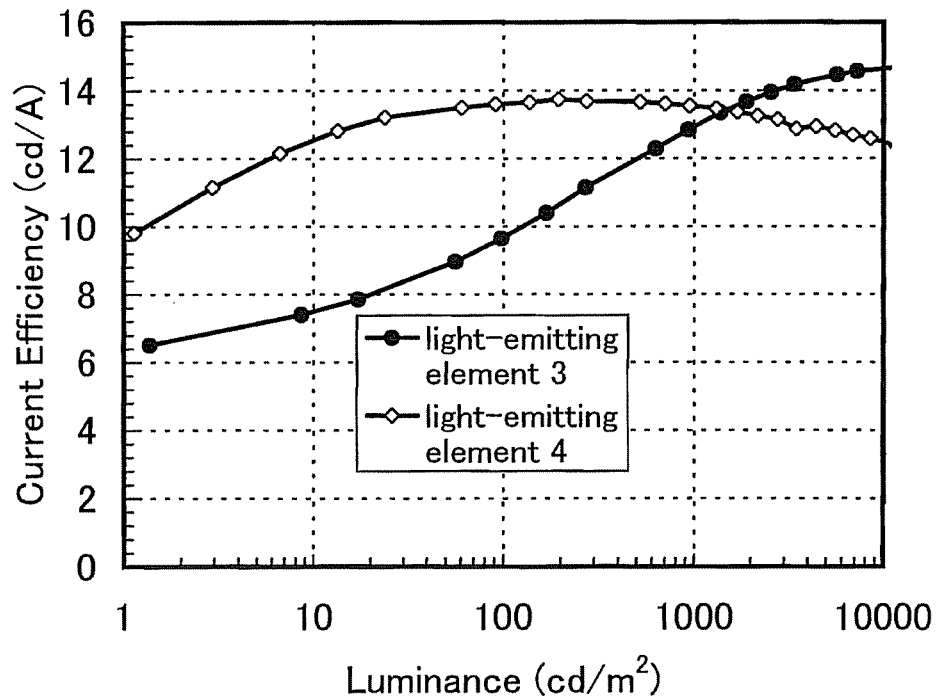
FIG. 35 shows the luminance vs. current efficiency characteristics of the light-emitting elements fabricated in Example 4.
Figure 36:
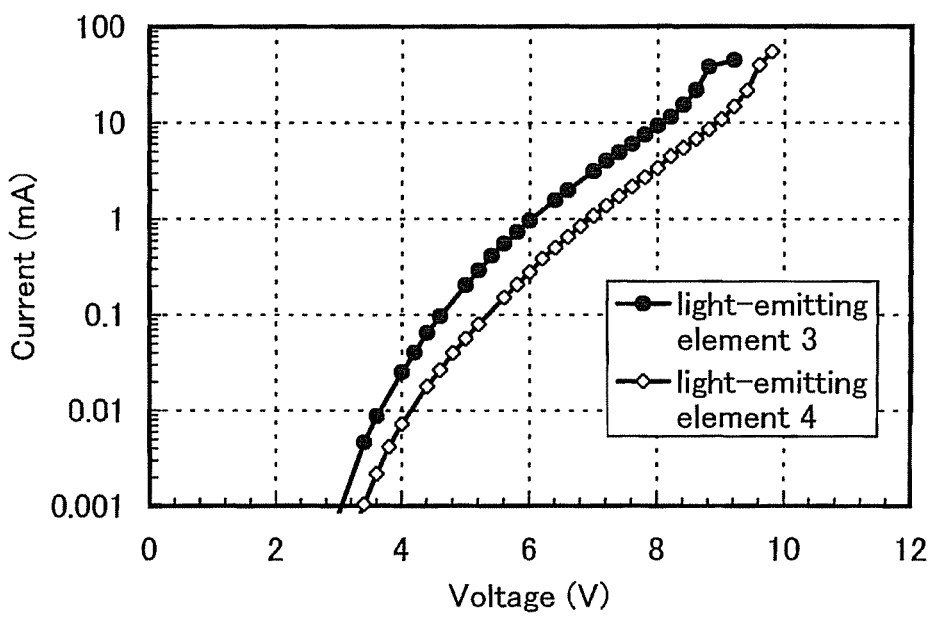
FIG. 36 shows the voltage vs. current characteristics of the light-emitting elements fabricated in Example 4.

FIG. 33 shows the current density vs. luminance characteristics of the light-emitting elements 3 and 4. FIG. 34 shows the voltage vs. luminance characteristics of the light-emitting elements 3 and 4. FIG. 35 shows the luminance vs. current efficiency characteristics of the light-emitting elements 3 and 4. FIG. 36 shows the voltage vs. current characteristics of the light-emitting elements 3 and 4.

Figure 37:
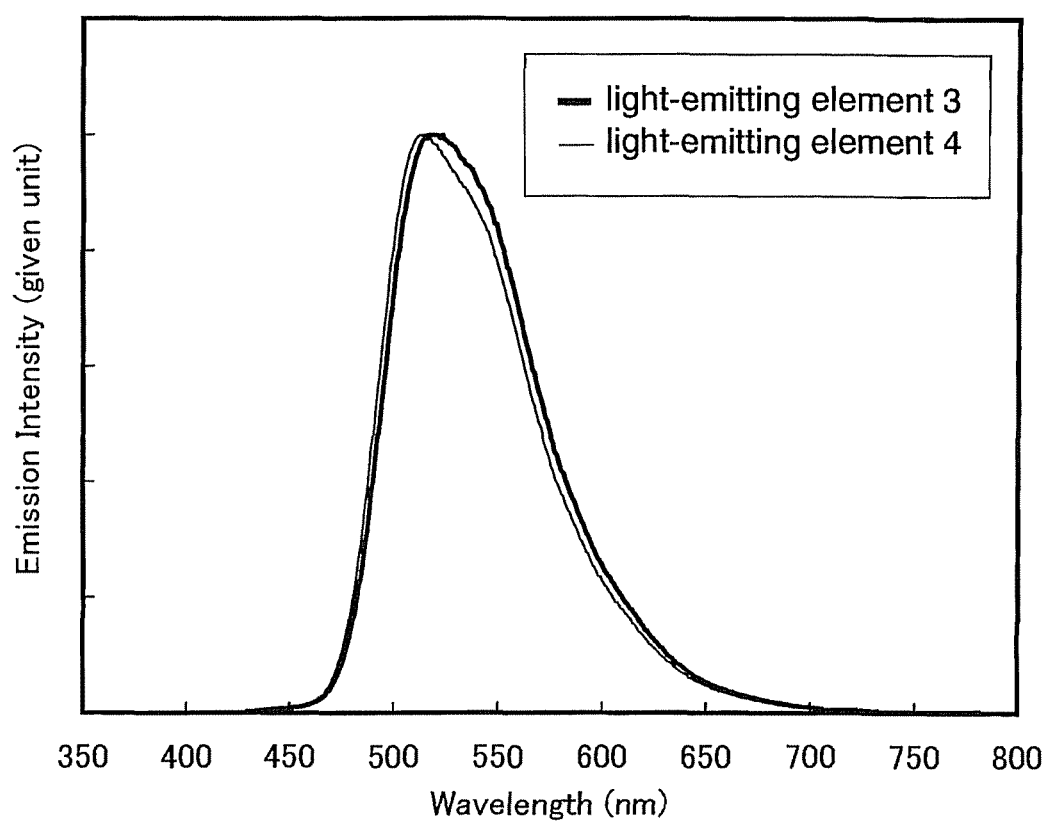
FIG. 37 shows emission spectra of the light-emitting elements fabricated in Example 4.

Further, FIG. 37 shows the emission spectra of the light-emitting elements 3 and 4 at a current of 1 mA. As apparent from FIG. 37, light emission from each of the light-emitting elements 3 and 4 were from 2PCAPA.

The CIE chromaticity coordinates of the light-emitting element 3 at a luminance of 3400 cd/m$^2$ were (x=0.30, y=0.62), and green light emission was exhibited. Further, at a luminance of 3400 cd/m$^2$, the current efficiency of the light-emitting element 3 was 14.2 cd/A. Furthermore, at a luminance of 3400 cd/m$^2$, the voltage, current density, and power efficiency of the light-emitting element 3 were 6.0 V, 24.0 mA/cm$^2$, and 7.4 lm/W, respectively.

The CIE chromaticity coordinates of the light-emitting element 4 at a luminance of 2800 cd/m$^2$ were (x, y)=(0.29, 0.62), and green light emission was exhibited. Further, at a luminance of 2800 cd/m$^2$, the current efficiency of the light-emitting element 4 was 13.2 cd/A. Furthermore, at a luminance of 2800 cd/m$^2$, the voltage, current density, and power efficiency of the light-emitting element 4 were 6.8 V, 21.0 mA/cm$^2$, and 6.1 lm/W, respectively.

Figure 38:
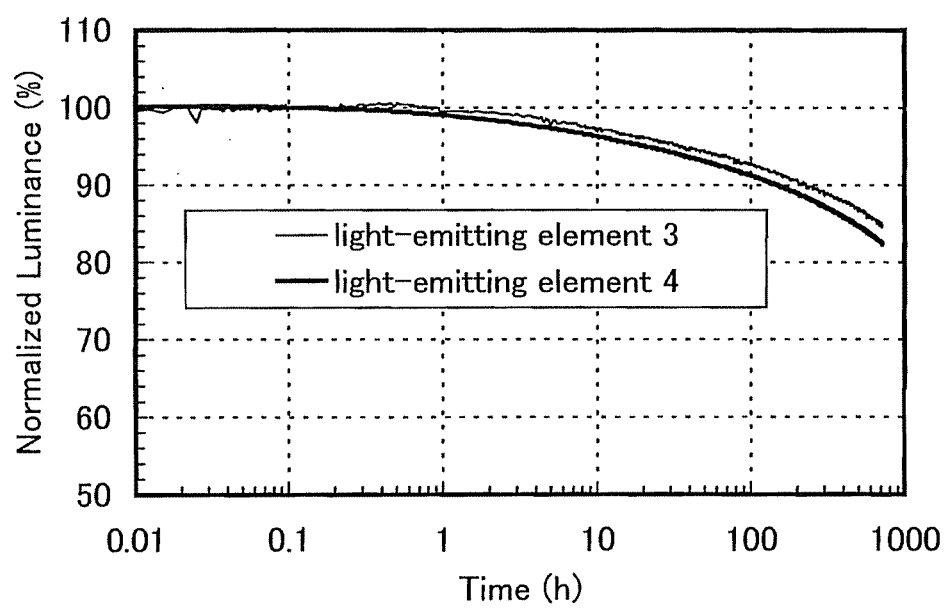
FIG. 38 shows a change in luminance with respect to driving time of the light-emitting elements fabricated in Example 4.

Further, FIG. 38 shows the results of continuous lighting tests in which the light-emitting elements 3 and 4 were continuously lit by constant current driving with the initial luminance thereof set to 3000 cd/m$^2$ (the vertical axis represents normalized luminance on condition that 3000 cd/m$^2$ was 100%). As can be seen from FIG. 38, the light-emitting elements 3 and 4 kept 85% and 82% of the initial luminance, respectively, after 710 hours. Therefore, it is understood that the light-emitting elements of the present invention have a long lifetime.

Thus, by using any of the anthracene derivatives of the present invention as a host material of the light-emitting layer, a light-emitting element with a long lifetime can be obtained.

Example 5

In Example 5, light-emitting elements of the present invention will be described using FIG. 27. Structural formulae of materials used in Example 5 are illustrated below. Note that the structural formulae of the materials which have already been illustrated are omitted.

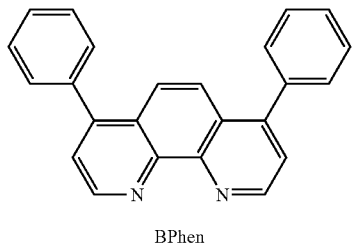 [SMILES: c1ccc(-c2ccnc3c2ccc2c(-c4ccccc4)ccnc23)cc1]

BPhen

Hereinafter, a method of fabricating light-emitting elements of Example 5 is described.
(Light-Emitting Element 5)

First, a film of indium tin oxide containing silicon oxide (ITSO) was formed on a glass substrate 2101 by a sputtering method, whereby a first electrode 2102 was formed. Note that the thickness of the first electrode 2102 was set to 110 nm and the area of the electrode was set to 2 mm×2 mm.

Next, the substrate provided with the first electrode was fixed to a substrate holder provided in a vacuum evaporation apparatus such that the surface on which the first electrode 2102 was formed faced downward. After the pressure in a film formation chamber was reduced to approximately $10^{-4}$ Pa, 4,4'-bis[N-(1-naphthyl)-N-phenylamino]biphenyl (abbreviation: NPB) and molybdenum(VI) oxide were co-evaporated on the first electrode 2102, whereby a layer 2111 including a composite material of an organic compound and an inorganic compound was formed. The thickness of the layer 2111 was set to 50 nm and the mass ratio of NPB to molybdenum(VI) oxide was adjusted so as to be 4:1 (=NPB:molybdenum oxide). Note that a co-evaporation method refers to an evaporation method by which evaporation is conducted from a plurality of evaporation sources at the same time in one treatment chamber.

Next, a 10-nm-thick film of 4,4'-bis[N-(1-naphthyl)-N-phenylamino]biphenyl (abbreviation: NPB) was formed on the layer 2111 including a composite material by an evaporation method with resistance heating, whereby the hole-transporting layer 2112 was formed.

Furthermore, 3-(9,10-diphenyl-2-anthryl)-9-phenyl-9H-carbazole (abbreviation: 2PCzPA) represented by the structural formula (101), which was one of the anthracene derivatives of the present invention, and N-(9,10-diphenyl-2-anthryl)-N,9-diphenyl-9H-carbazol-3-amine (abbreviation: 2PCAPA) were co-evaporated on the hole-transporting layer 2112, whereby the 40-nm-thick light-emitting layer 2113 was formed. Here, the mass ratio of 2PCzPA to 2PCAPA was adjusted to be 1:0.05 (=2PCzPA:2PCAPA).

Then, a 30-nm-thick film of bathophenanthroline (abbreviation: BPhen) was formed on the light-emitting layer 2113 by an evaporation method with resistance heating, whereby the electron-transporting layer 2114 was formed.

Then, a 1-nm-thick lithium fluoride film was formed on the electron-transporting layer 2114 by an evaporation method with resistance heating, whereby the electron-injecting layer 2115 was formed.

Lastly, a 200-nm-thick aluminum film was formed on the electron-injecting layer 2115 by an evaporation method with resistance heating, whereby the second electrode 2104 was formed. Thus, a light-emitting element 5 was fabricated.
(Light-Emitting Element 6)

A light-emitting element 6 was fabricated in a manner similar to that of the light-emitting element 5 by using the same kind of substrate as the light-emitting element 5 and 9-[4-(9,10-diphenyl-2-anthryl)phenyl]-9H-carbazole (abbreviation: 2CzPPA) represented by the structural formula (201), which was one of the anthracene derivatives of the present invention, instead of 2PCzPA. That is, by co-evaporation of 9-[4-(9,10-diphenyl-2-anthryl)phenyl]-9H-carbazole (abbreviation: 2CzPPA) represented by the structural formula (201), which was the anthracene derivative of the present invention, and N-(9,10-diphenyl-2-anthryl)-N,9-diphenyl-9H-carbazol-3-amine (abbreviation: 2PCAPA), the 40-nm-thick light-emitting layer 2113 was formed on the hole-transporting layer 2112. Here, the mass ratio of 2CzPPA to 2PCAPA was adjusted to be 1:0.05 (=2CzPPA:2PCAPA). The layers other than the light-emitting layer 2113 were formed in a manner similar to those of the light-emitting element 5.

The thus obtained light-emitting elements 5 and 6 were sealed in a glove box containing a nitrogen atmosphere so as not to be exposed to air. Then, operation characteristics of these light-emitting elements were measured. Note that the measurement was carried out at room temperature (in the atmosphere kept at 25° C.).

Figure 39:
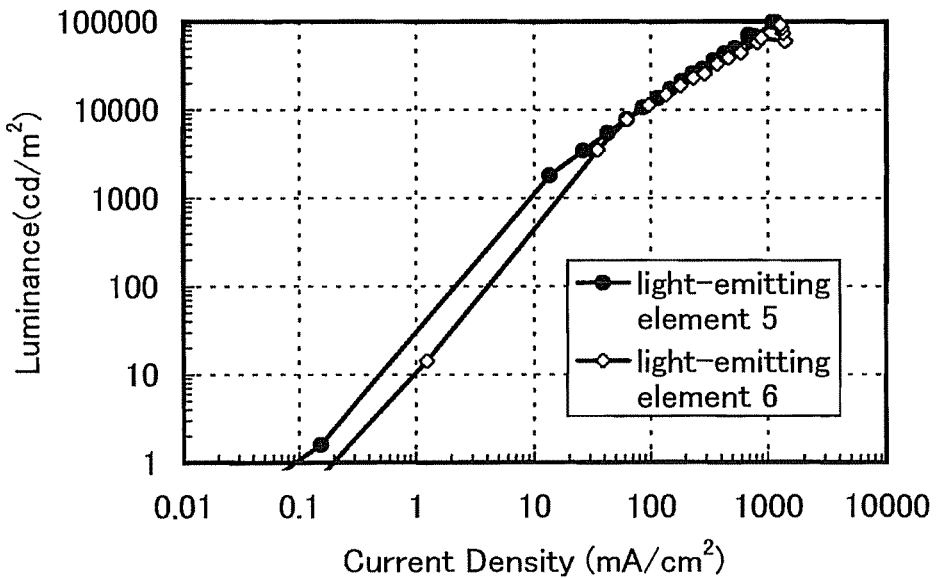
FIG. 39 shows the current density vs. luminance characteristics of light-emitting elements fabricated in Example 5.
Figure 40:
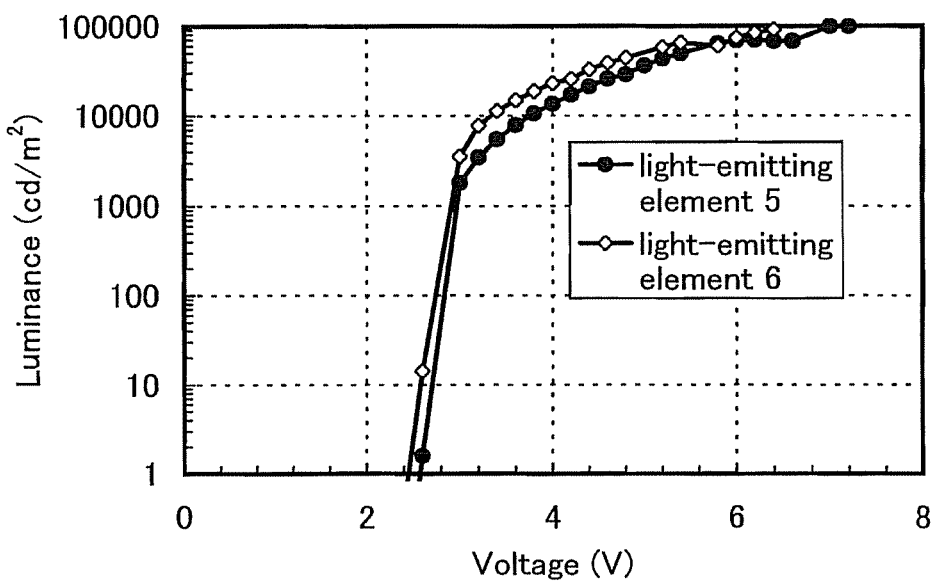
FIG. 40 shows the voltage vs. luminance characteristics of the light-emitting elements fabricated in Example 5.
Figure 41:
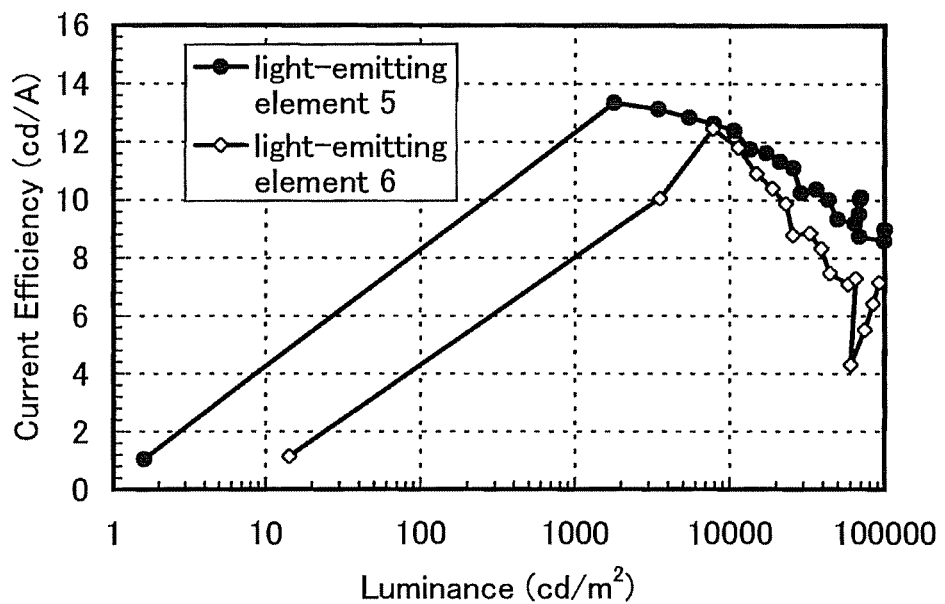
FIG. 41 shows the luminance vs. current efficiency characteristics of the light-emitting elements fabricated in Example 5.
Figure 42:
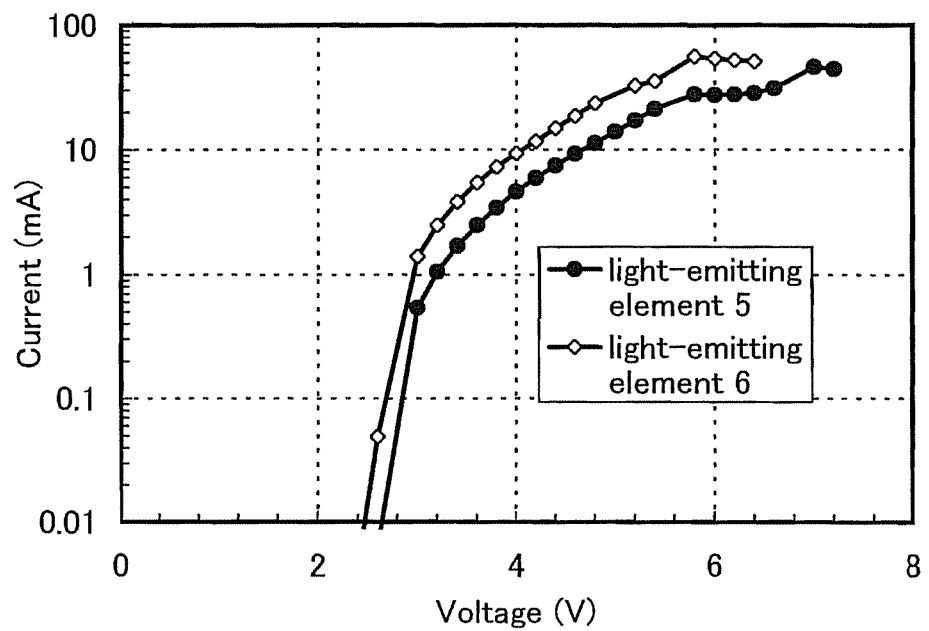
FIG. 42 shows the voltage vs. current characteristics of the light-emitting elements fabricated in Example 5.

FIG. 39 shows the current density vs. luminance characteristics of the light-emitting elements 5 and 6. FIG. 40 shows the voltage vs. luminance characteristics of the light-emitting elements 5 and 6. FIG. 41 shows the luminance vs. current efficiency characteristics of the light-emitting elements 5 and 6. FIG. 42 shows the voltage vs. current characteristics of the light-emitting elements 5 and 6.

Figure 43:
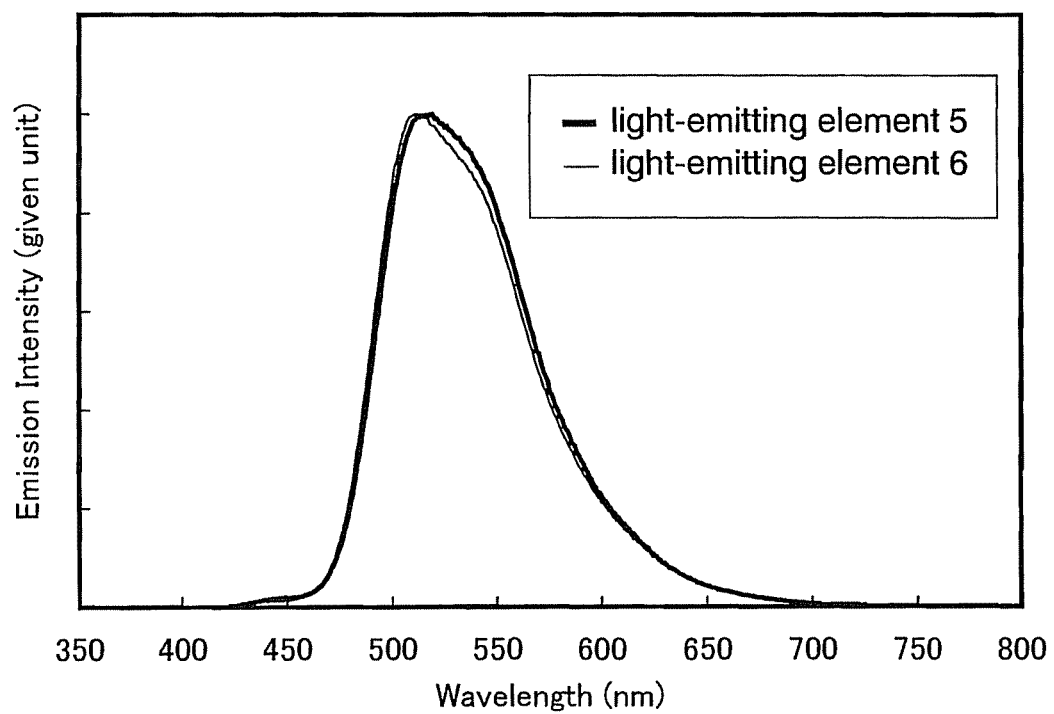
FIG. 43 shows emission spectra of the light-emitting elements fabricated in Example 5.

Further, FIG. 43 shows the emission spectra of the light-emitting elements 5 and 6 at a current of 1 mA. As apparent from FIG. 43, light emission from each of the light-emitting elements 5 and 6 were from 2PCAPA.

The CIE chromaticity coordinates of the light-emitting element 5 at a luminance of 3500 cd/m$^2$ were (x=0.28, y=0.61), and green light emission was exhibited. Further, at a luminance of 3500 cd/m$^2$, the current efficiency of the light-emitting element 5 was 13.1 cd/A. Furthermore, at a luminance of 3500 cd/m$^2$, the voltage, current density, and power efficiency of the light-emitting element 5 were 3.2 V, 26.3 mA/cm$^2$, and 12.9 lm/W, respectively.

The CIE chromaticity coordinates of the light-emitting element 6 at a luminance of 3500 cd/m$^2$ were (x=0.28, y=0.61), and green light emission was exhibited. Further, at a luminance of 3500 cd/m$^2$, the current efficiency of the light-emitting element 6 was 10.1 cd/A. Furthermore, at a luminance of 3500 cd/m$^2$, the voltage, current density, and power efficiency of the light-emitting element 6 were 3.0 V, 35.0 mA/cm$^2$, and 10.5 lm/W, respectively.

Figure 44:
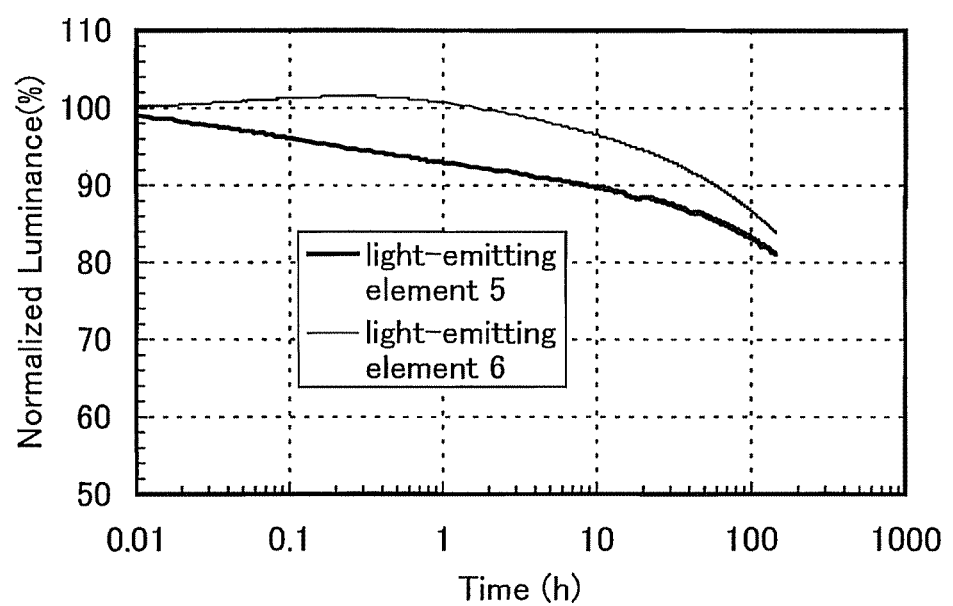
FIG. 44 shows a change in luminance with respect to driving time of the light-emitting elements fabricated in Example 5.

Further, FIG. 44 shows the results of continuous lighting tests in which the light-emitting elements 5 and 6 were continuously lit by constant current driving with the initial luminance thereof set to 3000 cd/m$^2$ (the vertical axis represents normalized luminance on condition that 3000 cd/m$^2$ was 100%). As can be seen from FIG. 44, the light-emitting elements 5 and 6 kept 81% and 84% of the initial luminance, respectively, after 140 hours. Therefore, it is understood that the light-emitting elements of the present invention have a long lifetime.

Thus, by using any of the anthracene derivatives of the present invention as a host material of the light-emitting layer, a light-emitting element with a long lifetime can be obtained.

Example 6

Figure 45:
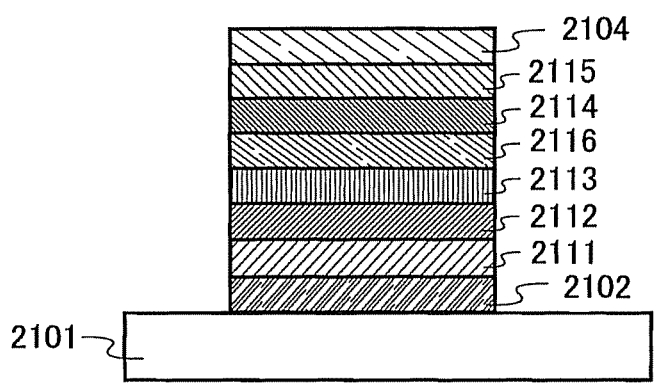
FIG. 45 illustrates a light-emitting element of Examples.

In Example 6, light-emitting elements of the present invention will be described using FIG. 45. Structural formulae of materials used in Example 6 are illustrated below. Note that the structural formulae of the materials which have already been illustrated are omitted.

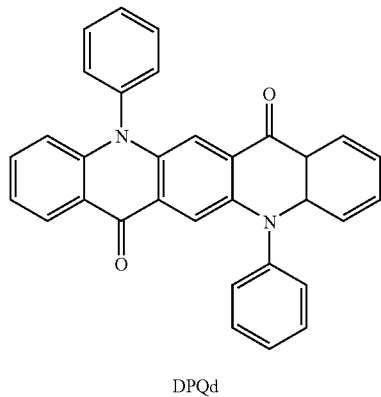 [SMILES: O=C1c2cc3c(cc2N(c2ccccc2)C2C=CC=CC12)c(=O)c1ccccc1n3-c1ccccc1]

DPQd

Hereinafter, a method of fabricating light-emitting elements of Example 6 is described.
(Light-Emitting Element 7)

First, a film of indium tin oxide containing silicon oxide (ITSO) was formed on the glass substrate 2101 by a sputtering method, whereby the first electrode 2102 was formed. Note that the thickness of the first electrode 2102 was set to 110 nm and the area of the electrode was set to 2 mm×2 mm.

Next, the substrate provided with the first electrode was fixed to a substrate holder provided in a vacuum evaporation apparatus such that the surface on which the first electrode 2102 was formed faced downward. After the pressure in a film formation chamber was reduced to approximately $10^{-4}$ Pa, 4,4'-bis[N-(1-naphthyl)-N-phenylamino]biphenyl (abbreviation: NPB) and molybdenum(VI) oxide were co-evaporated on the first electrode 2102, whereby the layer 2111 including a composite material of an organic compound and an inorganic compound was formed. The thickness of the layer 2111 was set to 50 nm and the mass ratio of NPB to molybdenum (VI) oxide was adjusted so as to be 4:1 (=NPB:molybdenum oxide). Note that a co-evaporation method refers to an evaporation method by which evaporation is conducted from a plurality of evaporation sources at the same time in one treatment chamber.

Next, a 10-nm-thick film of 4,4'-bis[N-(1-naphthyl)-N-phenylamino]biphenyl (abbreviation: NPB) was formed on the layer 2111 including a composite material by an evaporation method with resistance heating, whereby the hole-transporting layer 2112 was formed.

Furthermore, 3-(9,10-diphenyl-2-anthryl)-9-phenyl-9H-carbazole (abbreviation: 2PCzPA) represented by the structural formula (101), which was one of the anthracene derivatives of the present invention, and N-(9,10-diphenyl-2-anthryl)-N,9-diphenyl-9H-carbazol-3-amine (abbreviation: 2PCAPA) were co-evaporated on the hole-transporting layer 2112, whereby the 30-nm-thick light-emitting layer 2113 was formed. Here, the mass ratio of 2PCzPA to 2PCAPA was adjusted to be 1:0.05 (=2PCzPA:2PCAPA).

Furthermore, tris(8-quinolinolato)aluminum(III) (abbreviation: Alq) and N,N'-diphenylquinacridon (abbreviation: DPQd) were co-evaporated on the light-emitting layer 2113, whereby a 10 nm-thick functional layer 2116 for controlling transport of electrons was formed. Here, the mass ratio of Alq to DPQd was adjusted to be 1:0.005 (=Alq:DPQd).

Then, a 30-nm-thick bathophenanthroline (abbreviation: BPhen) film was formed on the functional layer 2116 by an evaporation method with resistance heating, whereby the electron-transporting layer 2114 was formed.

Furthermore, a 1-nm-thick lithium fluoride film was formed on the electron-transporting layer 2114, whereby the electron-injecting layer 2115 was formed.

Lastly, a 200-nm-thick aluminum film was formed on the electron-injecting layer 2115 by an evaporation method with resistance heating, whereby the second electrode 2104 was formed. Thus, a light-emitting element 7 was fabricated.
(Light-Emitting Element 8)

A light-emitting element 8 was fabricated in a manner similar to that of the light-emitting element 7 by using the same kind of substrate as the light-emitting element 7 and 9-[4-(9,10-diphenyl-2-anthryl)phenyl]-9H-carbazole (abbreviation: 2CzPPA) represented by the structural formula (201), which was one of the anthracene derivatives of the present invention, instead of 2PCzPA. That is, by co-evaporation of 9-[4-(9,10-diphenyl-2-anthryl)phenyl]-9H-carbazole (abbreviation: 2CzPPA) represented by the structural formula (201), which was the anthracene derivative of the present invention, and N-(9,10-diphenyl-2-anthryl)-N,9-diphenyl-9H-carbazol-3-amine (abbreviation: 2PCAPA), the 30-nm-thick light-emitting layer 2113 was formed on the hole-transporting layer 2112. Here, the mass ratio of 2CzPPA to 2PCAPA was adjusted to be 1:0.05 (=2CzPPA:2PCAPA). The layers other than the light-emitting layer 2113 were formed in a manner similar to those of the light-emitting element 7.

The thus obtained light-emitting elements 7 and 8 were sealed in a glove box containing a nitrogen atmosphere so as not to be exposed to air. Then, operation characteristics of these light-emitting elements were measured. Note that the measurement was carried out at room temperature (in the atmosphere kept at 25° C.).

Figure 46:
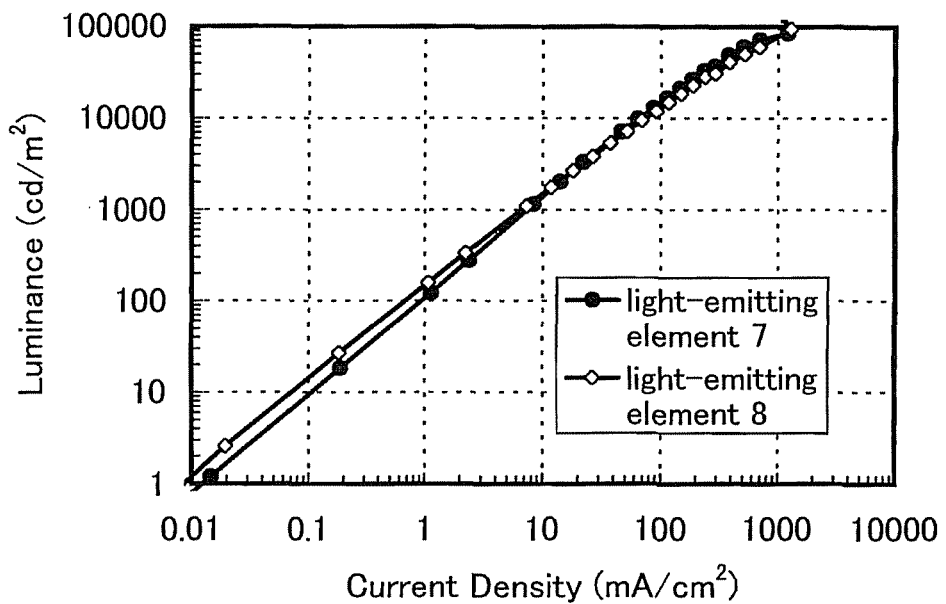
FIG. 46 shows the current density vs. luminance characteristics of light-emitting elements fabricated in Example 6.
Figure 47:
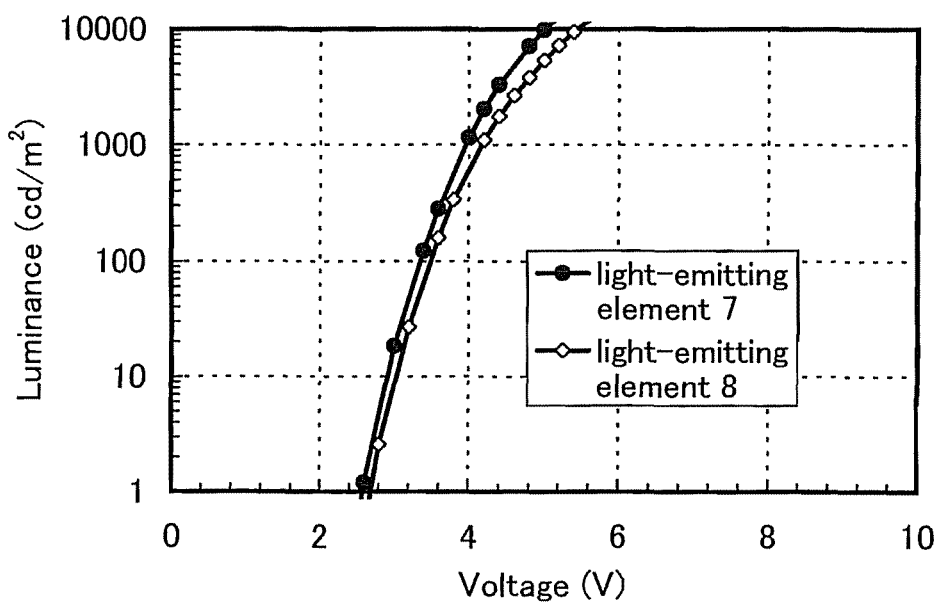
FIG. 47 shows the voltage vs. luminance characteristics of the light-emitting elements fabricated in Example 6.
Figure 48:
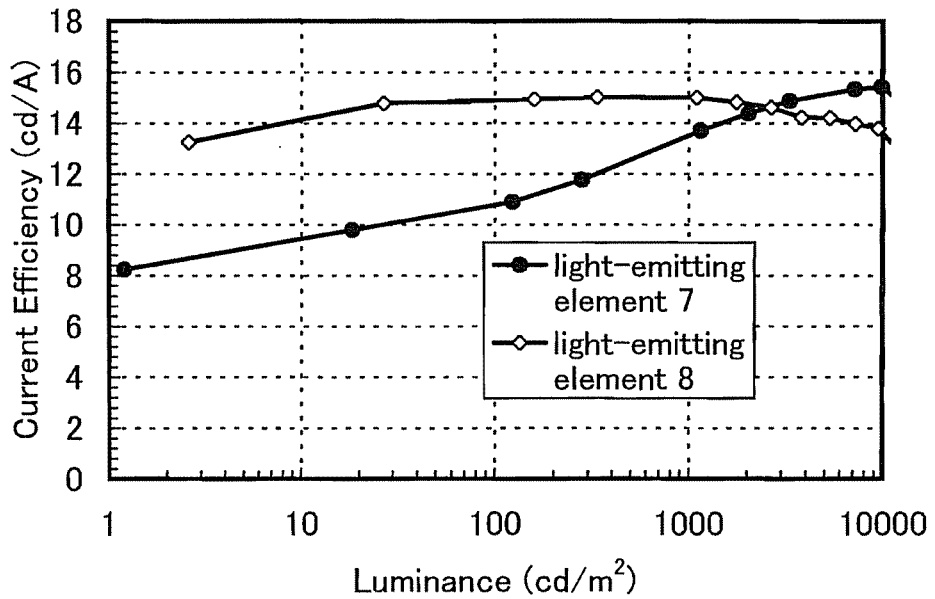
FIG. 48 shows the luminance vs. current efficiency characteristics of the light-emitting elements fabricated in Example 6.
Figure 49:
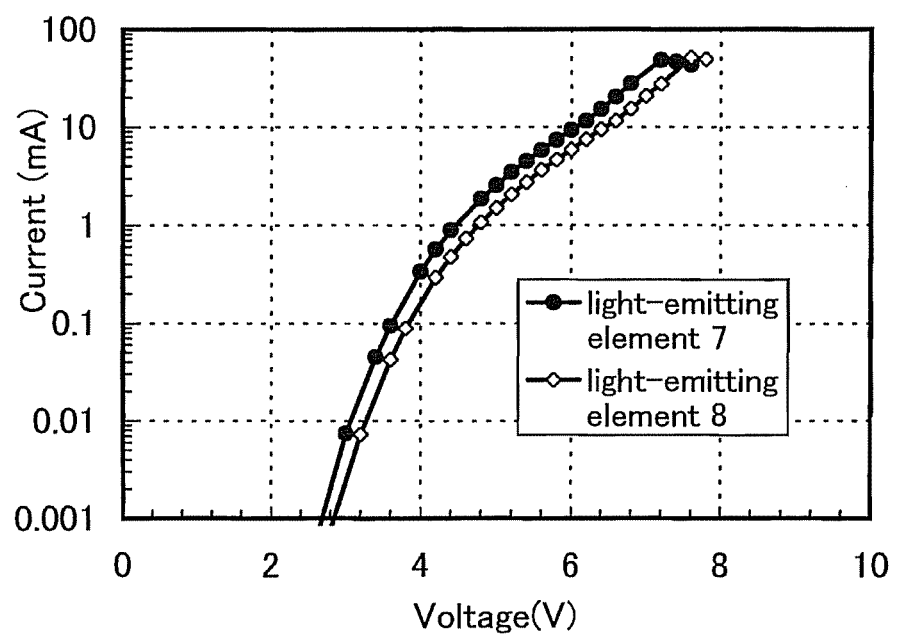
FIG. 49 shows the voltage vs. current characteristics of the light-emitting elements fabricated in Example 6.

FIG. 46 shows the current density vs. luminance characteristics of the light-emitting elements 7 and 8. FIG. 47 shows the voltage vs. luminance characteristics of the light-emitting elements 7 and 8. FIG. 48 shows the luminance vs. current efficiency characteristics of the light-emitting elements 7 and 8. FIG. 49 shows the voltage vs. current characteristics of the light-emitting elements 7 and 8.

Figure 50:
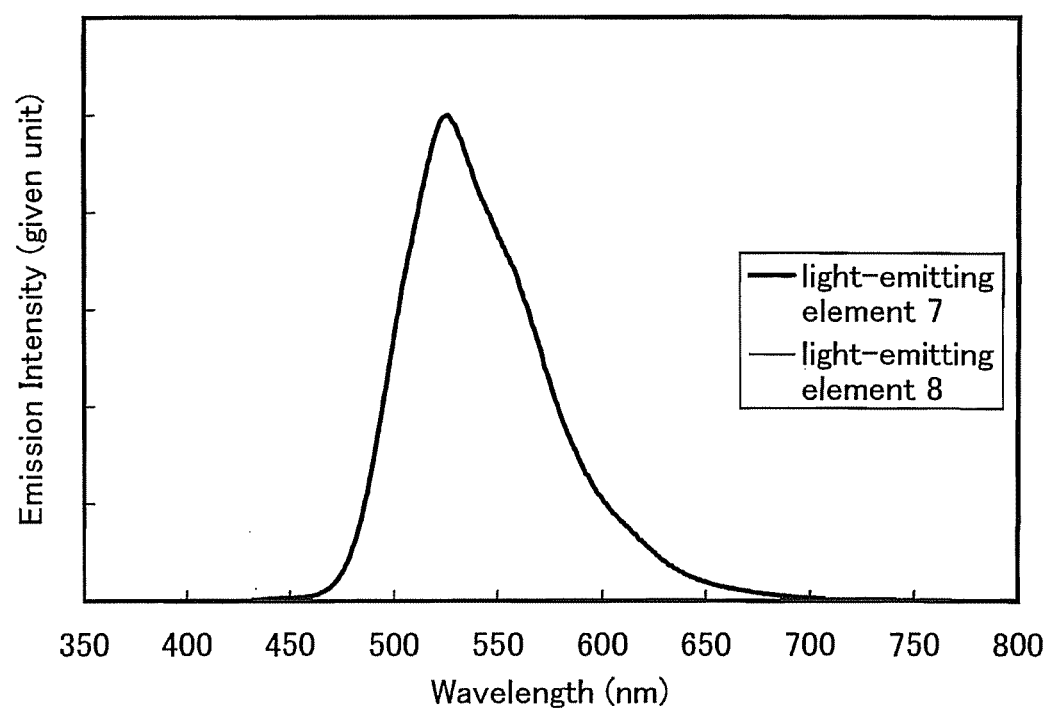
FIG. 50 shows emission spectra of the light-emitting elements fabricated in Example 6.

Further, FIG. 50 shows the emission spectra of the light-emitting elements 7 and 8 at a current of 1 mA. As apparent from FIG. 50, light emission from each of the light-emitting elements 7 and 8 were from 2PCAPA.

The CIE chromaticity coordinates of the light-emitting element 7 at a luminance of 3300 cd/m² were (x=0.31, y=0.62), and green light emission was exhibited. Further, at a luminance of 3300 cd/m², the current efficiency of the light-emitting element 7 was 14.9 cd/A. Furthermore, at a luminance of 3300 cd/m², the voltage, current density, and power efficiency of the light-emitting element 7 were 4.4 V, 22.2 mA/cm², and 10.6 lm/W, respectively.

The CE chromaticity coordinates of the light-emitting element 8 at a luminance of 2700 cd/m² were (x=0.29, y=0.62), and green light emission was exhibited. Further, at a luminance of 2700 cd/m², the current efficiency of the light-emitting element 8 was 14.6 cd/A. Furthermore, at a luminance of 2700 cd/m², the voltage, current density, and power efficiency of the light-emitting element 8 were 4.6 V, 18.2 mA/cm², and 10.0 lm/W, respectively.

Figure 51:
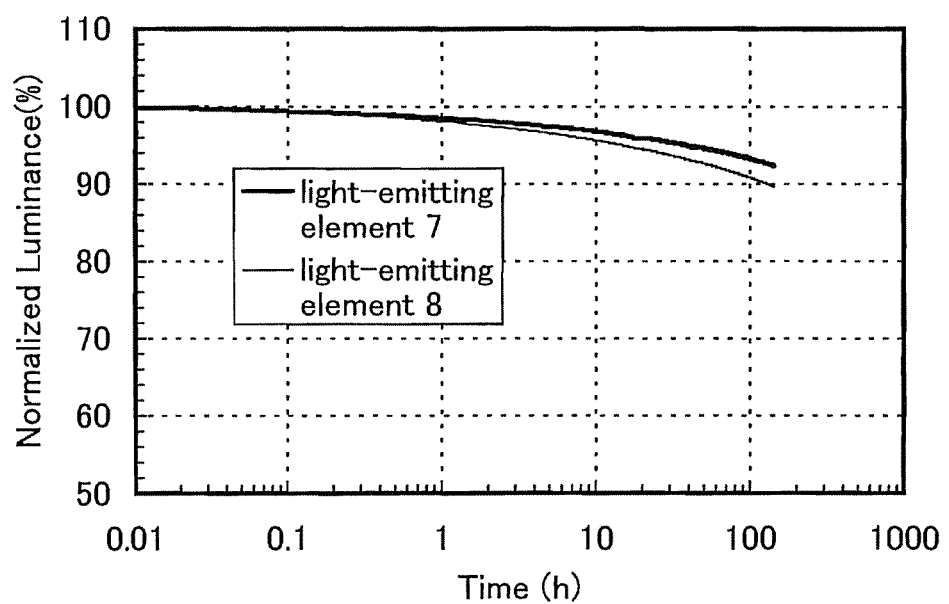
FIG. 51 shows a change in luminance with respect to driving time of the light-emitting elements fabricated in Example 6

Further, FIG. 51 shows the results of continuous lighting tests in which the light-emitting elements 7 and 8 were continuously lit by constant current driving with the initial luminance thereof set to 5000 cd/m² (the vertical axis represents normalized luminance on condition that 5000 cd/m² was 100%). As can be seen from FIG. 51, the light-emitting elements 7 and 8 kept 92% and 90% of the initial luminance, respectively, after 140 hours. Therefore, it is understood that the light-emitting elements of the present invention have a long lifetime even when the initial luminance was set to as high as 5000 cd/m².

Thus, by any of the anthracene derivatives of the present invention, a light-emitting element with a long lifetime can be obtained. In particular, by the anthracene derivative of the present invention together with the functional layer for controlling transport of electrons, a light-emitting element with a longer lifetime can be obtained.

Example 7

In Example 7, a method of synthesizing 9-{4-[9,10-bis(biphenyl-2-yl)-2-anthryl]phenyl}-9H-carbazole (abbreviation: 2CzPBPhA) represented by the structural formula (206), which is one of the anthracene derivatives of the present invention, is specifically described.

(206)

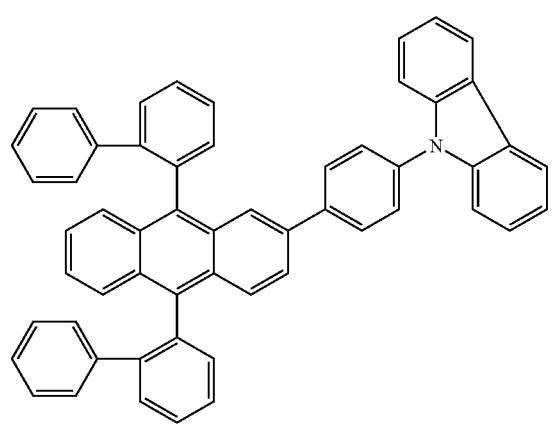

[Step 1] Synthesis of 9-{4-[9,10-bis(biphenyl-2-yl)-2-anthryl]phenyl}-9H-carbazole (abbreviation: 2CzPBPhA)

A synthesis scheme of 2CzPBPhA is illustrated in (E-1).

(E-1)

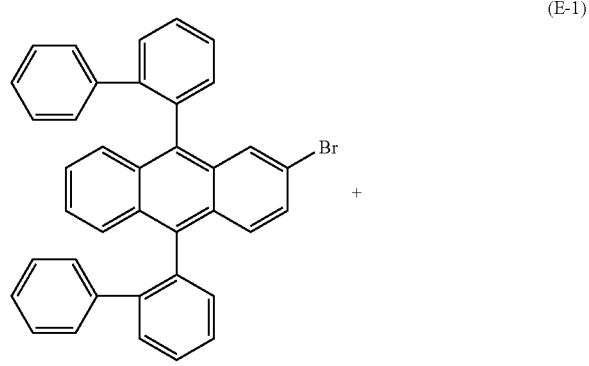

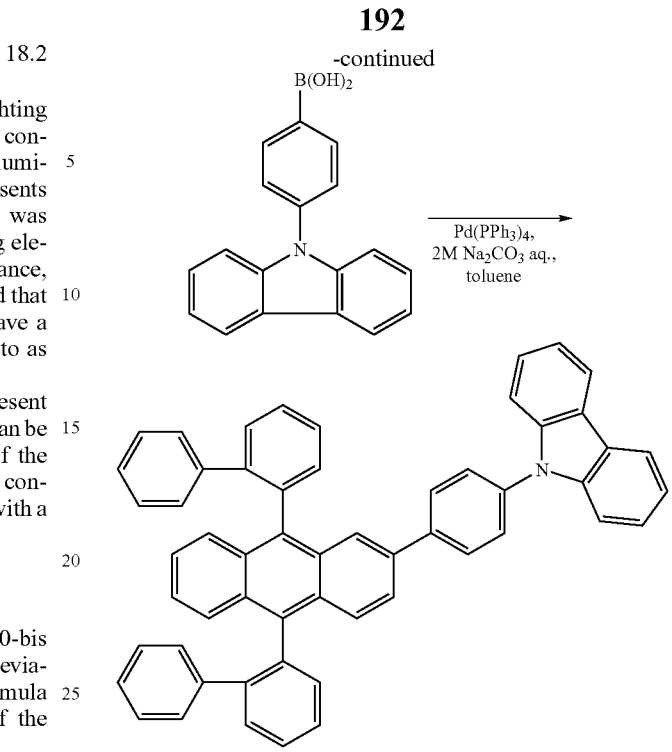

In a 100 mL three neck flask were put 1.7 g (30 mmol) of 2-bromo-9,10-bis(2-biphenyl)anthracene, 0.86 g (3.0 mmol) of 4-(9H-carbazol-9-yl)benzeneboronic acid, and 0.13 g (0.12 mmol) of tetrakis(triphenylphosphine)palladium(0), and the atmosphere in the flask was replaced with nitrogen. To this mixture were added 15 mL of toluene and 7 mL of an aqueous sodium carbonate solution (2.0 mol/L). This mixture was deaerated by being stirred under reduced pressure. This mixture was refluxed at 110° C. for 10 hours. Then, after the mixture was cooled to room temperature, about 100 mL of toluene was added thereto. This mixture was suction filtered through alumina, Florisil (a product of Wako Pure Chemical Industries, Ltd., Catalog No. 540-00135), and Celite (a product of Wako Pure Chemical Industries, Ltd., Catalog No. 531-16855). The obtained filtrate was washed with water and a saturated saline solution in that order, and the organic layer was dried with magnesium sulfate. This mixture was gravity filtered. The obtained filtrate was concentrated to give a solid, which was recrystallized with dichloromethane/hexane to give the object of the synthesis as 1.4 g of a light yellow powdered solid in a yield of 66%.

Then, 490 mg of the obtained light-yellow powdered solid was sublimated and purified by train sublimation. For sublimation purification conditions, the material was heated at 360° C. under a pressure of 200 Pa with argon gas at a flow rate of 15.0 mL/min. After the sublimation purification, 430 mg of 2CzPBPhA was recovered in a yield of 86%

By nuclear magnetic resonance (NMR) measurement, it was confirmed that this compound was 9-{4-[9,10-bis(biphenyl-2-yl)-2-anthryl]phenyl}-9H-carbazole (abbreviation: 2CzPBPhA).

Figure 52A:
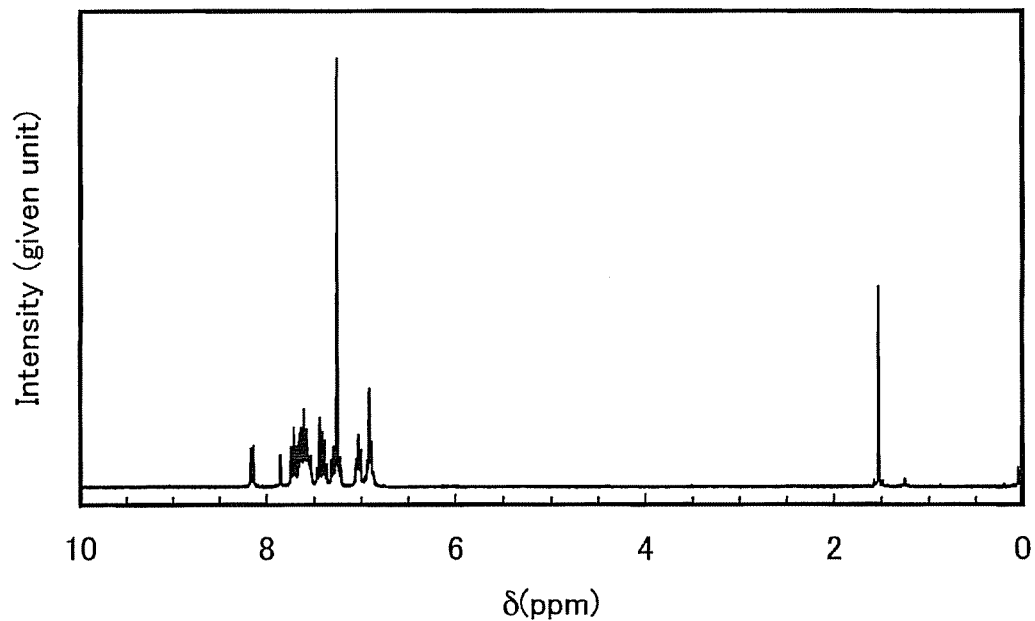
FIGS. 52A and 52B show $^1$H NMR charts of 9-{4-[9,10-bis(biphenyl-2-yl)-2-anthryl]phenyl}-9H-carbazole (abbreviation: 2CzPBPhA).
Figure 52B:
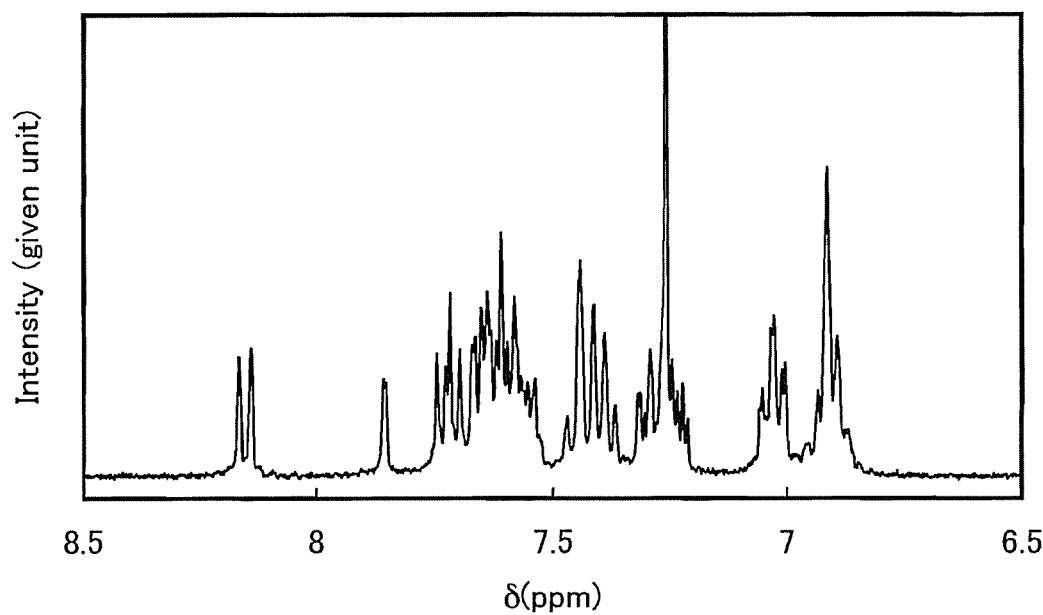

The $^1$H NMR data of 2CzPBPhA are shown as follows: $^1$H NMR (CDCl₃, 300 MHz): δ=6.89-6.96 (m, 6H), 7.00-7.06 (m, 4H), 7.21-7.32 (m, 4H), 7.37-7.45 (m, 7H), 7.54-7.74 (m, 15H), 7.85 (d, J=1.5 Hz, 1H), 8.15 (d, J=8.4 Hz, 2H). Further, FIGS. 52A and 52B show $^1$H NMR charts. Note that FIG. 52B is a chart in which the range of 6.5 to 8.5 ppm in FIG. 52A is enlarged.

Further, the decomposition temperature of 2CzPBPhA, which was obtained, was measured with a high vacuum differential type differential thermal balance (TG-DTA2410SA, a product of Bruker AXS K.K.). The temperature increase rate was set to 10° C./min, and the temperature was increased under normal pressure. Accordingly, a reduction in weight by 5% was seen at 455° C. Thus, 2CzPBPhA was found to have high thermal stability.

Further, the glass transition point of 2CzPBPhA was measured with a differential scanning calorimeter (DSC, a product of PerkinElmer, Inc., Pyris 1). After the sample was heated to 350° C. at 40° C./min to be melted, it is cooled to room temperature at 40° C./min. Then, by raising the temperature of the sample to 350° C. at 10° C./min, the measurement was conducted. Accordingly, the glass transition point (Tg) and melting point of 2CzPBPhA were 143° C. and 296° C., respectively. Thus, 2CzPBPhA was found to have a high glass transition point.

Figure 53:
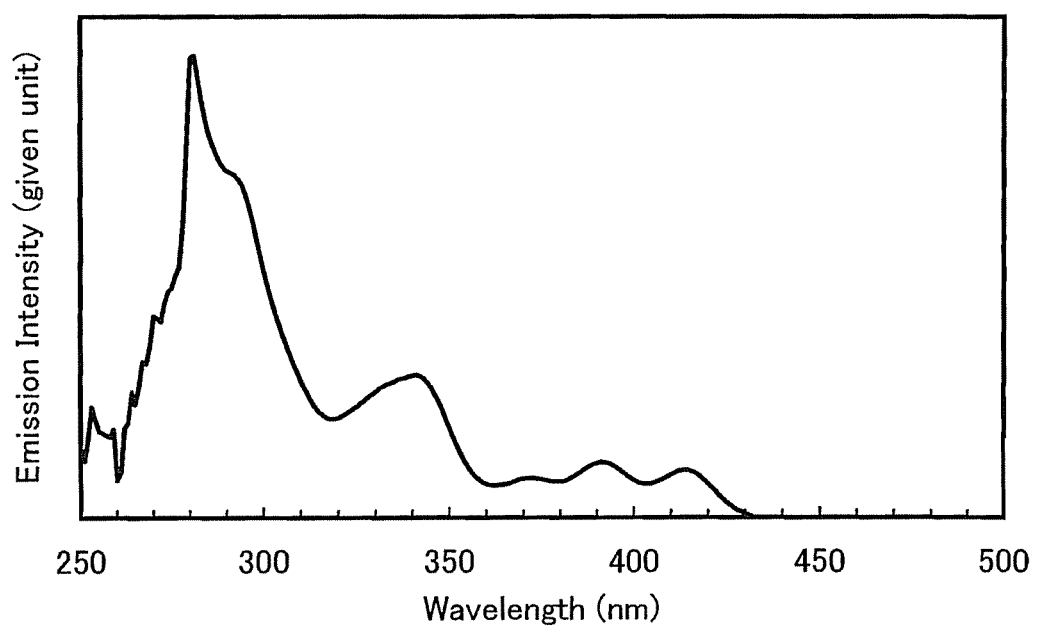
FIG. 53 shows an absorption spectrum of a toluene solution of 9-{4-[9,10-bis(biphenyl-2-yl)-2-anthryl]phenyl}-9H-carbazole (abbreviation: 2CzPBPhA).
Figure 54:
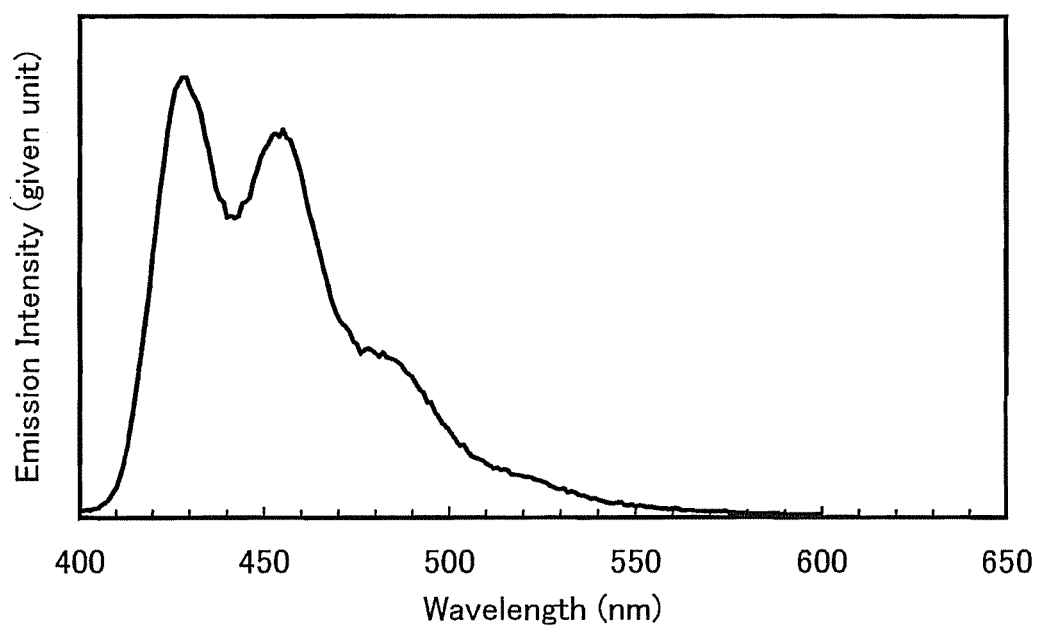
FIG. 54 shows an emission spectrum of the toluene solution of 9-{4-[9,10-bis(biphenyl-2-yl)-2-anthryl]phenyl}-9H-carbazole (abbreviation: 2CzPBPhA).

Further, FIG. 53 shows an absorption spectrum of a toluene solution of 2CzPBPhA, and FIG. 54 shows an emission spectrum of the toluene solution of 2CzPBPhA. An ultraviolet-visible spectrophotometer (V-550, a product of JASCO Corporation) was used for the measurement. The measurement was conducted with the solution put in the quartz cell. The absorption spectrum from which the absorption spectrum obtained with only toluene put in the quartz cell was subtracted is shown. In FIG. 53, the horizontal axis represents wavelength (nm) and the vertical axis represents absorption intensity (given unit). In FIG. 54, the horizontal axis represents wavelength (nm) and the vertical axis represents emission intensity (given unit). With the toluene solution, absorption was observed at around 291 nm, 340 nm, 369 nm, 389 nm, and 412 nm. In addition, with the toluene solution, the peak emission wavelengths were 429 nm and 455 nm (excitation wavelength of 370 nm).

Figure 55:
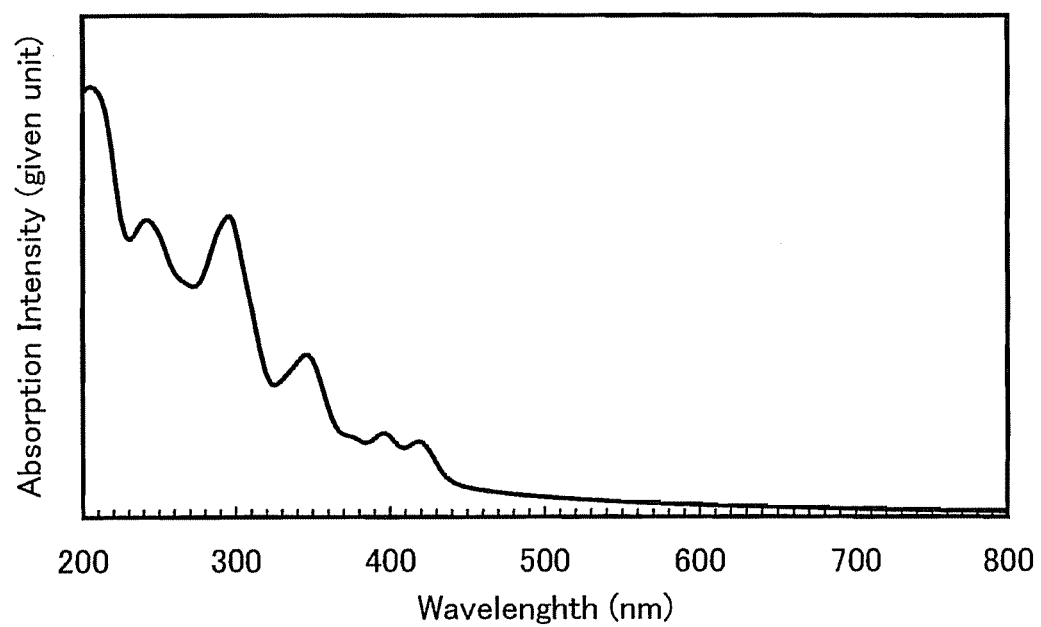
FIG. 55 shows an absorption spectrum of a thin film of 9-{4-[9,10-bis(biphenyl-2-yl)-2-anthryl]phenyl}-9H-carbazole (abbreviation: 2CzPBPhA).
Figure 56:
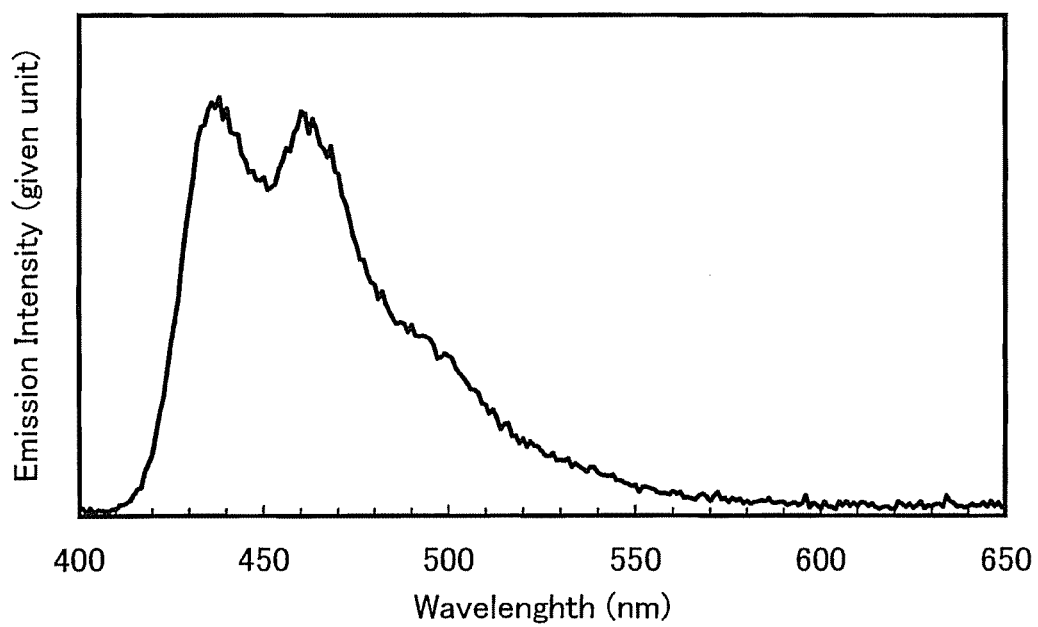
FIG. 56 shows an emission spectrum of the thin film of 9-{4-[9,10-bis(biphenyl-2-yl)-2-anthryl]phenyl}-9H-carbazole (abbreviation: 2CzPBPhA).

Further, FIG. 55 shows an absorption spectrum of a toluene solution of 2CzPBPhA, and FIG. 56 shows an emission spectrum of the toluene solution of 2CzPBPhA. An ultraviolet-visible spectrophotometer (V-550, a product of JASCO Corporation) was used for the measurement. A thin film sample was prepared by evaporation on a quartz substrate, and the absorption spectrum from which the absorption spectrum of quartz is subtracted is shown. In FIG. 55, the horizontal axis represents wavelength (nm) and the vertical axis represents absorption intensity (given unit). In FIG. 56, the horizontal axis represents wavelength (nm) and the vertical axis represents emission intensity (given unit). With the thin film, absorption was observed at around 293 nm, 344 nm, 398 nm, and 419 nm. In addition, with the thin film, the peak emission wavelengths were 438 nm and 463 nm (excitation wavelength of 380 nm).

Further, by measurement with a photoelectron spectrometer (AC-2, a product of Riken Keiki, Co., Ltd.) in the atmosphere, the ionization potential of the thin film of 2CzPBPhA was found to be 5.72 eV As a result, it was understood that the HOMO level was −5.72 eV. Furthermore, with the use of the absorption spectrum data of the thin film of 2CzPBPhA, the absorption edge was obtained by a Tauc plot assuming direct transition. The absorption edge was estimated as an optical energy gap, whereby the energy gap was 2.82 eV. From the obtained values of the energy gap and HOMO level, the LUMO level was −2.90 eV.

Further, the oxidation-reduction characteristics of 2CzPBPhA were measured by cyclic voltammetry (CV). Note that an electrochemical analyzer (ALS model 600A, a product of BAS Inc.) was used for the measurement.

For a solution used in the CV measurement, dehydrated dimethylformamide (DMF, a product of Sigma-Aldrich Inc., 99.8%, Catalog No. 22705-6) was used as a solvent, and tetra-n-butylammonium perchlorate (n-Bu$_4$NClO$_4$, a product of Tokyo Chemical Industry Co., Ltd., Catalog No. T0836), which was a supporting electrolyte, was dissolved in the solvent such that the concentration of tetra-n-butylammonium perchlorate was 100 mmol/L. Furthermore, 2CzPBPhA, which was the object of the measurement, was dissolved in the solution such that the concentration of 2CzPBPhA was 2 mmol/L. In addition, a platinum electrode (PTE platinum electrode, a product of BAS Inc.) was used as a working electrode, a platinum electrode (Pt counter electrode for VC-3, (5 cm), a product of BAS Inc.) was used as an auxiliary electrode, and an Ag/Ag$^+$ electrode (RE5 reference electrode for nonaqueous solvent, a product of BAS Inc.,) was used as a reference electrode. Note that the measurement was conducted at room temperature.

The oxidation characteristics of 2CzPBPhA were examined as follows. A scan for changing the potential of the working electrode with respect to the reference electrode from −0.26 V to 1.30 V and then from 1.30 V to −0.26 V was set to one cycle, and the measurement was performed for 100 cycles. Further, the reduction characteristics of 2CzPBPhA were examined as follows. A scan for changing the potential of the working electrode with respect to the reference electrode from −0.28 V to −2.40 V and then from −2.40 V to −0.28 V was set to one cycle, and the measurement was performed for 100 cycles. Note that the scan rate for the CV measurement was set to 0.1 V/s.

Figure 57:
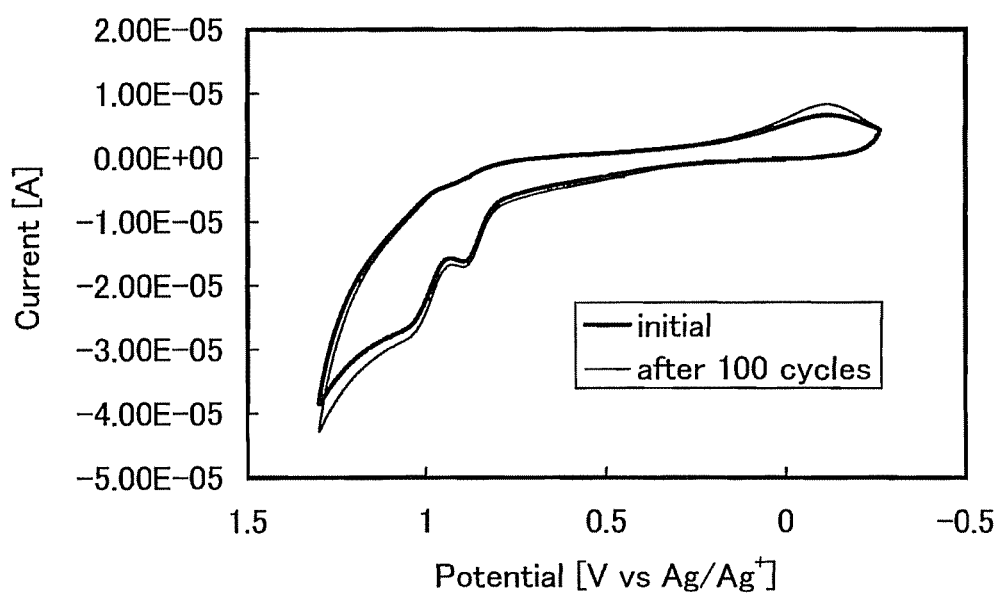
FIG. 57 shows the results of CV measurement of 9-{ 4-[9,10-bis(biphenyl-2-yl)-2-anthryl]phenyl}-9H-carbazole (abbreviation: 2CzPBPhA).
Figure 58:
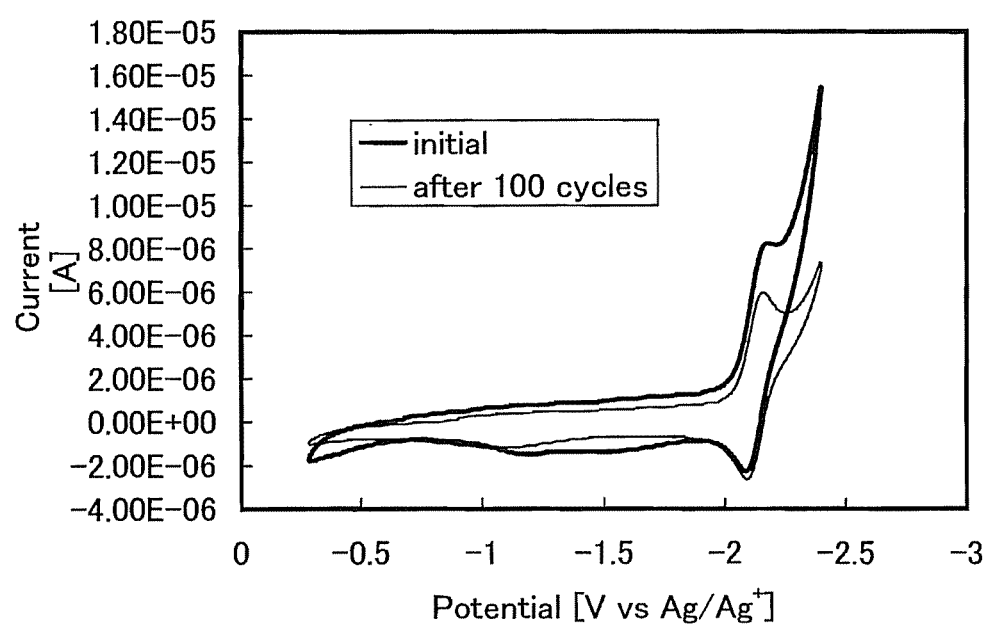
FIG. 58 shows the results of CV measurement of 9-{4-[9,10-bis(biphenyl-2-yl)-2-anthryl]phenyl}-9H-carbazole (abbreviation: 2CzPBPhA).

FIG. 57 shows CV measurement results of the oxidation characteristics of 2CzPBPhA. FIG. 58 shows CV measurement results of the reduction characteristics of 2CzPBPhA. In each of FIG. 57 and FIG. 58, the horizontal axis represents potential (V) of the working electrode with respect to the reference electrode, and the vertical axis represents the amount of current (μA) flowing between the working electrode and the auxiliary electrode. From FIG. 57, current exhibiting oxidation was observed at around 0.89 V (vs. the Ag/Ag$^+$ electrode). Further, from FIG. 58, current exhibiting reduction was observed at around −2.16 V (vs. the Ag/Ag$^+$ electrode).

Although the scan was repeated for as many as 100 cycles, significant changes in the peak position and peak intensity of the CV curves were not observed in each of the oxidation reactions and reduction reactions. This shows that the anthracene derivative of the present invention is significantly stable against repetition of oxidation reactions and reduction reactions.

The present application is based on Japanese Patent Application serial No. 2008-114057 filed with Japan Patent Office on Apr. 24, 2008, the entire contents of which are hereby incorporated by reference.

EXPLANATION OF REFERENCE

101: substrate, 102: first electrode, 103: EL layer, 104: second electrode, 111: hole-injecting layer, 112: hole-transporting layer, 113: light-emitting layer, 114: electron-transporting layer, 115: electron-injecting layer, 116: functional layer, 501: first electrode, 502: second electrode, 511: first light-emitting unit, 512: second light-emitting unit, 513: charge generation layer, 601: source side driver circuit, 602: pixel portion, 603: gate side driver circuit, 604: sealing substrate, 605: sealing material, 607: space, 608: wiring, 609: flexible printed circuit (FPC), 610: element substrate, 611: switching TFT, 612: current controlling TFT, 613: first electrode, 614: insulator, 616: EL layer, 617: second electrode, 618: light-emitting element, 623: n-channel TFT, 624: p-channel TFT, 701: main body, 702: display portion, 703: operation switch, 704: operation switch, 710: main body, 711: display portion, 712: memory portion, 713: operating portion, 714: earphone, 901: housing, 902: liquid crystal layer, 903: backlight, 904: housing, 905: driver IC, 906: terminal, 951: substrate, 952: electrode, 953: insulating layer, 954: partition layer, 955: EL layer, 956: electrode, 1001: housing, 1002: housing, 1101: display portion, 1102: speaker, 1103: microphone, 1104: operation key, 1105: pointing device, 1106: camera lens, 1107: external connection terminal, 1108: earphone terminal, 1201: keyboard, 1202: external memory slot, 1203: camera lens, 1204: light, 2001: housing, 2002: light source, 2101: glass substrate, 2102: first electrode, 2104: second electrode, 2111: layer including composite material, 2112: hole-transporting layer, 2113: light-emitting layer, 2114: electron-transporting layer, 2115: electron-injecting layer, 2116: functional layer, 3001: lighting apparatus, 3002: television set, 9101: housing, 9102: supporting base, 9103: display portion, 9104: speaker portion, 9105: video input terminal, 9201: main body, 9202: housing, 9203: display portion, 9204: keyboard, 9205: external connection port, 9206: pointing device, 9301: main body, 9302: display portion, 9303: housing, 9304: external connection port, 9305: remote control receiving portion, 9306: image receiving portion, 9307: battery, 9308: audio input portion, 9309: operation key, 9310: eye piece portion, 9401: main body, 9402: housing, 9403: display portion, 9404: audio input portion, 9405: audio output portion, 9406: operation key, 9407: external connection port, 9408: antenna.

The invention claimed is:

1. An anthracene derivative represented by a general formula (G12-1),

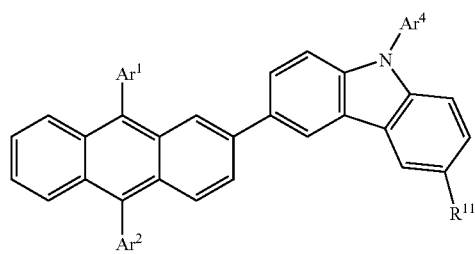

(G12-1)

wherein:
$Ar^1$ and $Ar^2$ independently represent a substituted or unsubstituted aryl group having 6 to 13 carbon atoms;
$Ar^4$ represents a substituted or unsubstituted aryl group having 6 to 13 carbon atoms; and
$R^{11}$ represents hydrogen, an alkyl group having 1 to 4 carbon atoms, or a substituted or unsubstituted aryl group having 6 to 13 carbon atoms.

2. An anthracene derivative represented by a general formula (G12-2),

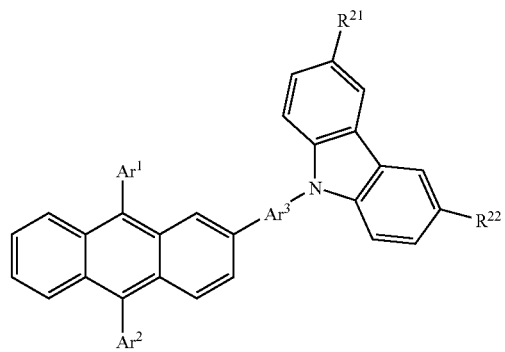

(G12-2)

wherein:
$Ar^1$ and $Ar^2$ independently represent a substituted or unsubstituted aryl group having 6 to 13 carbon atoms;
$Ar^3$ represents a substituted or unsubstituted arylene group having 6 to 13 carbon atoms; and
$R^{21}$ and $R^{22}$ independently represent hydrogen, an alkyl group having 1 to 4 carbon atoms, or a substituted or unsubstituted aryl group having 6 to 13 carbon atoms.

3. An anthracene derivative represented by a general formula (G13-1),

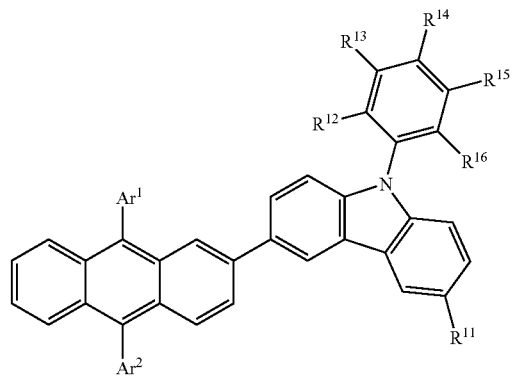

(G13-1)

wherein:
$Ar^1$ and $Ar^2$ independently represent a substituted or unsubstituted aryl group having 6 to 13 carbon atoms;
$R^{11}$ represents hydrogen, an alkyl group having 1 to 4 carbon atoms, or a substituted or unsubstituted aryl group having 6 to 13 carbon atoms; and
$R^{12}$ to $R^{16}$ independently represent hydrogen, an alkyl group having 1 to 4 carbon atoms, or a substituted or unsubstituted aryl group having 6 to 10 carbon atoms.-

4. An anthracene derivative represented by a general formula (G13-2),

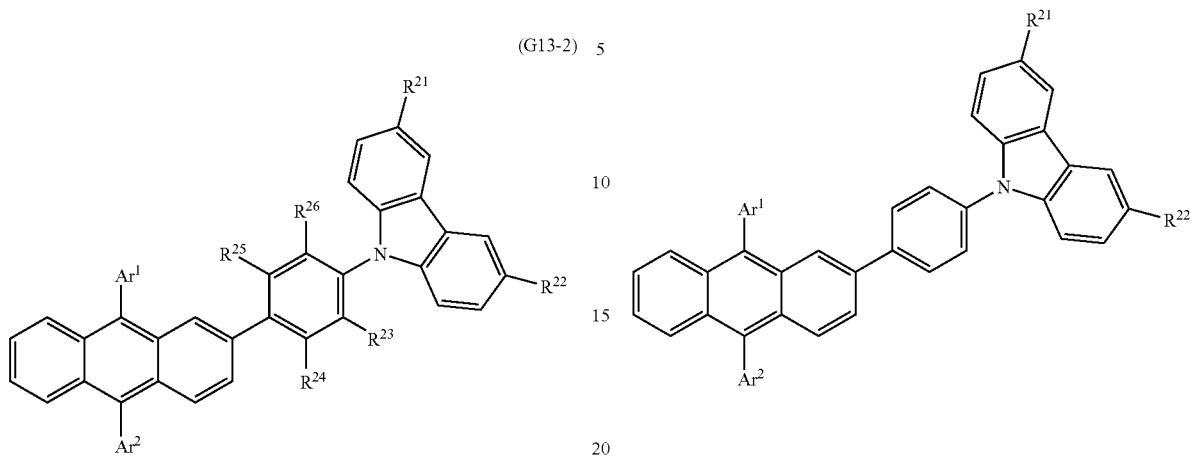

wherein:

Ar¹ and Ar² independently represent a substituted or unsubstituted aryl group having 6 to 13 carbon atoms;

$R^{21}$ and $R^{22}$ independently represent hydrogen, an alkyl group having 1 to 4 carbon atoms, or a substituted or unsubstituted aryl group having 6 to 13 carbon atoms; and $R^{23}$ to $R^{26}$ independently represent hydrogen, an alkyl group having 1 to 4 carbon atoms, or a substituted or unsubstituted phenyl group.

5. An anthracene derivative represented by a general formula (G14-1),

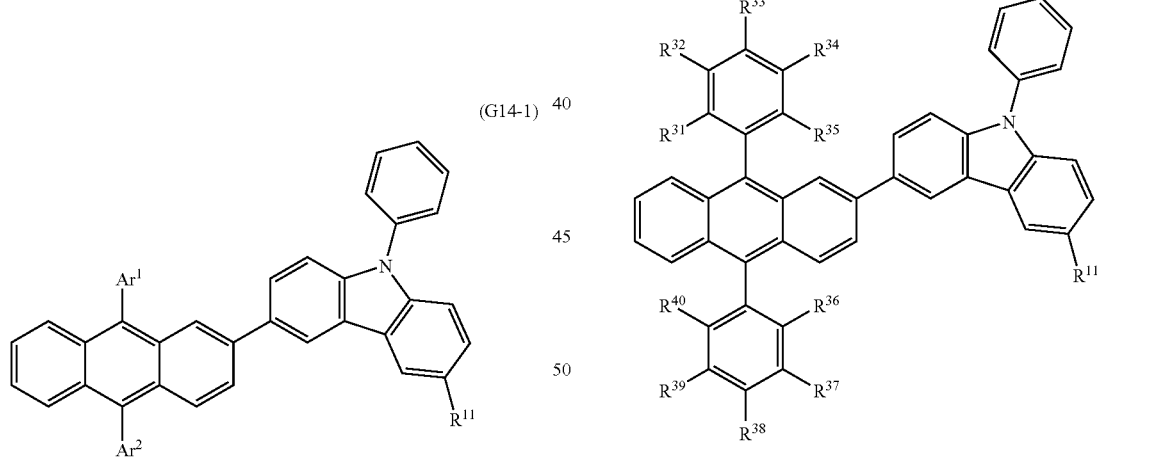

wherein:

Ar¹ and Ar² independently represent a substituted or unsubstituted aryl group having 6 to 13 carbon atoms; and $R^{11}$ represents hydrogen, an alkyl group having 1 to 4 carbon atoms, or a substituted or unsubstituted aryl group having 6 to 13 carbon atoms.

6. An anthracene derivative represented by a general formula (G14-2),

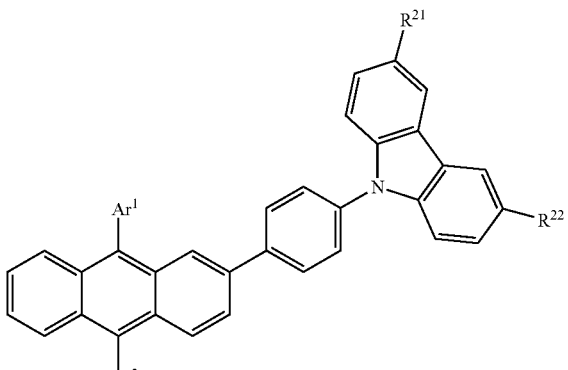

wherein:

Ar¹ and Ar² independently represent a substituted or unsubstituted aryl group having 6 to 13 carbon atoms; and $R^{21}$ and $R^{22}$ independently represent hydrogen, an alkyl group having 1 to 4 carbon atoms, or a substituted or unsubstituted aryl group having 6 to 13 carbon atoms.

7. An anthracene derivative represented by a general formula (G15-1),

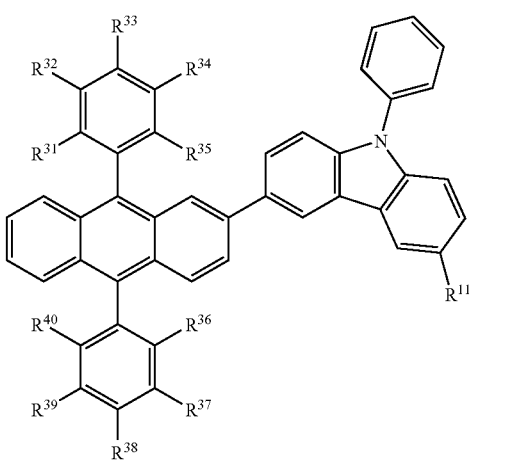

wherein:

$R^{11}$ represents hydrogen, an alkyl group having 1 to 4 carbon atoms, or a substituted or unsubstituted aryl group having 6 to 13 carbon atoms; and $R^{31}$ to $R^{40}$ independently represent hydrogen, an alkyl group having 1 to 4 carbon atoms; a substituted or unsubstituted aryl group having 6 to 10 carbon atoms; halogen, or a haloalkyl group having 1 to 4 carbon atoms.

8. An anthracene derivative represented by a general formula (G15-2),

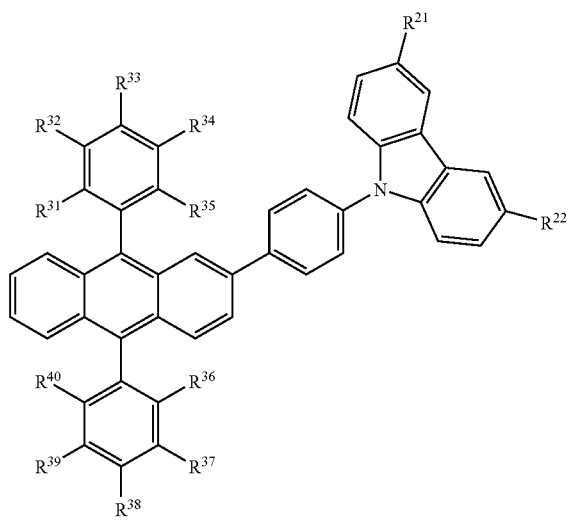

(G15-2)

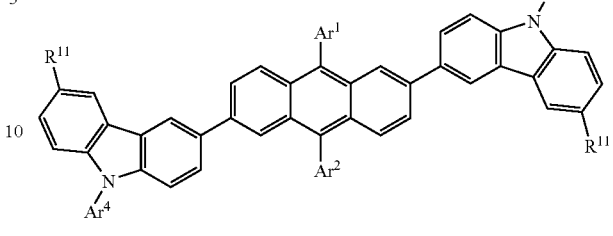

(G22-1)

wherein:

Ar$^1$ and Ar$^2$ independently represent a substituted or unsubstituted aryl group having 6 to 13 carbon atoms;

Ar$^4$ represents a substituted or unsubstituted aryl group having 6 to 13 carbon atoms; and R$^{11}$ represents hydrogen, an alkyl group having 1 to 4 carbon atoms, or a substituted or unsubstituted aryl group having 6 to 13 carbon atoms.

10. An anthracene derivative represented by a general formula (G23-1),

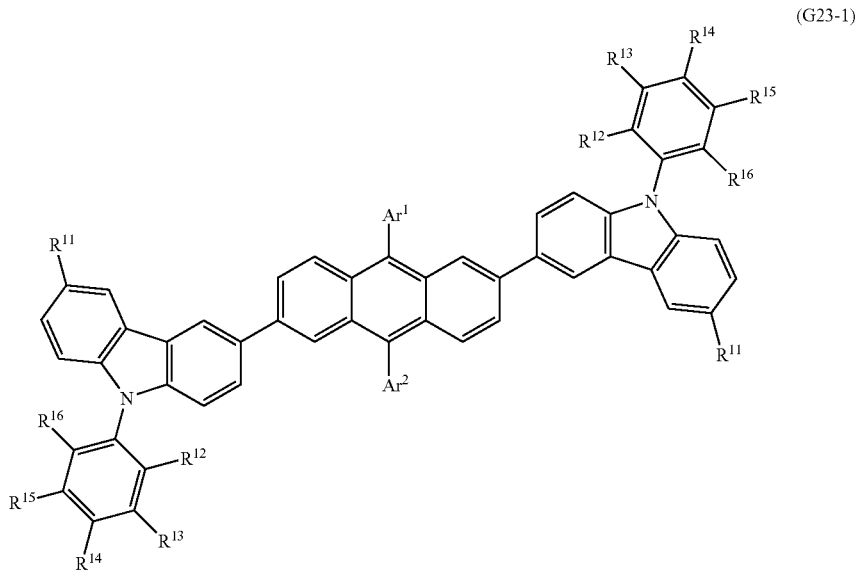

(G23-1)

wherein:

R$^{21}$ and R$^{22}$ independently represent hydrogen, an alkyl group having 1 to 4 carbon atoms, or a substituted or unsubstituted aryl group having 6 to 13 carbon atoms; and R$^{31}$ to R$^{40}$ independently represent hydrogen, an alkyl group having 1 to 4 carbon atoms; a substituted or unsubstituted aryl group having 6 to 10 carbon atoms; halogen, or a haloalkyl group having 1 to 4 carbon atoms.

9. An anthracene derivative represented by a general formula (G22-1), wherein:

Ar$^1$ and Ar$^2$ independently represent a substituted or unsubstituted aryl group having 6 to 13 carbon atoms;

R$^{11}$ represents hydrogen, an alkyl group having 1 to 4 carbon atoms, or a substituted or unsubstituted aryl group having 6 to 13 carbon atoms; and R$^{12}$ to R$^{16}$ independently represent hydrogen, an alkyl group having 1 to 4 carbon atoms, or a substituted or unsubstituted aryl group having 6 to 10 carbon atoms.

11. An anthracene derivative represented by a general formula (G24-1),

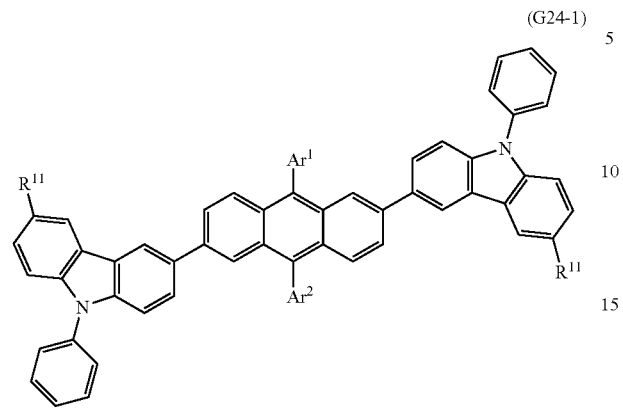

(G24-1)

wherein:
Ar$^1$ and Ar$^2$ independently represent a substituted or unsubstituted aryl group having 6 to 13 carbon atoms; and
R$^{10}$ represents hydrogen, an alkyl group having 1 to 4 carbon atoms, or a substituted or unsubstituted aryl group having 6 to 13 carbon atoms.

12. An anthracene derivative represented by a general formula (G25-1),

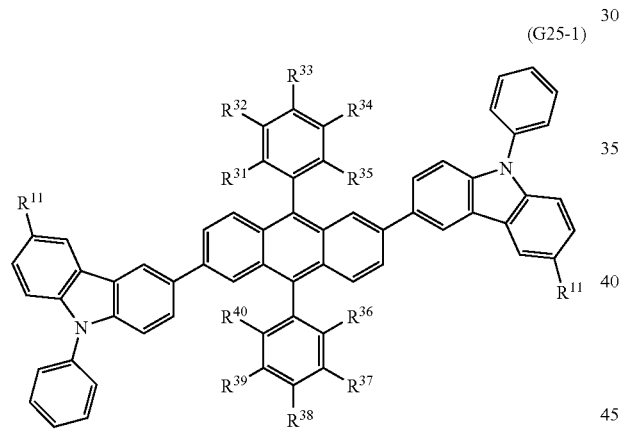

(G25-1)

wherein:
R$^{11}$ represents hydrogen, an alkyl group having 1 to 4 carbon atoms, or a substituted or unsubstituted aryl group having 6 to 13 carbon atoms; and
R$^{31}$ to R$^{40}$ independently represent hydrogen, an alkyl group having 1 to 4 carbon atoms; a substituted or unsubstituted aryl group having 6 to 10 carbon atoms; halogen, or a haloalkyl group having 1 to 4 carbon atoms.

13. The anthracene derivative according to any one of claims 1 to 8, wherein Ar$^1$ and Ar$^2$ are substituents each having a same structure.

14. An anthracene derivative represented by a structural formula (101)

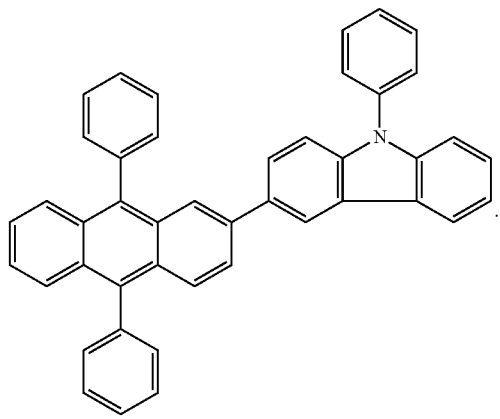

(101)

15. An anthracene derivative represented by a structural formula (201)

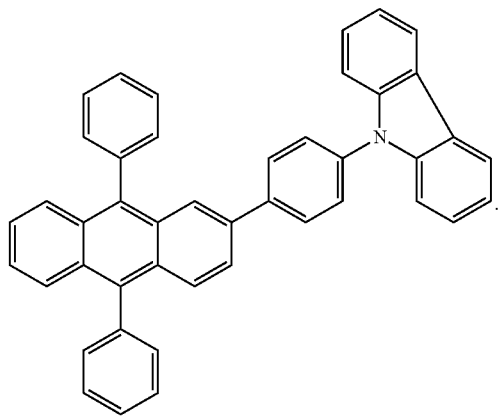

(201)

16. A light-emitting element comprising the anthracene derivative according to any one of claims 1 to 8, 14 and 15 between a pair of electrodes.

17. A light-emitting element comprising a light-emitting layer between a pair of electrodes, wherein the light-emitting layer comprises the anthracene derivative according to any one of claims 1 to 8, 14 and 15.

18. A light-emitting element comprising a light-emitting layer between a pair of electrodes,
wherein the light-emitting layer comprises the anthracene derivative according to any one of claims 1 to 8, 14 and 15, and
wherein the anthracene derivative emits light.

19. A light-emitting device comprising the light-emitting element according to claim 16 and a control circuit configured to control light emission from the light-emitting element.

20. An electronic device comprising a display portion, wherein the display portion comprises the light-emitting element according to claim 16 and a control circuit configured to control light emission from the light-emitting element.

* * * * *

UNITED STATES PATENT AND TRADEMARK OFFICE
CERTIFICATE OF CORRECTION

PATENT NO.       : 8,592,053 B2
APPLICATION NO.  : 12/427118
DATED            : November 26, 2013
INVENTOR(S)      : Sachiko Kawakami et al.

It is certified that error appears in the above-identified patent and that said Letters Patent is hereby corrected as shown below:

In the Specification:

Column 4, Line 17; Change "an 5 alkyl" to --an alkyl--.
Column 4, Line 43; Change "allyl" to --alkyl--.
Column 21, Line 17; Change "Spiro" to --spiro--.
Column 34, Line 16; Change "phenyl 5 group" to --phenyl group--.

Signed and Sealed this
Sixth Day of May, 2014

Michelle K. Lee
*Deputy Director of the United States Patent and Trademark Office*

CERTIFICATE OF CORRECTION (continued)
U.S. Pat. No. 8,592,053 B2

In the Specification:

Columns 109 to 110, Figure 347; Change

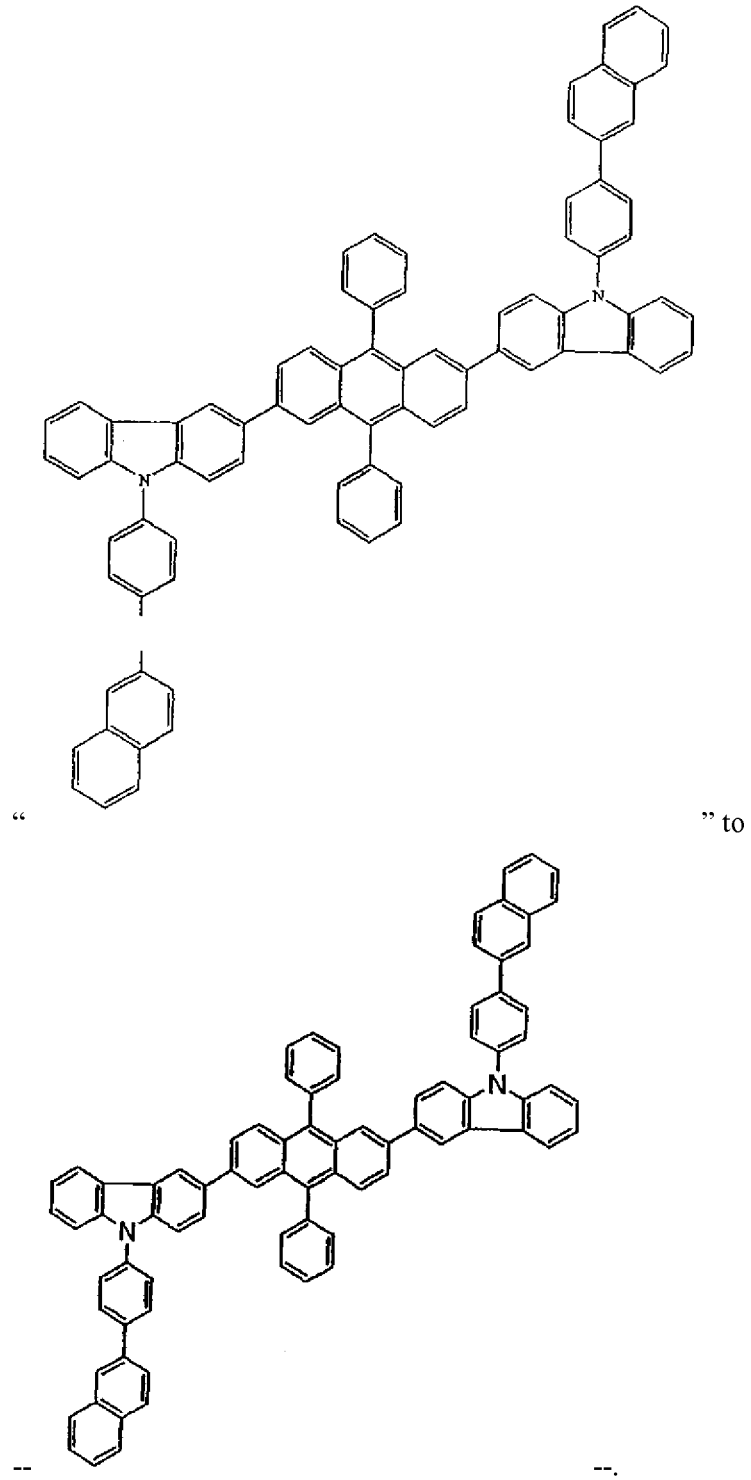

In the Specification:

CERTIFICATE OF CORRECTION (continued)
U.S. Pat. No. 8,592,053 B2

Columns 130 to 132, Figure 427; Change

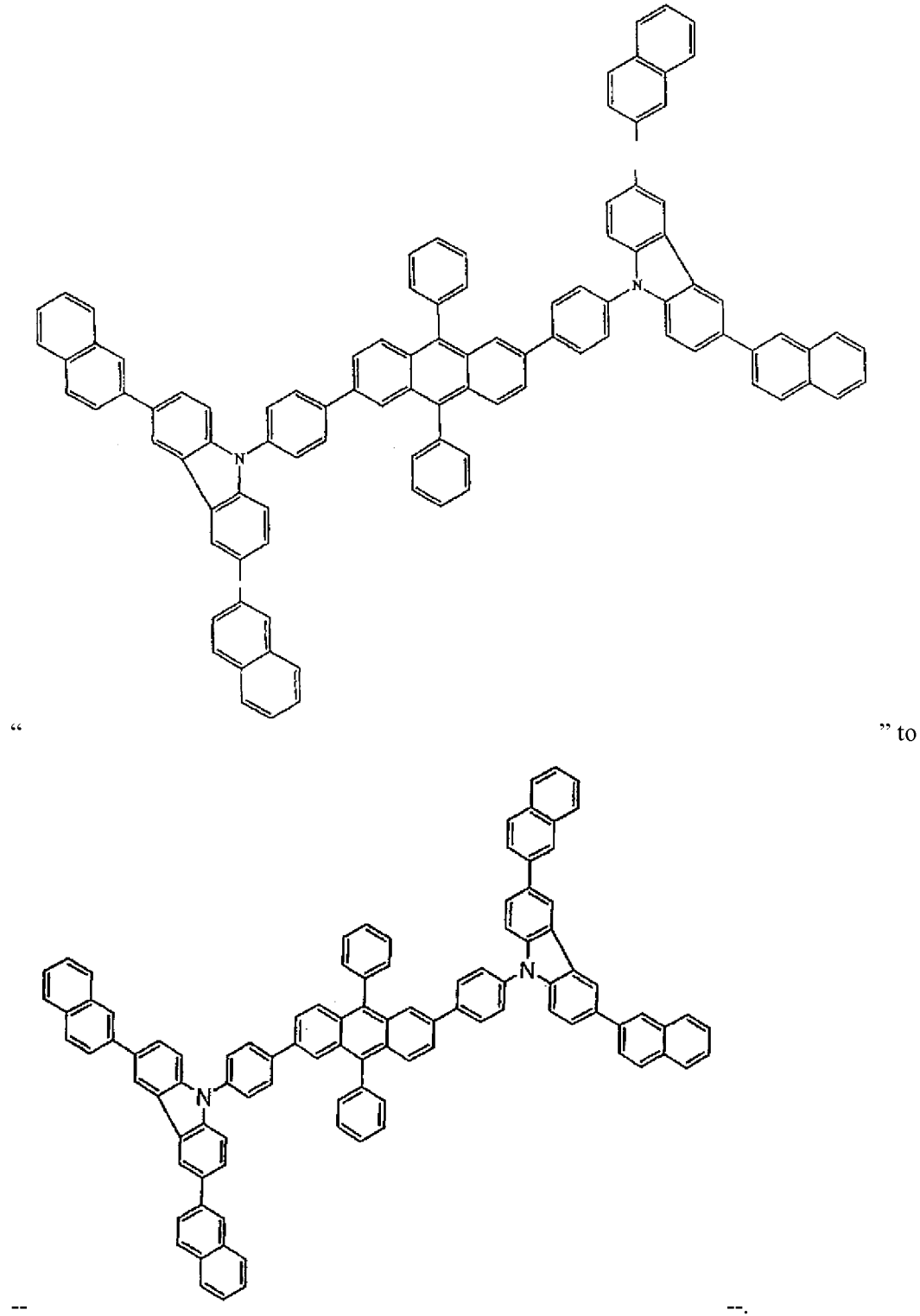

" to

" to

--                                                          --.

In the Specification:

Columns 131 to 132, Figure 428; Change
" 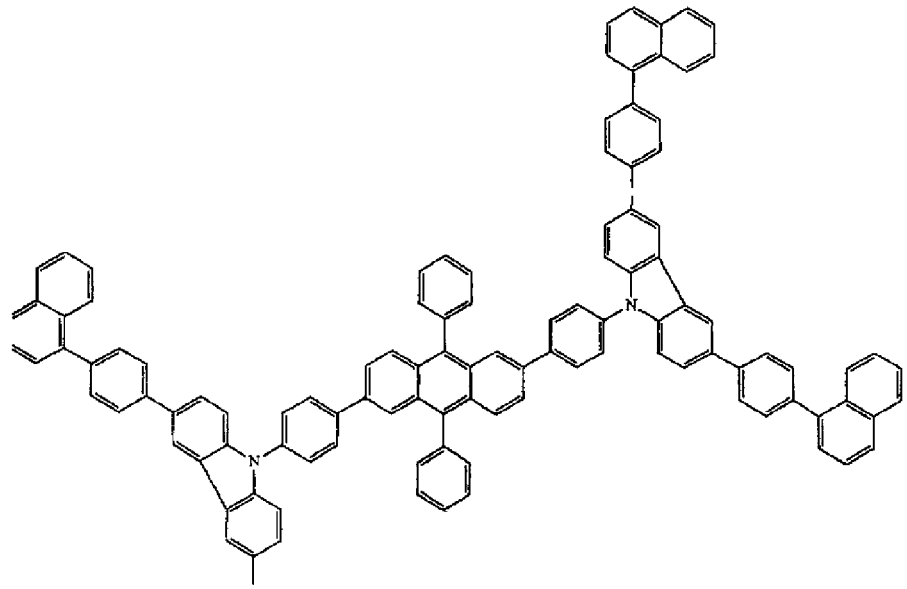 " to
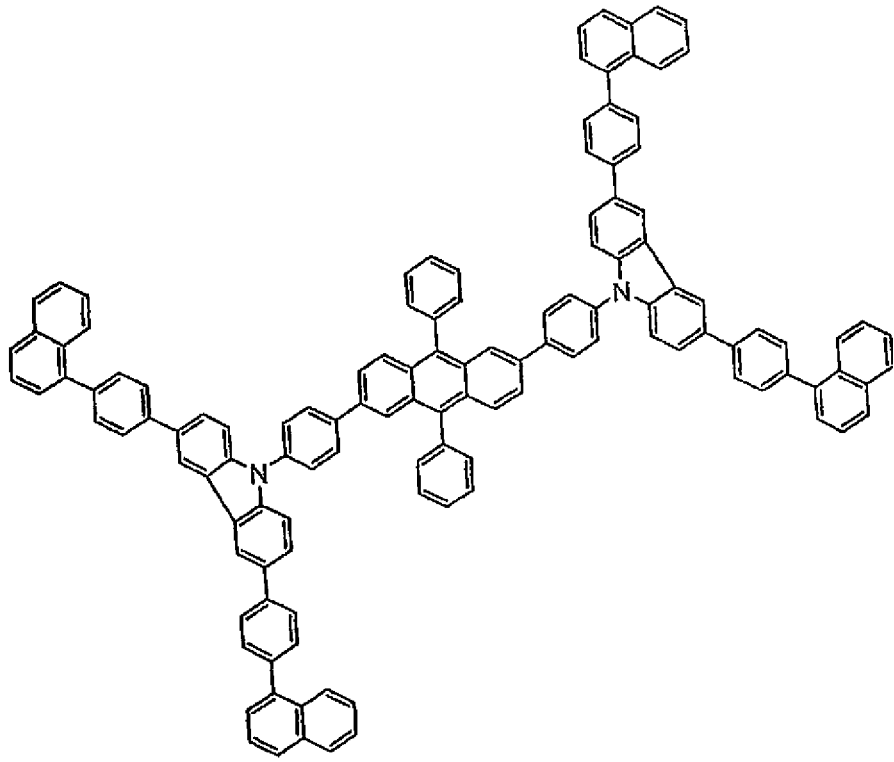
--  --.
In the Specification:

CERTIFICATE OF CORRECTION (continued)
U.S. Pat. No. 8,592,053 B2

Columns 133 to 134, Figure 429; Change

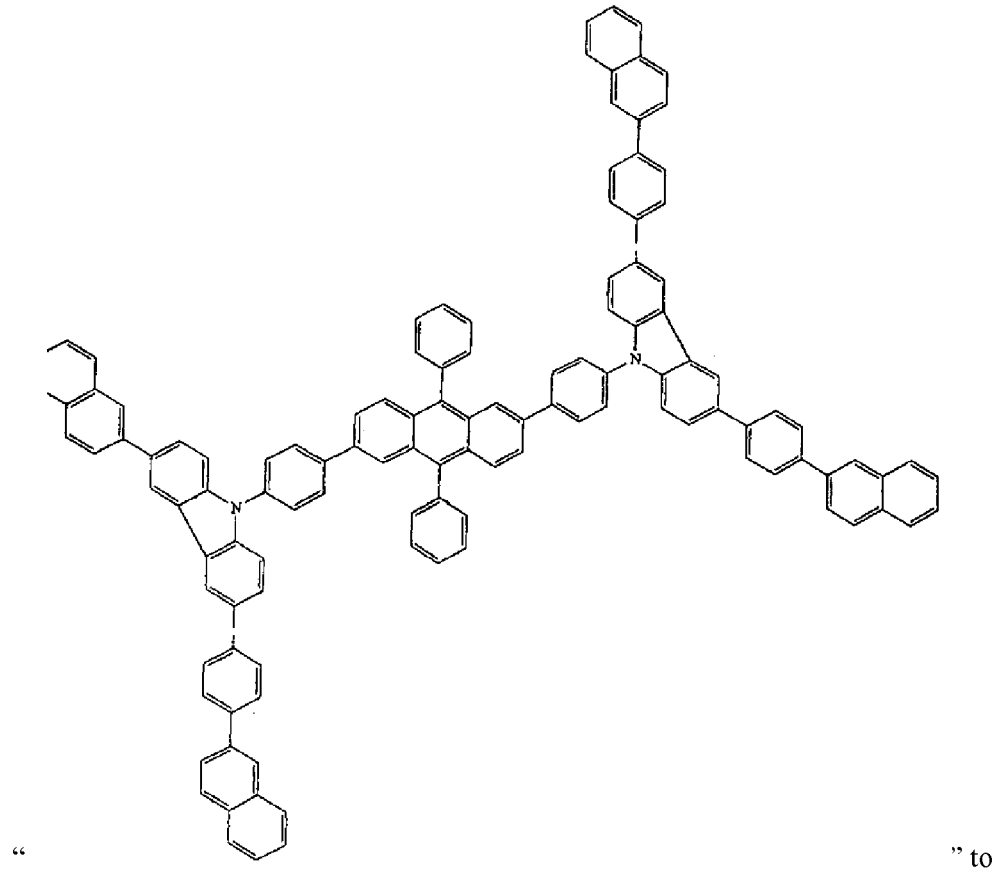

" to

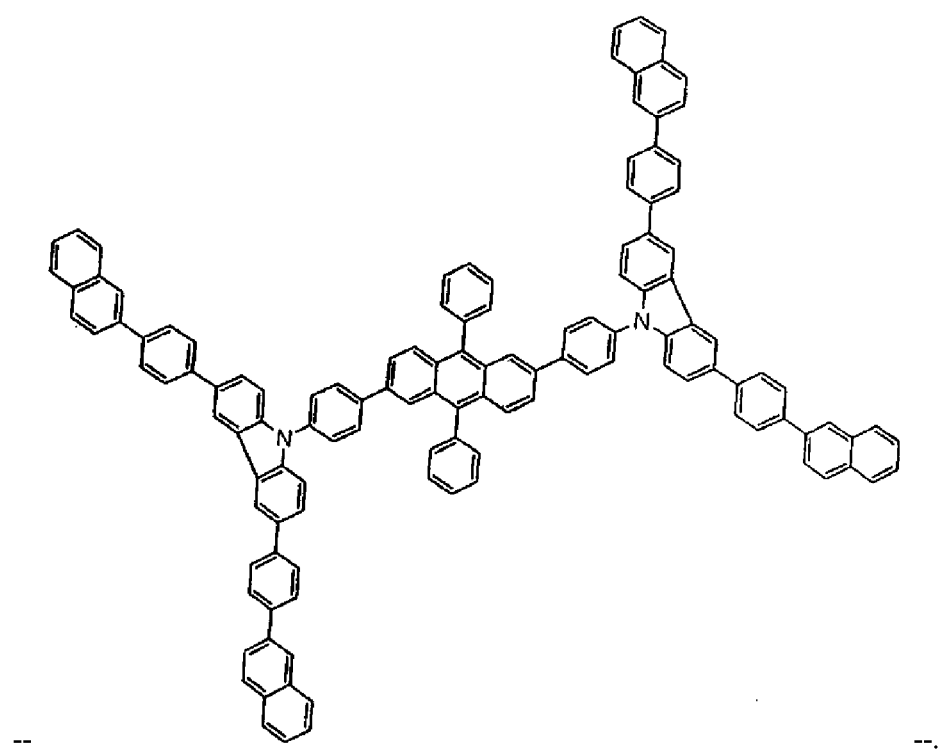

--.

In the Specification:

Columns 133 to 135, Figure 430; Change
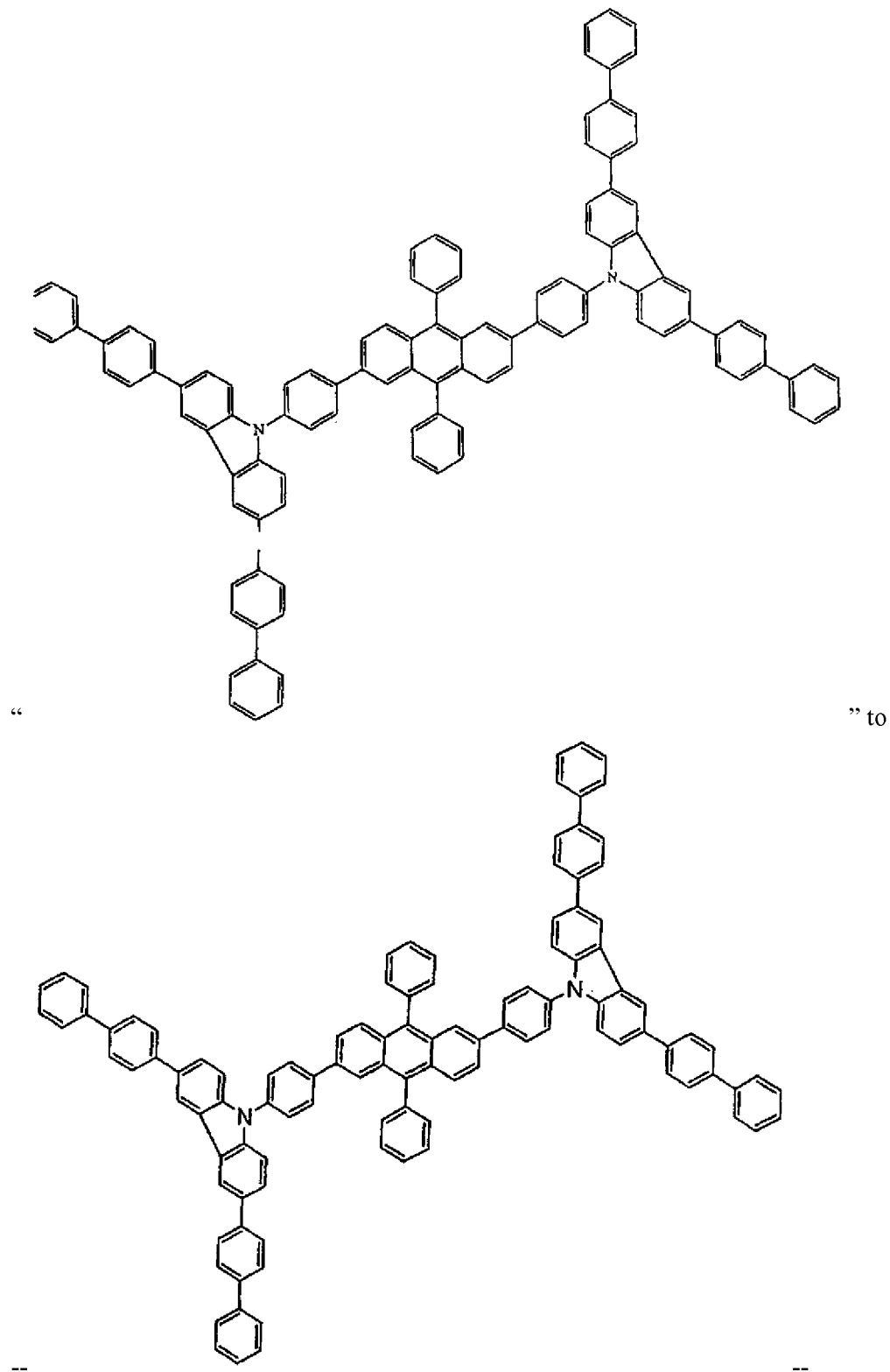
" "  to  " "
In the Specification:

Columns 135 to 136, Figure 431; Change
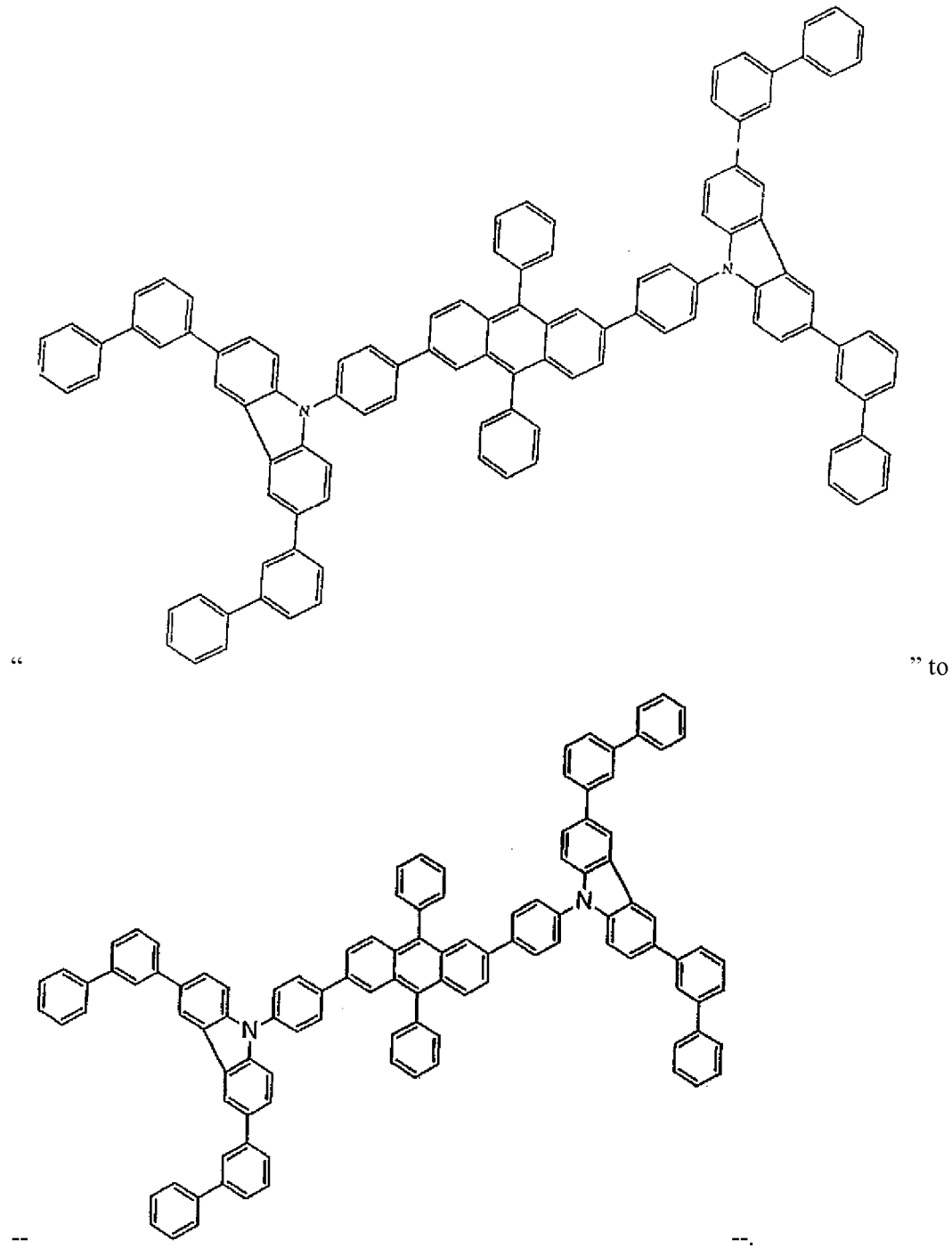
" to
--.
In the Specification:

CERTIFICATE OF CORRECTION (continued)
U.S. Pat. No. 8,592,053 B2

Columns 139 to 140, Figure 436; Change

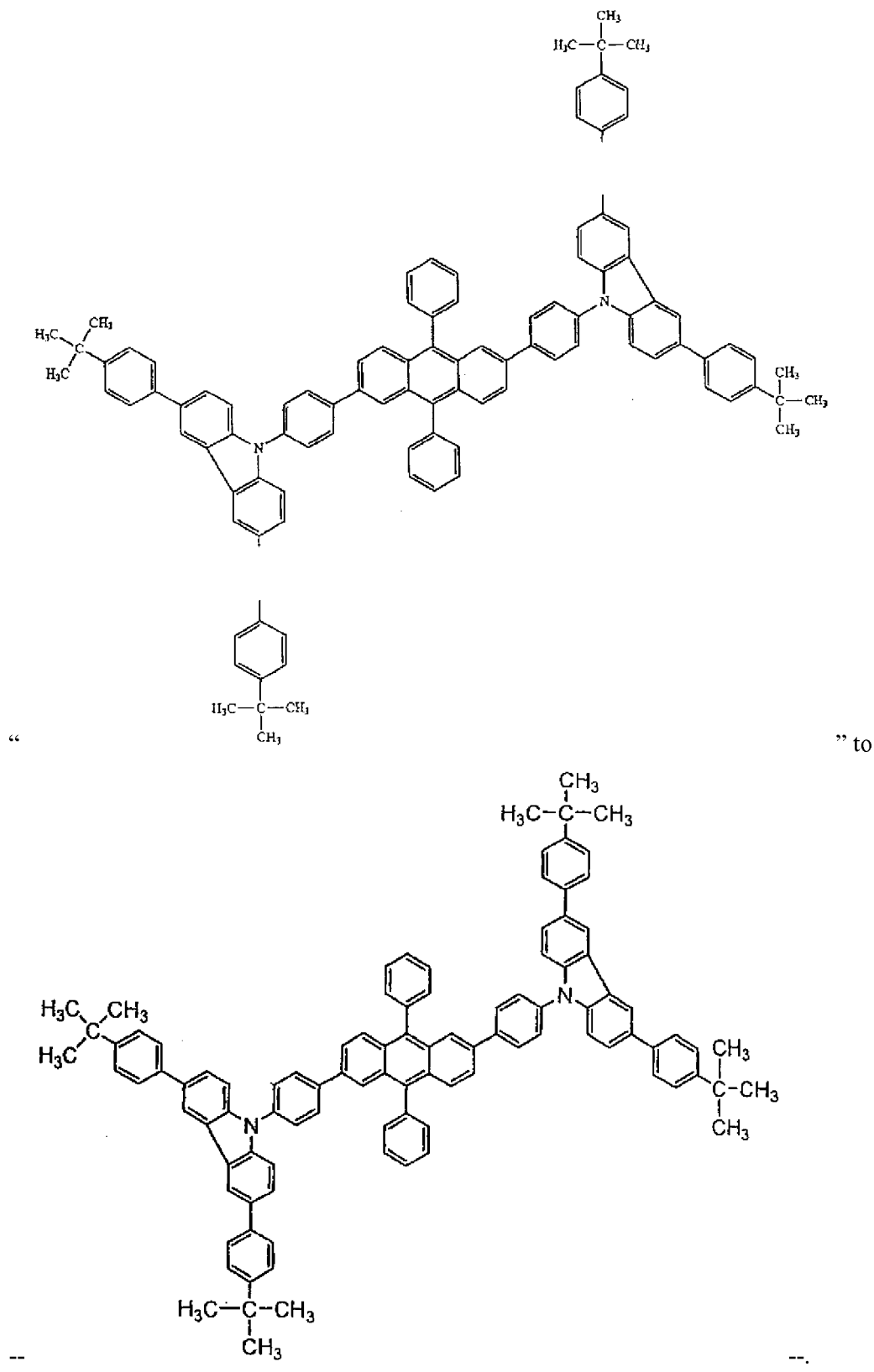

" to

"--.

In the Specification:

Column 142 to 144, Figure 439; Change
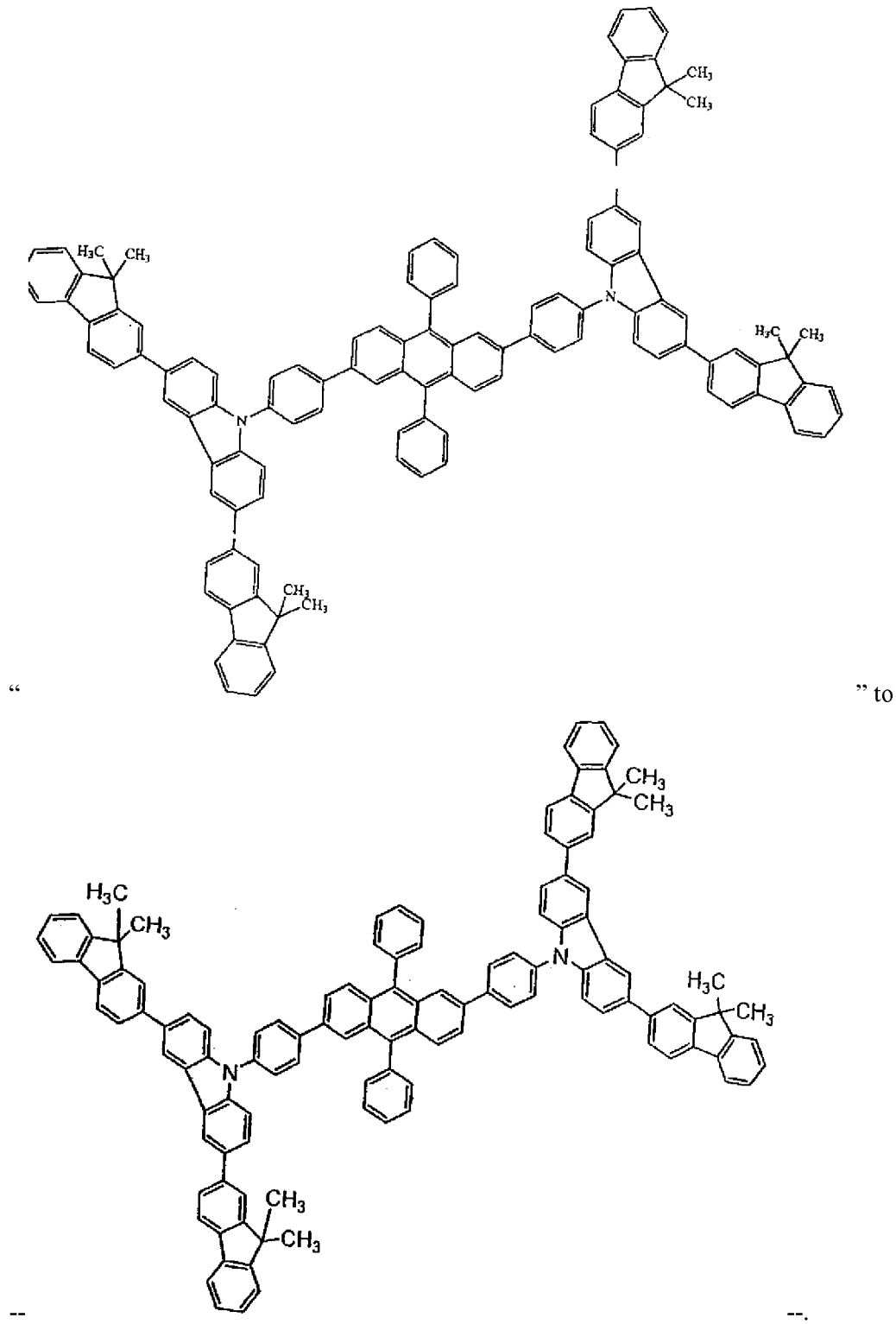
" to
-- --.
In the Specification:

Columns 143 to 144, Figure 440; Change
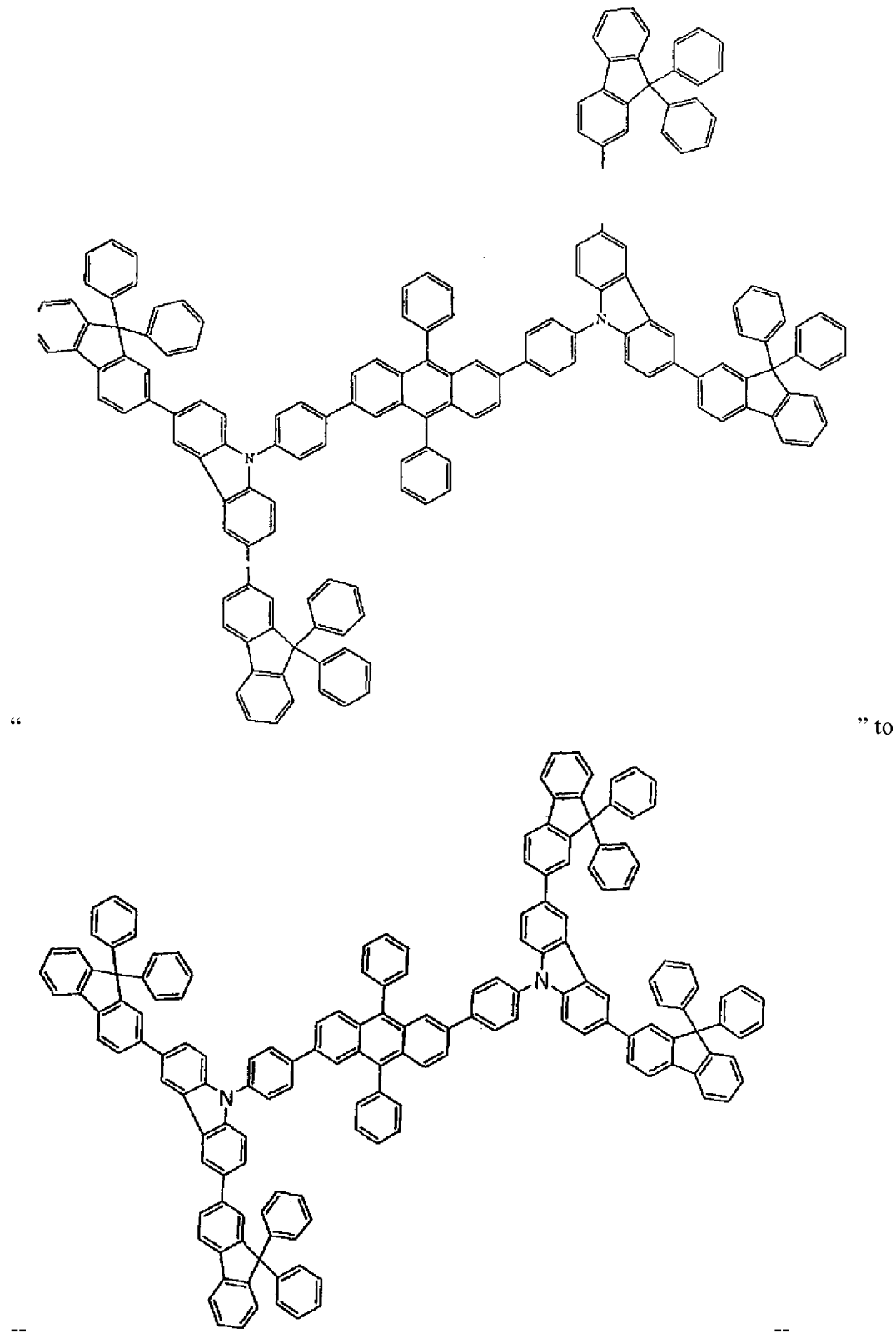
" to
" --.
In the Specification:

Columns 145 to 146, Figure 441; Change
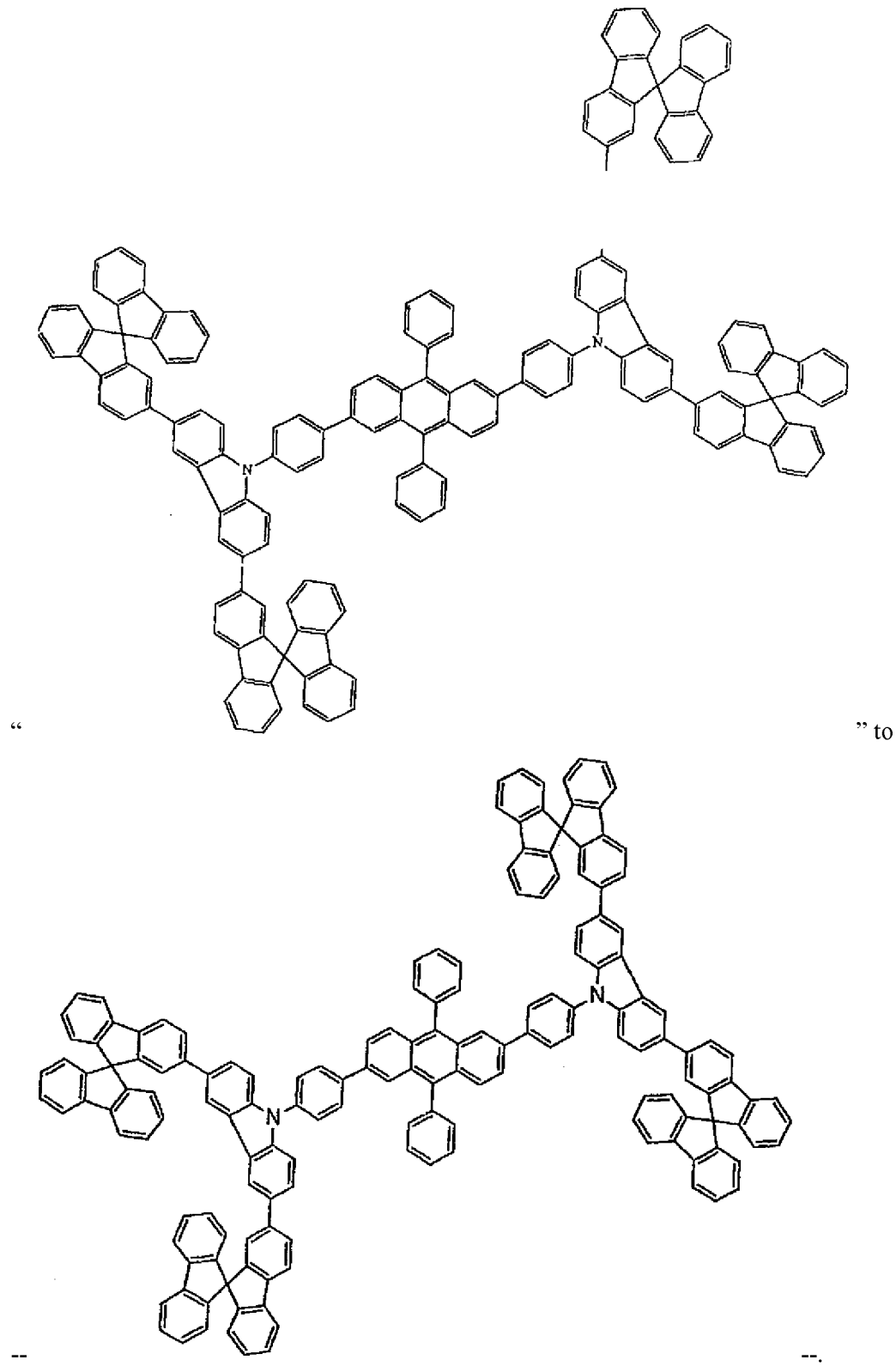
" to
In the Specification:

CERTIFICATE OF CORRECTION (continued)
U.S. Pat. No. 8,592,053 B2

Column 153, Line 36; Change "(g)" to --(Mg)--.
Column 156, Line 16; Change "9-antliryl)" to --9-anthryl)--.
Column 157, Line 15; Change "N,N'-diphenyl" to --N,9-diphenyl--.
Column 160, Line 43; Change "DPHPA)," to --DPhPA),--.
Column 173, Line 55; Change "IL" to --1L--.
Column 177, Line 42; Change "5 transition." to --transition.--.
Column 183, Line 61; Change ")aluminum(II)" to --)aluminum(III)--.

In the Claims:

Column 201, Line 24, Claim 11; Change "$R^{10}$" to --$R^{11}$--.